(12) United States Patent
Kawahata et al.

(10) Patent No.: US 9,522,947 B2
(45) Date of Patent: *Dec. 20, 2016

(54) PEPTIDOMIMETIC MACROCYCLES

(71) Applicant: Aileron Therapeutics, Inc., Cambridge, MA (US)

(72) Inventors: Noriyuki Kawahata, Wayland, MA (US); Vincent Guerlavais, Arlington, MA (US); Manoj Samant, Burlington, MA (US)

(73) Assignee: AILERON THERAPEUTICS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/750,649

(22) Filed: Jun. 25, 2015

(65) Prior Publication Data

US 2016/0137710 A1    May 19, 2016

Related U.S. Application Data

(63) Continuation of application No. 13/655,378, filed on Oct. 18, 2012, now Pat. No. 9,096,684.

(60) Provisional application No. 61/548,690, filed on Oct. 18, 2011.

(51) Int. Cl.
*C07K 14/60* (2006.01)
*A61K 38/00* (2006.01)

(52) U.S. Cl.
CPC .............. *C07K 14/60* (2013.01); *A61K 38/00* (2013.01)

(58) Field of Classification Search
None
See application file for complete search history.

(56) References Cited

U.S. PATENT DOCUMENTS

| | | |
|---|---|---|
| 4,000,259 A | 12/1976 | Garsky |
| 4,191,754 A | 3/1980 | Nutt et al. |
| 4,270,537 A | 6/1981 | Romaine |
| 4,438,270 A | 3/1984 | Bey et al. |
| 4,518,586 A | 5/1985 | Rivier et al. |
| 4,596,556 A | 6/1986 | Morrow et al. |
| 4,683,195 A | 7/1987 | Mullis et al. |
| 4,683,202 A | 7/1987 | Mullis |
| 4,728,726 A | 3/1988 | Rivier et al. |
| 4,730,006 A | 3/1988 | Bohme et al. |
| 4,737,465 A | 4/1988 | Bond et al. |
| 4,790,824 A | 12/1988 | Morrow et al. |
| 4,880,778 A | 11/1989 | Bowers et al. |
| 4,886,499 A | 12/1989 | Cirelli et al. |
| 4,940,460 A | 7/1990 | Casey, et al. |
| 4,941,880 A | 7/1990 | Burns |
| 5,015,235 A | 5/1991 | Crossman |
| 5,036,045 A | 7/1991 | Thorner |
| 5,043,322 A | 8/1991 | Rivier et al. |
| 5,064,413 A | 11/1991 | McKinnon et al. |
| 5,112,808 A | 5/1992 | Coy et al. |
| 5,120,859 A | 6/1992 | Webb |
| 5,141,496 A | 8/1992 | Dalto et al. |
| 5,169,932 A | 12/1992 | Hoeger et al. |
| 5,190,521 A | 3/1993 | Hubbard et al. |
| 5,245,009 A | 9/1993 | Kornreich et al. |
| 5,262,519 A | 11/1993 | Rivier et al. |
| 5,296,468 A | 3/1994 | Hoeger et al. |
| 5,310,910 A | 5/1994 | Drtina et al. |
| 5,312,335 A | 5/1994 | McKinnon et al. |
| 5,323,907 A | 6/1994 | Kalvelage |
| 5,328,483 A | 7/1994 | Jacoby |
| 5,334,144 A | 8/1994 | Alchas et al. |
| 5,339,163 A | 8/1994 | Homma et al. |
| 5,352,796 A | 10/1994 | Hoeger et al. |
| 5,364,851 A | 11/1994 | Joran |
| 5,371,070 A | 12/1994 | Koerber et al. |
| 5,383,851 A | 1/1995 | McKinnon, Jr. et al. |
| 5,416,073 A | 5/1995 | Coy et al. |
| 5,417,662 A | 5/1995 | Hjertman et al. |
| 5,446,128 A | 8/1995 | Kahn |
| 5,453,418 A | 9/1995 | Anderson et al. |
| 5,466,220 A | 11/1995 | Brenneman |
| 5,480,381 A | 1/1996 | Weston |
| 5,503,627 A | 4/1996 | McKinnon et al. |
| 5,506,207 A | 4/1996 | Rivier et al. |
| 5,520,639 A | 5/1996 | Peterson et al. |
| 5,527,288 A | 6/1996 | Gross et al. |
| 5,552,520 A | 9/1996 | Kim et al. |
| 5,569,189 A | 10/1996 | Parsons |
| 5,580,957 A | 12/1996 | Hoeger et al. |
| 5,599,302 A | 2/1997 | Lilley et al. |

(Continued)

FOREIGN PATENT DOCUMENTS

| | | |
|---|---|---|
| CN | 1252808 A | 5/2000 |
| CN | 1583730 A | 2/2005 |

(Continued)

OTHER PUBLICATIONS

Felix et al. Proceedings of the Twelfth American Peptide Symposium. p. 77-79:1991.*
Fry et al. Biopolymers. 32;349-666:1992.*
Adhikary et al., Transcriptional regulation and transformation by Myc proteins. Nat Rev Mol Cell Biol. 2005 Aug;6(8):635-45.
Agola et al., Rab GTPases as regulators of endocytosis, targets of disease and therapeutic opportunities. Clin Genet. 2011 Oct.; 80(4): 305-318.
Altschul et al. Basic local alignment search tool. J Mol Biol215(3):403-410 (1990).
Aman et al., cDNA cloning and characterization of the human interleukin 13 receptor alpha chain. J Biol Chem. Nov. 15, 1999;271(46):29265-70.
Andrews et al. Forming Stable Helical Peptide Using Natural and Artificial Amino Acids. Tetrahedron. 1999;55:11711-11743.
Andrews et al., Kinetic analysis of the interleukin-13 receptor complex. J Biol Chem. Nov. 29, 2002;277(48):46073-8. Epub Sep. 26, 2002.
Angel & Karin, "The Role of Jun, Fos and the AP-1 Complex in Cell-proliferation and Transformation," Biochim. Biophys. Acta 1072:129-157 (1991).
Angell, et al. Peptidomimetics via copper-catalyzed azide-alkyne cycloadditions. Chem Soc Rev. Oct. 2007;36(10):1674-89.
Angell, et al. Ring closure to beta-turn mimics via copper-catalyzed azide/alkyne cycloadditions. J Org Chem. Nov. 11, 2005;70(23):9595-8.

(Continued)

*Primary Examiner* — Karlheinz R Skowronek
*Assistant Examiner* — Schuyler Milton
(74) *Attorney, Agent, or Firm* — Wilson Sonsini Goodrich & Rosati

(57) ABSTRACT

The present invention provides peptidomimetic macrocycles capable of modulating growth hormone levels and methods of using such macrocycles for the treatment of disease.

56 Claims, 13 Drawing Sheets

(56) References Cited

U.S. PATENT DOCUMENTS

| | | |
|---|---|---|
| 5,620,708 A | 4/1997 | Amkraut et al. |
| 5,622,852 A | 4/1997 | Korsmeyer |
| 5,629,020 A | 5/1997 | Leone-Bay et al. |
| 5,635,371 A | 6/1997 | Stout et al. |
| 5,643,957 A | 7/1997 | Leone-Bay et al. |
| 5,649,912 A | 7/1997 | Peterson |
| 5,650,133 A | 7/1997 | Carvalho et al. |
| 5,650,386 A | 7/1997 | Leone-Bay et al. |
| 5,656,721 A | 8/1997 | Albert et al. |
| 5,663,316 A | 9/1997 | Xudong |
| 5,672,584 A | 9/1997 | Borchardt et al. |
| 5,681,928 A | 10/1997 | Rivier et al. |
| 5,700,775 A | 12/1997 | Gutniak et al. |
| 5,702,908 A | 12/1997 | Picksley et al. |
| 5,704,911 A | 1/1998 | Parsons |
| 5,708,136 A | 1/1998 | Burrell et al. |
| 5,710,245 A | 1/1998 | Kahn |
| 5,710,249 A | 1/1998 | Hoeger et al. |
| 5,731,408 A | 3/1998 | Hadley et al. |
| 5,744,450 A | 4/1998 | Hoeger et al. |
| 5,750,499 A | 5/1998 | Hoeger et al. |
| 5,750,767 A | 5/1998 | Carpino et al. |
| 5,756,669 A | 5/1998 | Bischoff et al. |
| 5,770,377 A | 6/1998 | Picksley et al. |
| 5,792,747 A | 8/1998 | Schally et al. |
| 5,807,983 A | 9/1998 | Jiang et al. |
| 5,811,515 A | 9/1998 | Grubbs et al. |
| 5,817,752 A | 10/1998 | Yu |
| 5,817,789 A | 10/1998 | Heartlein et al. |
| 5,824,483 A | 10/1998 | Houston, Jr. et al. |
| 5,834,209 A | 11/1998 | Korsmeyer |
| 5,837,845 A | 11/1998 | Hosokawa et al. |
| 5,840,833 A | 11/1998 | Kahn |
| 5,846,936 A | 12/1998 | Felix et al. |
| 5,847,066 A | 12/1998 | Coy et al. |
| 5,854,216 A | 12/1998 | Gaudreau |
| 5,856,445 A | 1/1999 | Korsmeyer |
| 5,859,184 A | 1/1999 | Kahn et al. |
| 5,861,379 A | 1/1999 | Ibea et al. |
| 5,874,529 A | 2/1999 | Gilon et al. |
| 5,893,397 A | 4/1999 | Peterson et al. |
| 5,922,863 A | 7/1999 | Grubbs et al. |
| 5,939,386 A | 8/1999 | Ibea et al. |
| 5,939,387 A | 8/1999 | Broderick et al. |
| 5,955,593 A | 9/1999 | Korsmeyer |
| 5,965,703 A | 10/1999 | Horne et al. |
| 5,993,412 A | 11/1999 | Deily et al. |
| 5,998,583 A | 12/1999 | Korsmeyer |
| 6,020,311 A | 2/2000 | Brazeau et al. |
| 6,030,997 A | 2/2000 | Eilat et al. |
| 6,031,073 A | 2/2000 | Yu |
| 6,043,339 A | 3/2000 | Lin et al. |
| 6,046,289 A | 4/2000 | Komazawa et al. |
| 6,051,513 A | 4/2000 | Kumazawa et al. |
| 6,051,554 A | 4/2000 | Hornik et al. |
| 6,054,556 A | 4/2000 | Huby et al. |
| 6,060,513 A | 5/2000 | Leone-Bay et al. |
| 6,066,470 A | 5/2000 | Nishimura et al. |
| 6,071,510 A | 6/2000 | Leone-Bay et al. |
| 6,071,538 A | 6/2000 | Milstein et al. |
| 6,071,926 A | 6/2000 | Van et al. |
| 6,090,958 A | 7/2000 | Leone-Bay et al. |
| 6,100,298 A | 8/2000 | Leone-Bay et al. |
| 6,118,010 A | 9/2000 | Ueda et al. |
| 6,123,964 A | 9/2000 | Asgharnejad et al. |
| 6,127,341 A | 10/2000 | Hansen et al. |
| 6,127,354 A | 10/2000 | Peschke et al. |
| 6,127,391 A | 10/2000 | Hansen et al. |
| 6,153,391 A | 11/2000 | Picksley et al. |
| 6,169,073 B1 | 1/2001 | Halazonetis et al. |
| 6,177,076 B1 | 1/2001 | Lattime et al. |
| 6,177,542 B1 | 1/2001 | Ruoslahti et al. |
| 6,184,344 B1 | 2/2001 | Kent et al. |
| 6,190,699 B1 | 2/2001 | Luzzi et al. |
| 6,194,384 B1 | 2/2001 | Brazeau et al. |
| 6,194,402 B1 | 2/2001 | Bach et al. |
| 6,204,361 B1 | 3/2001 | Carpino et al. |
| 6,245,359 B1 | 6/2001 | Milstein et al. |
| 6,245,886 B1 | 6/2001 | Halazonetis et al. |
| 6,248,358 B1 | 6/2001 | Bologna et al. |
| 6,271,198 B1 | 8/2001 | Braisted et al. |
| 6,274,584 B1 | 8/2001 | Peschke et al. |
| 6,287,787 B1 | 9/2001 | Houghten et al. |
| 6,307,017 B1 | 10/2001 | Coy et al. |
| 6,309,859 B1 | 10/2001 | Nishimura et al. |
| 6,313,088 B1 | 11/2001 | Leone-Bay et al. |
| 6,313,133 B1 | 11/2001 | Van et al. |
| 6,326,354 B1 | 12/2001 | Gross et al. |
| 6,331,318 B1 | 12/2001 | Milstein |
| 6,344,213 B1 | 2/2002 | Leone-Bay et al. |
| 6,346,264 B1 | 2/2002 | White |
| 6,348,558 B1 | 2/2002 | Harris et al. |
| 6,368,617 B1 | 4/2002 | Hastings et al. |
| 6,420,118 B1 | 7/2002 | Halazonetis et al. |
| 6,420,136 B1 | 7/2002 | Riabowol et al. |
| 6,444,425 B1 | 9/2002 | Reed et al. |
| 6,458,764 B1 | 10/2002 | Gravel et al. |
| 6,461,634 B1 | 10/2002 | Marshall |
| 6,495,589 B2 | 12/2002 | Hay et al. |
| 6,495,674 B1 | 12/2002 | Lemke et al. |
| 6,514,685 B1 | 2/2003 | Moro |
| 6,548,501 B2 | 4/2003 | Hakkinen |
| 6,555,156 B1 | 4/2003 | Loughman |
| 6,555,570 B2 | 4/2003 | Hansen et al. |
| 6,569,993 B1 | 5/2003 | Sledeski et al. |
| 6,572,856 B1 | 6/2003 | Taylor et al. |
| 6,579,967 B1 | 6/2003 | Rivier et al. |
| 6,610,657 B1 | 8/2003 | Goueli |
| 6,613,874 B1 | 9/2003 | Mazur et al. |
| 6,617,360 B1 | 9/2003 | Bailey et al. |
| 6,620,808 B2 | 9/2003 | Van Der Klish et al. |
| 6,635,740 B1 | 10/2003 | Enright et al. |
| 6,641,840 B2 | 11/2003 | Am Ende et al. |
| 6,686,148 B1 | 2/2004 | Shen et al. |
| 6,696,063 B1 | 2/2004 | Torres |
| 6,696,418 B1 | 2/2004 | Hay et al. |
| 6,703,382 B2 | 3/2004 | Wang et al. |
| 6,713,280 B1 | 3/2004 | Huang et al. |
| 6,720,330 B2 | 4/2004 | Hay et al. |
| 6,747,125 B1 | 6/2004 | Hoeger et al. |
| 6,784,157 B2 | 8/2004 | Halazonetis et al. |
| 6,849,428 B1 | 2/2005 | Evans et al. |
| 6,852,722 B2 | 2/2005 | Hakkinen |
| 6,875,594 B2 | 4/2005 | Muir et al. |
| 6,897,286 B2 | 5/2005 | Jaspers et al. |
| 6,939,880 B2 | 9/2005 | Hansen et al. |
| 7,019,109 B2 | 3/2006 | Rivier et al. |
| 7,034,050 B2 | 4/2006 | Deghenghi |
| 7,064,193 B1 | 6/2006 | Cory et al. |
| 7,083,983 B2 | 8/2006 | Lane et al. |
| 7,084,244 B2 | 8/2006 | Gilon et al. |
| 7,115,372 B2 | 10/2006 | Shen et al. |
| 7,144,577 B2 | 12/2006 | Torres |
| 7,166,461 B2 | 1/2007 | Schwartz et al. |
| 7,183,059 B2 | 2/2007 | Verdine et al. |
| 7,189,801 B2 | 3/2007 | Halazonetis et al. |
| 7,192,713 B1 | 3/2007 | Verdine et al. |
| 7,202,332 B2 | 4/2007 | Arora et al. |
| 7,238,775 B2 | 7/2007 | Rivier et al. |
| 7,247,700 B2 | 7/2007 | Korsmeyer et al. |
| 7,268,113 B2 | 9/2007 | Bridon et al. |
| 7,312,304 B2 | 12/2007 | Coy et al. |
| 7,316,997 B2 | 1/2008 | Abribat et al. |
| 7,414,107 B2 | 8/2008 | Larsen |
| 7,425,542 B2 | 9/2008 | Maggio |
| 7,445,919 B2 | 11/2008 | Jaspers et al. |
| 7,476,653 B2 | 1/2009 | Hoveyda et al. |
| 7,485,620 B2 | 2/2009 | Ghigo et al. |
| 7,491,695 B2 | 2/2009 | Fraser et al. |
| 7,521,420 B2 | 4/2009 | Fraser et al. |
| 7,538,190 B2 | 5/2009 | Robinson et al. |
| 7,566,777 B2 | 7/2009 | Enright et al. |

(56) References Cited

U.S. PATENT DOCUMENTS

| | | |
|---|---|---|
| 7,638,138 B2 | 12/2009 | Oki et al. |
| 7,655,447 B2 | 2/2010 | Jaspers et al. |
| 7,666,983 B2 | 2/2010 | Halazonetis et al. |
| 7,705,118 B2 | 4/2010 | Arora et al. |
| 7,723,469 B2 | 5/2010 | Walensky et al. |
| 7,737,174 B2 | 6/2010 | Wang et al. |
| 7,745,573 B2 | 6/2010 | Robinson et al. |
| 7,759,383 B2 | 7/2010 | Wang et al. |
| 7,786,072 B2 | 8/2010 | Verdine et al. |
| 7,829,724 B2 | 11/2010 | Perrissoud et al. |
| RE42,013 E | 12/2010 | Hoveyda |
| 7,884,073 B2 | 2/2011 | Guyon et al. |
| 7,884,107 B2 | 2/2011 | Ma et al. |
| 7,888,056 B2 | 2/2011 | Sheppard et al. |
| 7,893,025 B2 | 2/2011 | Lussier et al. |
| 7,893,278 B2 | 2/2011 | Haley et al. |
| 7,927,813 B2 | 4/2011 | Geneste et al. |
| 7,932,397 B2 | 4/2011 | Hock et al. |
| 7,960,342 B2 | 6/2011 | Rivier et al. |
| 7,960,506 B2 | 6/2011 | Nash |
| 7,964,724 B2 | 6/2011 | Fotouhi et al. |
| 7,981,998 B2 | 7/2011 | Nash |
| 7,981,999 B2 | 7/2011 | Nash |
| RE42,624 E | 8/2011 | Fraser |
| 7,994,329 B2 | 8/2011 | Ankerson |
| 7,998,927 B2 | 8/2011 | Maggio |
| 7,998,930 B2 | 8/2011 | Guyon et al. |
| 8,017,607 B2 | 9/2011 | Bartkovitz et al. |
| 8,039,456 B2 | 10/2011 | Polvino et al. |
| 8,039,457 B2 | 10/2011 | Polvino |
| 8,058,269 B2 | 11/2011 | Chen et al. |
| 8,071,541 B2 | 12/2011 | Arora et al. |
| 8,076,290 B2 | 12/2011 | Maggio |
| 8,076,482 B2 | 12/2011 | Chen et al. |
| 8,084,022 B2 | 12/2011 | Maggio |
| 8,088,733 B2 | 1/2012 | Fraser et al. |
| 8,088,815 B2 | 1/2012 | Bartkovitz et al. |
| 8,088,931 B2 | 1/2012 | Wang et al. |
| 8,124,356 B2 | 2/2012 | Sheppard et al. |
| 8,124,726 B2 | 2/2012 | Robinson et al. |
| 8,129,561 B2 | 3/2012 | Marsault et al. |
| 8,133,863 B2 | 3/2012 | Maggio |
| 8,173,594 B2 | 5/2012 | Maggio |
| 8,192,719 B2 | 6/2012 | Larsen |
| 8,198,405 B2 | 6/2012 | Walensky et al. |
| 8,217,051 B2 | 7/2012 | Zhang et al. |
| 8,222,209 B2 | 7/2012 | Guyon et al. |
| 8,226,949 B2 | 7/2012 | Maggio |
| 8,314,066 B2 | 11/2012 | Abribat et al. |
| 8,324,428 B2 | 12/2012 | Verdine et al. |
| 8,334,256 B2 | 12/2012 | Marsault et al. |
| 8,343,760 B2 | 1/2013 | Lu et al. |
| 8,349,887 B2 | 1/2013 | Fraser et al. |
| 8,389,484 B2 | 3/2013 | Shen et al. |
| 8,399,405 B2 | 3/2013 | Nash et al. |
| 8,435,945 B2 | 5/2013 | Abribat et al. |
| 8,450,268 B2 | 5/2013 | Fraser et al. |
| 8,524,653 B2 | 9/2013 | Nash et al. |
| 8,592,377 B2 | 11/2013 | Verdine et al. |
| 8,609,809 B2 | 12/2013 | Nash |
| 8,637,686 B2 | 1/2014 | Nash |
| 8,796,418 B2 | 8/2014 | Walensky et al. |
| 8,808,694 B2 | 8/2014 | Nash et al. |
| 8,859,723 B2 | 10/2014 | Guerlavais et al. |
| 8,871,899 B2 | 10/2014 | Wang et al. |
| 8,889,632 B2 | 11/2014 | Bernal et al. |
| 8,895,699 B2 | 11/2014 | Verdine et al. |
| 8,927,500 B2 | 1/2015 | Guerlavais et al. |
| 8,957,026 B2 | 2/2015 | Verdine et al. |
| 8,987,414 B2 | 3/2015 | Guerlavais et al. |
| 9,023,988 B2 | 5/2015 | Nash |
| 9,096,684 B2 | 8/2015 | Kawahata et al. |
| 9,163,330 B2 | 10/2015 | Verdine et al. |
| 9,175,045 B2 | 11/2015 | Nash et al. |
| 9,175,047 B2 | 11/2015 | Nash et al. |
| 9,175,056 B2 | 11/2015 | Nash |
| 9,206,223 B2 | 12/2015 | Nash et al. |
| 9,273,099 B2 | 3/2016 | Walensky et al. |
| 9,381,228 B2 | 7/2016 | Robson et al. |
| 9,394,336 B2 | 7/2016 | Nash et al. |
| 2001/0047030 A1 | 11/2001 | Hay et al. |
| 2002/0002198 A1 | 1/2002 | Parr |
| 2002/0013320 A1 | 1/2002 | Busch et al. |
| 2002/0016298 A1 | 2/2002 | Hay et al. |
| 2002/0028838 A1 | 3/2002 | MacLean et al. |
| 2002/0055156 A1 | 5/2002 | Jaspers et al. |
| 2002/0061838 A1 | 5/2002 | Holmquist et al. |
| 2002/0091090 A1 | 7/2002 | Cole et al. |
| 2002/0091125 A1 | 7/2002 | Hay et al. |
| 2002/0094992 A1 | 7/2002 | MacLean |
| 2002/0098580 A1 | 7/2002 | Nandabalan et al. |
| 2002/0103221 A1 | 8/2002 | Petrie et al. |
| 2002/0128206 A1 | 9/2002 | Hay et al. |
| 2002/0132977 A1 | 9/2002 | Yuan et al. |
| 2002/0137665 A1 | 9/2002 | Evans et al. |
| 2002/0173618 A1 | 11/2002 | Rivier et al. |
| 2003/0027766 A1 | 2/2003 | Ioannides et al. |
| 2003/0060432 A1 | 3/2003 | Tocque et al. |
| 2003/0074679 A1 | 4/2003 | Schwartz et al. |
| 2003/0083241 A1 | 5/2003 | Young |
| 2003/0105114 A1 | 6/2003 | Carpino et al. |
| 2003/0144331 A1 | 7/2003 | Gudkov et al. |
| 2003/0148948 A1 | 8/2003 | Schwartz et al. |
| 2003/0157717 A1 | 8/2003 | Draghia-Akli |
| 2003/0166138 A1 | 9/2003 | Kinsella et al. |
| 2003/0176318 A1 | 9/2003 | Gudkov et al. |
| 2003/0181367 A1 | 9/2003 | O'Mahony et al. |
| 2003/0186865 A1 | 10/2003 | Acosta et al. |
| 2003/0204063 A1 | 10/2003 | Gravel et al. |
| 2004/0018967 A1 | 1/2004 | Enright et al. |
| 2004/0023887 A1 | 2/2004 | Pillutla et al. |
| 2004/0038901 A1 | 2/2004 | Basler et al. |
| 2004/0038918 A1 | 2/2004 | Draghia-Akli et al. |
| 2004/0058877 A1 | 3/2004 | Hay et al. |
| 2004/0067503 A1 | 4/2004 | Tan et al. |
| 2004/0081652 A1 | 4/2004 | Zack et al. |
| 2004/0091530 A1 | 5/2004 | Am Ende et al. |
| 2004/0106159 A1 | 6/2004 | Kern et al. |
| 2004/0106548 A1 | 6/2004 | Schmidt et al. |
| 2004/0115135 A1 | 6/2004 | Quay |
| 2004/0122062 A1 | 6/2004 | MacLean et al. |
| 2004/0146971 A1 | 7/2004 | Lane et al. |
| 2004/0152708 A1 | 8/2004 | Li et al. |
| 2004/0157834 A1 | 8/2004 | Hay et al. |
| 2004/0170653 A1 | 9/2004 | Stanislawski et al. |
| 2004/0170971 A1 | 9/2004 | Kinzler et al. |
| 2004/0171530 A1 | 9/2004 | Coy et al. |
| 2004/0171809 A1 | 9/2004 | Korsmeyer et al. |
| 2004/0195413 A1 | 10/2004 | Reed et al. |
| 2004/0204358 A1 | 10/2004 | Brown et al. |
| 2004/0208866 A1 | 10/2004 | Jaspers et al. |
| 2004/0228866 A1 | 11/2004 | Lu |
| 2004/0235746 A1 | 11/2004 | Hawiger et al. |
| 2004/0248198 A1 | 12/2004 | Kriwacki et al. |
| 2004/0248788 A1 | 12/2004 | Vickers et al. |
| 2004/0265931 A1 | 12/2004 | Gu et al. |
| 2005/0009739 A1 | 1/2005 | Wang et al. |
| 2005/0013820 A1 | 1/2005 | Holoshitz et al. |
| 2005/0014686 A1 | 1/2005 | Albert et al. |
| 2005/0031549 A1 | 2/2005 | Quay et al. |
| 2005/0037383 A1 | 2/2005 | Taremi et al. |
| 2005/0043231 A1 | 2/2005 | Cutfield et al. |
| 2005/0048618 A1 | 3/2005 | Jaspers et al. |
| 2005/0049177 A1 | 3/2005 | Bachovchin et al. |
| 2005/0054581 A1 | 3/2005 | Hay et al. |
| 2005/0059605 A1 | 3/2005 | Peri et al. |
| 2005/0065180 A1 | 3/2005 | Lee |
| 2005/0080007 A1 | 4/2005 | Ghigo et al. |
| 2005/0089511 A1 | 4/2005 | Roth et al. |
| 2005/0119167 A1 | 6/2005 | Abbenante et al. |
| 2005/0137137 A1 | 6/2005 | Lane et al. |
| 2005/0147581 A1 | 7/2005 | Zamiri et al. |
| 2005/0164298 A1 | 7/2005 | Golz et al. |
| 2005/0176075 A1 | 8/2005 | Jones et al. |

(56) References Cited

U.S. PATENT DOCUMENTS

| | | |
|---|---|---|
| 2005/0203009 A1 | 9/2005 | Pan et al. |
| 2005/0222224 A1 | 10/2005 | Gudkov et al. |
| 2005/0222427 A1 | 10/2005 | Sharpless et al. |
| 2005/0227932 A1 | 10/2005 | Lu et al. |
| 2005/0245438 A1 | 11/2005 | Rivier et al. |
| 2005/0245457 A1 | 11/2005 | Deghenghi |
| 2005/0245764 A1 | 11/2005 | Yamashita et al. |
| 2005/0250680 A1 | 11/2005 | Walensky et al. |
| 2005/0261201 A1 | 11/2005 | Polvino et al. |
| 2005/0277764 A1 | 12/2005 | Boyd et al. |
| 2006/0008848 A1 | 1/2006 | Verdine et al. |
| 2006/0014675 A1 | 1/2006 | Arora et al. |
| 2006/0025344 A1 | 2/2006 | Lange et al. |
| 2006/0058219 A1 | 3/2006 | Miller et al. |
| 2006/0058221 A1 | 3/2006 | Miller et al. |
| 2006/0073518 A1 | 4/2006 | Timmerman et al. |
| 2006/0100143 A1 | 5/2006 | Lu et al. |
| 2006/0111411 A1 | 5/2006 | Cooper et al. |
| 2006/0128615 A1 | 6/2006 | Gaudreau |
| 2006/0142181 A1 | 6/2006 | Miller et al. |
| 2006/0142182 A1 | 6/2006 | Miller et al. |
| 2006/0148715 A1 | 7/2006 | Tweardy |
| 2006/0149039 A1 | 7/2006 | Hunter et al. |
| 2006/0155107 A1 | 7/2006 | Rivier et al. |
| 2006/0189511 A1 | 8/2006 | Koblish et al. |
| 2006/0210641 A1 | 9/2006 | Shalaby |
| 2006/0217296 A1 | 9/2006 | Jansson |
| 2006/0233779 A1 | 10/2006 | Ben-Avraham et al. |
| 2006/0247170 A1 | 11/2006 | Guyon et al. |
| 2006/0293380 A1 | 12/2006 | Nantermet et al. |
| 2007/0004765 A1 | 1/2007 | Graffner-Nordberg et al. |
| 2007/0006332 A1 | 1/2007 | O'Neill |
| 2007/0020620 A1 | 1/2007 | Finn et al. |
| 2007/0025991 A1 | 2/2007 | Pothoulakis et al. |
| 2007/0032417 A1 | 2/2007 | Baell |
| 2007/0037857 A1 | 2/2007 | Perrissoud et al. |
| 2007/0041902 A1 | 2/2007 | Goodman et al. |
| 2007/0060512 A1 | 3/2007 | Sadeghi et al. |
| 2007/0129324 A1 | 6/2007 | Boyd et al. |
| 2007/0161544 A1 | 7/2007 | Wipf et al. |
| 2007/0161551 A1 | 7/2007 | De Luca |
| 2007/0191283 A1 | 8/2007 | Polvino |
| 2007/0197772 A1 | 8/2007 | Arora et al. |
| 2007/0208061 A2 | 9/2007 | Perrissoud et al. |
| 2007/0238662 A1 | 10/2007 | Mintz |
| 2007/0274915 A1 | 11/2007 | Rao et al. |
| 2008/0015265 A1 | 1/2008 | Rubin et al. |
| 2008/0026993 A9 | 1/2008 | Guyon et al. |
| 2008/0032931 A1 | 2/2008 | Steward et al. |
| 2008/0081038 A1 | 4/2008 | Cho et al. |
| 2008/0085279 A1 | 4/2008 | Boyd et al. |
| 2008/0090756 A1 | 4/2008 | Coy et al. |
| 2008/0132485 A1 | 6/2008 | Wang et al. |
| 2008/0161426 A1 | 7/2008 | Gudkov et al. |
| 2008/0167222 A1 | 7/2008 | Lussier et al. |
| 2008/0171700 A1 | 7/2008 | Nilsson et al. |
| 2008/0194553 A1 | 8/2008 | Gillessen |
| 2008/0194672 A1 | 8/2008 | Hoveyda et al. |
| 2008/0213175 A1 | 9/2008 | Kolb et al. |
| 2008/0234183 A1 | 9/2008 | Hallbrink et al. |
| 2008/0242598 A1 | 10/2008 | Fairlie et al. |
| 2008/0250515 A1 | 10/2008 | Reed |
| 2008/0260638 A1 | 10/2008 | Rivier et al. |
| 2008/0260820 A1 | 10/2008 | Borrelly et al. |
| 2008/0261873 A1 | 10/2008 | Geesaman |
| 2008/0262200 A1 | 10/2008 | Nash |
| 2008/0299040 A1 | 12/2008 | Rivier et al. |
| 2008/0300193 A1 | 12/2008 | Ahn et al. |
| 2008/0300194 A1 | 12/2008 | Mann et al. |
| 2008/0305490 A1 | 12/2008 | Burrell et al. |
| 2008/0311608 A1 | 12/2008 | Tocque et al. |
| 2009/0011985 A1 | 1/2009 | Abribat et al. |
| 2009/0047711 A1 | 2/2009 | Nash |
| 2009/0069245 A1 | 3/2009 | Bowers et al. |
| 2009/0081168 A1 | 3/2009 | Sheppard et al. |
| 2009/0088383 A1 | 4/2009 | Abribat et al. |
| 2009/0088553 A1 | 4/2009 | Nash |
| 2009/0131478 A1 | 5/2009 | Dong et al. |
| 2009/0149630 A1 | 6/2009 | Walensky et al. |
| 2009/0156483 A1 | 6/2009 | Dong et al. |
| 2009/0156795 A1 | 6/2009 | Jaspers et al. |
| 2009/0170757 A1 | 7/2009 | Fraser et al. |
| 2009/0175821 A1 | 7/2009 | Bridon et al. |
| 2009/0176964 A1 | 7/2009 | Walensky et al. |
| 2009/0198050 A1 | 8/2009 | Marsault et al. |
| 2009/0221512 A1 | 9/2009 | Acosta et al. |
| 2009/0221689 A1 | 9/2009 | Marsault et al. |
| 2009/0240027 A1 | 9/2009 | Marsault et al. |
| 2009/0253623 A1 | 10/2009 | Abribat et al. |
| 2009/0275511 A1 | 11/2009 | Dong |
| 2009/0275519 A1 | 11/2009 | Nash et al. |
| 2009/0275648 A1 | 11/2009 | Fraser et al. |
| 2009/0305300 A1 | 12/2009 | Larsen |
| 2009/0311174 A1 | 12/2009 | Allen |
| 2009/0326192 A1 | 12/2009 | Nash et al. |
| 2009/0326193 A1 | 12/2009 | Maggio et al. |
| 2010/0010065 A1 | 1/2010 | Smith |
| 2010/0081611 A1 | 4/2010 | Bradner et al. |
| 2010/0087366 A1 | 4/2010 | Abribat et al. |
| 2010/0087381 A1 | 4/2010 | Polvino |
| 2010/0093057 A1 | 4/2010 | Beattie et al. |
| 2010/0093086 A1 | 4/2010 | Lin et al. |
| 2010/0152114 A1 | 6/2010 | Schally et al. |
| 2010/0158923 A1 | 6/2010 | Morimoto et al. |
| 2010/0168388 A1 | 7/2010 | Bernal et al. |
| 2010/0179168 A1 | 7/2010 | Blaney et al. |
| 2010/0184628 A1 | 7/2010 | Nash |
| 2010/0184645 A1 | 7/2010 | Verdine et al. |
| 2010/0204118 A1 | 8/2010 | Bevec |
| 2010/0210515 A1 | 8/2010 | Nash et al. |
| 2010/0216688 A1 | 8/2010 | Nash et al. |
| 2010/0234563 A1 | 9/2010 | Arora et al. |
| 2010/0239589 A1 | 9/2010 | Woods et al. |
| 2010/0267636 A1 | 10/2010 | Marsolais |
| 2010/0273704 A1 | 10/2010 | Korsmeyer et al. |
| 2010/0286362 A1 | 11/2010 | Boyd et al. |
| 2010/0298201 A1 | 11/2010 | Nash et al. |
| 2010/0298393 A1 | 11/2010 | Vanderklish et al. |
| 2010/0303791 A1 | 12/2010 | Francis et al. |
| 2010/0303794 A1 | 12/2010 | Francis et al. |
| 2010/0323964 A1 | 12/2010 | Vitali et al. |
| 2010/0331343 A1 | 12/2010 | Perrissoud et al. |
| 2011/0020435 A1 | 1/2011 | Maggio |
| 2011/0021529 A1 | 1/2011 | Lain et al. |
| 2011/0028753 A1 | 2/2011 | Verdine et al. |
| 2011/0046043 A1 | 2/2011 | Wang et al. |
| 2011/0065915 A1 | 3/2011 | Malcolmson et al. |
| 2011/0105389 A1 | 5/2011 | Hoveyda et al. |
| 2011/0105390 A1 | 5/2011 | Lussier et al. |
| 2011/0130331 A1 | 6/2011 | Guyon et al. |
| 2011/0143992 A1 | 6/2011 | Taub et al. |
| 2011/0144303 A1 | 6/2011 | Nash et al. |
| 2011/0144306 A1 | 6/2011 | Verdine et al. |
| 2011/0151480 A1 | 6/2011 | Sheppard et al. |
| 2011/0158973 A1 | 6/2011 | Madec et al. |
| 2011/0160135 A1 | 6/2011 | Johnstone et al. |
| 2011/0165137 A1 | 7/2011 | Madec et al. |
| 2011/0166063 A1 | 7/2011 | Bossard et al. |
| 2011/0171191 A1 | 7/2011 | Johnstone et al. |
| 2011/0183917 A1 | 7/2011 | Lu et al. |
| 2011/0195080 A1 | 8/2011 | Haffer et al. |
| 2011/0218155 A1 | 9/2011 | Walensky et al. |
| 2011/0223149 A1 | 9/2011 | Nash et al. |
| 2011/0230415 A1 | 9/2011 | Berlanga Acosta et al. |
| 2011/0243845 A1 | 10/2011 | Goodman et al. |
| 2011/0245159 A1 | 10/2011 | Hoveyda et al. |
| 2011/0245175 A1 | 10/2011 | Arora et al. |
| 2011/0245459 A1 | 10/2011 | Marsault et al. |
| 2011/0245477 A1 | 10/2011 | Hoveyda et al. |
| 2011/0250685 A1 | 10/2011 | Nash |
| 2011/0251252 A1 | 10/2011 | Wang et al. |
| 2011/0263815 A1 | 10/2011 | Nash |
| 2011/0269683 A1 | 11/2011 | Rivier et al. |
| 2011/0313167 A1 | 12/2011 | Doemling |

(56) References Cited

U.S. PATENT DOCUMENTS

| | | |
|---|---|---|
| 2012/0004174 A1 | 1/2012 | Abribat et al. |
| 2012/0010157 A1 | 1/2012 | Polvino et al. |
| 2012/0040889 A1 | 2/2012 | Nash et al. |
| 2012/0052548 A1 | 3/2012 | Steward et al. |
| 2012/0077745 A1 | 3/2012 | Polvino |
| 2012/0082636 A1 | 4/2012 | Walensky et al. |
| 2012/0083494 A1 | 4/2012 | Aicher et al. |
| 2012/0101047 A1 | 4/2012 | Nash et al. |
| 2012/0115783 A1 | 5/2012 | Nash et al. |
| 2012/0115793 A1 | 5/2012 | Nash et al. |
| 2012/0156197 A1 | 6/2012 | Errico et al. |
| 2012/0165566 A1 | 6/2012 | Marsault et al. |
| 2012/0172311 A1 | 7/2012 | Nash et al. |
| 2012/0178700 A1 | 7/2012 | Nash et al. |
| 2012/0226066 A1 | 9/2012 | Marsault et al. |
| 2012/0226067 A1 | 9/2012 | Marsault et al. |
| 2012/0226072 A1 | 9/2012 | Marsault et al. |
| 2012/0238507 A1 | 9/2012 | Fairlie et al. |
| 2012/0264674 A1 | 10/2012 | Nash et al. |
| 2012/0264738 A1 | 10/2012 | Sugimoto et al. |
| 2012/0270800 A1 | 10/2012 | Verdine et al. |
| 2012/0283269 A1 | 11/2012 | Blagosklonny et al. |
| 2012/0328692 A1 | 12/2012 | Lu et al. |
| 2013/0005943 A1 | 1/2013 | Arora et al. |
| 2013/0023646 A1 | 1/2013 | Nash et al. |
| 2013/0039851 A1 | 2/2013 | Maggio |
| 2013/0072439 A1 | 3/2013 | Nash et al. |
| 2013/0096050 A1 | 4/2013 | Shandler |
| 2013/0123196 A1 | 5/2013 | Arora et al. |
| 2013/0177979 A1 | 7/2013 | Turkson |
| 2013/0210743 A1 | 8/2013 | Guerlavais et al. |
| 2013/0211046 A1 | 8/2013 | Verdine et al. |
| 2013/0274205 A1 | 10/2013 | Guerlavais et al. |
| 2013/0330421 A1 | 12/2013 | Marine |
| 2014/0005118 A1 | 1/2014 | Verdine et al. |
| 2014/0011979 A1 | 1/2014 | Verdine et al. |
| 2014/0018302 A1 | 1/2014 | Walensky et al. |
| 2014/0051828 A1 | 2/2014 | Arora et al. |
| 2014/0128581 A1 | 5/2014 | Darlak et al. |
| 2014/0162339 A1 | 6/2014 | Verdine et al. |
| 2014/0235549 A1 | 8/2014 | Moellering et al. |
| 2014/0256912 A1 | 9/2014 | Moellering et al. |
| 2014/0296160 A1 | 10/2014 | Walensky et al. |
| 2014/0323701 A1 | 10/2014 | Nash et al. |
| 2014/0378390 A1 | 12/2014 | Guerlavais et al. |
| 2015/0038430 A1 | 2/2015 | Nash et al. |
| 2015/0051155 A1 | 2/2015 | Guerlavais et al. |
| 2015/0056612 A1 | 2/2015 | Shen et al. |
| 2015/0119551 A1 | 4/2015 | Bernal et al. |
| 2015/0183825 A1 | 7/2015 | Guerlavais et al. |
| 2015/0225471 A1 | 8/2015 | Liang et al. |
| 2015/0239937 A1 | 8/2015 | Verdine et al. |
| 2015/0284437 A1 | 10/2015 | Verdine et al. |
| 2015/0376227 A1 | 12/2015 | Verdine et al. |
| 2016/0024153 A1 | 1/2016 | Verdine et al. |
| 2016/0031936 A1 | 2/2016 | Nash |
| 2016/0052970 A1 | 2/2016 | Guerlavais et al. |
| 2016/0068573 A1 | 3/2016 | Nash et al. |
| 2016/0095896 A1 | 4/2016 | Nash |
| 2016/0096873 A1 | 4/2016 | Nash et al. |
| 2016/0101145 A1 | 4/2016 | Annis et al. |
| 2016/0108089 A1 | 4/2016 | Nash et al. |
| 2016/0115204 A1 | 4/2016 | Nash et al. |
| 2016/0193283 A1 | 7/2016 | Chen et al. |

FOREIGN PATENT DOCUMENTS

| | | |
|---|---|---|
| CN | 102399283 A | 4/2012 |
| CN | 102399284 A | 4/2012 |
| CZ | 9700369 A3 | 9/1998 |
| EP | 0467699 A2 | 1/1992 |
| EP | 0467699 A3 | 2/1993 |
| EP | 0528312 A2 | 2/1993 |
| EP | 0552417 A1 | 7/1993 |
| EP | 0352014 B1 | 3/1994 |
| EP | 0729972 A1 | 9/1996 |
| EP | 0643726 B1 | 8/1999 |
| EP | 0977580 B1 | 4/2003 |
| EP | 1321474 A1 | 6/2003 |
| EP | 1452868 A2 | 9/2004 |
| EP | 1541692 A1 | 6/2005 |
| EP | 1602663 A1 | 12/2005 |
| EP | 1609802 A1 | 12/2005 |
| EP | 1243923 B1 | 3/2006 |
| EP | 1180016 B1 | 9/2006 |
| EP | 0958305 B1 | 6/2008 |
| EP | 2091552 A2 | 8/2009 |
| EP | 2100901 A1 | 9/2009 |
| EP | 2310407 A2 | 4/2011 |
| EP | 1597585 B1 | 6/2011 |
| EP | 2377849 A2 | 10/2011 |
| JP | 2002524391 A | 8/2002 |
| JP | 2008096423 A | 4/2008 |
| JP | 2010120881 A | 6/2010 |
| WO | WO-8909233 A1 | 10/1989 |
| WO | WO-8912675 A1 | 12/1989 |
| WO | WO-9206998 A1 | 4/1992 |
| WO | WO-9213878 A2 | 8/1992 |
| WO | WO-9301203 A1 | 1/1993 |
| WO | WO-9307170 A1 | 4/1993 |
| WO | WO-9422910 A1 | 10/1994 |
| WO | WO-9425482 A1 | 11/1994 |
| WO | WO-9500534 A1 | 1/1995 |
| WO | WO-9522546 A1 | 8/1995 |
| WO | WO-9602642 A1 | 2/1996 |
| WO | WO-9620951 A1 | 7/1996 |
| WO | WO-9628449 A1 | 9/1996 |
| WO | WO-9632126 A1 | 10/1996 |
| WO | WO-9634878 A1 | 11/1996 |
| WO | WO-9700267 A1 | 1/1997 |
| WO | WO-9713537 A1 | 4/1997 |
| WO | WO-9714794 A1 | 4/1997 |
| WO | WO-9730072 A1 | 8/1997 |
| WO | WO-9737705 A1 | 10/1997 |
| WO | WO-9801467 A2 | 1/1998 |
| WO | WO-9817625 A1 | 4/1998 |
| WO | WO-9846631 A1 | 10/1998 |
| WO | WO-9847525 A1 | 10/1998 |
| WO | WO-9914259 A1 | 3/1999 |
| WO | WO-9934833 A1 | 7/1999 |
| WO | WO-9934850 A1 | 7/1999 |
| WO | WO-9963929 A2 | 12/1999 |
| WO | WO-0006187 A2 | 2/2000 |
| WO | WO-0006187 A3 | 5/2000 |
| WO | WO-02064790 A2 | 8/2002 |
| WO | WO-02070547 A1 | 9/2002 |
| WO | WO-02072597 A2 | 9/2002 |
| WO | WO-02064790 A3 | 5/2003 |
| WO | WO-03054000 A1 | 7/2003 |
| WO | WO-03059933 A2 | 7/2003 |
| WO | WO-03070892 A2 | 8/2003 |
| WO | WO-03102538 A2 | 12/2003 |
| WO | WO-03106491 A2 | 12/2003 |
| WO | WO-03059933 A3 | 1/2004 |
| WO | WO-2004026896 A2 | 4/2004 |
| WO | WO-2004041275 A1 | 5/2004 |
| WO | WO-2004058804 A1 | 7/2004 |
| WO | WO-2004077062 A2 | 9/2004 |
| WO | WO-03070892 A3 | 11/2004 |
| WO | WO-03106491 A3 | 12/2004 |
| WO | WO-2004077062 A3 | 1/2005 |
| WO | WO-2005007675 A2 | 1/2005 |
| WO | WO-2004077062 B1 | 2/2005 |
| WO | WO-2005012335 A1 | 2/2005 |
| WO | WO-2005040202 A2 | 5/2005 |
| WO | WO-2005044839 A2 | 5/2005 |
| WO | WO-2005040202 A3 | 6/2005 |
| WO | WO-2005007675 A3 | 7/2005 |
| WO | WO-2005044839 A3 | 7/2005 |
| WO | WO-2005074521 A2 | 8/2005 |
| WO | WO-2005085457 A2 | 9/2005 |
| WO | WO-2005090388 A1 | 9/2005 |
| WO | WO-2005097173 A2 | 10/2005 |
| WO | WO-2005118620 A2 | 12/2005 |

(56) References Cited

FOREIGN PATENT DOCUMENTS

| WO | WO-2005118625 A1 | 12/2005 |
|---|---|---|
| WO | WO-2005118634 A2 | 12/2005 |
| WO | WO-2006009645 A1 | 1/2006 |
| WO | WO-2006009674 A1 | 1/2006 |
| WO | WO-2006042408 A1 | 4/2006 |
| WO | WO-2005118634 A3 | 5/2006 |
| WO | WO-2005118620 A3 | 6/2006 |
| WO | WO-2006078161 A1 | 7/2006 |
| WO | WO-2006103666 A2 | 10/2006 |
| WO | WO-2006137974 A2 | 12/2006 |
| WO | WO-2006103666 A3 | 3/2007 |
| WO | WO-2007141533 A2 | 12/2007 |
| WO | WO-2008013454 A2 | 1/2008 |
| WO | WO-2008014216 A1 | 1/2008 |
| WO | WO-2008045238 A2 | 4/2008 |
| WO | WO-2008061192 A2 | 5/2008 |
| WO | WO-2008074895 A1 | 6/2008 |
| WO | WO2008076904 A1 | 6/2008 |
| WO | WO-2007141533 A3 | 7/2008 |
| WO | WO-2008061192 A3 | 7/2008 |
| WO | WO-2008092281 A1 | 8/2008 |
| WO | WO-2008095063 A1 | 8/2008 |
| WO | WO-2008104000 A2 | 8/2008 |
| WO | WO-2008106507 A2 | 9/2008 |
| WO | WO-2008121767 A2 | 10/2008 |
| WO | WO-2008130464 A1 | 10/2008 |
| WO | WO-2008137633 A2 | 11/2008 |
| WO | WO-2008121767 A3 | 1/2009 |
| WO | WO-2009009727 A2 | 1/2009 |
| WO | WO-2009031916 A1 | 3/2009 |
| WO | WO-2009033667 A2 | 3/2009 |
| WO | WO-2009033668 A2 | 3/2009 |
| WO | WO-2009042237 A2 | 4/2009 |
| WO | WO-2009009727 A3 | 5/2009 |
| WO | WO-2009089004 A1 | 7/2009 |
| WO | WO-2009033667 A3 | 8/2009 |
| WO | WO-2009033668 A3 | 8/2009 |
| WO | WO-2009099677 A2 | 8/2009 |
| WO | WO-2009110952 A2 | 9/2009 |
| WO | WO-2009126292 A2 | 10/2009 |
| WO | WO-2009129311 A2 | 10/2009 |
| WO | WO-2009137532 A1 | 11/2009 |
| WO | WO-2009149214 A2 | 12/2009 |
| WO | WO-2009149339 A2 | 12/2009 |
| WO | WO-2010011313 A2 | 1/2010 |
| WO | WO-2010013011 A1 | 2/2010 |
| WO | WO-2010033617 A2 | 3/2010 |
| WO | WO-2010033879 A2 | 3/2010 |
| WO | WO-2010034026 A1 | 3/2010 |
| WO | WO-2010034028 A1 | 3/2010 |
| WO | WO-2010034029 A1 | 3/2010 |
| WO | WO-2010034031 A1 | 3/2010 |
| WO | WO-2010034032 A2 | 3/2010 |
| WO | WO-2010034034 A1 | 3/2010 |
| WO | WO-2010058819 A1 | 5/2010 |
| WO | WO-2010060112 A1 | 5/2010 |
| WO | WO-2010065572 A1 | 6/2010 |
| WO | WO-2010068684 A2 | 6/2010 |
| WO | WO-2009129311 A3 | 7/2010 |
| WO | WO-2010083347 A2 | 7/2010 |
| WO | WO-2010083501 A2 | 7/2010 |
| WO | WO-2010100351 A1 | 9/2010 |
| WO | WO-2010107485 A1 | 9/2010 |
| WO | WO-2010132580 A2 | 11/2010 |
| WO | WO-2010011313 A3 | 12/2010 |
| WO | WO-2011005219 A1 | 1/2011 |
| WO | WO-2011008260 A2 | 1/2011 |
| WO | WO-2011008260 A3 | 3/2011 |
| WO | WO-2011023677 A1 | 3/2011 |
| WO | WO-2011038049 A1 | 3/2011 |
| WO | WO-2011047215 A1 | 4/2011 |
| WO | WO-2011060049 A2 | 5/2011 |
| WO | WO-2011061139 A1 | 5/2011 |
| WO | WO-2011076786 A1 | 6/2011 |
| WO | WO-2011090297 A2 | 7/2011 |
| WO | WO-2011101297 A1 | 8/2011 |
| WO | WO-2011106650 A2 | 9/2011 |
| WO | WO-2011133948 A2 | 10/2011 |
| WO | WO-2011143208 A1 | 11/2011 |
| WO | WO-2011143209 A1 | 11/2011 |
| WO | WO-2011153491 A2 | 12/2011 |
| WO | WO-2011159917 A2 | 12/2011 |
| WO | WO-2011161699 A2 | 12/2011 |
| WO | WO-2011162968 A1 | 12/2011 |
| WO | WO-2011163012 A2 | 12/2011 |
| WO | WO-2011133948 A3 | 1/2012 |
| WO | WO-2012012352 A2 | 1/2012 |
| WO | WO-2012016186 A1 | 2/2012 |
| WO | WO-2012021874 A1 | 2/2012 |
| WO | WO-2012021875 A1 | 2/2012 |
| WO | WO-2012021876 A2 | 2/2012 |
| WO | WO-2012033525 A2 | 3/2012 |
| WO | WO-2012034954 A1 | 3/2012 |
| WO | WO-2012037519 A2 | 3/2012 |
| WO | WO-2012038307 A1 | 3/2012 |
| WO | WO-2012040459 A2 | 3/2012 |
| WO | WO-2011153491 A3 | 4/2012 |
| WO | WO-2012045018 A1 | 4/2012 |
| WO | WO-2012047587 A2 | 4/2012 |
| WO | WO-2012051405 A1 | 4/2012 |
| WO | WO-2012059696 A1 | 5/2012 |
| WO | WO-2012065022 A2 | 5/2012 |
| WO | WO-2012065181 A2 | 5/2012 |
| WO | WO-2012066095 A1 | 5/2012 |
| WO | WO-2012040459 A3 | 6/2012 |
| WO | WO-2012076513 A1 | 6/2012 |
| WO | WO-2012080376 A1 | 6/2012 |
| WO | WO-2012080389 A1 | 6/2012 |
| WO | WO-2012083078 A2 | 6/2012 |
| WO | WO-2012083181 A1 | 6/2012 |
| WO | WO-2011159917 A3 | 7/2012 |
| WO | WO-2012094755 A1 | 7/2012 |
| WO | WO-2012037519 A3 | 8/2012 |
| WO | WO-2012121057 A1 | 9/2012 |
| WO | WO-2012122059 A1 | 9/2012 |
| WO | WO-2012149563 A1 | 11/2012 |
| WO | WO-2012173846 A2 | 12/2012 |
| WO | WO-2012174423 A1 | 12/2012 |
| WO | WO-2012175962 A1 | 12/2012 |
| WO | WO-2013033645 A1 | 3/2013 |
| WO | WO-2013036208 A1 | 3/2013 |
| WO | WO-2013049250 A1 | 4/2013 |
| WO | WO-2013059525 A1 | 4/2013 |
| WO | WO-2013059530 A2 | 4/2013 |
| WO | WO-2013123266 A1 | 8/2013 |
| WO | WO-2013123267 A1 | 8/2013 |
| WO | WO-2014052647 A2 | 4/2014 |
| WO | WO-2014055564 A1 | 4/2014 |
| WO | WO-2014071241 A1 | 5/2014 |
| WO | WO-2014138429 A2 | 9/2014 |
| WO | WO-2015157508 A1 | 10/2015 |
| WO | WO-2016049355 A1 | 3/2016 |
| WO | WO-2016049359 A1 | 3/2016 |

OTHER PUBLICATIONS

Annis, et al. A general technique to rank protein-ligand binding affinities and determine allosteric versus direct binding site competition in compound mixtures. J Am Chem Soc. Dec. 1, 2004;126(47):15495-503.

Annis, et al. Alis: An Affinity Selection-Mass Spectrometry System for the Discovery and Characterization of Protein-Ligand Interactions. In: Wanner, K. And Höfner, G. eds. Mass Spectrometry in Medicinal Chemistry. Wiley-VCH; 2007:121-156.

Armstrong et al., X=Y-Zh Systems as potential 1,3-dipoles. 5. Intramolecular cycloadditions of imines of a-amino acid esters. Tetrahedron. 1985;41(17):3547-58.

Arora, "Design, Synthesis, and Properties of the Hydrogen Bond Surrogate-based Artificial Alpha-helices," American Chemical Society Meeting, San Diego (Mar. 2005) (oral).

Arora, "Hydrogen Bond Surrogate Approach for the Synthesis of Short α-Helical Peptides," American Chemical Society Meeting, Philadelphia (Aug. 2004) (abstract of oral presentation).

(56) References Cited

OTHER PUBLICATIONS

Arosio, et al. Click chemistry to functionalise peptidomimetics. Tetrahedron Letters. 2006; 47:3697-3700.
Artavanis-Tsakonas et al., Notch signaling: cell fate control and signal integration in development. Science. Apr. 30, 1999;284(5415):770-6.
Attisano et al., TGFbeta and Wnt pathway cross-talk. Cancer Metastasis Rev. Jan.-Jun. 2004;23(1-2):53-61.
Austin et al., "A Template for Stabilization of a Peptide α-Helix: Synthesis and Evaluation of Conformational Effects by Circular Dichroism and NMR," J. Am. Chem. Soc. 119:6461-6472 (1997).
Avantaggiati, M.L. Molecular horizons of cancer therapeutics: 11th Pezcoller symposium. Biochim Biophys Acta. May 17, 2000;1470(3):R49-59.
Babcock, Proteins, radicals, isotopes, and mutants in photosynthetic oxygen evolution. Proc Natl Acad Sci USA. Dec. 1, 1993;90(23):10893-5.
Babine et aL, Molecular Recognition of Proteinminus signLigand Complexes: Applications to Drug Design. Chem Rev. Aug. 5, 1997;97(5):1359-1472.
Badyal, et al. A Simple Method for the Quantitative Analysis of Resin Bound Thiol Groups. Tetrahedron Lett. 2001; 42:8531-33.
Baell, J.B. Prospects for Targeting the Bcl-2 Family of Proteins to Develop Novel cytotoxic drugs. Biochem Pharmacol. Sep. 2002;64(5-6):851-63.
Bakhshi, et al. Cloning the chromosomal breakpoint of t(14;18) human lymphomas: clustering around JH on chromosome 14 and near a transcriptional unit on 18. Cell. Jul. 1985;41(3):899-906.
Balthaser et al., Remodelling of the natural product fumagillol employing a reaction discovery approach. Nat Chem. Dec. 2011;3(12):969-73.
Banerjee et aL, Structure of a Dna glycosylase searching for lesions. Science. Feb. 24, 2006;311(5764):1153-7.
Banerjee et al., Structure of a repair enzyme interrogating undamaged Dna elucidates recognition of damaged DNA. Nature. Mar. 31, 2005;434(7033):612-8.
Banerji et al. Synthesis of Cyclic β-Turn Mimics from L-Pro-Phe/Phe-L-Pro Derived Di- and Tripeptides via Ring Closing Metathesis: The Role of Chirality of the Phe Residue During Cyclization. Tetrahedron Lett. 2002; 43:6473-6477.
Bang et al., Total chemical synthesis of crambin. J Am Chem Soc. Feb. 11, 2004;126(5):1377-83.
Barandon et al., Reduction of infarct size and prevention of cardiac rupture in transgenic mice overexpressing FrzA. Circulation. Nov. 4, 2003;108(18):2282-9. Epub Oct. 27, 2003.
Barker, et al. Cyclic RGD peptide analogues as antiplatelet antithrombotics. J Med Chem. May 29, 1992;35(11):2040-8. (Abstract only).
Barker et al., Mining the Wnt pathway for cancer therapeutics. Nat Rev Drug Discov. Dec. 2006;5(12):997-1014.
Belokon et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon et al., Improved procedures for the synthesis of (S)-21N-(N'-benzyl-prolypaminolbenzophenone (BPB) and Ni(II) complexes of Schiff's bases derived from BPB and amino acids. Tetrahedron: Asymmetry. 1998;9:4249-52.
Belokon et al., "Halo-substituted (S)-N-(2-benzoylphenyl)-1-benzylpyrolidine-2 carboxamides as new chiral auxiliaries for the asymmetric synthesis of (S)-a-amino acids,"Russian Chemical Bulletin, International Edition, 51 (8): 1593-1599 (2002.
Bennett, et al. Regulation of osteoblastogenesis and bone mass by Wntl Ob. Proc Natl Acad Sci USA. Mar. 1, 2005;102(9):3324-9. Epub Feb. 22, 2005.
Berendsen et al., A glimpse of the Holy Grail? Science. Oct. 23, 1998;282(5389):642-3.
Berge et al. Pharmaceutical Salts. Journal of Pharmaceutical Sciences 66(1):1-19 (Jan. 1977).

Bernal, et al. A stapled p53 helix overcomes HDMX-mediated suppression of p53. Cancer Cell. Nov. 16, 2010;18(5):411-22. doi: 10.1016/j.ccr.2010.10.024.
Bernal, et al. Reactivation of the p53 tumor suppressor pathway by a stapled p53 peptide. J Am Chem Soc. Mar. 7, 2007;129(9):2456-7.
Biagini et al., Cross-metathesis of Unsaturated a-amino Acid Derivatives. J Chem Soc Perkin Trans. 1998;1:2485-99.
Bierzynski et al. A salt bridge stabilizes the helix formed by isolated C-Peptide of RNase A. PNAS USA. 1982;79:2470-2474.
Blackwell, et al. Highly Efficient Synthesis of Covalently Cross-Linked Peptide Helices by Ring-Closing Metathesis. Angewandte Chemie International Edition. 1998; 37(23):3281-3284.
Blackwell, et al. Ring-closing metathesis of olefinic peptides: design, synthesis, and structural characterization of macrocyclic helical peptides. J Org Chem. Aug. 10, 2001;66(16):5291-302.
Blundell et al., Atomic positions in rhombohedral 2-zinc insulin crystals. Nature. Jun. 25, 1971;231(5304):506-11.
Bock, et al. 1,2,3-Triazoles as peptide bond isosteres: synthesis and biological evaluation of cyclotetrapeptide mimics. Org Biomol Chem. Mar. 21, 2007;5(6):971-5.
Bode et al., Chemoselective amide ligations by decarboxylative condensations of N-alkylhydroxylamines and alpha-ketoacids. Angew Chem Int Ed Engl. Feb. 13, 2006;45(8):1248-52.
Boguslavsky, et al. Effect of peptide conformation on membrane permeability. J Pept Res. Jun. 2003;61(6):287-97.
Bossy-Wetzel, et al. Assays for cytochrome c release from mitochondria during apoptosis. Methods Enzymol. 2000;322:235-42.
Bossy-Wetzel, et al. Detection of apoptosis by annexin V labeling. Methods Enzymol. 2000;322:15-8.
Bottger, et al. Molecular characterization of the hdm2-p53 interaction. J Mol Biol. Jun. 27, 1997;269(5):744-56.
Boyden et al., High bone density due to a mutation in LDL-receptor-related protein 5. N Engl J Med. May 16, 2002;346(20):1513-21.
Bracken et al. Synthesis and nuclear magnetic resonance structure determination of an alpha-helical, bicyclic, lactam-bridged hexapeptide. JACS. 1994;116:6431-6432.
Bradley et al., Limits of cooperativity in a structurally modular protein: response of the Notch ankyrin domain to analogous alanine substitutions in each repeat. J Mol Biol. Nov. 22, 2002;324(2):373-86.
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Bray, Notch signalling: a simple pathway becomes complex. Nat Rev Mol Cell Biol. Sep. 2006;7(9):678-89.
Brea, et al. Synthesis of omega-(hetero)arylalkynylated alpha-amino acid by Sonogashira-type reactions in aqueous media. J Org Chem. Sep. 29, 2006;71(20):7870-3.
Brou et al., A novel proteolytic cleavage involved in Notch signaling: the role of the disintegrin-metalloprotease TACE. Mol Cell. Feb. 2000;5(2):207-16.
Brubaker et al., Solution structure of the interacting domains of the Mad-Sin3 complex: implications for recruitment of a chromatin-modifying complex. Cell. Nov. 10, 2000;103(4):655-65.
Brunel, et al. Synthesis of constrained helical peptides by thioether ligation: application to analogs of gp41. Chem Commun (Camb). May 28, 2005;(20):2552-4. Epub Mar. 11, 2005.
Brusselle et al., Allergen-induced airway inflammation and bronchial responsiveness in wild-type and interleukin-4-deficient mice. Am J Respir Cell Mol Biol. Mar. 1995;12(3):254.-9.
Burfield & Smithers, "Desiccant Efficiency in Solvent Drying. 3. Dipolar Aprotic Solvents," J. Org. Chem. 43(20):3966-3968 (1978).
Burger et aL, Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.
Burrage, et al. Biomimetic synthesis of lantibiotics. Chemistry. Apr. 14, 2000;6(8):1455-66.
Cabezas & Satterthwait, "The Hydrogen Bond Mimic Approach: Solid-phase Synthesis of a Peptide Stabilized as an α-Helix with a Hydrazone Link," J. Am. Chem. Soc. 121:3862-3875 (1999).

(56) References Cited

OTHER PUBLICATIONS

Campbell, et al. N-alkylated oligoamide alpha-helical proteomimetics. Org Biomol Chem. May 21, 2010;8(10):2344-51. doi: 10.1039/c001164a. Epub Mar. 18, 2010.
Cantel, et al. Synthesis and Conformational Analysis of a Cyclic Peptide Obtained via i to i+4 Intramolecular Side-Chain to Side-Chain Azide-Alkyne 1,3-Dipolar Cycloaddition. JOC Featured Article. Published on the web May 20, 2008.
Caricasole et al., The Wnt pathway, cell-cycle activation and beta-amyloid: novel therapeutic strategies in Alzheimer's disease? Trends Pharmacol Sci. May 2003;24(5):233-8.
Cariello, et al. Resolution of a missense mutant in human genomic DNA by denaturing gradient gel electrophoresis and direct sequencing using in vitro DNA amplification: HPRT Munich. Am J Hum Genet. May 1988;42(5):726-34.
Carrillo et al., The Multiple Sequence Alignment Problem in Biology. SIAM J Applied Math. 1988;48:1073-82.
Carlo-Stella, et al. Use of recombinant human growth hormone (rhGH) plus recombinant human granulocyte colony-stimulating factor (rhG-CSF) for the mobilization and collection of CD34+ cells in poor mobilizers. Blood. May 1, 2004;103(9):3287-95. Epub Jan. 15, 2004.
Carlson et al., Specificity landscapes of DNA binding molecules elucidate biological function. Proc Natl Acad Sci USA. Mar. 9, 2010;107(10):4544-9. doi: 10.1073/pnas.0914023107. Epub Feb. 22, 2010.
CAS Registry No. 2176-37-6, STN Entry Date Nov. 16, 1984.
CAS Registry No. 2408-85-7, STN Entry Date Nov. 16, 1984.
CAS Registry No. 4727-05-3, STN Entry Date Nov. 16, 1984.
CAS Registry No. 561321-72-0, STN Entry Date Aug. 6, 2003.
CAS Registry No. 721918-14-5, STN Entry Date Aug. 4, 2004.
Cervini, et al. Human growth hormone-releasing hormone hGHRH(1-29)-NH2: systematic structure-activity relationship studies. J Med Chem. Feb. 26, 1998;41(5):717-27.
Chakrabartty et al., "Helix Capping Propensities in Peptides Parallel Those in Proteins," Proc. Nat'l Acad. Sci. USA 90:11332-11336 (1993).
Chakrabartty et al., "Helix Propensities of the Amino Acids Measured in Alanine-based Peptides without Helix-stabilizing Side-chain Interactions," Protein Sci. 3:843-852 (1994).
Chapman et al., "A Highly Stable Short α-Helix Constrained by a Main-chain Hydrogen-bond Surrogate," J. Am. Chem. Soc. 126:12252-12253 (2004).
Chapman, et al. Optimized synthesis of hydrogen-bond surrogate helices: surprising effects of microwave heating on the activity of Grubbs catalysts. Org Lett. Dec. 7, 2006;8(25):5825-8.
Chapman, et al. Trapping a folding intermediate of the alpha-helix: stabilization of the pi-helix. Biochemistry. Apr. 8, 2008;47(14):4189-95. doi: 10.1021/bi800136m. Epub Mar. 13, 2008.
Chen et al., Determination of the helix and beta form of proteins in aqueous solution by circular dichroism. Biochemistry. Jul. 30, 1974;13(16):3350-9.
Chen, et al. Determination of the Secondary Structures of Proteins by Circular Dichroism and Optical Rotatory Dispersion. Biochemistry. 1972; 11(22):4120-4131.
Chen et al., Small molecule-mediated disruption of Wnt-dependent signaling in tissue regeneration and cancer. Nat Chem Biol. Feb. 2009;5(2):100-7. Epub Jan. 4, 2009.
Chen et al., "Structure of the DNA-binding Domains from NFAT, Fos and Jun Bound Specifically to DNA," Nature 392:42-48 (1998).
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Cheon et al., beta-Catenin stabilization dysregulates mesenchymal cell proliferation, motility, and invasiveness and causes aggressive fibromatosis and hyperplastic cutaneous wounds. Proc Natl Acad Sci USA. May 14, 2002;99(10):6973-8. Epub Apr. 30, 2002.
Chia et al., Emerging roles for Rab family GTPases in human cancer. Biochim Biophys Acta. Apr. 2009;1795(2):110-6.
Chiaramonte et al., Studies of murine schistosomiasis reveal interleukin-13 blockade as a treatment for established and progressive liver fibrosis. Hepatology. Aug. 2001;34(2):273-82.
Chin & Schepartz, "Design and Evolution of a Miniature Bcl-2 Binding Protein," Angew. Chem. Int. Ed. 40(20):3806-3809 (2001).
Chin et al., "Circular Dichroism Spectra of Short, Fixed-nucleus Alanine Helices," Proc. Nat'l Acad. Sci. USA 99(24):15416-15421 (2002).
Chittenden, et al. A conserved domain in Bak, distinct from BH1 and BH2, mediates cell death and protein binding functions. Embo J. Nov. 15, 1995;14(22):5589-96.
Chéne et al., "Study of the Cytotoxic Effect of a Peptidic Inhibitor of the p53-hdm2 Interaction in Tumor Cells," FEBS Lett. 529:293-297 (2002).
Chéne, P., "Inhibiting the p53-MDM2 Interaction: An Important Target for Cancer Therapy," Nat Rev. Cancer 3:102-109 (2003).
Choi, et al. Application of azide-alkyne cycloaddition 'click chemistry' for the synthesis of Grb2 SH2 domain-binding macrocycles. Bioorg Med Chem Lett. Oct. 15, 2006;16(20):5265-9.
Christodoulides et al., WNT10B mutations in human obesity. Diabetologia. Apr. 2006;49(4):678-84. Epub Feb. 14, 2006.
Chu, et al. Peptide-formation on cysteine-containing peptide scaffolds. Orig Life Evol Biosph. Oct. 1999;29(5):441-9.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.
Cleary, et al. Nucleotide sequence of a t(14;18) chromosomal breakpoint in follicular lymphoma and demonstration of a breakpoint-cluster region near a transcriptionally active locus on chromosome 18. Proc Natl Acad Sci USA. Nov. 1985;82(21):7439-43.
Clevers, Wnt/beta-catenin signaling in development and disease. Cell. Nov. 3, 2006;127(3):469-80.
Cline, et al. Effects of As(III) binding on alpha-helical structure. J Am Chem Soc. Mar. 12, 2003;125(10):2923-9.
Cohn et al., Cutting Edge: IL-4-independent induction of airway hyperresponsiveness by Th2, but not Th1, cells. J Immunol. Oct. 15, 1998;161(8):3813-6.
Colacino, et al. Evaluation of the anti-influenza virus activities of 1,3,4-thiadiazol-2-ylcyanamide (LY217896) and its sodium salt. Antimicrob Agents Chemother. Nov. 1990;34(11):2156-63.
Colaluca et al., Numb controls p53 tumour suppressor activity. Nature. Jan. 3, 2008;451(7174):76-80. doi: 10.1038/nature06412.
Cole et al., Transcription-independent functions of MYC: regulation of translation and DNA replication. Nat Rev Mol Cell Biol. Oct. 2008;9(10):810-5. Epub Aug. 13, 2008.
Cong et al., A protein knockdown strategy to study the function of beta-catenin in tumorigenesis. BMC Mol Biol. Sep. 29, 2003;4:10.
Co-pending U.S. Appl. No. 13/494,846, filed Jun. 12, 2012.
Co-pending U.S. Appl. No. 13/655,442, filed Oct. 18, 2010.
Co-pending U.S. Appl. No. 15/074,794, filed Mar. 18, 2016.
Co-pending U.S. Appl. No. 15/093,335, filed Apr. 7, 2016.
Co-pending U.S. Appl. No. 15/093,373, filed Apr. 7, 2016.
Co-pending U.S. Appl. No. 15/093,426, filed Apr. 7, 2016.
Co-pending U.S. Appl. No. 15/093,869, filed Apr. 8, 2016.
Co-pending U.S. Appl. No. 15/135,098, filed Apr. 21, 2016.
Cory et al., "The Bcl-2 Family: Roles in Cell Survival and Oncogenesis," Oncogene 22:8590-8607 (2003).
Cossu et al., Wnt signaling and the activation of myogenesis in mammals Embo J. Dec. 15, 1999;18(24):6867-72.
Cotton, et al. Reactivity of cytosine and thymine in single-base-pair mismatches with hydroxylamine and osmium tetroxide and its application to the study of mutations. Proc Natl Acad Sci USA. Jun. 1988;85(12):4397-401.
Cox et al., Insulin receptor expression by human prostate cancers. Prostate. Jan. 1, 2009;69(1):33-40. doi: 10.1002/pros.20852.
Coy, et al. Structural Simplification of Potent Growth Hormone-Releasing Hormone Analogs: Implications for Other Members of the VIP/GHRW PACAP Family. Annals of the New York Academy of Sciences. VIP, PACAP, Glucagon, and Related Peptides. Dec. 1996; 805:149-158.

(56) References Cited

OTHER PUBLICATIONS

Cummings, et al. Disrupting protein-protein interactions with non-peptidic, small molecule alpha-helix mimetics. Curr Opin Chem Biol. Jun. 2010;14(3):341-6. doi: 10.1016/j.cbpa.2010.04.001. Epub Apr. 27, 2010.
Cusack et al. 2,4,6-Tri-isopropylbenzenesulphonyl Hydrazide: A convenient source of Di-Imide. Tetrahedron. 1976;32:2157-2162.
Danial, et al. Cell death: critical control points. Cell. 2004; 116:204-219.
Danial et al., Dual role of proapoptotic BAD in insulin secretion and beta cell survival. Nat Med. Feb. 2008;14(2):144-53. doi: 10.1038/nm1717. Epub Jan. 27, 2008.
Darnell, Transcription factors as targets for cancer therapy. Nat Rev Cancer. Oct. 2002;2(10):740-9.
Daugherty & Gellman, "A Fluorescence Assay for Leucine Zipper Dimerization: Avoiding Unintended Consequences of Fluorophore Attachment," J. Am. Chem. Soc. 121:4325-4333 (1999).
David et al., Expressed protein ligation. Method and applications. EurJ Biochem. Feb. 2004;271(4):663-77.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
De La O et al., Notch and Kras reprogram pancreatic acinar cells to ductal intraepithelial neoplasia. Proc Natl Acad Sci USA. Dec. 2, 2008;105(48):18907-12. doi: 10.1073/pnas.0810111105. Epub Nov. 21, 2008.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.
De Strooper et al., A presenilin-I-dependent gamma-secretase-like protease mediates release of Notch intracellular domain. Nature. Apr. 8, 1999;398(6727):518-22.
Debinski et al., Retargeting interleukin 13 for radioimmunodetection and radioimmunotherapy of human high-grade gliomas. Clin Cancer Res. Oct. 1999;5(10 Suppl):3143s-3147s.
Definition of Analog from http://cancerweb.ncl.ac.uk/cgi-bin/omd?query=analog. pp. 1-5. Accessed Jul 7, 2005.
Degterev et al., "Identification of Small-molecule Inhibitors of Interaction between the BH3 Domain and Bcl-xL," Nature Cell Biol. 3:173-182 (2001).
Deiters, et al. Adding amino acids with novel reactivity to the genetic code of Saccharomyces cerevisiae. J Am Chem Soc. Oct. 1, 2003;125(39):11782-3.
Del Bianco et al., Mutational and energetic studies of Notch 1 transcription complexes. J Mol Biol. Feb. 8, 2008;376(1):131-40. Epub Nov. 28, 2007.
Deng, et al. Cross-Coupling Reaction of Iodo-1,2,3-triazoles Catalyzed by Palladium. Synthesis 2005(16): 2730-2738.
Denmark et al., Cyclopropanation with Diazomethane and Bis(oxazoline)palladium(II) Complexes. J Org Chem. May 16, 1997;62(10):3375-3389.
Designing Custom Peptide. from SIGMA Genosys, pp. 1-2. Accessed Dec. 16, 2004.
Devereux et al., A comprehensive set of sequence analysis programs for the VAX. Nucleic Acids Res. Jan. 11, 1984;12(1 Pt 1):387-95.
Dimartino et al, "A General Approach for the Stabilization of Peptide Secondary Structures," American Chemical Society Meeting, New York (Sep. 2003) (poster).
Dimartino et al. Solid-phase synthesis of hydrogen-bond surrogate-derived alpha-helices. Org Lett. Jun. 9, 2005;7(12):2389-92.
Dombroski et al., Isolation of an active human transposable element. Science. Dec. 20, 1991;254(5039):1805-8.
Doron, et al. Probiotics: their role in the treatment and prevention of disease. Expert Rev Anti Infect Ther. Apr. 2006;4(2):261-75.

Dovey et al., Functional gamma-secretase inhibitors reduce beta-amyloid peptide levels in brain. J Neurochem. Jan. 2001;76(1):173-81.
Dubreuil, et al. Growth hormone-releasing factor: structural modification or protection for more potent analogs. Comb Chem High Throughput Screen. Mar. 2006;9(3):171-4.
Duronio, Insulin receptor is phosphorylated in response to treatment of HepG2 cells with insulin-like growth factor I. Biochem J. Aug. 15, 1990;270(1):27-32.
Eckert & Kim, "Mechanisms of Viral Membrane Fusion and Its Inhibition," Annu. Rev. Biochem. 70:777-810 (2001).
Edlund, et al. Data-driven unbiased curation of the TP53 tumor suppressor gene mutation database and validation by ultradeep sequencing of human tumors. Pnas Early Edition, pp. 1-20.
Eglen et al., The use of AlphaScreen technology in HTS: current status. Curr Chem Genomics. Feb. 25, 2008;1:2-10. doi: 10.2174/1875397300801010002.
Eisenmesser et al., Solution structure of interleukin-13 and insights into receptor engagement. J Mol Biol. Jun. 29, 2001;310(1):231-41.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Ellisen et al., TAN-1, the human homolog of the Drosophila notch gene, is broken by chromosomal translocations in T lymphoblastic neoplasms. Cell. Aug. 23, 1991;66(4):649-61.
Ellman. Tissue sulfhydryl groups. Arch Biochem Biophys. May 1959;82(1):70-7.
Erlanson, et al. Facile synthesis of cyclic peptides containing di-, tri-, tetra-, and Pentasulfides. Tetrahedron Letters. 1998; 39(38):6799-6802.
Erlanson et al., The leucine zipper domain controls the orientation of AP-1 in the NFAT.AP- 1.DNA complex. Chem Biol. Dec. 1996;3(12):981-91.
Evans et al., The Rise of Azide—Alkyne 1,3-Dipolar 'Click' Cycloaddition and its Application to Polymer Science and Surface Modification. Australian Journal of Chemistry. 2007;60:384-95.
Favrin et al., Two-state folding over a weak free-energy barrier. Biophys J. Sep. 2003;85(3):1457- 65.
Felix et al., "Synthesis, Biological Activity and Conformational Analysis of Cyclic GRF Analogs," Int. J. Pep. Protein Res. 32:441-454 (1988).
Feng et al. Solid-phase SN2 macrocyclization reactions to form beta-turn mimics. Org Lett. Jul. 15, 1999;1(1):121-4.
Ferdinandi, et al. Non-clinical pharmacology and safety evaluation of TH9507, a human growth hormone-releasing factor analogue. Basic Clin Pharmacol Toxicol. Jan. 2007;100(1):49-58.
Fields, et al. Chapter 3 in Synthetic Peptides: A Users Guide. Grant W.H. Freeman & Co. New York, NY. 1992. p. 77.
Fieser, et al. Fieser and Fieser's Reagents for Organic Synthesis. John Wiley and Sons. 1994.
File Hcaplus on STN. AN No. 1986:572318. Armstrong et al. X=Y-Zh systems as potential 1,3-dipoles. 5. Intramolecular imines of α-amino acid esters. Tetrahedron. 1985; 41(17):3547-58. Abstract only. Abstract date Nov. 1986.
File Hcaplus on STN. AN No. 1990:532752. Burger et al. Synthesis of a-(trifluoromethyl)-substituted a-amino acids. Part 7. An efficient synthesis for a-trifluoromethyl-substituted w-carboxy a-amino acids. Chemiker-Zeitung (1990), 114(3), 101-4. Abstract only, date Oct. 1990.
File Hcaplus on STN. AN Number: 1979:168009. Greenlee et al. A general synthesis of alpha-vinyl-alpha-amino acids Tetrahedron Letters (1978), (42), 3999-4002. Abstract date 1984.
Fischbach et al., Specific biochemical inactivation of oncogenic Ras proteins by nucleoside diphosphate kinase. Cancer Res. Jul. 15, 2003;63(14):4089-94.
Fischer, et al. Apoptosis-based therapies and drug targets. Cell Death and Differentiation. 2005; 12:942-961.
Fischer et al., The HIV-1 Rev activation domain is a nuclear export signal that accesses an export pathway used by specific cellular RNAs. Cell. Aug. 11, 1995;82(3):475-83.

(56) References Cited

OTHER PUBLICATIONS

Fischer, P. Peptide, Peptidomimetic, and Small-molecule Antagonists of the p53-HDM2 Protein-Protein Interaction. Int J Pept Res Ther. Mar. 2006;12(1):3-19. Epub Mar. 15, 2006.
Fisher et al., Myc/Max and other helix-loop-helix/leucine zipper proteins bend DNA toward the minor groove. Proc Natl Acad Sci USA. Dec. 15, 1992;89(24):11779-83.
Folkers, et al. Methods and principles in medicinal chemistry. Eds. R. Mannhold, H. Kubinyi, and H. Timmerman. Wiley-VCH, 2001.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396- 402.
Freedman, et al. Structural basis for recruitment of CBP/p300 by hypoxia-inducible factor-1 alpha. Proc Natl Acad Sci USA. Apr. 16, 2002;99(8):5367-72.
Friedman-Einat, et al. Target gene identification: target specific transcriptional activation by three murine homeodomain/VP16 hybrid proteins in Saccharomyces cerevisiae. J Exp Zool. Feb. 15, 1996;274(3):145-56.
Friedmann et al., Ram-induced allostery facilitates assembly of a notch pathway active transcription complex. J Biol Chem. May 23, 2008;283(21):14781-91. doi: 10.1074/jbc.M709501200. Epub Apr. 1, 2008.
Fromme et al., Structural basis for removal of adenine mispaired with 8-oxoguanine by MutY adenine DNA glycosylase. Nature. Feb. 12, 2004;427(6975):652-6.
Fryer et al., Mastermind mediates chromatin-specific transcription and turnover of the Notch enhancer complex. Genes Dev. Jun. 1, 2002;16(11):1397-411.
Fuchs et al., Socializing with the neighbors: stem cells and their niche. Cell. Mar. 19, 2004;116(6):769-78.
Fulda, et al. Extrinsic versus intrinsic apoptosis pathways in anti-cancer chemotherapy. Oncogene. Aug. 7, 2006;25(34):4798-811.
Fung et al., Delta-like 4 induces notch signaling in macrophages: implications for inflammation. Circulation. Jun. 12, 2007;115(23):2948-56. Epub May 28, 2007.
Furstner et al., Alkyne Metathesis: Development of a Novel Molybdenum-Based Catalyst System and Its Application to the Total Synthesis of Epothilone A and C. Chem Euro J. 2001;7(24):5299-5317.
Furstner, et al. Mo[N(t-Bu)(AR)]3 Complexes as catalyst precursors: in situ activation and application to metathesis reactions of alkynes and diynes. J Am chem Soc. 1999; 121:9453-54.
Furstner, et al. Nozaki—Hiyama—Kishi reactions catalytic in chromium. J Am Chem Soc. 1996; 118:12349-57.
Fustero, et al. Asymmetric synthesis of new beta,beta-difluorinated cyclic quaternary alpha-amino acid derivatives. Org Lett. Aug. 31, 2006;8(18):4129-32.
Galande, et al. Thioether side chain cyclization for helical peptide formation: inhibitors of estrogen receptor-coactivator interactions. Journal of Peptide Research. 2004; 63(3): 297-302.
Galande, et al. An effective method of on-resin disulfide bond formation in peptides. J Comb Chem. Mar.-Apr. 2005;7(2):174-7.
Gallivan et al., A neutral, water-soluble olefin metathesis catalyst based on an N-heterocyclic carbene ligand. Tetrahedron Letters. 2005;46:2577-80.
Galluzzi, et al. Guidelines for the use and interpretation of assays for monitoring cell death in higher eukaryotes. Cell Death Differ. Aug. 2009;16(8):1093-107. Epub Apr. 17, 2009.
Gante, Peptidomimetics—Tailored Enzyme Inhibitors. J Angew Chem Int Ed Engl. 1994;33:1699-1720.
García-Echeverría et al., "Discovery of Potent Antagonists of the Interaction between Human Double Minute 2 and Tumor Suppressor p53," J. Med. Chem. 43:3205-3208 (2000).
Garg et al., Mutations in NOTCH1 cause aortic valve disease. Nature. Sep. 8, 2005;437(7056):270-4. Epub Jul. 17, 2005.
Gat et al., De Novo hair follicle morphogenesis and hair tumors in mice expressing a truncated beta-catenin in skin. Cell. Nov. 25, 1998;95(5):605-14.
Gavathiotis et al., Bax activation is initiated at a novel interaction site. Nature. Oct. 23, 2008;455(7216):1076-81.
Geistlinger & Guy, "An Inhibitor of the Interaction of Thyroid Hormone Receptor β and Glucocorticoid Interacting Protein 1," J. Am. Chem. Soc. 123:1525-1526 (2001).
Gemperli et al., "Paralog-selective Ligands for Bcl-2 Proteins," J. Am. Chem. Soc. 127:1596-1597 (2005).
Gentle et al., Direct production of proteins with N-terminal cysteine for site-specific conjugation. Bioconjug Chem. May-Jun. 2004;15(3):658-63.
Gerber-Lemaire et al., Glycosylation pathways as drug targets for cancer: glycosidase inhibitors. Mini Rev Med Chem. Sep. 2006;6(9):1043-52.
Ghadiri & Choi, "Secondary Structure Nucleation in Peptides. Transition Metal Ion Stabilized α-Helices," J. Am. Chem. Soc. 112:1630-1632 (1990).
Giannis et aL, Peptidomimetics for Receptor Ligands—Discovery, Development, and Medical Perspectives. Angew Chem Int Ed Engl. 1993;32:1244-67.
Glover & Harrison, "Crystal Structure of the Heterodimeric bZIP Transcription Factor c-Fos-c-Jun Bound to DNA," Nature 373:257-261 (1995).
Goncalves, et al. On-resin cyclization of peptide ligands of the Vascular Endothelial Growth Factor Receptor 1 by copper(I)-catalyzed 1,3-dipolar azide-alkyne cycloaddition. Bioorg Med Chem Lett. Oct. 15, 2007;17(20):5590-4.
Gong et al., LDL receptor-related protein 5 (LRP5) affects bone accrual and eye development. Cell. Nov. 16, 2001;107(4):513-23.
Goodson et al., Potential Growth Antagonists. I. Hydantoins and Disubstituted Glycines. J Org Chem. 1960;25:1920-24.
Gorlich et al., Transport between the cell nucleus and the cytoplasm. Annu Rev Cell Dev Biol. 1999;15:607-60.
Goun et al., Molecular transporters: synthesis of oligoguanidinium transporters and their application to drug delivery and real-time imaging. Chembiochem. Oct. 2006;7(10):1497-515.
Greene, et al. Protective Groups in Organic Synthesis, 2nd Ed. John Wiley and Sons. 1991.
Greenfield et al. Computed circular dichroism spectra for the evaluation of protein conformation. Biochemistry. Oct. 8, 1969;(10):4108-4116.
Greenlee et al., A General Synthesis of a-vinyl-a-amino acids. Tetrahedron Letters. 1978;42:3999-40002.
Grubbs, et al. Ring-Closing Metathesis and Related Processes in Organic Synthesis. Acc. Chem. Res., 1995, 28 (11), pp. 446-452.
Grunig et al., Requirement for IL-13 independently of IL-4 in experimental asthma. Science. Dec. 18, 1998;282(5397):2261-3.
Guinn et al., Synthesis and characterization of polyamides containing unnatural amino acids. Biopolymers. May 1995;35(5):503-12.
Guo et al., Probing the alpha-helical structural stability of stapled p53 peptides: molecular dynamics simulations and analysis. Chem Biol Drug Des. Apr. 2010;75(4):348-59. doi: 10.1111/j.1747-0285. 2010.00951.x.
Gupta et al., Long-term effects of tumor necrosis factor-alpha treatment on insulin signaling Gupta pathway in HepG2 cells and HepG2 cells overexpressing constitutively active Akt/Pkb. J Cell Biochem. Feb. 15, 2007;100(3):593-607.
Hanessian, et al. Structure-based design and synthesis of macroheterocyclic peptidomimetic inhibitors of the aspartic protease beta-site amyloid precursor protein cleaving enzyme (BACE). J Med Chem. Jul. 27, 2006;49(15):4544-67.
Hara, S. et al. 'Synthetic studies on halopeptins, anti-inflammatory cyclodepsipeptides', Peptide Science. 2006 (vol. date 2005), 42nd, pp. 39-42.
Harper et al., Efficacy of a bivalent Li virus-like particle vaccine in prevention of infection with human papillomavirus types 16 and 18 in young women: a randomized controlled trial. Lancet. Nov. 13-19, 2004;364(9447):1757-65.
Harris et al., Synthesis of proline-modified analogues of the neuroprotective agent glycyl-1-prolyl-glutamic acid (GPE). Tetrahedron. 2005;61:10018-35.
Harrison, et al. Downsizing human, bacterial, and viral proteins to short water-stable alpha helices that maintain biological potency.

(56) References Cited

OTHER PUBLICATIONS

Proc Natl Acad Sci USA. Jun. 29, 2010;107(26):11686-91. doi: 10.1073/pnas.1002498107. Epub Jun. 11, 2010.
Hartmann, A Wnt canon orchestrating osteoblastogenesis. Trends Cell Biol. Mar. 2006;16(3):151-8. Epub Feb. 7, 2006.
Hartmann et al., Dual roles of Wnt signaling during chondrogenesis in the chicken limb. Development. Jul. 2000;127(14):3141-59.
Hase; et al., "1,6-Aminosuberic acid analogs of lysine- and arginine-vasopressin and -vasotocin. Synthesis and biological properties. J Am Chem Soc. May 17, 1972;94(10):3590-600."
Hein, et al. Copper(I)-Catalyzed Cycloaddition of Organic Azides and 1-Iodoalkynes. Angew Chem Int Ed Engl. 2009;48(43):8018-21.
Hellman et al., Electrophoretic mobility shift assay (EMSA) for detecting protein-nucleic acid interactions. Nat Protoc. 2007;2(8):1849-61.
Hemerka, et al. Detection and characterization of influenza A virus PA-PB2 interaction through a bimolecular fluorescence complementation assay. J Virol. Apr. 2009;83(8):3944-55. doi: 10.1128/Jvi.02300-08. Epub Feb. 4, 2009.
Henchey et al., Contemporary strategies for the stabilization of peptides in the a-helical conformation. Curr Opin Chem Biol. 2008;12:692-97.
Henchey, et al. High specificity in protein recognition by hydrogen-bond-surrogate a-helices: selective inhibition of the p53/MDM2 complex. Chembiochem. Oct. 18, 2010;11(15):2104-7. doi: 10.1002/cbic.201000378.
Henchey, et al. Inhibition of Hypoxia Inducible Factor 1-Transcription Coactivator Interaction by a Hydrogen Bond Surrogate α-Helix. J Am Chem Soc. Jan. 27, 2010;132(3):941-3.
Hessa, et al. Recognition of transmembrane helices by the endoplasmic reticulum translocon. Nature. Jan. 27, 2005;433(7024):377-81.
Hilton et al., Notch signaling maintains bone marrow mesenchymal progenitors by suppressing osteoblast differentiation. Nat Med. Mar. 2008;14(3):306-14. doi: 10.1038/nm1716. Epub Feb. 24, 2008.
Hipfner et al., Connecting proliferation and apoptosis in development and disease. Nat Rev Mol Cell Biol. Oct. 2004;5(10):805-15.
Hiroshige, et al. Palladium-mediated macrocyclisations on solid support and its applica-tions to combinatorial synthesis. J. Am. Chem. Soc. 1995; 117:11590-11591.
Hoang et al., Dickkopf 3 inhibits invasion and motility of Saos-2 osteosarcoma cells by modulating the Wnt-beta-catenin pathway. Cancer Res. Apr. 15, 2004;64(8):2734-9.
Holford et al., Adding 'splice' to protein engineering. Structure. Aug. 15, 1998;6(8):951-6.
Horiguchi, et al. Identification and characterization of the ER/lipid droplet-targeting sequence in 17beta-hydroxysteroid dehydrogenase type 11. Arch Biochem Biophys. Nov. 15, 2008;479(2):121-30. doi: 10.1016/j.abb.2008.08.020. Epub Sep. 10, 2008.
Horne, et al. Foldamers with heterogeneous backbones. Acc Chem Res. Oct. 2008;41(10):1399-408. doi: 10.1021/ar800009n. Epub Jul. 1, 2008.
Horne, et al. Heterocyclic peptide backbone modifications in an alpha-helical coiled coil. J Am Chem Soc. Dec. 1, 2004;126(47):15366-7.
Horne, et al. Structural and biological mimicry of protein surface recognition by alpha/beta-peptide foldamers. Proc Natl Acad Sci USA. Sep. 1, 2009;106(35):14751-6. doi: 10.1073/pnas.0902663106. Epub Aug. 17, 2009.
Hossain, et al. Solid phase synthesis and structural analysis of novel A-chain dicarba analogs of human relaxin-3 (INSL7) that exhibit full biological activity. Org Biomol Chem. Apr. 21, 2009;7(8):1547-53. doi: 10.1039/b821882j. Epub Feb. 24, 2009.
Hoveyda et al., "Ru Complexes Bearing Bidentate Carbenes: From Innocent Curiosity to Uniquely Effective Catalysts for Olefin Metathesis," Org. Biomolec. Chem. 2:8-23 (2004).
Hu, et al. Efficient p53 activation and apoptosis by simultaneous disruption of binding to MDM2 and MDMX. Cancer Res. Sep. 15, 2007;67(18):8810-7.

Huang et al., How insulin binds: the B-chain alpha-helix contacts the Li beta-helix of the insulin receptor. J Mol Biol. Aug. 6, 2004;341(2):529-50.
Huang et al., Tankyrase inhibition stabilizes axin and antagonizes Wnt signalling. Nature. Oct. 1, 2009;461(7264):614-20. Epub Sep. 16, 2009.
Hunt, S. The Non-Protein Amino Acids. In: Barrett G.C., ed. Chemistry and Biochemistry of the Amino Acids. New York; Chapman and Hall; 1985.
International search report and written opinion dated Feb. 7, 2013 for PCT Application No. US12/60913.
International search report and written opinion dated Mar. 3, 2014 for PCT/US2013/068147.
International search report and written opinion dated May 23, 2013 for PCT/US2013/026241.
International search report and written opinion dated May 29, 2013 for PCT/US2013/026238.
International search report and written opinion dated Oct. 12, 2011 for PCT/US2011/047692.
Isidro-Llobet, et al. Amino acid-protecting groups. Chem Rev. Jun. 2009;109(6):2455-504. doi: 10.1021/cr800323s.
Izdebski, et al. Synthesis and biological evaluation of superactive agonists of growth hormone-releasing hormone. Proc Natl Acad Sci USA. May 23, 1995;92(11):4872-6.
Jackson et al. General approach to the synthesis of short alpha-helical peptides. JACS. 1991;113:9391-9392.
Jamieson et al., Granulocyte-macrophage progenitors as candidate leukemic stem cells in blast-crisis CML. N. Engl J Med. Aug. 12, 2004;351(7):657-67.
Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.
Jin, et al. Structure-based design, synthesis, and activity of peptide inhibitors of RGS4 GAP activity. Methods Enzymol. 2004;389:266-77.
Jin, et al. Structure-based design, synthesis, and pharmacologic evaluation of peptide RGS4 inhibitors. J Pept Res. Feb. 2004;63(2):141-6.
Joerger, et al. Structural biology of the tumor suppressor p53. Annu Rev Biochem. 2008;77:557-82. doi: 10.1146/annurev.biochem.77.060806.091238.
Johannesson, et al. Vinyl sulfide cyclized analogues of angiotensin II with high affinity and full agonist activity at the AT(1) receptor. J Med Chem. Apr. 25, 2002;45(9):1767-77.
Jordan et al., Wnt4 overexpression disrupts normal testicular vasculature and inhibits testosterone synthesis by repressing steroidogenic factor 1/beta-catenin synergy. Proc Natl Acad Sci USA. Sep. 16, 2003;100(19):10866-71. Epub Aug. 29, 2003.
Joutel et al., Notch3 mutations in CADASIL, a hereditary adult-onset condition causing stroke and dementia. Nature. Oct. 24, 1996;383(6602):707-10.
Junutula et al., Molecular characterization of Rab11 interactions with members of the family of Rab11-interacting proteins. J Biol Chem. Aug. 6, 2004;279(32):33430-7. Epub Jun. 1, 2004.
Kallen, et al. Crystal structures of human MdmX(HdmX) in complex with p53 peptide analogues reveal surprising conformational changes. Journal of Biological Chemistry. Mar. 27, 2009; 284:8812-8821.
Kanan et al. Reaction discovery enabled by DNA-templated synthesis and in vitro selection. Nature. Sep. 30, 2004;431(7008):545-9.
Karle, et al. Structural charateristics of alpha-helical peptide molecules containing Aib residues. Biochemistry. Jul. 24, 1990;29(29):6747-56.
Karle. Flexibility in peptide molecules and restraints imposed by hydrogen bonds, the Aib residue, and core inserts. Biopolymers. 1996;40(1):157-80.
Karwoski et al., Lysinonorleucine cross-link formation in alpha amino heptenoic acid-substituted peptide derivatives. Biopolymers. 1978;17(5):1119-27.

(56) References Cited

OTHER PUBLICATIONS

Katoh et al., Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.

Katsu et al., the human frizzled-3 (FZD3) gene on chromosome 8p21, a receptor gene for Wnt ligands, is associated with the susceptibility to schizophrenia. Neurosci Lett. Dec. 15, 2003;353(1):53-6.

Kaul & Balaram, "Stereochemical Control of Peptide Folding," Bioorg. Med. Chem. 7:105-117 (1999).

Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.

Kazmaier, Sythesis of Quaternary Amino Acids Containing 13, y- as well as 7,6-Unsaturated Side Chains via Chelate-Enolate Claisen Rearrangement. Tetrahedron Letters. 1996;37(30):5351-4.

Kedrowski, B.L. et al. 'Thiazoline ring formation from 2-methylcysteines and 2- halomethylalanines', Heterocycles. 2002, vol. 58, pp. 601-634.

Kelly-Welch et al, Interleukin-4 and Interleukin-13 Signaling Connections Maps. Science. 2003;300:1527-28.

Kelso et al., "A Cyclic Metallopeptide Induces α Helicity in Short Peptide Fragments of Thermolysin," Angew. Chem. Int. Ed. 42(4):421-424 (2003).

Kelso et al., "α-Turn Mimetics: Short Peptide a-Helices Composed of Cyclic Metallopentapeptide Modules," J. Am. Chem. Soc. 126:4828-4842 (2004).

Kemp et al., "Studies of N-Terminal Templates for α-Helix Formation. Synthesis and Conformational Analysis of (2S,5S,8S,11S)-1-Acetyl-1,4-diaza-3-keto-5-carboxy-10-thiatricyclo[2.8.1.04,8]-tridecane (Ac-Hel1-OH)," J. Org. Chem. 56:6672-6682 (1991).

Kemp et al., "Studies of N-Terminal Templates for 60 -Helix Formation. Synthesis and Conformational Analysis of Peptide Conjugates of (2S,5S,8S,11S)-1-Acetyl-1,4-diaza-3-keto-5-carboxy-10-thiatricyclo[2.8.1.04,8]-tridecane (Ac-Hel1-OH)," J. Org. Chem. 56:6683-6697 (1991).

Kent. Advanced Biology. Oxford University Press. 2000.

Khalil et al., An efficient and high yield method for the N-tert-butoxycarbonyl protection of sterically hindered amino acids. Tetrahedron Lett. 1996;37(20):3441-44.

Kilby et al., "Potent Suppression of HIV-1 Replication in Humans by T-20, a Peptide Inhibitor of gp41-Mediated Virus Entry," Nat. Med. 4(11):1302-1307 (1998).

Kim et al., Introduction of all-hydrocarbon i,i+3 staples into alpha-helices via ring-closing olefin metathesis. Org Lett. Jul. 2, 2010;12(13):3046-9. doi: 10.1021/011010449.

Kim et al., Stereochemical effects of all-hydrocarbon tethers in i,i+4 stapled peptides. Bioorg Med Chem Lett. May 1, 2009;19(9):2533-6. Epub Mar. 13, 2009.

Kim et al., Synthesis of all-hydrocarbon stapled a-helical peptides by ring-closing olefin metathesis. Nat Protoc. Jun. 2011;6(6):761-71. doi: 10.1038/nprot.2011.324. Epub May 12, 2011.

Kimmerlin et al., '100 years of peptide synthesis': ligation methods for peptide and protein synthesis with applications to beta-peptide assemblies. J Pept Res. Feb. 2005;65(2):229-60.

Kinage, et al. Highly regio-selective synthesis of beta-amino alcohol by reaction with aniline and propylene carbonate in self solvent systems over large pore zeolite catalyst. Green and Sustainable Chem. Aug. 2011;1: 76-84.

Kinzler et al., Identification of FAP locus genes from chromosome 5q21. Science. Aug. 9, 1991;253(5020):661-5.

Kinzler et al., Lessons from hereditary colorectal cancer. Cell. Oct. 18, 1996;87(2):159-70.

Knackmuss et al., Specific inhibition of interleukin-13 activity by a recombinant human single-chain immunoglobulin domain directed against the IL-13 receptor alpha! chain. Biol Chem. Mar. 2007;388(3):325-30.

Kohler et al., DNA specificity enhanced by sequential binding of protein monomers. Proc Natl Acad Sci USA. Oct. 12, 1999;96(21):11735-9.

Kolb et al., Click Chemistry: Diverse Chemical Function from a Few Good Reactions. Angew Chem Int Ed Engl. Jun. 1, 2001;40(11):2004-2021.

Kondo et al., Frizzled 4 gene (FZD4) mutations in patients with familial exudative vitreoretinopathy with variable expressivity. Br J Ophthalmol. Oct. 2003;87(10):1291-5.

Konishi et al Gamma-secretase inhibitor prevents Notch3 activation and reduces proliferation in human lung cancers. Cancer Res. Sep. 1, 2007;67(17):8051-7.

Korcsmaros et al., Uniformly curated signaling pathways reveal tissue-specific cross-talks and support drug target discovery. Bioinformatics. Aug. 15, 2010;26(16):2042-50. Epub Jun. 11, 2010.

Korinek et al., Depletion of epithelial stem-cell compartments in the small intestine of mice lacking Tcf-4. Nat Genet. Aug. 1998;19(4):379-83.

Kosir, et al. Breast Cancer. Available at https://www.merckmanuals.com/home/women-s-health-issues/breast-disorders/breast-cancer. Accessed on Jun. 29, 2016.

Kotha et al., Modification of constrained peptides by ring-closing metathesis reaction. Bioorg Med Chem Lett. Jun. 4, 2001;11(11):1421-3.

Kouzarides, Acetylation: a regulatory modification to rival phosphorylation? EMBO J. Mar. 15, 2000;19(6):1176-9.

Kovall et al., Crystal structure of the nuclear effector of Notch signaling, CSL, bound to DNA. EMBO J. Sep. 1, 2004;23(17):3441-51. Epub Aug. 5, 2004.

Kozlovsky et aL, GSK-3 and the neurodevelopmental hypothesis of schizophrenia. Eur Neuropsychopharmacol. Feb. 2002:12(1):13-25.

Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.

Kristensen et al., Functional reconstitution of insulin receptor binding site from non-binding receptor fragments. J Biol Chem. May 24, 2002;277(21):18340-5. Epub Mar. 18, 2002.

Kritzer et al., "Helical β-Peptide Inhibitors of the p53-hDM2 Interaction," J. Am. Chem. Soc. 126:9468-9469 (2004).

Kudaj, et al. An efficient synthesis of optically pure alpha-alkyl-beta-azido- and alpha-alkylbeta-aminoalanines via ring opening of 3-amino-3-alkyl-2-oxetanones. Tetrahedron Letters. 2007; 48:6794-6797.

Kung, et al. Suppression of tumor growth through disruption of hypoxia-inducible transcription. Nature Medicine. 2000; 6(12):1335-1340.

Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.

Kussie et al, "Structure of the MDM2 Oncoprotein Bound to the p53 Tumor Suppressor Transactivation Domain," Science 274:948-953 (1996).

Kutchukian et al., All-atom model for stabilization of alpha-helical structure in peptides by hydrocarbon staples. J Am Chem Soc. Apr. 8, 2009;131(13):4622-7.

Kutzki et al., "Development of a Potent Bcl-xL Antagonist Based on α-Helix Mimicry," J. Am. Chem. Soc. 124:11838-11839 (2002).

Kwon, et al. Quantitative comparison of the relative cell permeability of cyclic and linear peptides. Chem Biol. Jun. 2007;14(6):671-7.

Lacombe et al. Reduction of olefins on solid support using diimide. Tetrahedron Letters. 1998;39:6785-6786.

Lammi et al., Mutations in AXIN2 cause familial tooth agenesis and predispose to colorectal cancer. Am J Hum Genet. May 2004;74(5):1043-50. Epub Mar. 23, 2004.

Laporte et al., Molecular and structural basis of cytokine receptor pleiotropy in the interleukin-4/13 system. Cell. Jan. 25, 2008;132(2):259-72.

Larock, R.C. Comprehensive Organic Transformations, New York: VCH Publishers; 1989.

(56) References Cited

OTHER PUBLICATIONS

Le Guezennec et al., Molecular characterization of Sin3 PAH-domain interactor specificity and identification of PAH partners. Nucleic Acids Res. 2006;34(14):3929-37. Epub Aug. 12, 2006.

Le Guezennec et al., Molecular determinants of the interaction of Mad with the PAH2 domain of mSin3. J Biol Chem. Jun. 11, 2004;279(24):25823-9. Epub Mar. 26, 2004.

Leduc et al., Helix-stabilized cyclic peptides as selective inhibitors of steroid receptor-coactivator interactions. Proc Natl Acad Sci USA. 2003;100(20):11273-78.

Lee, et al. A novel BH3 ligand that selectively targets Mcl-1 reveals that apoptosis can proceed without Mcl-1 degradation. J Cell Biol. Jan. 28, 2008;180(2):341-355.

Lee, et al. Novel pyrrolopyrimidine-based a-helix mimetics: cell-permeable inhibitors of protein-protein interactions. J Am Chem Soc. Feb. 2, 2011;133(4):676-9. doi: 10.1021/ja108230s.

Letai, et al. Distinct BH3 Domains Either Sensitize or Activate Mitochondrial Apoptosis, Serving as Prototype Cancer Therapeutics. Cancer Cell. 2002; 2:183-192.

Lewis et al., Apoptosis in T cell acute lymphoblastic leukemia cells after cell cycle arrest induced by pharmacological inhibition of notch signaling. Chem Biol. Feb. 2007;14(2):209-19.

Li, et al. A convenient preparation of 5-iodo-1,4-disubstituted-1,2,3-triazole: multicomponent one-pot reaction of azide and alkyne mediated by CuI-NBS. J Org Chem. May 2, 2008;73(9):3630-3. doi: 10.1021/jo800035v. Epub Mar. 22, 2008.

Li et al., Alagille syndrome is caused by mutations in human Jagged!, which encodes a ligand for Notch1. Nat Genet. Jul. 1997;16(3):243-51.

Li et al., Modulation of Notch signaling by antibodies specific for the extracellular negative regulatory region of NOTCH3. J Biol Chem. Mar. 21, 2008;283(12):8046-54. doi: 10.1074/jbc.M800170200. Epub Jan. 8, 2008.

Li et al., Notch3 signaling promotes the development of pulmonary arterial hypertension. Nat Med. Nov. 2009;15(11):1289-97. doi: 10.1038/nm.2021. Epub Oct. 25, 2009.

Li, et al. Structure-based design of thioether-bridged cyclic phosphopeptides binding to Grb2-SH2 domain. Bioorg Med Chem Lett. Mar. 10, 2003;13(5):895-9.

Li, et al. Systematic mutational analysis of peptide inhibition of the p53-MDM2/Mdmx interactions. J Mol Biol. Apr. 30, 2010;398(2):200-13. doi: 10.1016/j.jmb.2010.03.005. Epub Mar. 10, 2010.

Liang et al., Wnt5a inhibits B cell proliferation and functions as a tumor suppressor in hematopoietic tissue. Cancer Cell. Nov. 2003;4(5):349-60.

Lifson & Roig, "On the Theory of Helix-coil Transition in Polypeptides," J. Chem. Phys. 34(6):1963-1974 (1961).

Lindsay et al., Rab coupling protein (RCP), a novel Rab4 and Rab11 effector protein. J Biol Chem. Apr. 5, 2002;277(14):12190-9. Epub Jan. 10, 2002.

Liskamp, et al. Conformationally restricted amino acids and dipeptides, (non)peptidomimetics and secondary structure mimetics. Recl Travl Chim Pays-Bas. 1994; 113:1-19.

Litowski & Hodges, "Designing Heterodimeric Two-stranded a-Helical Coiled-coils: Effects of Hydrophobicity and a-Helical Propensity on Protein Folding, Stability, and Specificity," J. Biol. Chem. 277(40):37272-37279 (2002).

Little et aL, a Mutation in the LDL Receptor-Related Protein 5 Gene Results in the Autosomal Dominant High-Bone-Mass Trait. Am J Hum Genet. 2002;70:11-19.

Liu et al., Chemical Ligation Approach to Form a Peptide Bond between Unprotected Peptide Segments. Concept and Model Study. J Am Chem Soc. 1994;116(10):4149-53.

Liu et al., Targeted degradation of beta-catenin by chimeric F-box fusion proteins. Biochem Biophys Res Commun. Jan. 23, 2004;313(4):1023-9.

Lo et al., Phosphorylation by the beta-catenin/MAPK complex promotes 14-3-3-mediated nuclear export of TCF/POP-1 in signal-responsive cells in C. elegans. Cell. Apr. 2, 2004;117(1):95-106.

Logan et al., The Wnt signaling pathway in development and disease. Annu Rev Cell Dev Biol. 2004;20:781-810.

Lohmar, et al. α-Aminosäuren als nucleophile Acyläquivalente, IV. Synthese symmetrischer Ketone unter Verwendung von 2-Phenyl-2-oxazolin-5-on. Chemische Berichte 113.12 (1980): 3706-3715.

Losey et al., Crystal structure of Staphylococcus aureus tRNA adenosine deaminase TadA in complex with RNA. Nat Struct Mol Biol. Feb. 2006;13(2):153-9. Epub Jan. 15, 2006.

Lou et al., The first three domains of the insulin receptor differ structurally from the insulin-like growth factor 1 receptor in the regions governing ligand specificity. Proc Natl Acad Sci USA. Aug. 15, 2006;103(33):12429-34. Epub Aug. 7, 2006.

Loughlin et al., Functional variants within the secreted frizzled-related protein 3 gene are associated with hip osteoarthritis in females. Proc Natl Acad Sci USA. Jun. 29, 2004;101(26):9757-62. Epub Jun. 21, 2004.

Lu et al., Both Pbxl and E2A-Pbx1 bind the DNA motif ATCAATCAA cooperatively with the products of multiple murine Hox genes, some of which are themselves oncogenes. Mol Cell Biol. Jul. 1995;15(7):3786-95.

Lu, et al. Proteomimetic libraries: design, synthesis, and evaluation of p53-MDM2 interaction inhibitors. J Comb Chem. May-Jun. 2006;8(3):315-25.

Lubman et al., Quantitative dissection of the Notch:CSL interaction: insights into the Notch-mediated transcriptional switch. J Mol Biol. Jan. 19, 2007;365(3):577-89. Epub Oct. 3, 2006.

Luo, et al. Mechanism of helix induction by trifluoroethanol: a framework for extrapolating the helix-forming properties of peptides from trifluoroethanol/water mixtures back to water. Biochemistry. Jul. 8, 1997;36(27):8413-21.

Luo et al., Wnt signaling and human diseases: what are the therapeutic implications? Lab Invest. Feb. 2007;87(2):97-103. Epub Jan. 8, 2007.

Luscher et al., the basic region/helix-loop-helix/leucine zipper domain of Myc proto-oncoproteins: function and regulation. Oncogene. May 13, 1999;18(19):2955-66.

Luu et al, Wnt/beta-catenin signaling pathway as a novel cancer drug target. Curr Cancer Drug Targets. Dec. 2004;4(8):653-71.

Lyu, et al. Capping Interactions in Isolated α Helices: Position-dependent Substitution Effects and Structure of a Serine-capped Peptide Helix. Biochemistry. 1993; 32:421-425.

Lyu et al, "α-Helix Stabilization by Natural and Unnatural Amino Acids with Alkyl Side Chains," Proc. Nat'l Acad. Sci. USA 88:5317-5320 (1991).

MacMillan, Evolving strategies for protein synthesis converge on native chemical ligation. Angew Chem Int Ed Engl. Nov. 27, 2006;45(46):7668-72.

Madden, et al. Synthesis of cell-permeable stapled peptide dual inhibitors of the p53- Mdm2/Mdmx interactions via photoinduced cycloaddition. Bioorg Med Chem Lett. Mar. 1, 2011;21(5):1472-5. doi: 10.1016/j.bmcl.2011.01.004. Epub Jan. 7, 2011.

Mai, et al. A proapoptotic peptide for the treatment of solid tumors. Cancer Research. 2001; 61:7709-7712.

Makimura, et al. Reduced growth hormone secretion is associated with increased carotid intima-media thickness in obesity. J Clin Endocrinol Metab. Dec. 2009;94(12):5131-8. doi: 10.1210/jc.2009-1295. Epub Oct. 16, 2009.

Mangold, et al. Azidoalanine mutagenicity in Salmonella: effect of homologation and alpha-Mutat Res. Feb. 1989;216(1):27-33.methyl substitution.

Mannhold, R., Kubinyi, H., Folkers, G., series eds. Molecular Drug Properties: Measurement and Prediction (Methods and Principles in Medicinal Chemistry). Wiley-VCH; 2007.

Marquesee & Baldwin, "Helix Stabilization by Glu- . . . Lys+ Salt Bridges in Short Peptides of De Novo Design," Proc. Nat'l Acad. Sci. USA 84:8898-8902 (1987).

Marshall et al., Back to the future: ribonuclease A. Biopolymers. 2008;90(3):259-77.

Martin, et al. Thermal [2+2] intramolecular cycloadditions of fuller-1,6-enynes. Angew Chem Int Ed Engl. Feb. 20, 2006;45(9):1439-42.

Mayo, et al. International Union of Pharmacology. XXXV. The glucagon receptor family. Pharmacol Rev. Mar. 2003;55(1):167-94.

(56) References Cited

OTHER PUBLICATIONS

McGahon, et al. The end of the (cell) line: Methods for the study of apoptosis in vitro. Methods Cell Biol. 1995;46:153-85.

McKern et al., Structure of the insulin receptor ectodomain reveals a folded-over conformation. Nature. Sep. 14, 2006;443(7108):218-21. Epub Sep. 6, 2006.

McNamara et al. Peptides constrained by an aliphatic linkage between two C(alpha) sites: design, synthesis, and unexpected conformational properties of an i,(i+4)-linked peptide. J Org Chem. Jun. 29, 2001;66(13):4585-95.

Mellegaard-Waetzig et al., Allylic amination via decarboxylative c—n. bond formation Syn Jett. 2005;18:2759-2762.

Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.

Meyers et al., Formation of mutually exclusive Rab11 complexes with members of the family of Rab11-interacting proteins regulates Rab11 endocytic targeting and function. J Biol Chem. 2002 Dec 13;277(50):49003-10. Epub Oct. 9, 2002.

Miller & Scanlan, "oNBS-SPPS: A New Method for Solid-phase Peptide Synthesis," J. Am. Chem. Soc. 120:2690-2691 (1998).

Miller et al., Application of Ring-Closing Metathesis to the Synthesis of Rigidified Amino Acids and Peptides. J Am Chem Soc. 1996;118(40):9606-9614.

Miller et al., Synthesis of Conformationally Restricted Amino Acids and Peptides Employing Olefin Metathesis. J Am Chem Soc. 1995;117(21):5855-5856.

Miloux et al., Cloning of the human IL-13R alpha! chain and reconstitution with the IL4R alpha of a functional IL-4/IL-13 receptor complex. FEBS Lett. Jan. 20, 1997;401(2-3):163-6.

Min, et al. Structure of an HIF-1alpha -pVHL complex: hydroxyproline recognition in signaling. Science. Jun. 7, 2002;296(5574):1886-9.

Miyaoka et al., Increased expression of Wnt-1 in schizophrenic brains. Schizophr Res. Jul. 27, 1999;38(1):1-6.

Moellering et al., Abstract 69. Computational modeling and molecular optimization of stabilized alpha-helical peptides targeting NOTCH-CSL transcriptional complexes. Nov. 2010; 8(7):30. Doi: 10.1016/S1359-6349(10)71774-2. Abstract Only, European Journal of Cancer Supplements, 2010, 8(7).

Moellering et al., Direct inhibition of the Notch transcription factor complex. Nature. Nov. 12, 2009;462(7270):182-8. Erratum in: Nature. Jan. 21, 2010;463(7279):384.

Moon et al., WNT and beta-catenin signalling: diseases and therapies. Nat Rev Genet. Sep. 2004;5(9):689-701.

Morin, beta-catenin signaling and cancer. Bioessays. Dec. 1999;21(12):1021-30.

Morita, et al. Cyclolinopeptides B-E, new cyclic peptides from Linum usitatissimum. Tetrahedron 55.4 (1999): 967-976.

Mosberg, et al. Dithioether-containing cyclic peptides. J. Am. Chem. Soc. 1985;107(10):2986-2987.

Moses, et al. The growing applications of click chemistry. Chem Soc Rev. Aug. 2007;36(8):1249-62.

Moy et al., Solution structure of human IL-13 and implication for receptor binding. J Mol Biol. Jun. 29, 2001;310(1):219-30.

Muchmore, et al. X-ray and NMR structure of human Bcl-xL, an inhibitor of programmed cell death. Nature. May 23, 1996;381(6580):335-41.

Mudher et al., Alzheimer's disease-do tauists and baptists finally shake hands! Trends Neurosci. Jan. 2002;25(1):22-6.

Muir et al., Expressed protein ligation: a general method for protein engineering. Proc Natl Acad Sci USA. Jun. 9, 1998;95(12):6705-10.

Muir, Semisynthesis of proteins by expressed protein ligation. Annu Rev Biochem. 2003;72:249-89. Epub Feb. 27, 2003.

Muller, P. Glossary of terms used in physical organic chemistry. Pure and Applied Chemistry, 1994, vol. 66, pp. 1077-1184.

Mulqueen et al. Synthesis of the thiazoline-based siderophore (S)-desferrithiocin. 1993;48(24):5359-5364.

Muppidi et al., Conjugation of spermine enhances cellular uptake of the stapled peptide-based inhibitors of p53-Mdm2 interaction. Bioorg Med Chem Lett. Dec. 15, 2011;21(24):7412-5. doi: 10.1016/j.bmcl.2011.10.009. Epub Oct. 12, 2011.

Murphy, et al. Growth hormone exerts hematopoietic growth-promoting effects in vivo and partially counteracts the myelosuppressive effects of azidothymidine. Blood. Sep. 15, 1992;80(6):1443-7.

Murray, et al. Targeting protein-protein interactions: lessons from p53/MDM2. Biopolymers. 2007;88(5):657-86.

Mustapa, et al. Synthesis of a Cyclic Peptide Containing Norlanthionine: Effect of the Thioether Bridge on Peptide Conformation. J. Org. Chem. 2003;68(21):8193-8198.

Mynarcik et al., Alanine-scanning mutagenesis of a C-terminal ligand binding domain of the insulin receptor alpha subunit. J Biol Chem. Feb. 2, 1996;271(5):2439-42.

Mynarcik et al., Identification of common ligand binding determinants of the insulin and insulin-like growth factor 1 receptors. Insights into mechanisms of ligand binding. J Biol Chem. Jul. 25, 1997;272(30):18650-5.

Myriem, V. One pot iodination click reaction: A Convenient Preparation of 5-Iodo-1,4-disubstituted-1,2,3-triazole. Date unknown.

Myung et al., The ubiquitin-proteasome pathway and proteasome inhibitors. Med Res Rev. Jul. 2001;21(4):245-73.

Nair et al., X-ray structures of Myc-Max and Mad-Max recognizing DNA. Molecular bases of regulation by proto-oncogenic transcription factors. Cell. Jan. 24, 2003;112(2):193-205.

Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.

Nam et al., Structural basis for cooperativity in recruitment of MAML coactivators to Notch transcription complexes. Cell. Mar. 10, 2006;124(5):973-83.

Nam et al., Structural requirements for assembly of the CSL. intracellular Notch1.Mastermind-like 1 transcriptional activation complex. J Biol Chem. Jun. 6, 2003;278(23):21232-9. Epub Mar. 18, 2003.

Nefedova et al., Involvement of Notch-1 signaling in bone marrow stroma-mediated de novo drug resistance of myeloma and other malignant lymphoid cell lines. Blood. May 1, 2004;103(9):3503-10. Epub Dec. 11, 2003.

Nelson & Kallenbach, "Persistence of the α-Helix Stop Signal in the S-Peptide in Trifluoroethanol Solutions," Biochemistry 28:5256-5261 (1989).

Ngo et al. Computational complexity, protein structure prediction, and the levinthal paradox. In: The Protein Folding Problem and Tertiary Structure Prediction. K. Merz, Jr., et al. Eds. 1994:433-506.

Ngo et al. Computational complexity, protein structure prediction and the Levinthal Paradox.In: The Protein Folding Problem and Tertiary Structure Prediction. K.Merz, Jr. and S. LeGrand, eds., 1994, pp. 491-495.

Nicole, et al. Identification of key residues for interaction of vasoactive intestinal peptide with human VPAC1 and VPAC2 receptors and development of a highly selective VPAC1 receptor agonist. Alanine scanning and molecular modeling of the peptide. J Biol Chem. Aug. 4, 2000;275(31):24003-12.

Niemann et al., Homozygous WNT3 mutation causes tetra-amelia in a large consanguineous family. Am J Hum Genet. Mar. 2004;74(3):558-63. Epub Feb. 5, 2004.

Nilsson et al., Staudinger ligation: a peptide from a thioester and azide. Org Lett. Jun. 29, 2000;2(13):1939-41.

Niranjan et al., The Notch pathway in podocytes plays a role in the development of glomerular disease. Nat Med. Mar. 2008;14(3):290-8. doi: 10.1038/nm1731. Epub Mar. 2, 2008.

Nishisho et al., Mutations of chromosome 5q21 genes in FAP and colorectal cancer patients. Science. Aug. 9, 1991;253(5020):665-9.

Noah, et al. A cell-based luminescence assay is effective for high-throughput screening of potential influenza antivirals. Antiviral Res. Jan. 2007;73(1):50-9. Epub Jul. 28, 2006.

Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.

(56) References Cited

OTHER PUBLICATIONS

Noguera-Troise et al., Blockade of Dll4 inhibits tumour growth by promoting non-productive angiogenesis. Nature. Dec. 21, 2006;444(7122):1032-7.
Notice of allowance dated Jan. 7, 2015 for U.S. Appl. No. 13/370057.
Notice of allowance dated Mar. 30, 2015 for U.S. Appl. No. 13/655,378.
Office action dated Nov. 26, 2013 for U.S. Appl. No. 13/655,378.
O'Shea et al., "Mechanism of Specificity in the Fos-Jun Oncoprotein Heterodimer," Cell 68:699-708 (1992).
Okamura et al., Redundant regulation of T cell differentiation and TCRalpha gene expression by the transcription factors LEF-1 and TCF-1. Immunity. Jan. 1998;8(1):11-20.
Olson et al., Sizing up the heart: development redux in disease. Genes Dev. Aug. 15, 2003;17(16):1937-56. Epub Jul. 31, 2003.
O'Neil & DeGrado, "A Thermodynamic Scale for the Helix-forming Tendencies of the Commonly Occurring Amino Acids," Science 250:646-651(1990).
O'Neil et al., FBW7 mutations in leukemic cells mediate NOTCH pathway activation and resistance to gamma-secretase inhibitors. J Exp Med. Aug. 6, 2007;204(8):1813-24. Epub Jul. 23, 2007.
Or et al. Cysteine alkylation in unprotected peptides: synthesis of a carbavasopressin analogue by intramolecular cystein alkylation. J. Org. Chem. Apr. 1991;56(9):3146-3149.
Oswald et al., RBP-Jkappa/SHARP recruits CtIP/CtBP corepressors to silence Notch target genes. Mol Cell Biol. Dec. 2005;25(23):10379-90.
Pakotiprapha et al., Crystal structure of Bacillus stearothermophilus UvrA provides insight into ATP-modulated dimerization, UvrB interaction, and DNA binding. Mol Cell. Jan. 18, 2008;29(1):122-33. Epub Dec. 27, 2007.
Palomero et al., Mutational loss of PTEN induces resistance to NOTCH1 inhibition in T-cell leukemia. Nat Med. Oct. 2007;13(10):1203-10. Epub Sep. 16, 2007.
Pangborn et al., "Safe and Convenient Procedure for Solvent Purification," Organometallics 15:1518-1520 (1996).
Paquette, L.A., ed. Encyclopedia of Reagents for Organic Synthesis. New York; John Wiley & Sons; 1995.
Park et al., Notch3 gene amplification in ovarian cancer. Cancer Res. Jun. 15, 2006;66(12):6312-8.
Parrish et al., Perspectives on alkyl carbonates in organic synthesis. Tetrahedron, 2000; 56(42): 8207-8237.
Parthier, et al. Passing the baton in class B GPCRs: peptide hormone activation via helix induction? Trends Biochem Sci. Jun. 2009;34(6):303-10. doi: 10.1016/j.tibs.2009.02.004. Epub May 14, 2009.
Patgiri, et al. A hydrogen bond surrogate approach for stabilization of short peptide sequences in alpha-helical conformation. Acc Chem Res. Oct. 2008;41(10):1289-300. Epub Jul. 17, 2008.
Patgiri, et al. An orthosteric inhibitor of the Ras-Sos interaction. Nat Chem Biol. Jul. 17, 2011;7(9):585-7. doi: 10.1038/nchembio.612.
Patgiri, et al. Solid phase synthesis of hydrogen bond surrogate derived alpha-helices: resolving the case of a difficult amide coupling. Org Biomol Chem. Apr. 21, 2010;8(8):1773-6.
Pattenden, et al. Enantioselective synthesis of 2-alkyl substituted cysteines. 1993;49(10):2131-2138.
Pattenden, et al. Naturally occurring linear fused thiazoline-thiazole containing metabolites: total synthesis of (-)-didehydromirabazole A, a cytotoxic alkaloid from blue-green algae. J Chem Soc. 1993;14:1629-1636.
Pazgier, et al. Structural basis for high-affinity peptide inhibition of p53 interactions with MDM2 and MDMX. Proc Natl Acad Sci USA. Mar. 24, 2009;106(12):4665-70. doi: 10.1073/pnas.0900947106. Epub Mar. 2, 2009.
Pellois et al., Semisynthetic proteins in mechanistic studies: using chemistry to go where nature can't. Curr Opin Chem Biol. Oct. 2006;10(5):487-91. Epub Aug. 28, 2006.
Perantoni, Renal development: perspectives on a Wnt-dependent process. Semin Cell Dev Biol. Aug. 2003;14(4):201-8.

Peryshkov, et al. Z-Selective olefin metathesis reactions promoted by tungsten oxo alkylidene complexes. Am Chem Soc. Dec. 28, 2011;133(51):20754-7. doi: 10.1021/ja210349m. Epub Nov. 30, 2011.
Petros et al., "Rationale for Bcl-xL/Bad Peptide Complex Formation from Structure, Mutagenesis, and Biophysical Studies," Protein Sci. 9:2528-2534 (2000).
Phan, et al. Structure-based design of high affinity peptides inhibiting the interaction of p53 with MDM2 and Mdmx. J Biol Chem. Jan. 15, 2010;285(3):2174-83. doi: 10.1074/jbc.M109.073056. Epub Nov. 12, 2009.
Phelan, et al. A General Method for Constraining Short Peptides to an α-Helical Conformation. J. Am. Chem. Soc. 1997;119:455-460.
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Pinnix et al., Active Notch1 confers a transformed phenotype to primary human melanocytes. Cancer Res. Jul. 1, 2009;69(13):5312-20. doi: 10.1158/0008-5472.CAN-08-3767. Epub Jun. 23, 2008.
Plenat, et al. [Formaldehyde fixation in the third millennium]. Ann Pathol. Feb. 2001;21(1):29- 47.
Polakis, The oncogenic activation of beta-catenin. Curr Opin Genet Dev. Feb. 1999;9(1):15- 21.
Lu et al., Structural determinants within Pbxl that mediate cooperative DNA binding with pentapeptide-containing Hox proteins: proposal for a model of a Pbxl-Hox-DNA complex. Mol Cell Biol. Apr. 1996;16(4):1632-40.
Punna, et al. Head-to-tail peptide cyclodimerization by copper-catalyzed azide-alkyne cycloaddition. Angew Chem Int Ed Engl. Apr. 8, 2005;44(15):2215-20.
Qian & Schellman, "Helix-coil Theories: A Comparative Study for Finite Length Polypeptides," J. Phys. Chem. 96:3987-3994 (1992).
Qiu et al., Convenient, Large-Scale Asymmetric Synthesis of Enantiomerically Pure trans-Cinnamylglycine and -a-Alanine. Tetrahedron. 2000;56:2577-82.
Rao et al., Inhibition of Notch signaling by gamma secretase inhibitor engages the RB pathway and elicits cell cycle exit in T-cell acute lymphoblastic leukemia cells. Cancer Res. Apr. 1, 2009;69(7):3060-8. doi: 10.1158/0008-5472.CAN-08-4295. Epub Mar. 24, 2009.
Rasmussen, et al. Ruthenium-catalyzed cycloaddition of aryl azides and alkynes. Org Lett. Dec. 20, 2007;9(26):5337-9.
Rawlinson et al., CRM1-mediated nuclear export of dengue virus RNA polymerase NS5 modulates interleukin-8 induction and virus production. J Biol Chem. Jun. 5, 2009;284(23):15589-97. Epub Mar. 18, 2009.
Remington: The Science and Practice of Pharmacy. 19th Edition, 1995.
Reya et al., Wnt signalling in stem cells and cancer. Nature. Apr. 14, 2005;434(7035):843-50.
Rich et al., Synthesis of the cytostatic cyclic tetrapeptide, chlamydocin. Tetranderon Letts. 1983;24(48):5305-08.
Riddoch, et al. A solid-phase labeling strategy for the preparation of technetium and rhenium bifunctional chelate complexes and associated peptide conjugates. Bioconjug Chem. Jan.-Feb. 2006;17(1):226-35.
Ridgway et al., Inhibition of Dll4 signalling inhibits tumour growth by deregulating angiogenesis. Nature. Dec. 21, 2006;444(7122):1083-7.
Rink, et al. Lantibiotic Structures as Guidelines for the Design of Peptides That Can Be Modified by Lantibiotic Enzymes. Biochemistry. 2005; 44:8873-8882.
Rivlin, et al. Mutations in the p53 Tumor Suppressor Gene: Important Milestones at the Various Steps of Tumorigenesis. Genes & Cancer 2011, 2:466. Originally published online May 18, 2011.
Robberecht, et al. Structural requirements for the activation of rat anterior pituitary adenylate cyclase by growth hormone-releasing factor (GRF): discovery of (N—Ac—Tyr1, D-Arg2)-Grf(1-29)—NH2 as a GRF antagonist on membranes. Endocrinology. Nov. 1985;117(5):1759-64.

(56) References Cited

OTHER PUBLICATIONS

Robert, A hierarchical "nesting" approach to describe the stability of alpha helices with side-chain interactions. Biopolymers. 1990;30(3-4):335-47.
Roberts, et al. Efficient synthesis of thioether-based cyclic peptide libraries. Tetrahedon Letters. 1998; 39: 8357-8360.
Roberts, et al. Examination of methodology for the synthesis of cyclic thioether peptide libraries derived from linear tripeptides. J Pept Sci. Dec. 2007;13(12):811-21.
Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.
Roehrl et al., "A General Framework for Development and Data Analysis of Competitive High-throughput Screens for Small-molecule Inhibitors of Protein-Protein Interactions by Fluorescence Polarization," Biochemistry 43:16056-16066 (2004).
Roehrl et al., "Discovery of Small-molecule Inhibitors of the NFAT-Calcineurin Interaction by Competitive High-throughput Fluorescence Polarization Screening," Biochemistry 43:16067-16075 (2004).
Roice, et al. High Capacity Poly(ethylene glycol) Based Amino Polymers for Peptide and Organic Synthesis. QSAR & Combinatorial Science. 2004;23(8):662-673.
Rojo, et al. Macrocyclic peptidomimetic inhibitors of β-secretase (BACE): First X-ray structure of a macrocyclic peptidomimetic-Bace complex. Bioorg. Med. Chem. Lett. 2006; 16:191-195.
Roof, et al. Mechanism of action and structural requirements of constrained peptide inhibitors of RGS proteins. Chem Biol Drug Des. Apr. 2006;67(4):266-74.
Roos et al., Synthesis of a-Substituted a-Amino Acids via Cationic Intermediates. J Org Chem. 1993;58:3259-68.
Ross et aL, Inhibition of adipogenesis by Wnt signaling. Science. Aug. 11, 2000;289(5481):950-3.
Rostovtsev, et al. A stepwise huisgen cycloaddition process: copper (i)-catalyzed regioselective "ligation" of azides and terminal alkynes. Angew. Chem. Int. Ed. Engl. Jul. 15, 2002;41(14):2596-2599.
Ruan et al., "Metal Ion Enhanced Helicity in Synthetic Peptides Containing Unnatural, Metal-ligating Residues," J. Am. Chem. Soc. 112:9403-9404 (1990).
RudingerJ, "Characteristics of the amino acids as components of a peptide hormone sequence," Peptide Hormones, JA Parsons Edition, University Park Press, Jun. 1976, pp. 1-7.
Ruffolo and Shore. BCL-2 Selectively Interacts with the BID-Induced Open Conformer of BAK, Inhibiting BAK Auto-Oligomerization. J. Biol. Chern. 2003;278(27):25039-25045.
Rutledge et al., "A View to a Kill: Ligands for Bcl-2 Family Proteins," Curr. Opin. Chem. Biol. 6:479-485 (2002).
Rytting, et al. Overview of Leukemia. Available at http://www.merckmanuals.com/home/blood-disorders/leukemias/overview-of%20leukemia?qt=Leukemia&%2520alt=sh. Accessed on Jun. 29, 2016.
Sadot et al., Down-regulation of beta-catenin by activated p53. Mol Cell Biol. Oct. 2001;21(20):6768-81.
Saghiyan, A. S., et al., "New chiral Niii complexes of Schiffs bases of glycine and alanine for efficient asymmetric synthesis of a-amino acids," Tedrahedron: Asymmetry 17: 455-467 (2006).
Saghiyan, et al. Novel modified (S)-N-(benzoylphenyI)-1-(3,4-dichlorobenzyl)-pyrolidine-2-carboxamide derived chiral auxiliarie for asymmetric synthesis of (S)-alpha-amino acids. Chemical Journal of Armenia. Aug. 2002; 55(3):150-161. (abstract only).
Saiki, et al. Primer-directed enzymatic amplification of DNA with a thermostable DNA polymerase. Science. Jan. 29, 1998;239(4839):487-91.
Sali et al., Stabilization of protein structure by interaction of alpha-helix dipole with a charged side chain. Nature. Oct. 20, 1988;335(6192):740-3.
Sampietro et al., Crystal structure of a beta-catenin/BCL9/Tcf4 complex. Mol Cell. Oct. 20, 2006;24(2):293-300.
Sanchez-Garcia, et al. Tumorigenic activity of the BCR-ABL oncogenes is mediated by BCL2. Proc Natl Acad Sci USA. Jun. 6, 1995;92(12):5287-91.
Ösapay & Taylor, "Multicyclic Polypeptide Model Compounds. 2. Synthesis and Conformational Properties of a Highly α-Helical Uncosapeptide Constrained by Three Side-chain to Side-chain Lactam Bridges," J. Am. Chem. Soc. 114:6966-6973 (1992).
Satoh et al., AXIN1 mutations in hepatocellular carcinomas, and growth suppression in cancer cells by virus-mediated transfer of AXIN1. Nat Genet. Mar. 2000;24(3):245-50.
Sattler et al. Structure of Bcl-xL-Back peptide complex: recognition between regulators of apoptosis. Science. 1997;275:983-986.
Saxon et al., Cell surface engineering by a modified Staudinger reaction. Science. Mar. 17, 2000;287(5460):2007-10.
Schaffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schaffer et al., Assembly of high-affinity insulin receptor agonists and antagonists from peptide building blocks. Proc Natl Acad Sci USA. Apr. 15, 2003;100(8):4435-9. Epub Apr. 8, 2003.
Schafmeister et al. An all-hydrocarbon crosslinking system for enhancing the helicity and metabolic stability of peptides. J. Am Chem. Soc. 2000;122:5891-5892.
Scheffzek et al., The Ras-RasGAP complex: structural basis for GTPase activation and its loss in oncogenic Ras mutants. Science. Jul. 18, 1997;277(5324):333-8.
Schinzel et al., the phosphate recognition site of *Escherichia coli* maltodextrin phosphorylase. Febs Lett. Jul. 29, 1991;286(1-2):125-8.
Schmiedeberg et al. Reversible backbone protection enables combinatorial solid-phase ring-closing metathesis reaction (RCM) in peptides. Org Lett. Jan. 10, 2002;4(1):59-62.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Schwarzer et al., Protein semisynthesis and expressed protein ligation: chasing a protein's tail. Curr Opin Chem Biol. Dec. 2005;9(6):561-9. Epub Oct. 13, 2005.
Scorrano, et al. A distinct pathway remodels mitochondrial cristae and mobilizes cytochrome c during apoptosis. Dev Cell. Jan. 2002;2(1):55-67.
Scott, et al. A Solid-Phase Synthetic Route to Unnatural Amino Acids with Diverse Side-Chain Substitutions. Journal of Organic Chemistry. 2002, vol. 67, No. 9, pp. 2960-2969.
Scott et al., Evidence of insulin-stimulated phosphorylation and activation of the mammalian target of rapamycin mediated by a protein kinase B signaling pathway. Proc Natl Acad Sci USA. Jun. 23, 1998;95(13):7772-7.
Seabra et al., Rab GTPases, intracellular traffic and disease. Trends Mol Med. Jan. 2002;8(1):23-30.
Seebach, et al. Beta-peptidic peptidomimetics. Acc Chem Res. Oct. 2008;41(10):1366-75. doi: 10.1021/ar700263g. Epub Jun. 26, 2008.
Seebach, et al. Self-Regeneration of Stereocenters (SRS)—Applications, Limitations, and Abandonment of a Synthetic Principle. Angew. Chem. Int. Ed. Engl. 1996;35:2708-2748.
Seebeck, et al. Ribosomal synthesis of dehydroalanine-containing peptides. J Am Chem Soc. Jun. 7, 2006;128(22):7150-1.
Seiffert et al., Presenilin-1 and -2 are molecular targets for gamma-secretase inhibitors. J Biol Chem. Nov. 3, 2000;275(44):34086-91.
Shair, A closer view of an oncoprotein-tumor suppressor interaction. Chem Biol. Nov. 1997;4(11):791-4.
Shangary, et al. Targeting the MDM2-p53 interaction for cancer therapy. Clin Cancer Res. Sep. 1, 2008;14(17):5318-24. doi: 10.1158/1078-0432.CCR-07-5136.
Shenk, et al. Biochemical method for mapping mutational alterations in DNA with S1 nuclease: the location of deletions and temperature-sensitive mutations in simian virus 40. Proc Natl Acad Sci USA. Mar. 1975;72(3):989-93.

(56) References Cited

OTHER PUBLICATIONS

Shepherd et al., "Single Turn Peptide Alpha Helices with Exceptional Stability in Water," J. Am. Chem. Soc. 127:2974-2983 (2005).
Shi, et al. The role of arsenic-thiol interactions in metalloregulation of the ars operant. J Biol Chem. Apr. 19, 1996;271(16):9291-7.
Shiba et al., Structural basis for Rab11-dependent membrane recruitment of a family of Rab11-interacting protein 3 (FIP3)/Arfophilin-1. Proc Natl Acad Sci USA. Oct. 17, 2006;103(42):15416-21. Epub Oct. 9, 2006.
Si et aL, CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Sia et al., "Short Constrained Peptides that Inhibit HIV-1 Entry," Proc. Nat'l Acad. Sci. USA 99(23):14664-14669 (2002).
Siddle et al., Specificity in ligand binding and intracellular signalling by insulin and insulin-like growth factor receptors. Biochem Soc Trans. Aug. 2001;29(Pt 4):513-25.
Singh et al., Iridium(I)-catalyzed regio- and enantioselective allylic amidation.Tet. Lett. 2007;48 (40): 7094-7098.
Singh, et al. Efficient asymmetric synthesis of (S)- and (R)-N-Fmoc-S-trityl-alpha-methylcysteine using camphorsultam as a chiral auxiliary. J Org Chem. Jun. 25, 2004;69(13):4551-4.
Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.
Smith, et al. Design, Synthesis, and Binding Affinities of Pyrrolinone-Based Somatostatin Mimetics. Organic Letters. Jan. 8, 2005, vol. 7, No. 3, pp. 399-402, plus Supporting Information, pp. S1-S39.
Smith et al., Structural resolution of a tandem hormone-binding element in the insulin receptor and its implications for design of peptide agonists. Proc Natl Acad Sci USA. Apr. 13, 2010;107(15):6771-6. doi: 10.1073/pnas.1001813107. Epub Mar. 26, 2010.
Solution phase synthesis from http://www.combichemistry.com/solution_phase_synthesis.html. P.1. Accessed Aug. 6, 2009.
Soucek et al., Modelling Myc inhibition as a cancer therapy. Nature. Oct. 2, 2008;455(7213):679-83. Epub Aug 17, 2008.
Sparey et al., Cyclic sulfamide gamma-secretase inhibitors. Bioorg Med Chem Lett. Oct. 1, 2005;15(19):4212-6.
Spierings, et al. Connected to death: the (unexpurgated) mitochondrial pathway of apoptosis. Science. 2005; 310:66-67.
Stein et al., Rab proteins and endocytic trafficking: potential targets for therapeutic intervention. Adv Drug Deliv Rev. Nov. 14, 2003;55(11):1421-37.
Stenmark et al., The Rab GTPase family. Genome Biol. 2001;2(5):3007.1-3007.7.
Stewart, et al. Cell-penetrating peptides as delivery vehicles for biology and medicine. Org Biomol Chem. Jul. 7, 2008;6(13):2242-55. doi: 10.1039/b719950c. Epub Apr. 15, 2008.
Still et al., "Rapid Chromatographic Technique for Preparative Separations with Moderate Resolution," J. Org. Chem. 43(14):2923-2925 (1978).
Still et al., Semianalytical Treatment of Solvation for Molecular Mechanics and Dynamics. J Am Chem Soc. 1990;112:6127-29.
STN search notes for Lu reference, 4 pages, 2006.
Struhl et al., Presenilin is required for activity and nuclear access of Notch in Drosophila. Nature. Apr. 8, 1999;398(6727):522-5.
Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.
Su et al., Eradication of pathogenic beta-catenin by Skp1/Cullin/F box ubiquitination machinery. Proc Natl Acad Sci USA. Oct. 28, 2003;100(22):12729-34. Epub Oct. 16, 2003.
Su, et al. In vitro stability of growth hormone releasing factor (GRF) analogs in porcine plasma. Horm Metab Res. Jan. 1991;23(1):15-21.

Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Suzuki, et al. Structure of Bax: coregulation of dimer formation and intracellular localization. Cell. Nov. 10, 2000;103(4):645-54.
Szewczuk, et al. Synthesis and Biological activity of new conformationally restricted analogues of pepstatin. Int. J. Peptide Protein. Res. 1992; 40:233-242.
Takeda et al., Human sebaceous tumors harbor inactivating mutations in LEF I. Nat Med. Apr. 2006;12(4):395-7. Epub Mar. 26, 2006.
Tam, et al. Protein prosthesis: 1,5-disubstituted[1,2,3]triazoles as cis-peptide bond surrogates. J Am Chem Soc. Oct. 24, 2007;129(42):12670-1.
Tanaka, Design and synthesis of non-proteinogenic amino acids and secondary structures of their peptides. Yakugaku Zasshi. Oct. 2006:126(10):931-44. Japanese.
Tang, et al. Construction and activity of a novel GHRH analog, Pro-Pro-hGHRH(1-44)-Gly-Gly-Cys. Acta Pharmacol Sin. Nov. 2004;25(11):1464-70.
Taylor. The synthesis and study of side-chain lactam-bridged peptides. Biopolymers. 2002;66(1):49-75.
Thallinger, et al. Mcl-1 is a novel therapeutic target for human sarcoma: synergistic inhibition of human sarcoma xenotransplants by a combination of mcl-1 antisense oligonucleotides with low-dose cyclophosphamide. Clin Cancer Res. Jun. 15, 2004;10(12 Pt 1):4185-91.
Therasse, et al. New guidelines to evaluate the response to treatment in solid tumors. European Organization for Research and Treatment of Cancer, National Cancer Institute of the United States, National Cancer Institute of Canada. J Natl Cancer Inst. Feb. 2, 2000;92(3):205-16.
Thompson et al., Mutants of interleukin 13 with altered reactivity toward interleukin 13 receptors. J Biol Chem. Oct. 15, 1999;274(42):29944-50.
Tian et al., Linear non-competitive inhibition of solubilized human gamma-secretase by pepstatin A methylester, L685458, sulfonamides, and benzodiazepines. J Biol Chem. Aug. 30, 2002;277(35):31499-505. Epub Jun. 18, 2002.
Tian, et al. Recombinant human growth hormone promotes hematopoietic reconstitution after syngeneic bone marrow transplantation in mice. Stem Cells. 1998;16(3):193-9.
Tian et aL, The role of the Wnt-signaling antagonist DKK1 in the development of osteolytic lesions in multiple myeloma. N Engl J Med. Dec. 25, 2003;349(26):2483-94.
Titus, et al. Human K/natural killer cells targeted with hetero-cross-linked antibodies specifically lyse tumor cells in vitro and prevent tumor growth in vivo. J Immunol. Nov. 1, 1987;139(9):3153-8.
Tolbert et al., New methods for proteomic research: preparation of proteins with N-terminal cysteines for labeling and conjugation. Angew Chem Int Ed Engl. Jun. 17, 2002;41(12):2171-4.
Toniolo, Conformationally restricted peptides through short-range cyclizations. Int J Pept Protein Res. Apr. 1990;35(4):287-300.
Toomes et al., Mutations in LRP5 or FZD4 underlie the common familial exudative vitreoretinopathy locus on chromosome 11q. Am J Hum Genet. Apr. 2004;74(4):721-30. Epub Mar. 11, 2004.
Tornoe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Torrance et al., Combinatorial chemoprevention of intestinal neoplasia. Nat Med. Sep. 2000;6(9):1024-8.
Torres, et al. Peptide tertiary structure nucleation by side-chain crosslinking with metal complexation and double "click" cycloaddition. Chembiochem. Jul. 21, 2008;9(11):1701-5.
Trnka & Grubbs, "The Development of L2X2Ru=CHR Olefin Metathesis Catalysts: An Organometallic Success Story," Acc. Chem. Res. 34:18-29 (2001).
Tsuji et al., Antiproliferative activity of REIC/Dkk-3 and its significant down-regulation in non-small-cell lung carcinomas. Biochem Biophys Res Commun. Nov. 23, 2001;289(1):257-63.
Tsuji et al., Synthesis of γ, δ-unsaturated ketones by the intramolecular decarboxylative allylation of allylβ-keto carboxylates and

(56) References Cited

OTHER PUBLICATIONS alkenyl allyl carbonates catalyzed by molybdenum, nickel, and rhodium complexes. Chemistry Letters. 1984; 13(10):1721-1724.
Tsuruzoe et al., Insulin receptor substrate 3 (IRS-3) and IRS-4 impair IRS-1- and IRS-2- mediated signaling. Mol Cell Biol. Jan. 2001;21(1):26-38.
Tugyi, et al. The effect of cyclization on the enzymatic degradation of herpes simplex virus glycoprotein D derived epitope peptide. J Pept Sci. Oct. 2005;11(10):642-9.
Turner et al., "Mitsunobu Glycosylation of Nitrobenzenesulfonamides: Novel Route to Amadori Rearrangement Products," Tetrahedron Lett. 40:7039-7042 (1999).
Tyndall et al. Macrocycles mimic the extended peptide conformation recognized by aspartic, serine, cysteine and metallo proteases. Curr Med Chem. Jul. 2001;8(8):893-907.
Tyndall, et al. Over one hundred peptide-activated G protein-coupled receptors recognize ligands with turn structure. Chem Rev. Mar. 2005;105(3):793-826.
Tyndall, et al., "Proteases Universally Recognize Beta Strands in Their Active Sites," Chem. Rev. 105:973-999 (2005).
Ueki, et al. Improved synthesis of proline-derived Ni(II) complexes of glycine: versatile chiral equivalents of nucleophilic glycine for general asymmetric synthesis of alpha-amino acids. J Org Chem. Sep. 5, 2003;68(18):7104-7.
Ueki et al., Increased insulin sensitivity in mice lacking p85beta subunit of phosphoinositide 3-kinase. Proc Natl Acad Sci USA. Jan. 8, 2002;99(1):419-24. Epub Dec. 18, 2001.
Ueki et al., Positive and negative regulation of phosphoinositide 3-kinase-dependent signaling pathways by three different gene products of the p85alpha regulatory subunit. Mol Cell Biol. Nov. 2000;20(21):8035-46.
Uesugi et al., The alpha-helical FXXPhiPhi motif in p53: TAF interaction and discrimination by MDM2. Proc Natl Acad Sci USA. Dec. 21, 1999;96(26):14801-6.
Ullman et al., Luminescent oxygen channeling immunoassay: measurement of particle binding kinetics by chemiluminescence. Proc Natl Acad Sci USA. Jun. 7, 1994;91(12):5426-30.
Vaickus et al., Immune markers in hematologic malignancies. Crit Rev Oncol Hematol. Dec. 1991; 11(4):267-97.
Van Genderen et al., Development of several organs that require inductive epithelial-mesenchymal interactions is impaired in LEF-1-deficient mice. Genes Dev. Nov. 15, 1994;8(22):2691-703.
Van Gijn et al., The wnt-frizzled cascade in cardiovascular disease. Cardiovasc Res. Jul. 2002;55(1):16-24.
Van Hoof, et al. Identification of cell surface proteins for antibody-based selection of human embryonic stem cell-derived cardiomyocytes. J Proteome Res. Mar. 5, 2010;9(3):1610-8. doi: 10.1021/pr901138a.
Van Maarseveen, et al. Efficient route to C2 symmetric heterocyclic backbone modified cyclic peptides. Org Lett. Sep. 29, 2005;7(20):4503-6.
Varallo et al., Beta-catenin expression in Dupuytren's disease: potential role for cell-matrix interactions in modulating beta-catenin levels in vivo and in vitro. Oncogene. Jun. 12, 2003;22(24):3680-4.
Vartak et al., Allosteric Modulation of the Dopamine Receptor by Conformationally Constrained Type VI (3-Turn Peptidomimetics of Pro-Leu-Gly-NH2. J Med Chem. 2007;50(26):6725-6729.
Vassilev, et al. In Vivo Activation of the p53 Pathway by Small-molecule Antagonists of MDM2. Science. 2004; 303:844-848.
Venancio et al., Reconstructing the ubiquitin network: cross-talk with other systems and identification of novel functions. Genome Biol. 2009;10(3):R33. Epub Mar. 30, 2009.
Verdine et al., Stapled peptides for intracellular drug targets. Methods Enzymol. 2012;503:3-33. doi: 10.1016/B978-0-12-396962-0.00001-X.
Verdine et al., The challenge of drugging undruggable targets in cancer: lessons learned from targeting BCL-2 family members. Clin Cancer Res. Dec. 15, 2007;13(24):7264-70.

Verma et al., Small interfering RNAs directed against beta-catenin inhibit the in vitro and in vivo growth of colon cancer cells. Clin Cancer Res. Apr. 2003;9(4):1291-300.
Viallet, et al. Tallimustine is inactive in patients with previously treated small cell lung cancer. A phase II trial of the National Cancer Institute of Canada Clinical Trials Group. Lung Cancer. Nov. 1996;15(3):367-73.
Vila-Perello, et al. A minimalist design approach to antimicrobial agents based on a thionin template. J Med Chem. Jan. 26, 2006;49(2):448-51.
Voet D, Voet JG, Biochemistry, Second Edition, John Wiley & Sons, Inc., 1995, pp. 235-241.
Walensky, et al. A stapled Bid BH3 helix directly binds and activates BAX. Mol. Cell. Oct. 20, 2006;24(2):199-210.
Walensky, et al. Activation of apoptosis in vivo by a hydrocarbon-stapled BH3 helix. Science. Sep. 3, 2004;305(5689):1466-70.
Walker, et al. General method for the synthesis of cyclic peptidomimetic compounds. Tetrahedron Letters. 2001; 42(34):5801-5804.
Walter et al., Critical role for IL-13 in the development of allergen-induced airway hyperreactivity. J Immunol. Oct. 15, 2001;167(8):4668-75.
Wang, 4-Alkyl-2-trichloromethyloxazolidin-5-ones: Valuable Precursors to Enantiomerically Pure C- and N-Protected a-Alkyl Prolines. Synlett. 1999;1:33-36.
Wang, et al. Bid: a novel BH3 domain-only death agonist. Genes Dev. Nov. 15, 1996;10(22):2859-69.
Wang et al. Cell permeable Bcl-2 binding peptides: a chemical approach to apoptosis induction in tumor cells. Cancer Res. Mar. 15, 2000;60(6):1498-502.
Wang, et al. "Click" synthesis of small molecule probes for activity-based fingerprinting of matrix metalloproteases. Chem Commun (Camb). Sep. 28, 2006;(36):3783-5.
Wang et al. Enhanced metabolic stability and protein-binding properties of artificial alpha helices derived from a hydrogen-bond surrogate: application to Bcl-xL. Angew Chem Int Ed Engl. Oct. 14, 2005;44(40):6525-9.
Wang, et al. Evaluation of biologically relevant short alpha-helices stabilized by a main-chain hydrogen-bond surrogate. J Am Chem Soc. Jul. 19, 2006;128(28):9248-56.
Wang, et al. Inhibition of HIV-1 fusion 1-15 by hydrogen-bond-surrogate-based alpha helices. Angewandte Chemie International Edition. 2008; 47(10):1879-1882.
Wang et al. Inhibition of p53 degradation by Mdm2 acetylation. Febs Lett. Mar. 12, 2004;561(1-3):195-201.
Wang, et al. Nucleation and stability of hydrogen-bond surrogate-based alpha-helices. Org Biomol Chem. Nov. 21, 2006;4(22):4074-81.
Wang et al., "Recognition of a Protein Receptor with the Hydrogen Bond Surrogate-based Artificial Alpha-helices," American Chemical Society Meeting, San Diego (Mar. 2005) (poster).
Wang et al., "Recognition of a Protein Receptor with the Hydrogen Bond Surrogate-based Artificial Alpha-helices," Chemical Biology Symposium, Hunter College (Jan. 2005) (poster).
Weaver et al.,Transition metal-catalyzed decarboxylative allylation and benzylation reactions.Chemical Rev. Mar. 9, 2011;111(3):1846-913.
Website: http://www.onelook.com/?w=span&ls=a&loc=home_ac_span, 1 page, Retrieved on Jan. 23, 2016.
Wei et al., Disorder and structure in the Rab11 binding domain of Rab11 family interacting protein 2. Biochemistry. Jan. 27, 2009;48(3):549-57. doi: 10.1021/bi8020197.
Wei, et al. tBID, a membrane-targeted death ligand, oligomerizes BAK to release cytochrome c. Genes Dev. Aug. 15, 2000;14(16):2060-71.
Wels, et al. Synthesis of a novel potent cyclic peptide MC4-ligand by ring-closing metathesis. Bioorg. Med. Chem. Lett. 2005; 13: 4221-4227.
Weng et al., Activating mutations of NOTCH1 in human T cell acute lymphoblastic leukemia. Science. Oct. 8, 2004;306(5694):269-71.
Weng et al., Growth suppression of pre-T acute lymphoblastic leukemia cells by inhibition of notch signaling. Mol Cell Biol. Jan. 2003;23(2):655-64.

(56) References Cited

OTHER PUBLICATIONS

Wenninger, et al. International Cosmetic Ingredient Dictionary and Handbook. vol. 2, 7th Edition, 1997, published by The Cosmetic, Toiletry, and Fragrance Association.
Westhoff et al., Alterations of the Notch pathway in lung cancer. Proc Natl Acad Sci USA. Dec. 29, 2009;106(52):22293-8. doi: 10.1073/pnas.0907781106. Epub Dec. 10, 2009.
Wikipedia The Free Encyclopedia. Willgerodt Rearrangement. Available at https://en.wikipedia.org/wiki/Willgerodt_rearrangement. Accessed on Feb. 12, 2013.
Wild et al., "Peptides Corresponding to a Predictive α-Helical Domain of Human Immunodeficiency Virus Type 1 gp41 are Potent Inhibitors of Virus Infection," Proc. Nat'l Acad. Sci. USA 91:9770-9774 (1994).
Wilen et al., Strategies in Optical Resolution. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Williams and Im. Asymmetric Synthesis of Nonsubstituted and α,α-Disubstituted α-Amino Acids via Disatereoselective Glycine Enolate Alkylations. JACS. 1991;113:9276-9286.
Williams et al., Asymmetric synthesis of 2,6-diamino-6-(hydroxymethyl)pimelic acid: assignment of stereochemistry. J Am Chem Soc. 1991;113(18):6976-6981.
Wills-Karp et al., Interleukin-13: central mediator of allergic asthma. Science. Dec. 18, 1998;282(5397):2258-61.
Wills-Karp, Interleukin-13 in asthma pathogenesis. Immunol Rev. Dec. 2004;202:175-90.
Wills-Karp, The gene encoding interleukin-13: a susceptibility locus for asthma and related traits. Respir Res. 2000;1(1):19-23. Epub Jul. 17, 2000.
Wilson et al., Crystal structure of the CSL-Notch-Mastermind ternary complex bound to DNA. Cell. Mar. 10, 2006;124(5):985-96.
Wilson et al., The FIP3-Rabll protein complex regulates recycling endosome targeting to the cleavage furrow during late cytokinesis. Mol Biol Cell. Feb. 2005;16(2):849-60. Epub Dec. 15, 2004.
Wu et al., MAML1, a human homologue of Drosophila mastermind, is a transcriptional co-activator for NOTCH receptors. Nat Genet. Dec. 2000;26(4):484-9.
Wu, et al. Regiospecific Synthesis of 1,4,5-Trisubstituted-1,2,3-triazole via One-Pot Reaction Promoted by Copper(I) Salt. Synthesis. 2005(8): 1314-1318.
Wu, et al. Studies on New Strategies for the Synthesis of Oligomeric 1,2,3-Triazoles. Synlett 2006(4): 0645-0647.
Wu et al., Therapeutic antibody targeting of individual Notch receptors. Nature. Apr. 15, 2010;464(7291):1052-7. doi: 10.1038/nature08878.
Xi et al., Use of DNA and peptide nucleic acid molecular beacons for detection and quantification of rRNA in solution and in whole cells. Appl Environ Microbiol. Sep. 2003;69(9):5673-8.
Xing, et al. Crystal structure of a beta-catenin/axin complex suggests a mechanism for the beta-'catenin destruction complex. Genes Dev. Nov. 15, 2003;17(22):2753-64. Epub Nov. 4, 2003.

Yang, et al. Calculation of protein conformation from circular dichroism. Methods Enzymol. 1986;130:208-69.
Yang et al. Synthesis and helical structure of lactam bridged BH3 peptides derived from pro-apoptotic Bcl-2 family proteins. Bioorg Med Chem Lett. Mar. 22, 2004;14(6):1403-6.
Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.
Ye et al., Neurogenic phenotypes and altered Notch processing in Drosophila Presenilin mutants. Nature. Apr. 8, 199;398(6727):525-9.
Yin et al., "Terphenyl-based Helical Mimetics That Disrupt the p53/HDM2 Interaction," Angew. Chem. Int. Ed. 44:2704-2707 (2005).
Yu, et al. Synthesis of macrocyclic natural products by catalyst-controlled stereoselective ring-closing metathesis. Nature. Nov. 2, 2011;479(7371):88-93. doi: 10.1038/nature10563.
Yu et al., The role of Axin2 in calvarial morphogenesis and craniosynostosis. Development. Apr. 2005; 132(8): 1995-2005.
Zamzami et al. The thiol crosslinking agent diamide overcomes the apoptosis-inhibitory effect of Bcl-2 by enforcing mitochondrial permeability transition. Oncogene. Feb. 26, 1998;16(8):1055-63.
Zhang, et al. 310 Helix versus alpha-helix: a molecular dynamics study of conformational preferences of Aib and Alanine. J. American Cancer Society. Dec. 1994; 116(26):11915-11921.
Zhang et al., A cell-penetrating helical peptide as a potential HIV-1 inhibitor. J Mol Biol. May 2, 2008;378(3):565-80. doi: 10.1016/j jmb.2008.02.066. Epub Mar. 6, 2008.
Zhang, et al. A triazole-templated ring-closing metathesis for constructing novel fused and bridged triazoles. Chem Commun (Camb). Jun. 21, 2007;(23):2420-2.
Zhang, et al. Development of a High-throughput Fluorescence Polarization Assay for Bcl-xL. Anal. Biochem. 2002; 307:70-75.
Zhang, et al. Ruthenium-catalyzed cycloaddition of alkynes and organic azides. J Am Chem Soc. Nov. 23, 2005;127(46):15998-9.
Zhou, et al. Identification of ubiquitin target proteins using cell-based arrays. J Proteome Res. 2007; 6:4397-4406.
Zhou et al., Lymphoid enhancer factor 1 directs hair follicle patterning and epithelial cell fate. Genes Dev. Mar. 15, 1995;9(6):700-13.
Zhou et aL, Tyrosine kinase inhibitor STI-571/Gleevec downregulates the beta-catenin signaling activity. Cancer Lett. Apr. 25, 2003;193(2):161-70.
Zimm & Bragg, "Theory of the Phase Transition between Helix and Random Coil in Polypeptide Chains," J. Chem. Phys. 31(2):526-535 (1959).
Zitzow, et al. Pathogenesis of avian influenza A (H5N1) viruses in ferrets. J Virol. May 2002;76(9):4420-9.
Zor et aL, Solution structure of the KIX domain of CBP bound to the transactivation domain of c-Myb. J Mol Biol. Mar. 26, 2004;337(3):521-34.
Notice of allowance dated Jul. 19, 2015 for U.S. Appl. No. 14/068,844.

* cited by examiner

Figure 3

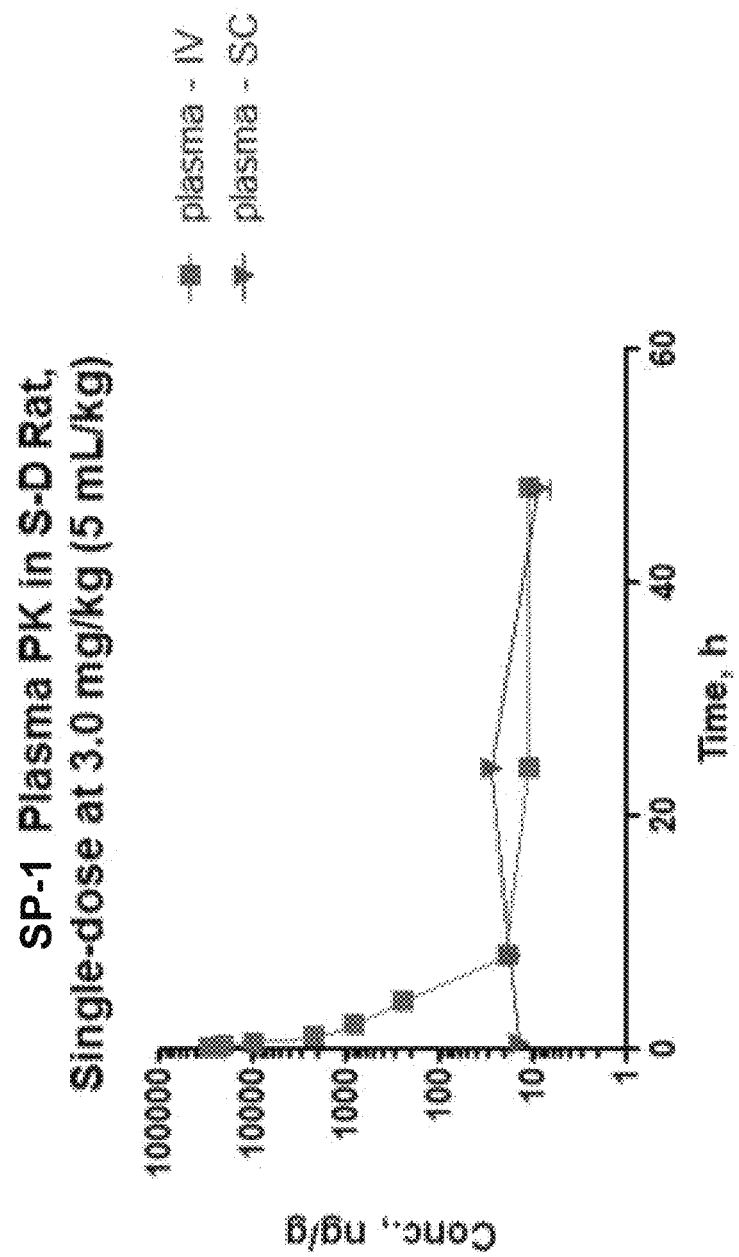

Figure 9

| Compound | AUClnf hr*ng/mL | AUCExt(%) % | t1/2 hr | MRT hr | Vdss mL/kg | CP mL/hr/kg |
|---|---|---|---|---|---|---|
| SP-1 | 17329 | 13.8 | 55.1 | 1.6 | 267 | 171 |
| SP-6 | 23477 | 16.3 | 20.6 | 3.7 | 474 | 128 |
| SP-8 | 12575 | 4.8 | 10.2 | 1.6 | 390 | 239 |
| SP-21 | 30455 | 9.4 | 10.1 | 5.3 | 524 | 99 |
| SP-32 | 36963 | 3.0 | 9.7 | 2.3 | 190 | 81 |
| Tesamorelin, dog 0.1 μg/kg IV** | 5301 | | 0.4 | | | |
| Tesamorelin, human 0.5, 1, or 2 mg SC** | | | 2-5h | | | |
| ** literature values | | | | | | |

PEPTIDOMIMETIC MACROCYCLES

CROSS-REFERENCE TO RELATED APPLICATIONS

This application is a continuation of U.S. Non-Provisional application Ser. No. 13/655,378 filed Oct. 18, 2012 which application claims the priority benefit of U.S. Provisional Application Ser. No. 61/548,690, filed on Oct. 18, 2011, the content of each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jan. 8, 2016, is named 35224-769 301 SL.txt and is 225,340 bytes in size.

BACKGROUND OF THE INVENTION

Human GHRH (Growth Hormone-Releasing Hormone) is a 44-amino-acid peptide whose full biological activity resides in its first 29 amino acids ("GHRH 1-29"). GHRH binds to the GHRH receptor and stimulates pulsatile GH [Growth Hormone] secretion, and with this mechanism of action GHRH represents an alternative to GH therapy in patients with an intact pituitary that may minimize the side effects associated with long-term GH administration. Because the quantity of GH release induced by GHRH is limited by IGF-1 levels, which exert a negative feedback effect, the risk of side effects associated with excessive GH secretion may also be lower with GHRH therapy than with GH therapy. In addition, treatment with GHRH may result in the pituitary secretion of a broader set of GH proteins, and not just the 22-kDa form provided by recombinant human GH, which may also have beneficial effects. Clinically, GHRH has been shown to be safe and effective in increasing GH levels in adults and children, and the growth-promoting effect of GHRH is correlated with the dose and frequency of administration. However, the half-life of GHRH after intravenous injection is only 10-12 min, which has significantly limited its use as a therapeutic agent. Thus there is a clinical need for analogs of GHRH that possess extended half-life in vivo that could provide greater therapeutic benefit with an improved (less frequent) dosing regimen.

SUMMARY OF THE INVENTION

The present invention provides GHRH-derived peptidomimetic macrocycles that are designed to possess improved pharmaceutical properties relative to GHRH. These improved properties include enhanced chemical stability, extended in vivo half-life, increased potency and reduced immunogenicity. These peptidomimetic macrocycles are useful to increase circulating levels of GH as a treatment for muscle wasting diseases, lipodystrophies, growth hormone disorders, gastroparesis/short bowel syndrome, and other conditions for which an increase in GH would provide therapeutic benefit.

Described below are stably cross-linked peptides derived from the GHRH peptide. These cross-linked peptides contain at least two modified amino acids that together form an intramolecular cross-link that can help to stabilize the alpha-helical secondary structures of a portion of GHRH that is thought to be important for agonist activity at the GHRH receptor. Relative to the amino acid sequence of the wild-type peptide, any amino acid which is not essential to the growth-hormone releasing activity of the peptide may be replaced with any other amino acids, while amino acids which are essential to the growth-hormone releasing activity of the peptide may be replaced only with amino acid analogs which do not substantially decrease said activity.

Accordingly, a cross-linked polypeptide described herein can have improved biological activity relative to a corresponding polypeptide that is not cross-linked Without being bound by theory, the GHRH peptidomimetic macrocycles are thought to activate the GHRH receptor, thereby stimulating production and release of growth hormone, which can increase lean muscle mass or reduce adipose tissue (such as abdominal adipose tissue). For example, adipose tissue can be reduced in subjects suffering from obesity, including abdominal obesity. The GHRH peptidomimetic macrocycles described herein can be used therapeutically, for example, to treat muscle wasting diseases that include anorexias, cachexias (such as cancer cachexia, chronic heart failure cachexia, chronic obstructive pulmonary disease cachexia, rheumatoid arthritis cachexia) and sarcopenias, to treat lipodystrophies that include HIV lipodystrophy, to treat growth hormone disorders that include adult and pediatric growth hormone deficiencies, or to treat gastroparesis or short bowel syndrome. Pediatric growth hormone deficiency may be, for example, linked with or associated to idiopathic short stature, SGA (infant small for gestational age), chronic kidney disease, Prader-Willi syndrome Turner syndrome, short stature homeobox (SHOX) gene deficiency, or primary IGF-1 deficiency.

In one aspect, the present invention provides a peptidomimetic macrocycle comprising an amino acid sequence which is at least about 60%, 65%, 70%, 75%, 80%, 85%, 90%, 95%, 96%, 97%, 98%, or 99% identical to GHRH 1-44, GHRH 1-29 and/or to an amino acid sequence chosen from the group consisting of the amino acid sequences in Table 1, 2 or 4. Alternatively, an amino acid sequence of said peptidomimetic macrocycle is chosen from the group consisting of the amino acid sequences in Table 1, 2 or 4. The peptidomimetic macrocycle may comprise one, two, three, four, five or more macrocycle-forming linkers, wherein each macrocycle-forming linker connects one amino acid to another amino acid within the peptidomimetic macrocycle. For example, a peptidomimetic macrocycle comprises at least two macrocycle-forming linkers wherein the first of said at least two macrocycle-forming linkers connects a first amino acid to a second amino acid, and the second of said at least two macrocycle-forming linkers connects a third amino acid to a fourth amino acid. In some embodiments, the peptidomimetic macrocycle comprises exactly two macrocycle-forming linkers. In other embodiments, the peptidomimetic macrocycle comprises exactly one macrocycle-forming linker.

Macrocycle-forming linkers connect any two amino acids which can be crosslinked without impairing the activity of the peptidomimetic macrocycle. In some embodiments, a macrocycle-forming linker connects one of the following pairs of amino acids (numbered with reference to any sequences aligned to GHRH 1-29): 4 and 8; 5 and 12; 8 and 12; 8 and 15; 9 and 16; 12 and 16; 12 and 19; 15 and 22; 18 and 25; 21 and 25; 21 and 28; 22 and 29; 25 and 29. For example, a macrocycle-forming linkers connects of the following pairs of amino acids: 4 and 8; 5 and 12; 12 and 19;

15 and 22; 18 and 25; 21 and 25; 21 and 28. In some embodiments, a first macrocycle-forming linker connects amino acid pairs 4 and 8; 5 and 12; 8 and 12; 8 and 15; 9 and 16; 12 and 16; or 12 and 19; and a second macrocycle-forming linker connects amino acid pairs 15 and 22; 18 and 25; 21 and 25; 21 and 28; 22 and 29; or 25 and 29. For example, the first macrocycle-forming linker connects amino acid pairs 4 and 8; 5 and 12; or 12 and 19; and the second macrocycle-forming linker connects amino acid pairs 15 and 22; 18 and 25; 21 and 25; or 21 and 28. In some embodiments, the first macrocycle-forming linker connects amino acid pairs 4 and 8 and the second macrocycle-forming linker connects amino acid pairs 21 and 25.

In some embodiments, a peptidomimetic macrocycle comprises an amino acid sequence which is at least about 60%, 65%, 70%, 75%, 80%, 85%, 90%, 95%, 96%, 97%, 98%, or 99% identical to GHRH 1-44, GHRH 1-29 and/or to an amino acid sequence chosen from the group consisting of the amino acid sequences in Table 1, 2 or 4, and further comprises a macrocycle-forming linker connecting a first amino acid to a second amino acid, wherein the first and second amino acids are selected from the following pairs of amino acids: 4 and 8; 5 and 12; 8 and 12; 8 and 15; 9 and 16; 12 and 16; 12 and 19; 15 and 22; 18 and 25; 21 and 25; 21 and 28; 22 and 29. For example, the macrocycle-forming linker connects amino acids 12 and 19.

In some embodiments, a peptidomimetic macrocycle comprises a sequence chosen from the group consisting of the amino acid sequences in Tables 1, 2 or 4, or the amino acid sequence of the peptidomimetic macrocycle is chosen from the group consisting of the amino acid sequences in Tables 1, 2 or 4.

In some embodiments, the peptidomimetic macrocycle comprises a helix, such as an α-helix or a $3_{10}$ helix. In other embodiments, the peptidomimetic macrocycle comprises an α,α-disubstituted amino acid. For example, at least one amino acid, or each amino acid, connected by the macrocycle-forming linker is an α,α-disubstituted amino acid.

In some embodiments, a peptidomimetic macrocycle of the invention comprises a crosslinker linking the α-positions of at least two amino acids.

In some embodiments, the peptidomimetic macrocycle has the formula:

Formula (I)

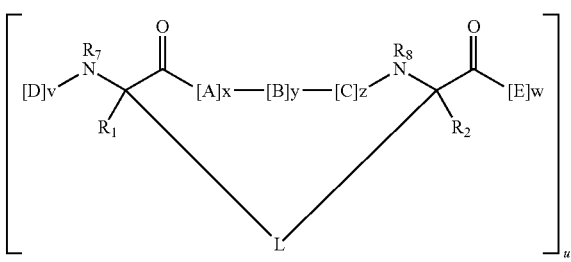

wherein:
each A, C, D, and E is independently an amino acid;
B is an amino acid,

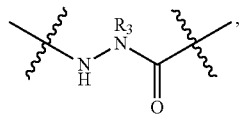

[—NH-$L_3$-CO—], [—NH-$L_3$-$SO_2$—], or [—NH-$L_3$-]; $R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

L is a macrocycle-forming linker of the formula -$L_1$-$L_2$-;

and wherein A, B, C, D, and E, taken together with the crosslinked amino acids connected by the macrocycle-forming linker L, form the amino acid sequence of the peptidomimetic macrocycle which is at least about 60%, 65%, 70%, 75%, 80%, 85%, 90%, 95%, 96%, 97%, 98%, or 99% identical to GHRH 1-44, GHRH 1-29 and/or to an amino acid sequence chosen from the group consisting of the amino acid sequences in Table 1, 2 or 4;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

v and w are independently integers from 1-1000, for example 1-500, 1-200, 1-100, 1-50, 1-40, 1-25, 1-20, 1 to 15, or 1 to 10;

u, x, y and z are independently integers from 0-10, for example u is 1, 2, or 3; and n is an integer from 1-5. For example, u is 2. In some embodiments, the sum of x+y+z is 2, 3 or 6, for example 3 or 6.

In some embodiments, the peptidomimetic macrocycle of Formula (I) has the Formula:

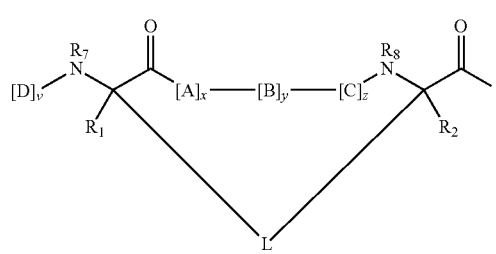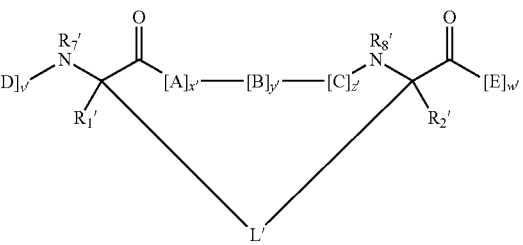

wherein each A, C, D, and E is independently an amino acid;

B is an amino acid,

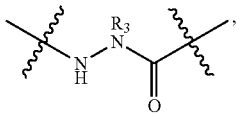

[—NH-L₃-CO—], [—NH-L₃-SO₂—], or [—NH-L₃-]; L' is a macrocycle-forming linker of the formula -L₁'-L₂'-;

and wherein A, B, C, D, and E, taken together with the crosslinked amino acids connected by the macrocycle-forming linkers L and L', form the amino acid sequence of the peptidomimetic macrocycle;

$R_1'$ and $R_2'$ are independently —H, alkyl, alkenyl, alkynyl, arylalkyl, cycloalkyl, cycloalkylalkyl, heteroalkyl, or heterocycloalkyl, unsubstituted or substituted with halo-;

$L_1'$ and $L_2'$ are independently alkylene, alkenylene, alkynylene, heteroalkylene, cycloalkylene, heterocycloalkylene, cycloarylene, heterocycloarylene, or $[-R_4-K-R_4-]_n$, each being optionally substituted with $R_5$;

each K is independently O, S, SO, SO₂, CO, CO₂, or CONR₃;

$R_7'$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

$R_8'$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

v' and w' are independently integers from 1-1000, for example 1-500, 1-200, 1-100, 1-50, 1-40, 1-25, 1-20, 1 to 15, or 1 to 10;

x', y' and z' are independently integers from 0-10; and n is an integer from 1-5. In some embodiments, the sum of x'+y'+z' is 2, 3 or 6, for example 3 or 6.

In some embodiments of any of the peptidomimetic macrocycles described herein, each K is O, S, SO, SO₂, CO, or CO₂.

In other embodiments, the peptidomimetic macrocycle may comprise a crosslinker linking a backbone amino group of a first amino acid to a second amino acid within the peptidomimetic macrocycle. For example, the invention provides peptidomimetic macrocycles of the Formula (II) or (IIa):

Formula (II)

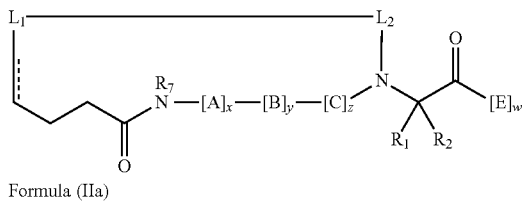

Formula (IIa)

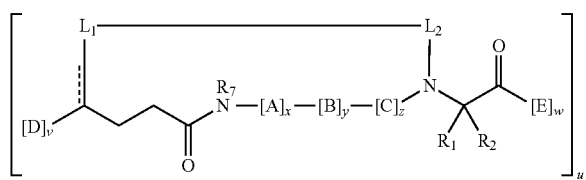

wherein:
each A, C, D, and E is independently an amino acid;
B is an amino acid,

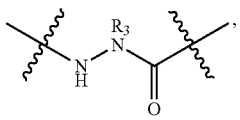

[—NH-L₃-CO—], [—NH-L₃-SO₂—], or [—NH-L₃-]; $R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

$L_1$ and $L_2$ are independently alkylene, alkenylene, alkynylene, heteroalkylene, cycloalkylene, heterocycloalkylene, cycloarylene, heterocycloarylene, or $[-R_4-K-R_4-]_n$, each being optionally substituted with $R_5$;

and wherein A, B, C, D, and E, taken together with the crosslinked amino acids connected by the macrocycle-forming linker -L₁-L₂-, form the amino acid sequence of the peptidomimetic macrocycle which is at least about 60%, 65%, 70%, 75%, 80%, 85%, 90%, 95%, 96%, 97%, 98%, or 99% identical to GHRH 1-44, GHRH 1-29 and/or to an amino acid sequence chosen from the group consisting of the amino acid sequences in Table 1, 2 or 4;

each $R_4$ is alkylene, alkenylene, alkynylene, heteroalkylene, cycloalkylene, heterocycloalkylene, arylene, or heteroarylene;

each K is O, S, SO, SO₂, CO, CO₂, or CONR₃;

each $R_5$ is independently halogen, alkyl, —OR₆, —N(R₆)₂, —SR₆, —SOR₆, —SO₂R₆, —CO₂R₆, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$;

v and w are independently integers from 1-1000, for example 1-500, 1-200, 1-100, 1-50, 1-40, 1-25, 1-20, 1 to 15, or 1 to 10;

u, x, y and z are independently integers from 0-10, for example u is 1-3; and n is an integer from 1-5.

Also provided herein is a peptidomimetic macrocycle comprising an amino acid sequence of Formula:

X1-X2-X3-X4-X5-X6-X7-X8-X9-X10-X11-X12-
X13-X14-X15-X16-X17-X18-X19-X20-X21-
X22-X23-X24-X25-X26-X27-X28-X29    (SEQ ID NO: 1)

wherein:
X1 is Tyr or His;
X2 is Ala, D-Ala, or Val;
X3 is Asp;
X4 is Ala or a crosslinked amino acid;
X5 is Ile;
X6 is Phe;
X7 is Thr;
X8 is Gln, Asn, or a crosslinked amino acid;
X9 is Ser or a crosslinked amino acid;
X10 is Tyr;
X11 is Arg, Ala or Gln;

X12 is Lys, Ala, Gln or a crosslinked amino acid;
X13 is Val or Ile;
X14 is Leu;
X15 is Gly, Ala or a crosslinked amino acid;
X16 is Gln, Glu or a crosslinked amino acid;
X17 is Leu;
X18 is Ser, Tyr or a crosslinked amino acid;
X19 is Ala or a crosslinked amino acid;
X20 is Arg or Gln;
X21 is Lys, Gln or a crosslinked amino acid;
X22 is Leu, Ala, or a crosslinked amino acid;
X23 is Leu;
X24 is Gln, Glu or His;
X25 is Asp, Glu or a crosslinked amino acid;
X26 is Ile;
X27 is Met, Ile, Leu or Nle;
X28 is Ser or a crosslinked amino acid;
X29 is Arg, Ala, Gln or a crosslinked amino acid;
wherein the peptidomimetic macrocycle comprises at least one macrocycle-forming linker connecting at least one pair of amino acids selected from X1-X29;

L is a macrocycle-forming linker of the formula $-L_1-L_2-$;

$L_1$ and $L_2$ are independently alkylene, alkenylene, alkynylene, heteroalkylene, cycloalkylene, heterocycloalkylene, cycloarylene, heterocycloarylene, or $[-R_4-K-R_4-]_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, or $CO_2$;

each $R_5$ is independently halogen, alkyl, $-OR_6$, $-N(R_6)_2$, $-SR_6$, $-SOR_6$, $-SO_2R_6$, $-CO_2R_6$, a fluorescent moiety, a radioisotope or a therapeutic agent; and each $R_6$ is independently —H, alkyl, alkenyl, alkynyl, arylalkyl, cycloalkylalkyl, heterocycloalkyl, a fluorescent moiety, a radioisotope or a therapeutic agent.

For example, the polypeptide comprises at least one, or at least two, macrocycle-forming linkers which connect one of the following pairs of amino acids: X4 and X8; X5 and X12; X8 and X12; X8 and X15; X9 and X16; X12 and X16; X12 and X19; X15 and X22; X18 and X25; X21 and X25; X21 and X28; X22 and X29; X25 and X29. For example, each macrocycle-forming linker connects one of the following pairs of amino acids: X4 and X8; X5 and X12; X12 and X19; X15 and X22; X18 and X25; X21 and X25; X21 and X28.

In some embodiments, peptidomimetic macrocycles comprise a macrocycle-forming linker of Formula $-L_1-L_2-$, wherein $L_1$ and $L_2$ are independently alkylene, alkenylene or alkynylene. For example, $L_1$ and $L_2$ are independently $C_3-C_{10}$ alkylene or alkenylene, or $C_3-C_6$ alkylene or alkenylene.

In some embodiments, $R_1$ and $R_2$ are independently H or alkyl, for example methyl.

Additionally, the invention provides a method of increasing the circulating level of growth hormone (GH) in a subject, a method of increasing lean muscle mass in a subject, and a method of reducing adipose tissue (such as abdominal adipose tissue) in a subject comprising administering to the subject a peptidomimetic macrocycle of the invention. For example, subjects suffering from obesity, including abdominal obesity, are treated using a peptidomimetic macrocycle of the invention. The invention also provides a method of treating muscle wasting diseases that include anorexias, cachexias (such as cancer cachexia, chronic heart failure cachexia, chronic obstructive pulmonary disease cachexia, rheumatoid arthritis cachexia) and sarcopenias, a method of treating lipodystrophies that include HIV lipodystrophy, a method of treating growth hormone disorders that include adult and pediatric growth hormone deficiencies, or a method of treating gastroparesis or short bowel syndrome. Pediatric growth hormone deficiency may be, for example, linked with or associated to idiopathic short stature, SGA (infant small for gestational age), chronic kidney disease, Prader-Willi syndrome Turner syndrome, short stature homeobox (SHOX) gene deficiency, or primary IGF-1 deficiency. The invention also provides a method of treating muscle wasting diseases, lipodystrophies, growth hormone disorders or gastroparesis/short bowel syndrome in a subject by administering an agonist of the GHRH receptor, such as an analog of GHRH, wherein the agonist is administered no more frequently than once daily, no more frequently than every other day, no more frequently than twice weekly, no more frequently than weekly, or no more frequently than every other week. The invention also provides a method of increasing the circulating level of growth hormone (GH) in a subject by administering an agonist of the GHRH receptor, such as an analog of GHRH, wherein the agonist is administered no more frequently than once daily, no more frequently than every other day, no more frequently than twice weekly, no more frequently than weekly, or no more frequently than every other week.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3 and 3a show GHRH receptor agonist activities measured by cAMP release and trypsin half-lives of the peptidomimetic macrocycles of the invention. For cAMP values, "+" represents values greater than 50 nM; "++" represents values between 10-50 nM; "+++" represents values between 1-10 nM; "++++" represents values lower than 1 nM. For trypsin half-lives, "+" represents values lower than 50 min.; "++" represents values between 50-100 min.; "+++" represents values between 100-200 min.; "++++" represents values greater than 200 min.; and "NT" signifies "not tested". FIG. 3 discloses SEQ ID NOS 89-131, respectively, in order of appearance. FIG. 3a discloses SEQ ID NOS 132-137, respectively, in order of appearance.

FIG. 4 shows the result of a plasma PK study performed with peptidomimetic macrocycle SP-1.

FIG. 9 shows the result of a plasma PK study performed with peptidomimetic macrocycles SP-1, SP-6, SP-8, SP-21, and SP-32.

DETAILED DESCRIPTION OF THE INVENTION

Figure 1A:
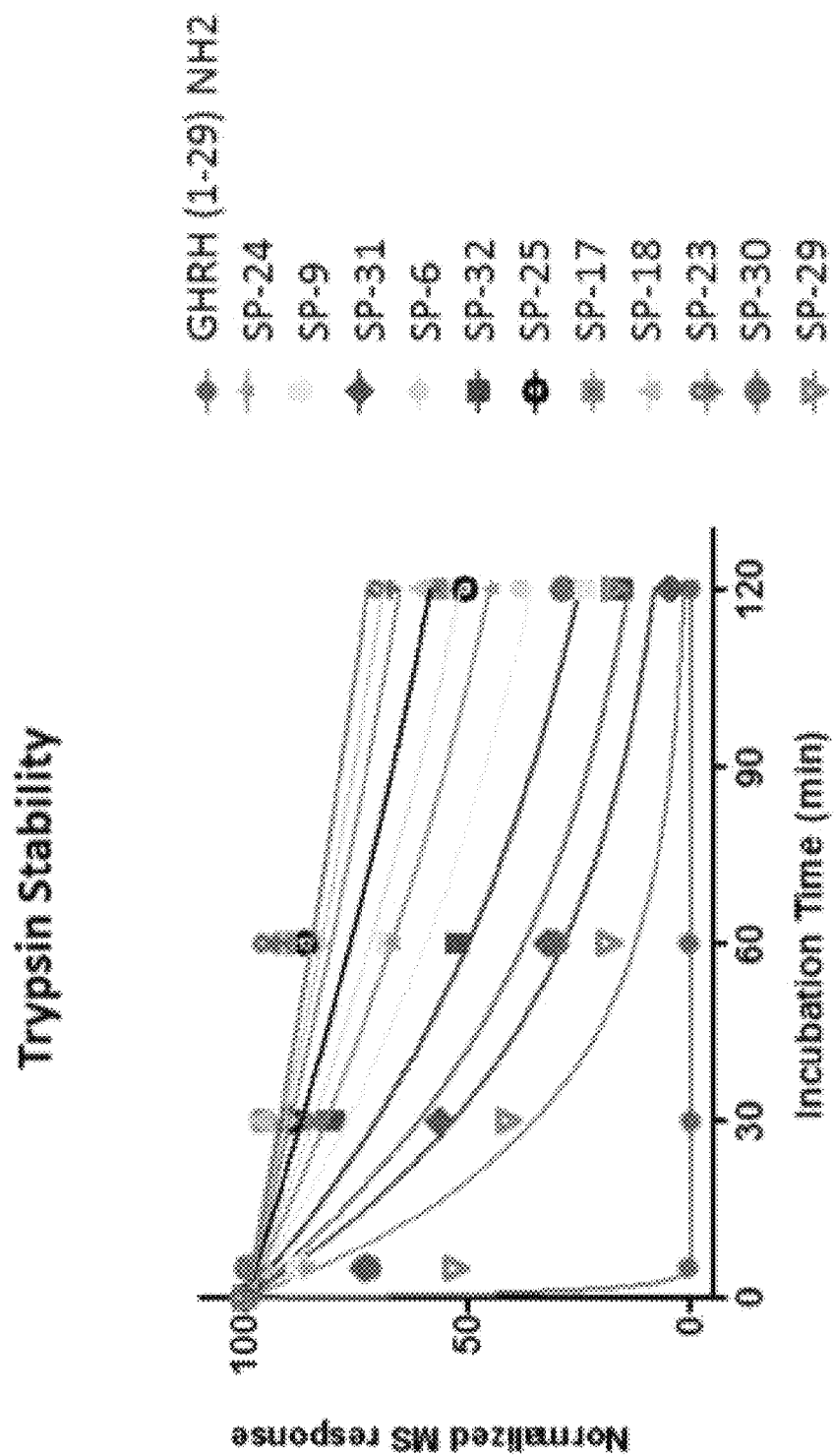
FIGS. 1A and 1B show improved stabilities to trypsin proteolysis of the peptidomimetic macrocycles of the invention.

As used herein, the term "macrocycle" refers to a molecule having a chemical structure including a ring or cycle formed by at least 9 covalently bonded atoms.

As used herein, the term "peptidomimetic macrocycle" or "crosslinked polypeptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycle include embodiments where the macrocycle-forming linker connects the α carbon of the first amino acid residue (or analog) to the α carbon of the second amino acid residue (or analog). The peptidomimetic macrocycles optionally include one or more non-peptide bonds between one or more amino acid residues and/or amino acid analog residues, and optionally include one or more non-naturally-occurring amino acid residues or amino acid analog residues in addition to any which form the macrocycle. A "corresponding uncrosslinked polypeptide" when referred to in the context of a peptidomimetic macrocycle is understood to relate to a polypeptide of the same length as the macrocycle and comprising the equivalent natural amino acids of the wild-type sequence corresponding to the macrocycle.

As used herein, the term "stability" refers to the maintenance of a defined secondary structure in solution by a peptidomimetic macrocycle of the invention as measured by circular dichroism, NMR or another biophysical measure, or resistance to proteolytic degradation in vitro or in vivo. Non-limiting examples of secondary structures contemplated in this invention are α-helices, $3_{10}$ helices, β-turns, and β-pleated sheets.

As used herein, the term "helical stability" refers to the maintenance of a helical structure by a peptidomimetic macrocycle of the invention as measured by circular dichroism or NMR. For example, in some embodiments, the peptidomimetic macrocycles of the invention exhibit at least a 1.25, 1.5, 1.75 or 2-fold increase in α-helicity as determined by circular dichroism compared to a corresponding uncrosslinked macrocycle.

The term "amino acid" refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes without limitation, α-amino acids, natural amino acids, non-natural amino acids, and amino acid analogs.

The term "α-amino acid" refers to a molecule containing both an amino group and a carboxyl group bound to a carbon which is designated the α-carbon.

The term "β-amino acid" refers to a molecule containing both an amino group and a carboxyl group in a β configuration.

The term "naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
| --- | --- | --- | --- | --- | --- |
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive(10%) neutral(90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acid" are glycine, alanine, proline, and analogs thereof. "Large hydrophobic amino acids" are valine, leucine, isoleucine, phenylalanine, methionine, tryptophan, and analogs thereof. "Polar amino acids" are serine, threonine, asparagine, glutamine, cysteine, tyrosine, and analogs thereof. "Charged amino acids" are lysine, arginine, histidine, aspartate, glutamate, and analogs thereof.

The term "amino acid analog" refers to a molecule which is structurally similar to an amino acid and which can be substituted for an amino acid in the formation of a peptidomimetic macrocycle. Amino acid analogs include, without limitation, β-amino acids and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P, S, T, W, Y and V. Non-natural amino acids or amino acid analogs include, without limitation, structures according to the following:

-continued
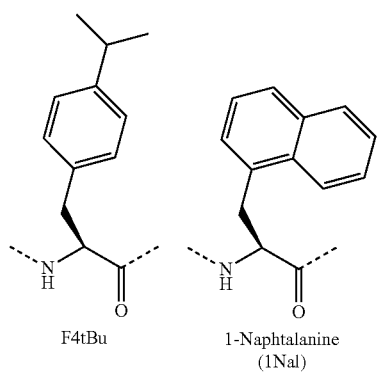
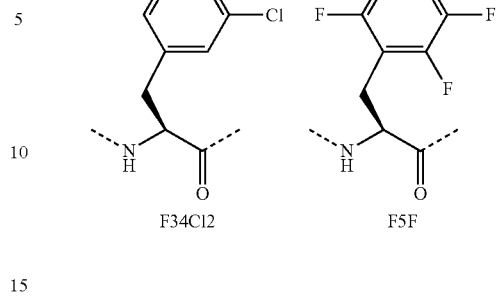
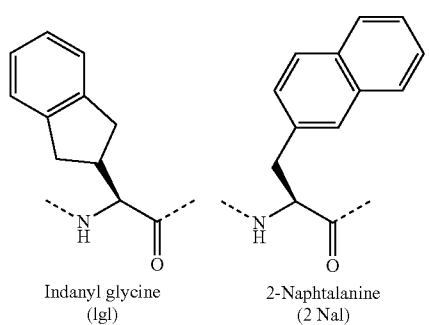
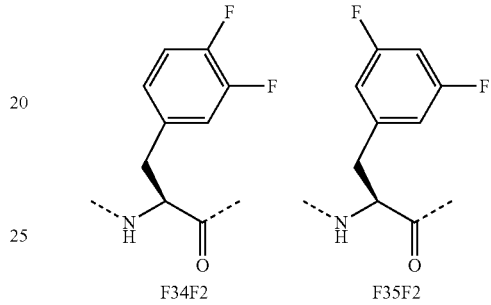
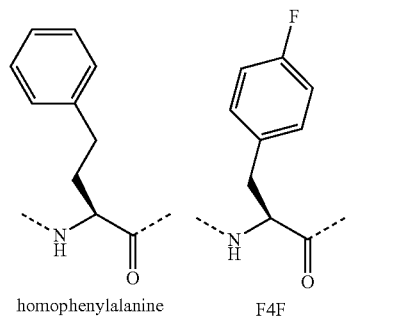
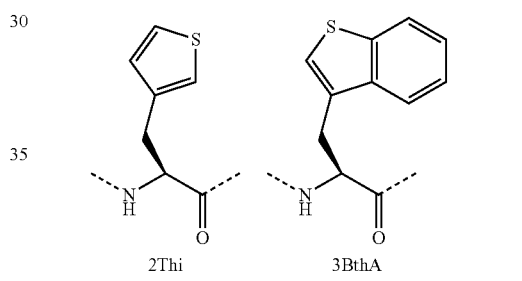
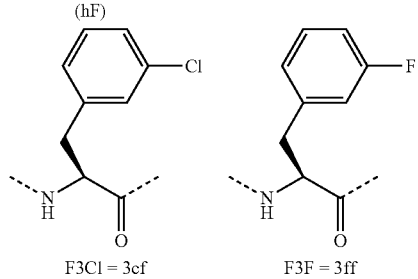
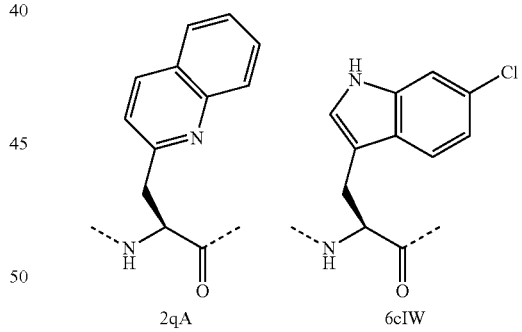
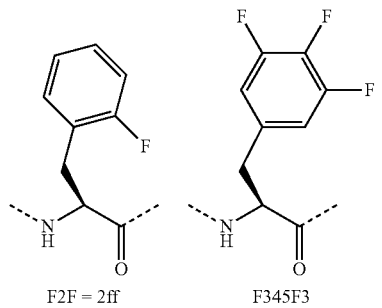
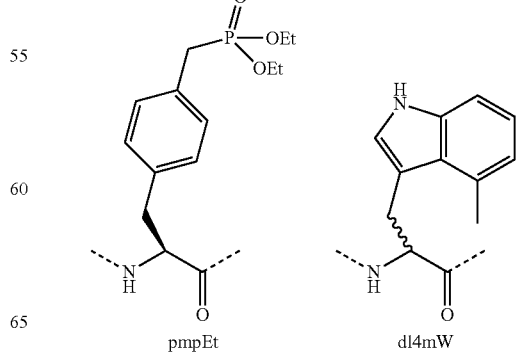

-continued
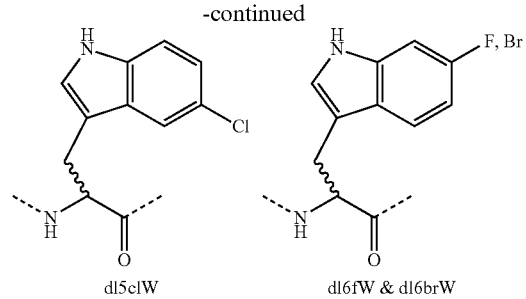
dl5clW  dl6fW & dl6brW
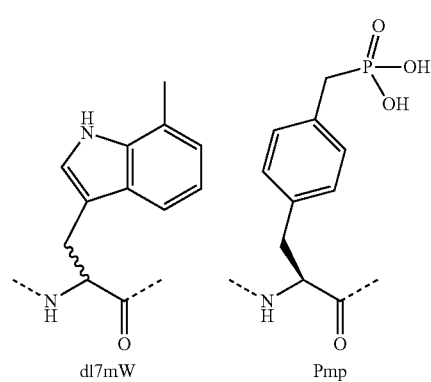
dl7mW  Pmp
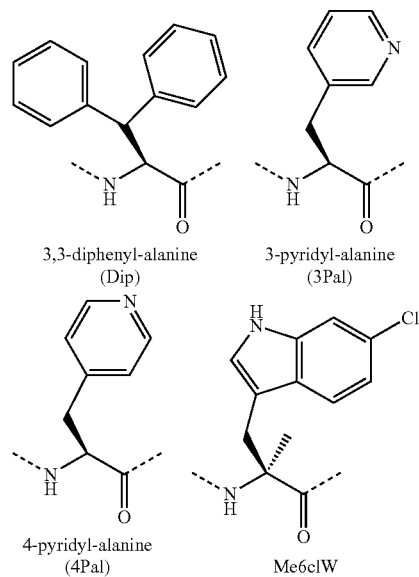
3,3-diphenyl-alanine (Dip)  3-pyridyl-alanine (3Pal)
4-pyridyl-alanine (4Pal)  Me6clW
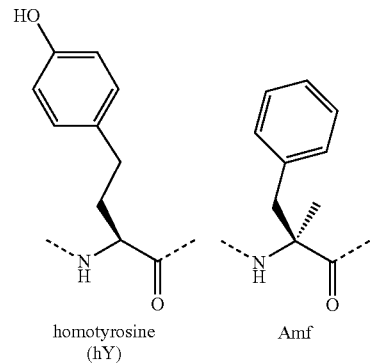
homotyrosine (hY)  Amf
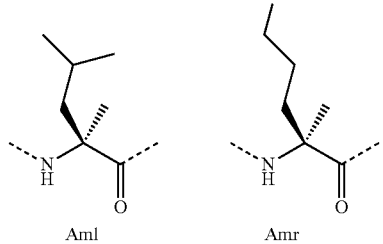
Aml  Amr
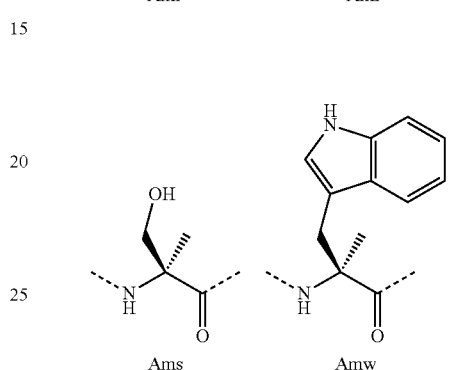
Ams  Amw
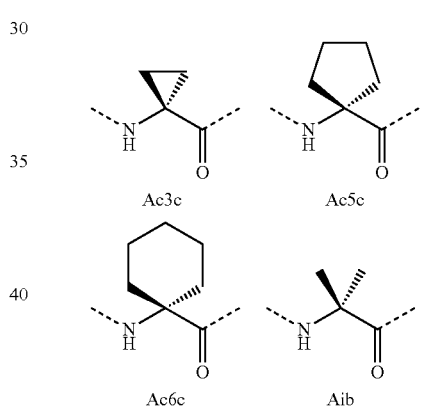
Ac3c  Ac5c
Ac6c  Aib
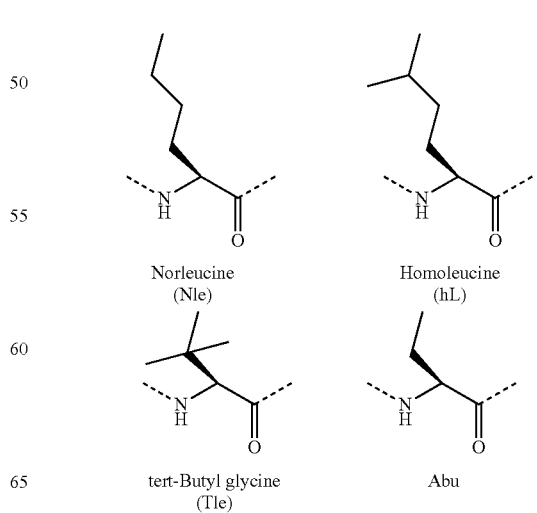
Norleucine (Nle)  Homoleucine (hL)
tert-Butyl glycine (Tle)  Abu

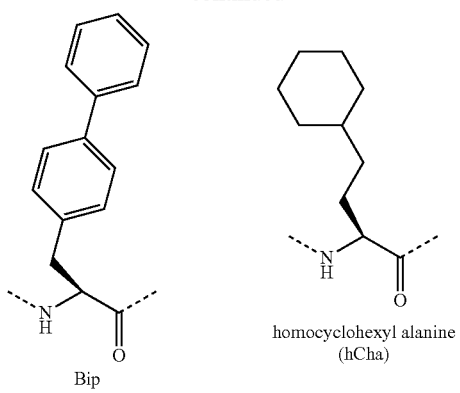
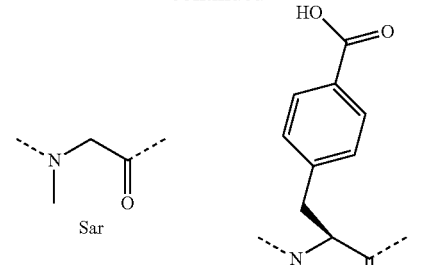
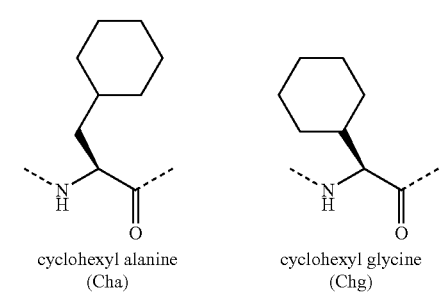
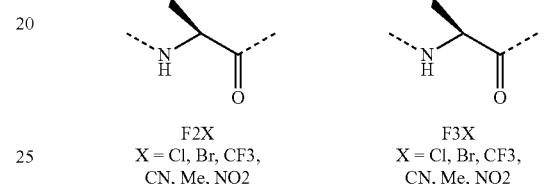
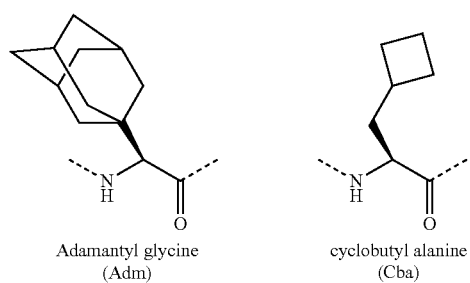
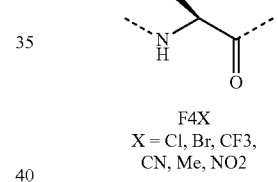
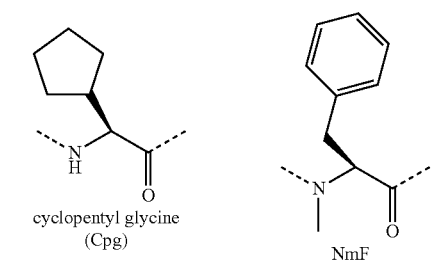
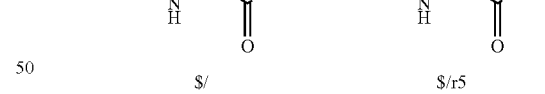
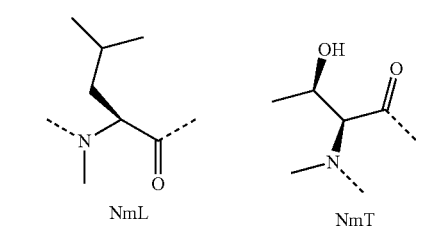
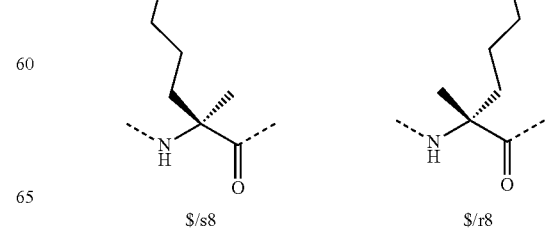

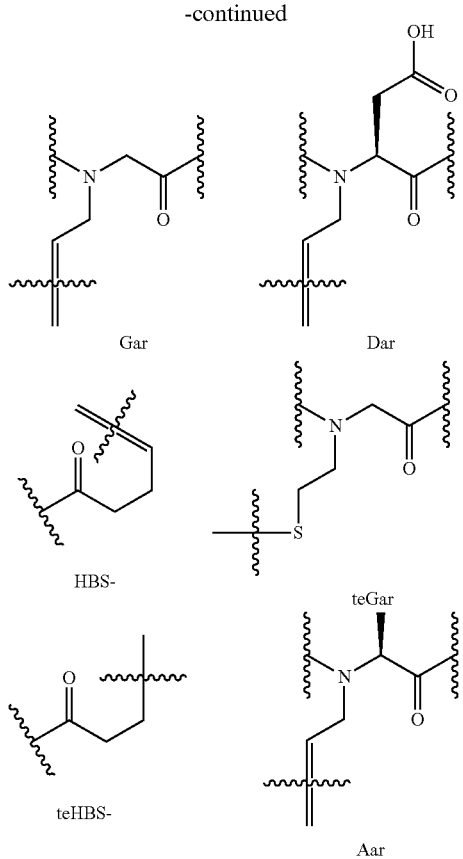

Amino acid analogs include β-amino acid analogs. Examples of β-amino acid analogs include, but are not limited to, the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl)butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl)-butyric acid; (S)-3-amino-4-(4-cyanophenyl)-butyric acid; (S)-3-amino-4-(4-fluorophenyl)-butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homolysine; Nδ-trityl-L-β-homoglutamine; No)-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

Amino acid analogs include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanin; β-cyclohexyl-D-alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH.dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-(3-thienyl)glycine; D-2-aminocaproic acid; D-2-indanylglycine; D-allylglycine.dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-(3-thienyl)glycine; L-2-amino-3-(dimethylamino)-propionic acid; L-2-aminocaproic acid dicyclohexyl-ammonium salt; L-2-indanylglycine; L-allylglycine-dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene)ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α,γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

Amino acid analogs include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)$_2$-OH; Lys(N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxocyclohex-1-ylidene)ethyl)-D-ornithine; (Nδ-1-(4,4-dimethyl-2,6-dioxo-cyclohex-1-ylidene)ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH (asymmetrical); Arg(Me)2-OH (symmetrical); Lys(ivDde)-OH; Lys(Me)2-OH.HCl; Lys(Me3)-OH chloride; Nω-nitro-D-arginine; and Nω-nitro-L-arginine.

Amino acid analogs include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

Amino acid analogs include analogs of cysteine and methionine. Examples of amino acid analogs of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthioninesulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

Amino acid analogs include analogs of phenylalanine and tyrosine. Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichlorophenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2; 4; 5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L tyrosine, 3-cyano-D-phenylalanine, 3-cyano-L-phenylalanine, 3-fluoro-D-phenylalanine, 3-fluoro-L-phenylalanine, 3-fluoro-L-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

Amino acid analogs include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

Amino acid analogs include analogs of serine and threonine. Examples of amino acid analogs of serine and threonine include, but are not limited to, 3-amino-2-hydroxy-5-methylhexanoic acid, 2-amino-3-hydroxy-4- methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

Amino acid analogs include analogs of tryptophan. Examples of amino acid analogs of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-β-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some embodiments, amino acid analogs are racemic. In some embodiments, the D isomer of the amino acid analog is used. In some embodiments, the L isomer of the amino acid analog is used. In other embodiments, the amino acid analog comprises chiral centers that are in the R or S configuration. In still other embodiments, the amino group (s) of a β-amino acid analog is substituted with a protecting group, e.g., tert-butyloxycarbonyl (BOC group), 9-fluorenylmethyloxycarbonyl (FMOC), tosyl, and the like. In yet other embodiments, the carboxylic acid functional group of a β-amino acid analog is protected, e.g., as its ester derivative. In some embodiments the salt of the amino acid analog is used.

A "non-essential" amino acid residue is a residue that can be altered from the wild-type sequence of a polypeptide without abolishing or substantially abolishing its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., K, R, H), acidic side chains (e.g., D, E), uncharged polar side chains (e.g., G, N, Q, S, T, Y, C), nonpolar side chains (e.g., A, V, L, I, P, F, M, W), beta-branched side chains (e.g., T, V, I) and aromatic side chains (e.g., Y, F, W, H). Thus, a predicted nonessential amino acid residue in a polypeptide, for example, is replaced with another amino acid residue from the same side chain family. Other examples of acceptable substitutions are substitutions based on isosteric considerations (e.g. norleucine for methionine) or other properties (e.g. 2-thienylalanine for phenylalanine).

The term "capping group" refers to the chemical moiety occurring at either the carboxy or amino terminus of the polypeptide chain of the subject peptidomimetic macrocycle. The capping group of a carboxy terminus includes an unmodified carboxylic acid (ie —COOH) or a carboxylic acid with a substituent. For example, the carboxy terminus can be substituted with an amino group to yield a carboxamide at the C-terminus. Various substituents include but are not limited to primary and secondary amines, including pegylated secondary amines. Representative secondary amine capping groups for the C-terminus include:

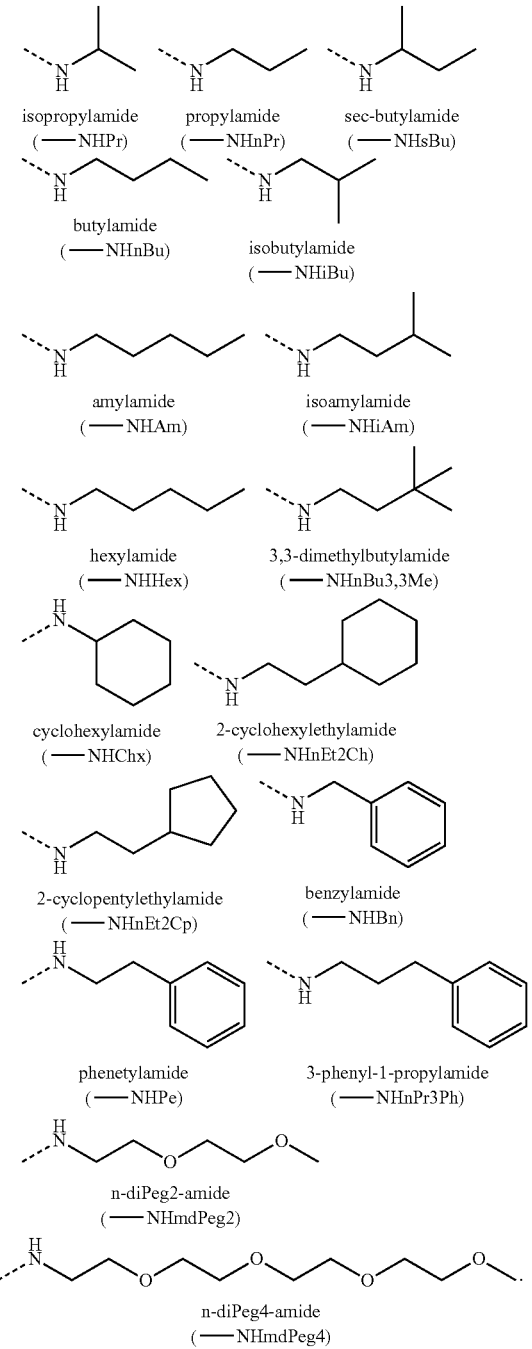

The capping group of an amino terminus includes an unmodified amine (ie —NH$_2$) or an amine with a substituent. For example, the amino terminus can be substituted with an acyl group to yield a carboxamide at the N-terminus. Various substituents include but are not limited to substituted acyl groups, including $C_1$-$C_6$ carbonyls, $C_7$-$C_{30}$ carbonyls, and pegylated carbamates. Representative capping groups for the N-terminus include:

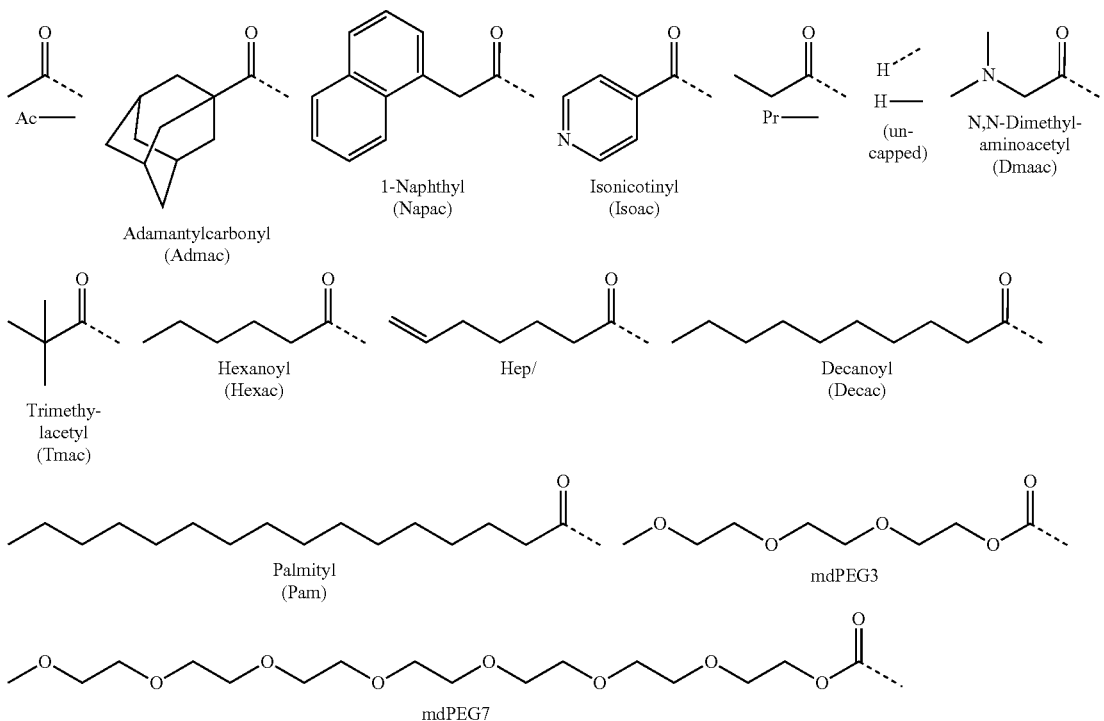

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-dimethyl cyclodecane are all considered ten-membered macrocycles as the hydrogen or fluoro substituents or methyl side chains do not participate in forming the macrocycle.

The symbol  when used as part of a molecular structure refers to a single bond or a trans or cis double bond.

The term "amino acid side chain" refers to a moiety attached to the α-carbon (or another backbone atom) in an amino acid. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an α,α di-substituted amino acid).

The term "α,α di-substituted amino" acid refers to a molecule or moiety containing both an amino group and a carboxyl group bound to a carbon (the α-carbon) that is attached to two natural or non-natural amino acid side chains.

The term "polypeptide" encompasses two or more naturally or non-naturally-occurring amino acids joined by a covalent bond (e.g., an amide bond). Polypeptides as described herein include full length proteins (e.g., fully processed proteins) as well as shorter amino acid sequences (e.g., fragments of naturally-occurring proteins or synthetic polypeptide fragments).

The term "macrocyclization reagent" or "macrocycle-forming reagent" as used herein refers to any reagent which may be used to prepare a peptidomimetic macrocyte of the invention by mediating the reaction between two reactive groups. Reactive groups may be, for example, an azide and alkyne, in which case macrocyclization reagents include, without limitation, Cu reagents such as reagents which provide a reactive Cu(I) species, such as CuBr, CuI or CuOTf, as well as Cu(II) salts such as $Cu(CO_2CH_3)_2$, $CuSO_4$, and $CuCl_2$ that can be converted in situ to an active Cu(I) reagent by the addition of a reducing agent such as ascorbic acid or sodium ascorbate. Macrocyclization reagents may additionally include, for example, Ru reagents known in the art such as Cp*RuCl(PPh$_3$)$_2$, [Cp*RuCl]$_4$ or other Ru reagents which may provide a reactive Ru(II) species. In other cases, the reactive groups are terminal olefins. In such embodiments, the macrocyclization reagents or macrocycle-forming reagents are metathesis catalysts including, but not limited to, stabilized, late transition metal carbene complex catalysts such as Group VIII transition metal carbene catalysts. For example, such catalysts are Ru and Os metal centers having a +2 oxidation state, an electron count of 16 and pentacoordinated. In other examples, catalysts have W or Mo centers. Various catalysts are disclosed in Grubbs et al., "Ring Closing Metathesis and Related Processes in Organic Synthesis" Acc. Chem. Res. 1995, 28, 446-452, and U.S. Pat. No. 5,811,515; U.S. Pat. No. 7,932, 397; U.S. Application No. 2011/0065915; U.S. Application No. 2011/0245477; Yu et al., "Synthesis of Macrocyclic Natural Products by Catalyst-Controlled Stereoselective Ring-Closing Metathesis," Nature 2011, 479, 88; and Peryshkov et al., "Z-Selective Olefin Metathesis Reactions Promoted by Tungsten Oxo Alkylidene Complexes," J. Am. Chem. Soc. 2011, 133, 20754. In yet other cases, the reactive groups are thiol groups. In such embodiments, the macrocyclization reagent is, for example, a linker functionalized with two thiol-reactive groups such as halogen groups.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like. The term "arylalkoxy" refers to an alkoxy substituted with aryl.

"Arylalkyl" refers to an aryl group, as defined above, wherein one of the aryl group's hydrogen atoms has been replaced with a $C_1$-$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH2-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl, "Alkylheterocycle" refers to a $C_1$-$C_5$ alkyl group, as defined above, wherein one of the $C_1$-$C_5$ alkyl group's hydrogen atoms has been replaced with a heterocycle. Representative examples of an alkylheterocycle group include, but are not limited to, —CH$_2$CH$_2$-morpholine, —CH$_2$CH$_2$-piperidine, —CH$_2$CH$_2$CH$_2$-morpholine, and —CH$_2$CH$_2$-imidazole.

"Alkylamido" refers to a $C_1$-$C_5$ alkyl group, as defined above, wherein one of the $C_1$-$C_5$ alkyl group's hydrogen atoms has been replaced with a —C(O)NH$_2$ group. Representative examples of an alkylamido group include, but are not limited to, —CH$_2$—C(O)NH$_2$, —CH$_2$CH$_2$—C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH$_2$)CH$_3$, —CH$_2$CH(C(O)NH$_2$)CH$_2$CH$_3$, —CH(C(O)NH$_2$)CH$_2$CH$_3$, —C(CH$_3$)$_2$CH$_2$C(O)NH$_2$, —CH$_2$—CH$_2$—NH—C(O)—CH$_3$, —CH$_2$—CH$_2$—NH—C(O)—CH$_3$—CH3, and —CH$_2$—CH$_2$—NH—C(O)—CH=CH$_2$.

"Alkanol" refers to a $C_1$-$C_5$ alkyl group, as defined above, wherein one of the $C_1$-$C_5$ alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_3$ and —C(CH$_3$)$_2$CH$_2$OH.

"Alkylcarboxy" refers to a $C_1$-$C_5$ alkyl group, as defined above, wherein one of the $C_1$-$C_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thio-alkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included in the present invention unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included in the present invention unless expressly provided otherwise. All crystal forms of the compounds described herein are included in the present invention unless expressly provided otherwise.

As used herein, the terms "increase" and "decrease" mean, respectively, to cause a statistically significantly (i.e., p<0.1) increase or decrease of at least 5%.

As used herein, the recitation of a numerical range for a variable is intended to convey that the variable is equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values ≥0 and ≤2 if the variable is inherently continuous.

As used herein, unless specifically indicated otherwise, the word "or" is used in the inclusive sense of "and/or" and not the exclusive sense of "either/or."

The term "on average" represents the mean value derived from performing at least three independent replicates for each data point.

The term "biological activity" encompasses structural and functional properties of a macrocycle of the invention. Biological activity is, for example, structural stability, alpha-helicity, affinity for a target, resistance to proteolytic degradation, cell penetrability, intracellular stability, in vivo stability, or any combination thereof.

The details of one or more particular embodiments of the invention are set forth in the accompanying drawings and the description below. Other features, objects, and advantages of the invention will be apparent from the description and drawings, and from the claims.

In some embodiments, the peptide sequences are derived from a GHRH peptide. For example, the peptide sequences are derived from human GHRH (1-29) or human GHRH (1-44).

A non-limiting exemplary list of suitable GHRH peptides for use in the present invention is given in Table 1 and Table 2 below. In Tables 1 and 2, all peptides possess a free amino terminus (shown as H—) and all peptides possess an carboxamide terminus (shown as —NH2). X residues form cross-links to one other X residue, Z residues form cross-links to one other Z residue, and XX residues form cross-links with two other X residues. In Tables 1 and 2, amino acid A2 is either L-Ala or D-Ala, A8 is either L-Asn or L-Gln, A15 is either L-Ala or Gly, and A27 is either L-Nle or L-Leu.

TABLE 1

H-Y-A2-D-X-IFT-X-SYRKVL-A15-QLSAR-Z-LLQ-Z-I-A27-SR-NH2

H-Y-A2-D-X-IFT-X-SYRKVL-A15-QLSARKLLQ-Z-I-A27-S-Z-NH2

H-Y-A2-DAIFT-X-SYR-X-VL-A15-QLSAR-Z-LLQ-Z-I-A27-SR-NH2

H-Y-A2-DAIFT-X-SYR-X-VL-A15-QLSARKLLQ-Z-I-A27-S-Z-NH2

H-Y-A2-DAIFT-A8-SY-X-KVL-X-QLSAR-Z-LLQ-Z-I-A27-SR-NH2

H-Y-A2-DAIFT-A8-SY-X-KVL-X-QLSARKLLQ-Z-I-A27-S-Z-NH2

H-Y-A2-DAIFT-A8-SYR-X-VL-A15-X-LSAR-Z-LLQ-Z-I-A27-SR-NH2

H-Y-A2-DAIFT-A8-SYR-X-VL-A15-X-LSARKLLQ-Z-I-A27-S-Z-NH2

H-Y-A2-D-X-IFT-A8-SY-X-KVL-A15-QLSARKLLQDI-A27-SR-NH2

H-Y-A2-DA-X-FT-A8-SYR-X-VL-A15-QLSARKLLQDI-A27-SR-NH2

H-Y-A2-DAI-X-T-A8-SYRK-X-L-A15-QLSARKLLQDI-A27-SR-NH2

H-Y-A2-DAIF-X-A8-SYRKV-X-A15-QLSARKLLQDI-A27-SR-NH2

H-Y-A2-DAIFT-X-SYRKVL-X-QLSARKLLQDI-A27-SR-NH2

H-Y-A2-DAIFT-A8-X-YRKVL-A15-X-LSARKLLQDI-A27-SR-NH2

H-Y-A2-DAIFT-A8-S-X-RKVL-A15-Q-X-SARKLLQDI-A27-SR-NH2

H-Y-A2-DAIFT-A8-SY-X-KVL-A15-QL-X-ARKLLQDI-A27-SR-NH2

H-Y-A2-DAIFT-A8-SYR-X-VL-A15-QLS-X-RKLLQDI-A27-SR-NH2

H-Y-A2-DAIFT-A8-SYRK-X-L-A15-QLSA-X-KLLQDI-A27-SR-NH2

H-Y-A2-DAIFT-A8-SYRKV-X-A15-QLSAR-X-LLQDI-A27-SR-NH2

H-Y-A2-DAIFT-A8-SYRKVL-X-QLSARK-X-LQDI-A27-SR-NH2

H-Y-A2-DAIFT-A8-SYRKVL-A15-X-LSARKL-X-QDI-A27-SR-NH2

H-Y-A2-DAIFT-A8-SYRKVL-A15-Q-X-SARKLL-X-DI-A27-SR-NH2

H-Y-A2-DAIFT-A8-SYRKVL-A15-QL-X-ARKLLQ-X-I-A27-SR-NH2

H-Y-A2-DAIFT-A8-SYRKVL-A15-QLS-X-RKLLQD-X-A27-SR-NH2

H-Y-A2-DAIFT-A8-SYRKVL-A15-QLSA-X-KLLQDI-X-SR-NH2

H-Y-A2-DAIFT-A8-SYRKVL-A15-QLSAR-X-LLQDI-A27-X-R-NH2

H-Y-A2-DAIFT-A8-SYRKVL-A15-QLSARK-X-LQDI-A27-S-X-NH2

TABLE 1-continued

H-Y-A2-D-X-IFT-A8-SY-X-KVL-A15-QLSAR-Z-LLQ-Z-I-A27-SR-NH2

H-Y-A2-D-X-IFT-A8-SY-X-KVL-A15-QLSARKLLQ-Z-I-A27-S-Z-NH2

H-Y-A2-DA-X-FT-A8-SYR-X-VL-A15-QLSAR-Z-LLQ-Z-I-A27-SR-NH2

H-Y-A2-DA-X-FT-A8-SYR-X-VL-A15-QLSARKLLQ-Z-I-A27-S-Z-NH2

H-Y-A2-DAI-X-T-A8-SYRK-X-L-A15-QLSAR-Z-LLQ-Z-I-A27-SR-NH2

H-Y-A2-DAI-X-T-A8-SYRK-X-L-A15-QLSARKLLQ-Z-I-A27-S-Z-NH2

H-Y-A2-DAIF-X-A8-SYRKV-X-A15-QLSAR-Z-LLQ-Z-I-A27-SR-NH2

H-Y-A2-DAIF-X-A8-SYRKV-X-A15-QLSARKLLQ-Z-I-A27-S-Z-NH2

H-Y-A2-DAIFT-X-SYRKVL-X-QLSAR-Z-LLQ-Z-I-A27-SR-NH2

H-Y-A2-DAIFT-X-SYRKVL-X-QLSARKLLQ-Z-I-A27-S-Z-NH2

H-Y-A2-DAIFT-A8-X-YRKVL-X-LSARKLLQ-Z-I-A27-S-Z-NH2

H-Y-A2-DAIFT-A8-X-YRKVL-A15-X-LSAR-Z-LLQ-Z-I-A27-SR-NH2

H-Y-A2-DAIFT-A8-SYR-X-VL-A15-QLS-X-RKLLQ-Z-I-A27-S-Z-NH2

H-Y-A2-D-X-IFT-X-SYRKVL-Z-QLSARK-Z-LQDI-A27-SR-NH2

H-Y-A2-D-X-IFT-X-SYRKVL-A15-QL-Z-ARKLLQ-Z-I-A27-SR-NH2

H-Y-A2-D-X-IFT-X-SYRKVL-A15-QLSAR-Z-LLQDI-A27-Z-R-NH2

H-Y-A2-D-X-IFT-X-SYRKVL-A15-QLSARK-Z-LQDI-A27-S-Z-NH2

H-Y-A2-DAIFT-X-SYR-X-VL-Z-QLSARK-Z-LQDI-A27-SR-NH2

H-Y-A2-DAIFT-X-SYR-X-VL-A15-QL-Z-ARKLLQ-Z-I-A27-SR-NH2

H-Y-A2-DAIFT-X-SYR-X-VL-A15-QLSAR-Z-LLQDI-A27-Z-R-NH2

H-Y-A2-DAIFT-X-SYR-X-VL-A15-QLSARK-Z-LQDI-A27-S-Z-NH2

H-Y-A2-DAIFT-A8-SYR-X-VL-A15-X-LSAR-Z-LLQDI-A27-Z-R-NH2

H-Y-A2-DAIFT-A8-SYR-X-VL-A15-X-LSARK-Z-LQDI-A27-S-Z-NH2

H-Y-A2-DAIFT-A8-SY-X-KVL-X-QLSAR-Z-LLQDI-A27-Z-R-NH2

H-Y-A2-DAIFT-A8-SY-X-KVL-X-QLSARK-Z-LQDI-A27-S-Z-NH2

H-Y-A2-D-X-IFT-XX-SYR-X-VL-A15-QLSARKLLQDI-A27-SR-NH2

H-Y-A2-DAIFT-X-SYR-XX-VL-A15-X-LSARKLLQDI-A27-SR-NH2

H-Y-A2-DAIFT-A8-SYR-X-VL-A15-XX-LSA-X-KLLQDI-A27-SR-NH2

H-Y-A2-DAIFT-A8-SYRKVL-A15-QLSAR-X-LLQ-XX-I-A27-S-X-NH2

H-Y-A2-D-X-IFT-XX-SYRKVL-X-QLSARKLLQDI-A27-SR-NH2

H-Y-A2-D-X-IFT-A8-SY-XX-KVL-X-QLSARKLLQDI-A27-SR-NH2

H-Y-A2-DAIFT-X-SYR-XX-VL-A15-QLS-X-RKLLQDI-A27-SR-NH2

H-Y-A2-DAIFT-X-SYRKVL-XX-QLS-X-RKLLQDI-A27-SR-NH2

H-Y-A2-DAIFT-A8-X-YRKVL-A15-XX-LSA-X-KLLQDI-A27-SR-NH2

H-Y-A2-DAIFT-A8-X-YRK-XX-L-A15-QLSA-X-KLLQDI-A27-SR-NH2

H-Y-A2-DAIFT-A8-SYR-X-VL-A15-QLS-XX-RKL-X-QDI-A27-SR-NH2

H-Y-A2-DAIFT-A8-SYR-X-VL-A15-XX-LSARKL-X-QDI-A27-SR-NH2

H-Y-A2-DAIFT-A8-SYRKVL-A15-X-LSARKL-XX-QDI-X-SR-NH2

H-Y-A2-DAIFT-A8-SYRKVL-A15-X-LSA-XX-KLLQDI-X-SR-NH2

H-Y-A2-DAIFT-A8-SYRKVL-A15-QL-X-ARK-XX-LQDI-A27-S-X-NH2

H-Y-A2-DAIFT-A8-SYRKVL-A15-QL-X-ARKLLQ-XX-I-A27-S-X-NH2

H-Y-A2-D-X-IFT-A8-SY-XX-KVL-A15-QL-X-ARKLLQDI-A27-SR-NH2

H-Y-A2-DAIFT-X-SYRKVL-XX-QLSARK-X-LQDI-A27-SR-NH2

H-Y-A2-DAIFT-A8-X-YRKVL-A15-XX-LSARKL-X-QDI-A27-SR-NH2

H-Y-A2-DAIFT-A8-SYR-X-VL-A15-QLS-XX-RKLLQD-X-A27-SR-NH2

H-Y-A2-DAIFT-A8-SYRKVL-X-QLSARK-XX-LQDI-A27-S-X-NH2

TABLE 2

H-Y-A2-D-X-IFT-X-SYRKVL-A15-QLSAR-Z-LLQ-Z-I-A27-SRQQGESNQERGARARL-NH2

H-Y-A2-D-X-IFT-X-SYRKVL-A15-QLSARKLLQ-Z-I-A27-S-Z-QQGESNQERGARARL-NH2

H-Y-A2-D-X-IFT-X-SYRKVL-Z-QLSARK-Z-LQDI-A27-SRQQGESNQERGARARL-NH2

H-Y-A2-D-X-IFT-X-SYRKVL-A15-QL-Z-ARKLLQ$I-A27-SRQQGESNQERGARARL-NH2

H-Y-A2-D-X-IFT-X-SYRKVL-A15-QLSAR-Z-LLQDI-A27--Z-RQQGESNQERGARARL-NH2

TABLE 2-continued

```
H-Y-A2-D-X-IFT-X-SYRKVL-A15-QLSARK-Z-LQDI-A27-
S-Z-QQGESNQERGARARL-NH2

H-Y-A2-DAIFT-X-SYR-X-VL-A15-QLSAR-Z-LLQ-Z-I-A27-
SRQQGESNQERGARARL-NH2

H-Y-A2-DAIFT-X-SYR-X-VL-A15-QLSARKLLQ-Z-I-A27-S-
Z-QQGESNQERGARARL-NH2

H-Y-A2-DAIFT-A8-SY-X-KVL-X-QLSAR-Z-LLQ-Z-I-A27-
SRQQGESNQERGARARL-NH2

H-Y-A2-DAIFT-A8-SY-X-KVL-X-QLSARKLLQ-Z-I-A27-S-
Z-QQGESNQERGARARL-NH2

H-Y-A2-DAIFT-A8-SYR-X-VL-A15--X-LSAR-Z-LLQ-Z-I-
A27-SRQQGESNQERGARARL-NH2

H-Y-A2-DAIFT-A8-SYR-X-VL-A15--X-LSARKLLQ-Z-I-
A27-S-Z-QQGESNQERGARARL-NH2

H-Y-A2-DAIFT-X-SYRKVL-X-QLSAR-Z-LLQ-Z-I-A27-
SRQQGESNQERGARARL-NH2

H-Y-A2-DAIFT-X-SYRKVL-X-QLSARKLLQ-Z-I-A27-S-Z-
QQGESNQERGARARL-NH2
```

Peptidomimetic Macrocycles of the Invention

In some embodiments, a peptidomimetic macrocycle of the invention has the Formula (I):

Formula (I)

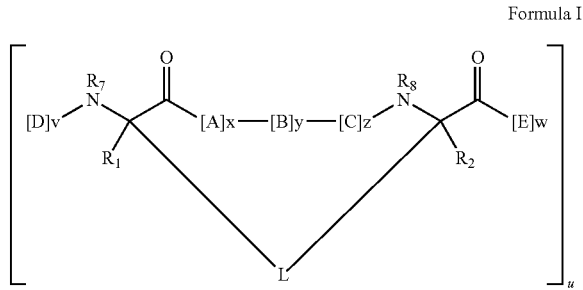

wherein:

each A, C, D, and E is independently an amino acid (including natural or non-natural amino acids and amino acid analogs) and the terminal D and E independently optionally include a capping group;

B is an amino acid (including natural or non-natural amino acids and amino acid analogs),

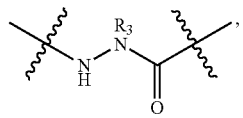

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

L is a macrocycle-forming linker of the formula -$L_1$-$L_2$-;

and wherein A, B, C, D, and E, taken together with the crosslinked amino acids connected by the macrocycle-forming linker L, form the amino acid sequence of the peptidomimetic macrocycle which is at least about 60%, 65%, 70%, 75%, 80%, 85%, 90%, 95%, 96%, 97%, 98%, or 99% identical to GHRH 1-44, GHRH 1-29 and/or to an amino acid sequence chosen from the group consisting of the amino acid sequences in Table 1, 2 or 4;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

v and w are independently integers from 1-1000, for example 1-500, 1-200, 1-100, 1-50, 1-40, 1-25, 1-20, 1 to 15, or 1 to 10;

u, x, y and z are independently integers from 0-10, for example u is 1, 2, or 3; and n is an integer from 1-5, for example 1. For example, u is 2. In some embodiments, the sum of x+y+z is 2, 3 or 6, for example 3 or 6.

In some embodiments, the peptidomimetic macrocycle of Formula (I) has the Formula:

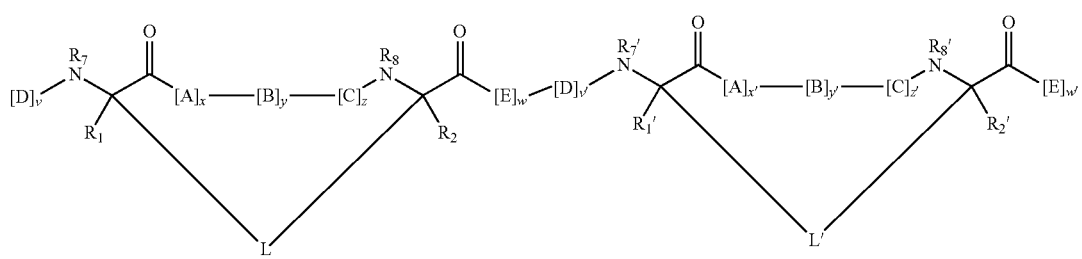

wherein each A, C, D, and E is independently an amino acid;

B is an amino acid,

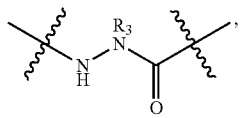

[—NH-L$_3$-CO—], [—NH-L$_3$-SO$_2$—], or [—NH-L$_3$-];

L' is a macrocycle-forming linker of the formula -L$_1$'-L$_2$'-;

and wherein A, B, C, D, and E, taken together with the crosslinked amino acids connected by the macrocycle-forming linkers L and L', form the amino acid sequence of the peptidomimetic macrocycle;

R$_1$' and R$_2$' are independently —H, alkyl, alkenyl, alkynyl, arylalkyl, cycloalkyl, cycloalkylalkyl, heteroalkyl, or heterocycloalkyl, unsubstituted or substituted with halo-;

L$_1$' and L$_2$' are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

each K is independently O, S, SO, SO$_2$, CO, CO$_2$, or CONR$_3$; R$_7$' is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with a D residue;

R$_8$' is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with an E residue;

v' and w' are independently integers from 1-1000, for example 1-500, 1-200, 1-100, 1-50, 1-40, 1-25, 1-20, 1 to 15, or 1 to 10;

x', y' and z' are independently integers from 0-10; and n is an integer from 1-5. In some embodiments, the sum of x'+y'+z' is 2, 3 or 6, for example 3 or 6.

In some embodiments of any of the peptidomimetic macrocycles described herein, each K is O, S, SO, SO$_2$, CO, or CO$_2$.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments of the invention, the sum of the sum of x+y+z is at least 3, and/or the sum of x'+y'+z' is at least 3. In other embodiments of the invention, the sum of the sum of x+y+z is 1, 2, 3, 4, 5, 6, 7, 8, 9 or 10 (for example 2, 3 or 6) and/or the sum of x'+y'+z' is 1, 2, 3, 4, 5, 6, 7, 8, 9 or 10 (for example 2, 3 or 6).

Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges. Similarly, when u is greater than 1, each compound of the invention may encompass peptidomimetic macrocycles which are the same or different. For example, a compound of the invention may comprise peptidomimetic macrocycles comprising different linker lengths or chemical compositions.

In some embodiments, the peptidomimetic macrocycle of the invention comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

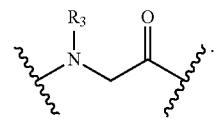

In other embodiments, the length of the macrocycle-forming linker L as measured from a first Cα to a second Cα is selected to stabilize a desired secondary peptide structure, such as an α-helix formed by residues of the peptidomimetic macrocycle including, but not necessarily limited to, those between the first Cα to a second Cα.

In one embodiment, the peptidomimetic macrocycle of Formula (I) is:

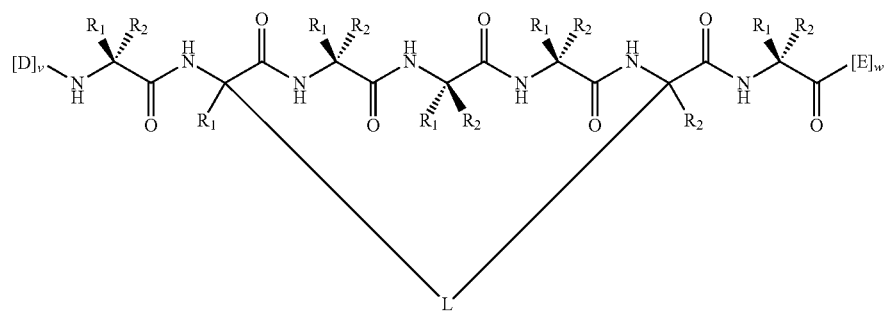

wherein each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-.

In related embodiments, the peptidomimetic macrocycle comprises a structure of Formula (I) which is:

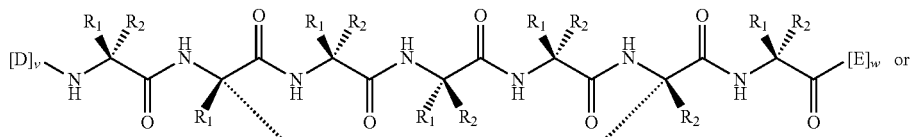

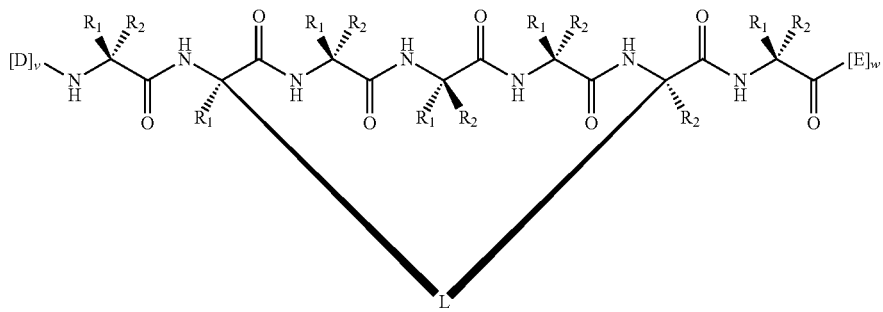

In other embodiments, the peptidomimetic macrocycle of Formula (I) is a compound of any of the formulas shown below:

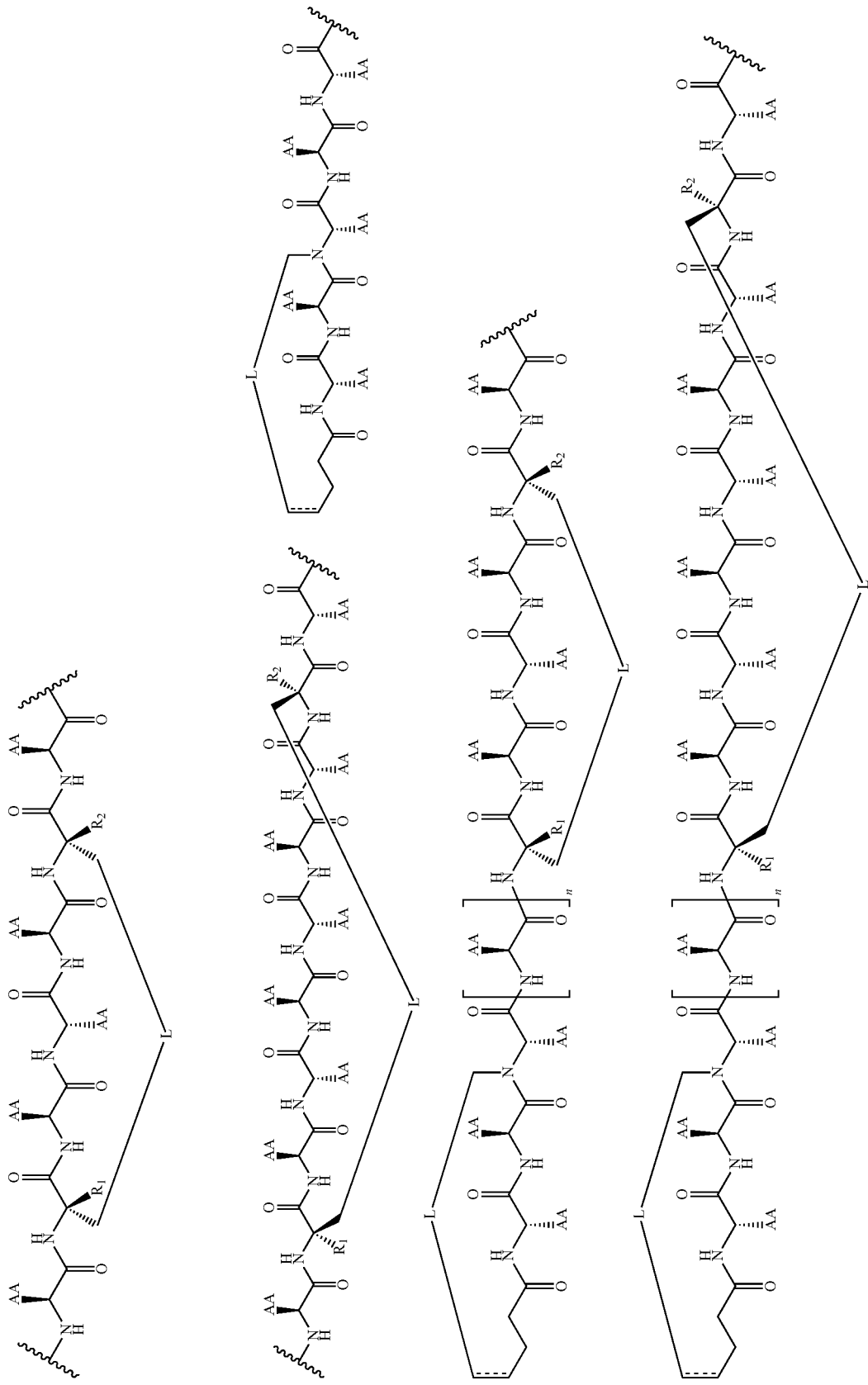

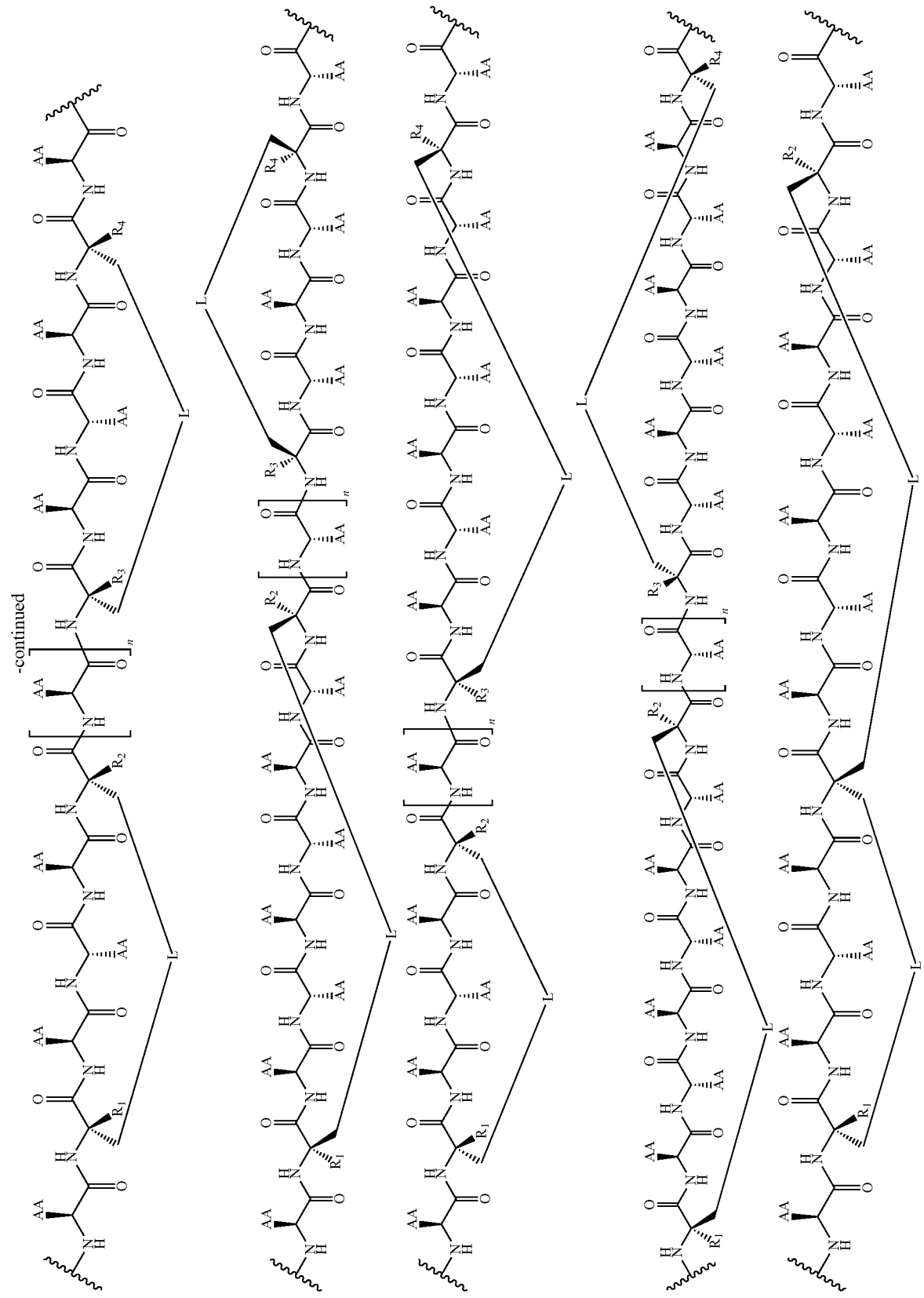

-continued
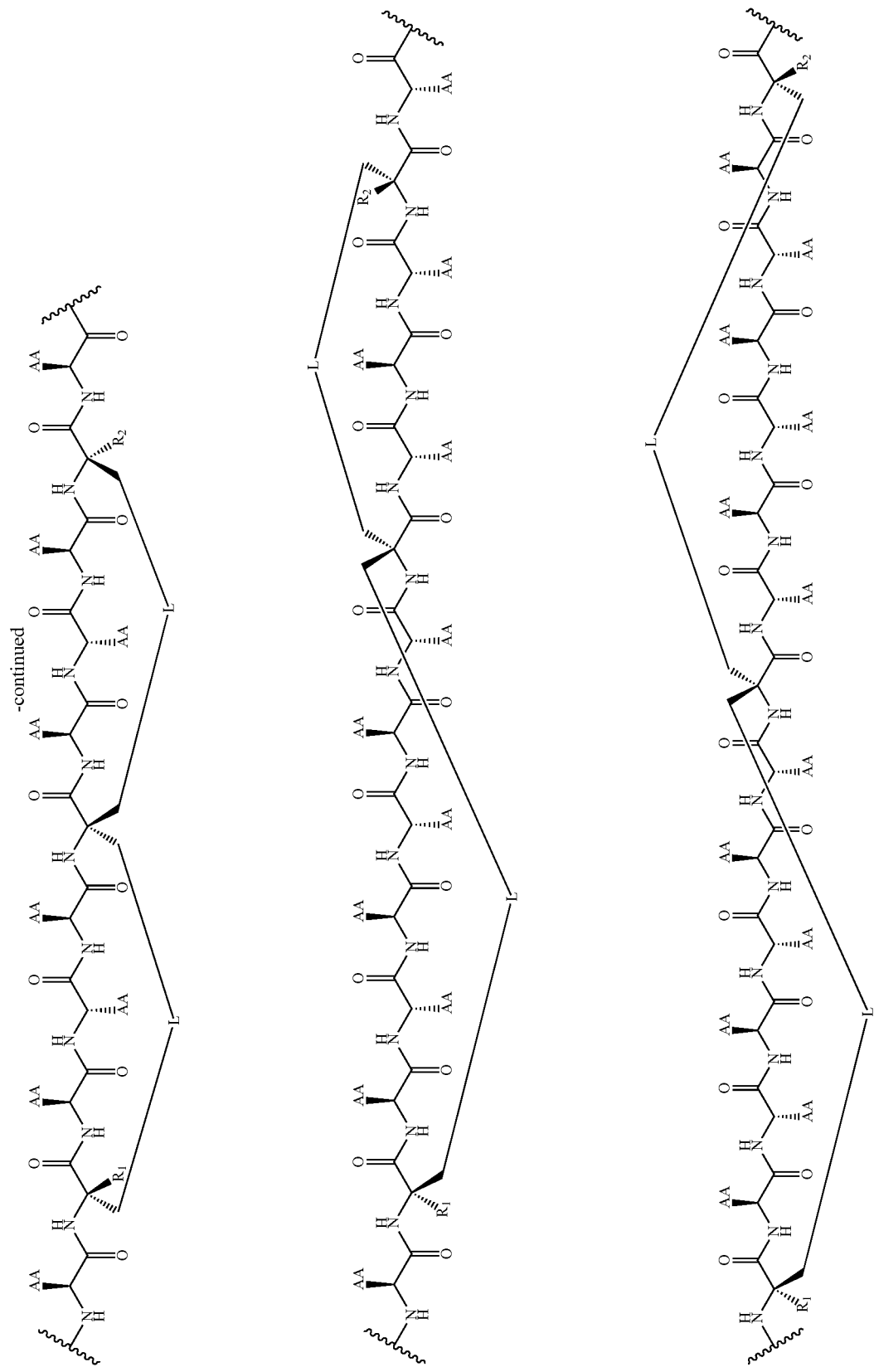

wherein "AA" represents any natural or non-natural amino acid side chain and "⸺" is [D]$_v$, [E]$_w$ as defined above, and n is an integer between 0 and 20, 50, 100, 200, 300, 400 or 500. In some embodiments, the substituent "n" shown in the preceding paragraph is 0. In other embodiments, the substituent "n" shown in the preceding paragraph is less than 50, 40, 30, 20, 10, or 5.

Exemplary embodiments of the macrocycle-forming linker L are shown below.

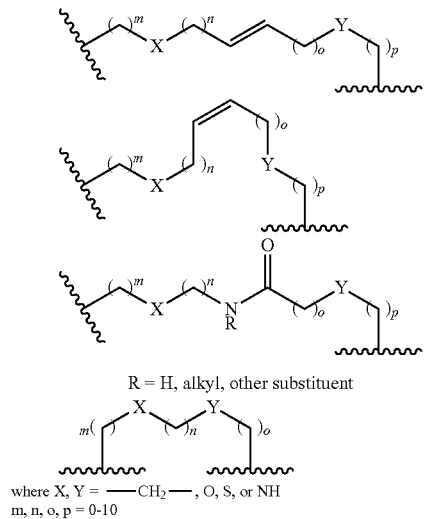

In other embodiments, D and/or E in the compound of Formula I are further modified in order to facilitate cellular uptake. In some embodiments, lipidating or PEGylating a peptidomimetic macrocycle facilitates cellular uptake, increases bioavailability, increases blood circulation, alters pharmacokinetics, decreases immunogenicity and/or decreases the needed frequency of administration.

In other embodiments, at least one of [D] and [E] in the compound of Formula I represents a moiety comprising an additional macrocycle-forming linker such that the peptidomimetic macrocycle comprises at least two macrocycle-forming linkers. In a specific embodiment, a peptidomimetic macrocycle comprises two macrocycle-forming linkers.

In the peptidomimetic macrocycles of the invention, any of the macrocycle-forming linkers described herein may be used in any combination with any of the sequences shown in Tables 1-3 and also with any of the R— substituents indicated herein.

In some embodiments, the peptidomimetic macrocycle comprises at least one α-helix motif. For example, A, B and/or C in the compound of Formula I include one or more α-helices. As a general matter, α-helices include between 3 and 4 amino acid residues per turn. In some embodiments, the α-helix of the peptidomimetic macrocycle includes 1 to 5 turns and, therefore, 3 to 20 amino acid residues. In specific embodiments, the α-helix includes 1 turn, 2 turns, 3 turns, 4 turns, or 5 turns. In some embodiments, the macrocycle-forming linker stabilizes an α-helix motif included within the peptidomimetic macrocycle. Thus, in some embodiments, the length of the macrocycle-forming linker L from a first Cα to a second Cα is selected to increase the stability of an α-helix. In some embodiments, the macrocycle-forming linker spans from 1 turn to 5 turns of the α-helix. In some embodiments, the macrocycle-forming linker spans approximately 1 turn, 2 turns, 3 turns, 4 turns, or 5 turns of the α-helix. In some embodiments, the length of the macrocycle-forming linker is approximately 5 Å to 9 Å per turn of the α-helix, or approximately 6 Å to 8 Å per turn of the α-helix. Where the macrocycle-forming linker spans approximately 1 turn of an α-helix, the length is equal to approximately 5 carbon-carbon bonds to 13 carbon-carbon bonds, approximately 7 carbon-carbon bonds to 11 carbon-carbon bonds, or approximately 9 carbon-carbon bonds. Where the macrocycle-forming linker spans approximately 2 turns of an α-helix, the length is equal to approximately 8 carbon-carbon bonds to 16 carbon-carbon bonds, approximately 10 carbon-carbon bonds to 14 carbon-carbon bonds, or approximately 12 carbon-carbon bonds. Where the macrocycle-forming linker spans approximately 3 turns of an α-helix, the length is equal to approximately 14 carbon-carbon bonds to 22 carbon-carbon bonds, approximately 16 carbon-carbon bonds to 20 carbon-carbon bonds, or approximately 18 carbon-carbon bonds. Where the macrocycle-forming linker spans approximately 4 turns of an α-helix, the length is equal to approximately 20 carbon-carbon bonds to 28 carbon-carbon bonds, approximately 22 carbon-carbon bonds to 26 carbon-carbon bonds, or approximately 24 carbon-carbon bonds. Where the macrocycle-forming linker spans approximately 5 turns of an α-helix, the length is equal to approximately 26 carbon-carbon bonds to 34 carbon-carbon bonds, approximately 28 carbon-carbon bonds to 32 carbon-carbon bonds, or approximately 30 carbon-carbon bonds. Where the macrocycle-forming linker spans approximately 1 turn of an α-helix, the linkage contains approximately 4 atoms to 12 atoms, approximately 6 atoms to 10 atoms, or approximately 8 atoms. Where the macrocycle-forming linker spans approximately 2 turns of the α-helix, the linkage contains approximately 7 atoms to 15 atoms, approximately 9 atoms to 13 atoms, or approximately 11 atoms. Where the macrocycle-forming linker spans approximately 3 turns of the α-helix, the linkage contains approximately 13 atoms to 21 atoms, approximately 15 atoms to 19 atoms, or approximately 17 atoms. Where the macrocycle-forming linker spans approximately 4 turns of the α-helix, the linkage contains approximately 19 atoms to 27 atoms, approximately 21 atoms to 25 atoms, or approximately 23 atoms. Where the macrocycle-forming linker spans approximately 5 turns of the α-helix, the linkage contains approximately 25 atoms to 33 atoms, approximately 27 atoms to 31 atoms, or approximately 29 atoms. Where the macrocycle-forming linker spans approximately 1 turn of the α-helix, the resulting macrocycle forms a ring containing approximately 17 members to 25 members, approximately 19 members to 23 members, or approximately 21 members. Where the macrocycle-forming linker spans approximately 2 turns of the α-helix, the resulting macrocycle forms a ring containing approximately 29 members to 37 members, approximately 31 members to 35 members, or approximately 33 members. Where the macrocycle-forming linker spans approximately 3 turns of the α-helix, the resulting macrocycle forms a ring containing approximately 44 members to 52 members, approximately 46 members to 50 members, or approximately 48 members. Where the macrocycle-forming linker spans approximately 4 turns of the α-helix, the resulting macrocycle forms a ring containing approximately 59 members to 67 members, approximately 61 members to 65 members, or approximately 63 members. Where the macrocycle-forming linker spans approximately 5 turns of the α-helix, the resulting macrocycle forms a ring containing approximately 74 members to 82 members, approximately 76 members to 80 members, or approximately 78 members.
In some embodiments, L is a macrocycle-forming linker of the formula
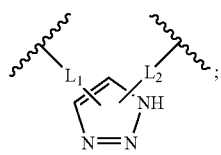
Exemplary embodiments of such macrocycle-forming linkers L are shown below.
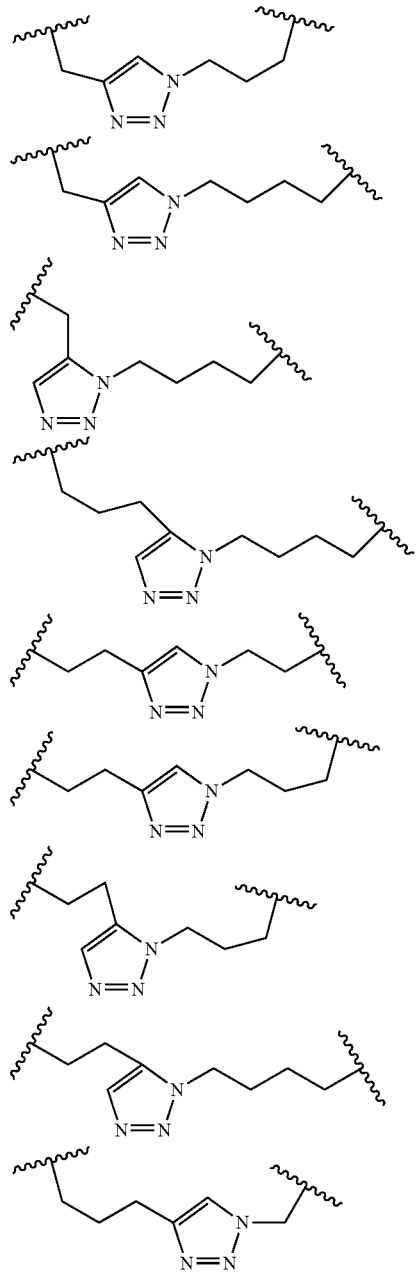
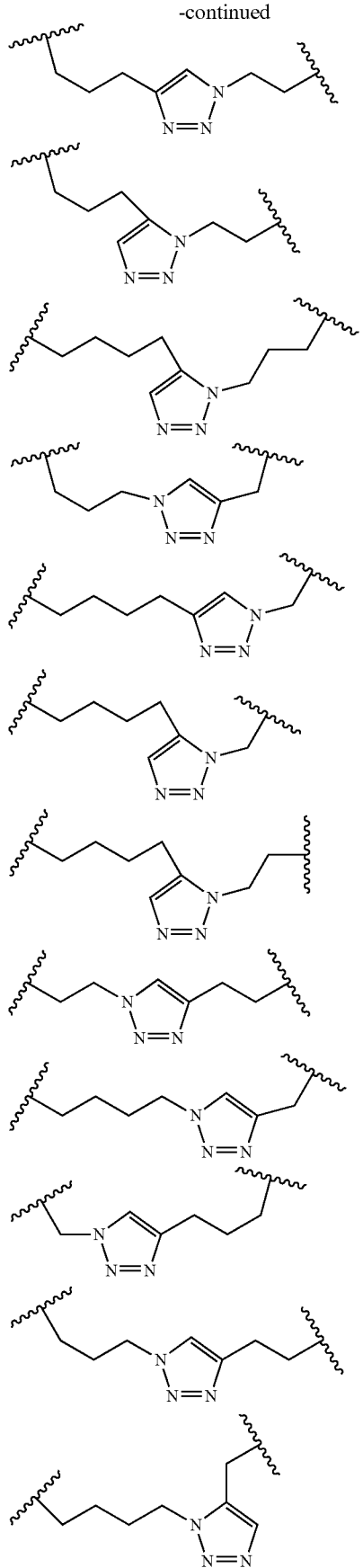

47
-continued
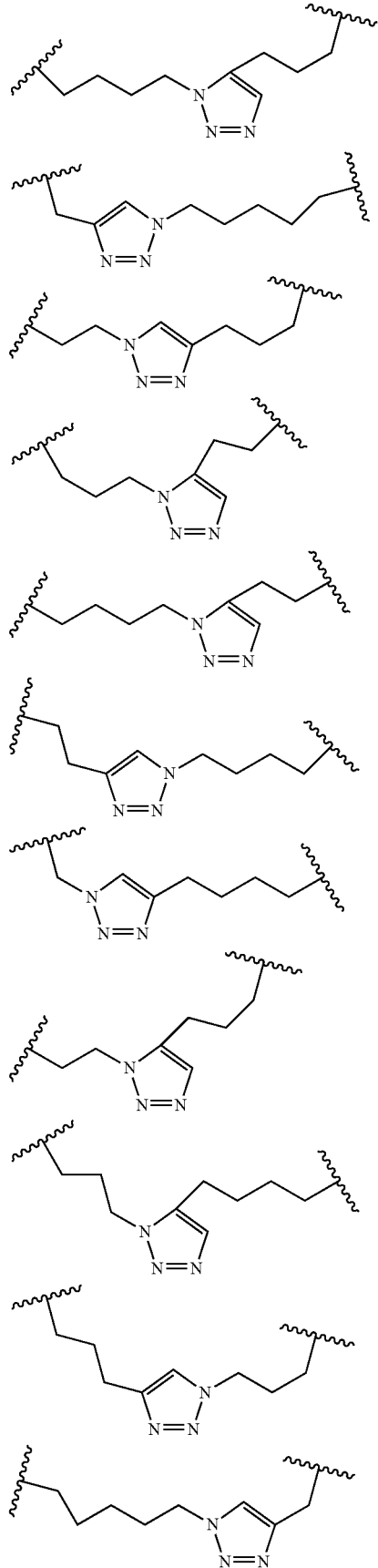
48
-continued
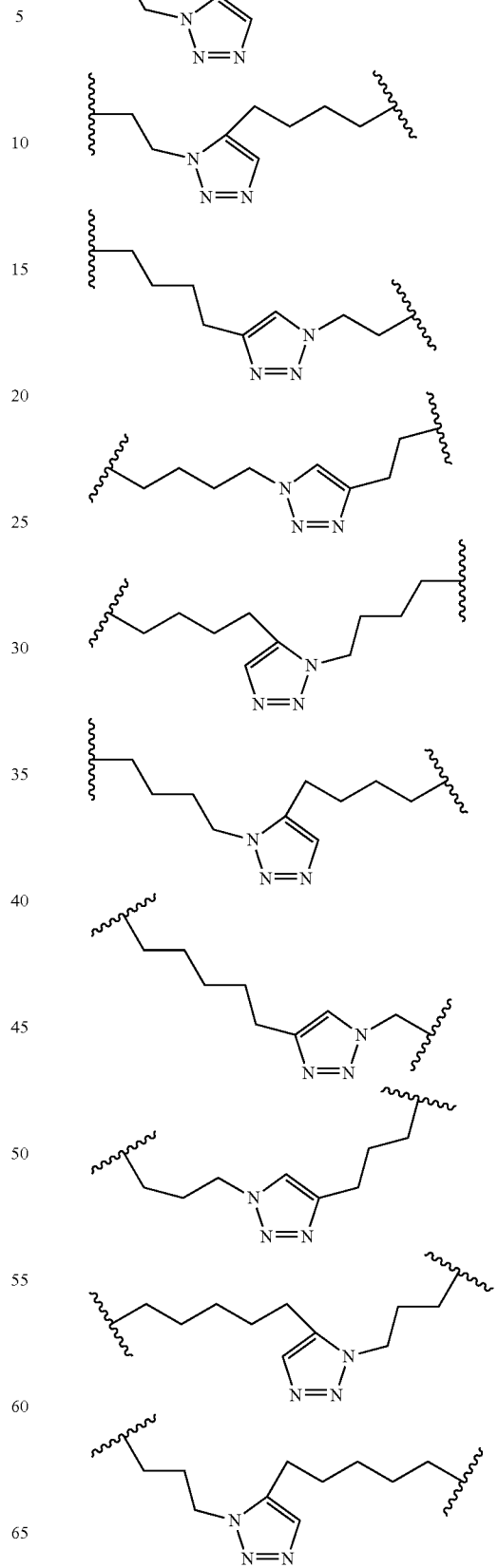

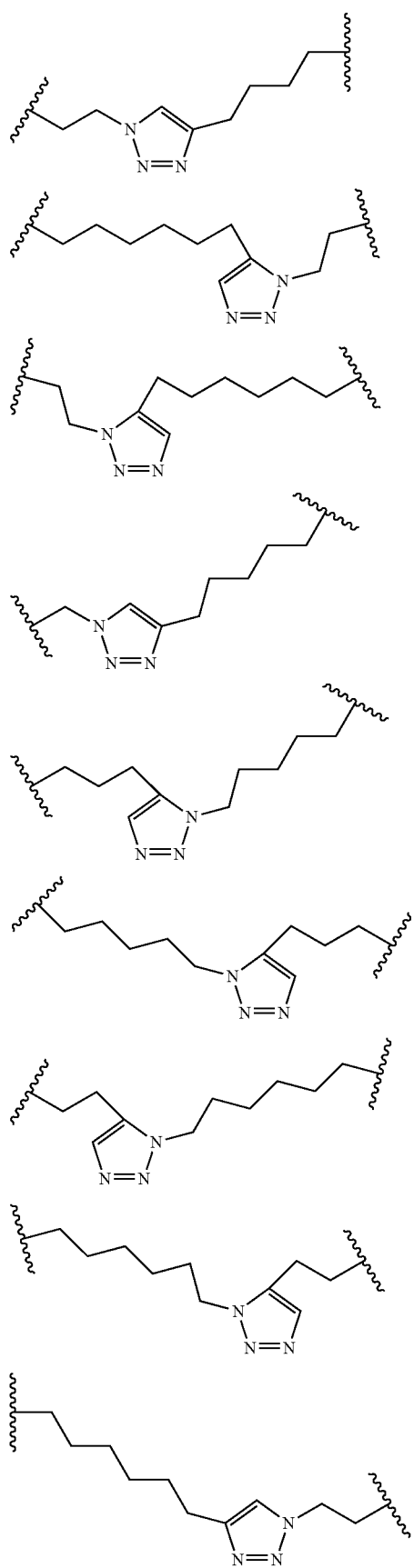
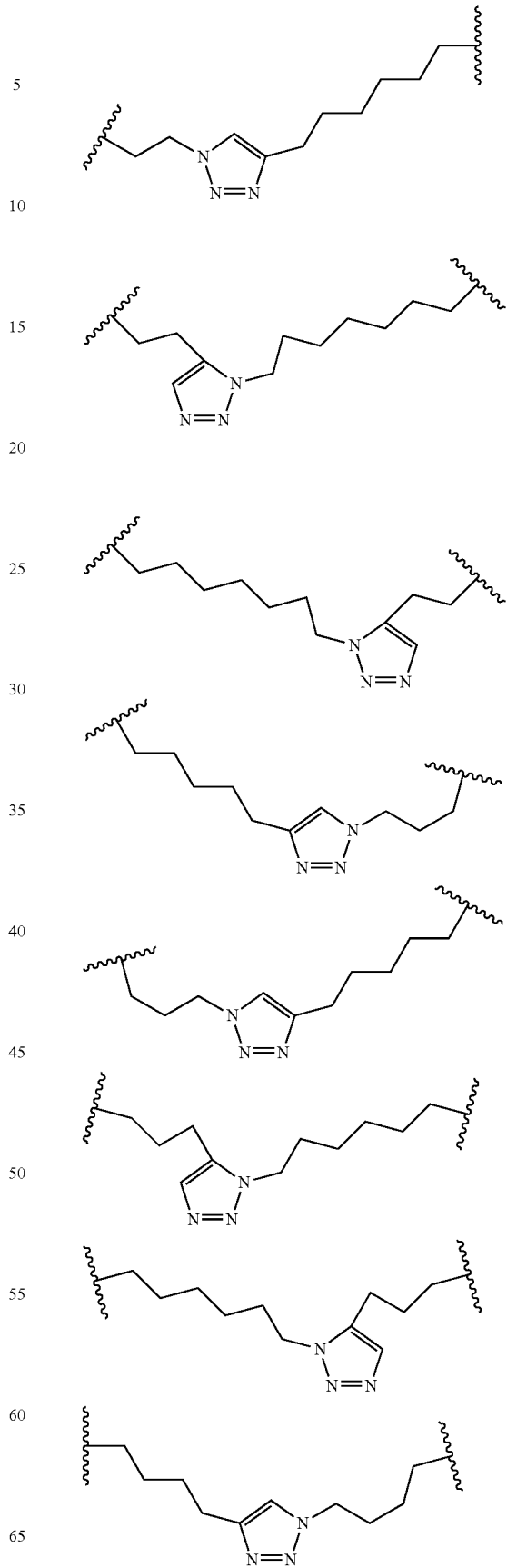

51
-continued
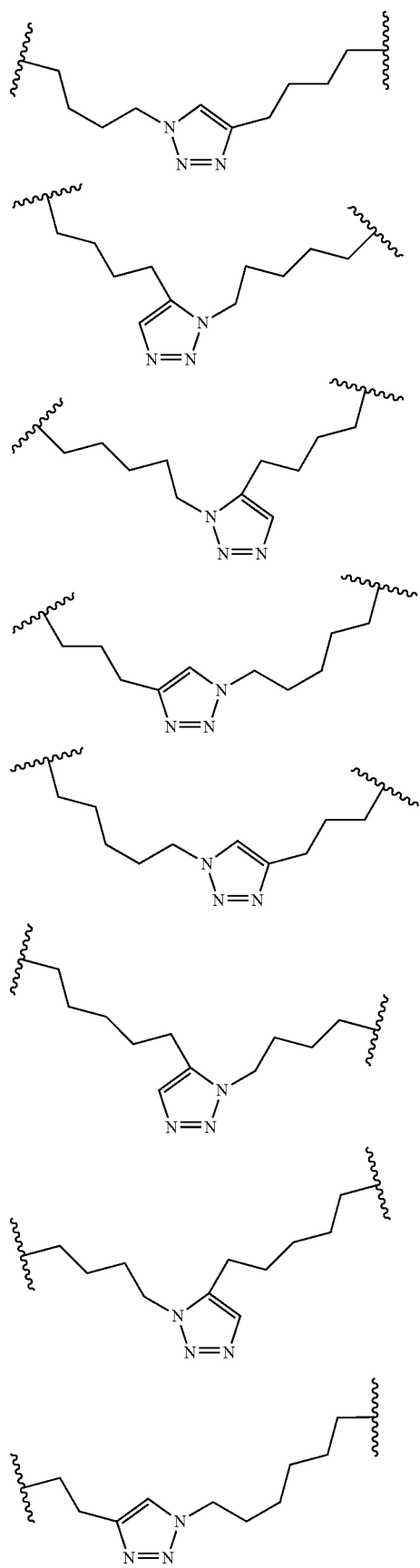
52
-continued
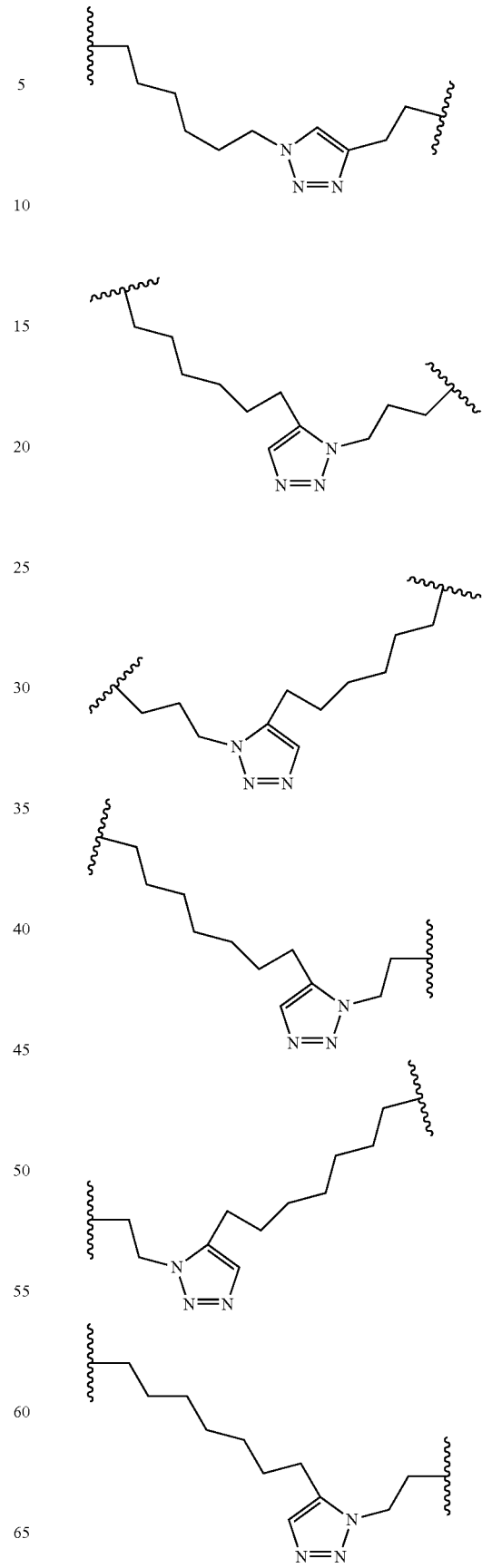

-continued

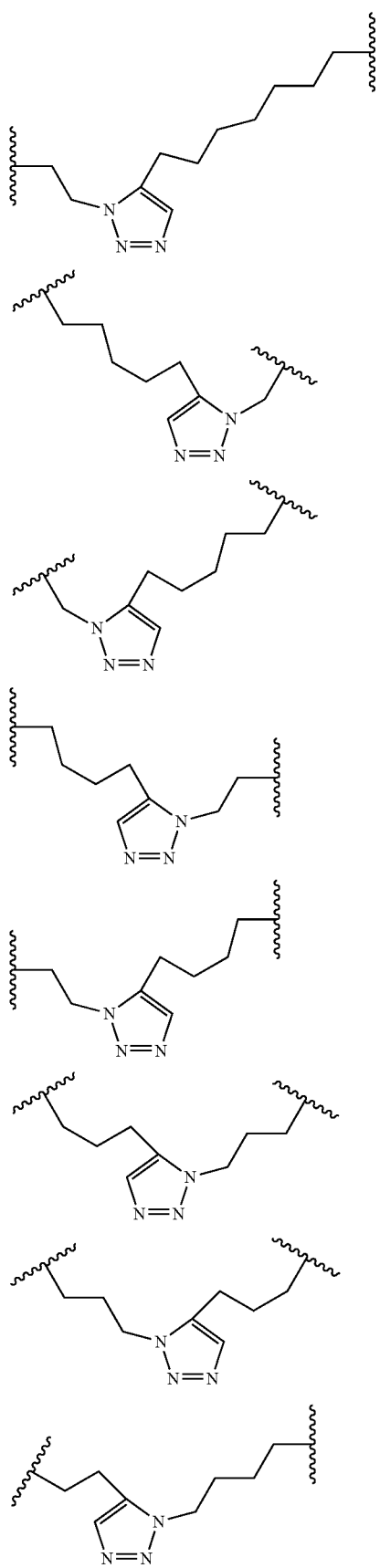

-continued

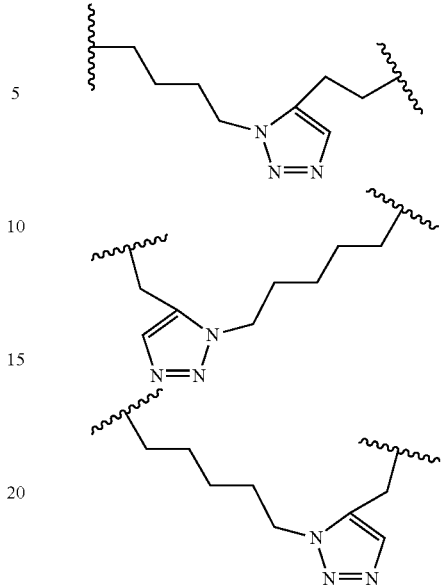

In other embodiments, the invention provides peptidomimetic macrocycles of Formula (II) or (IIa):

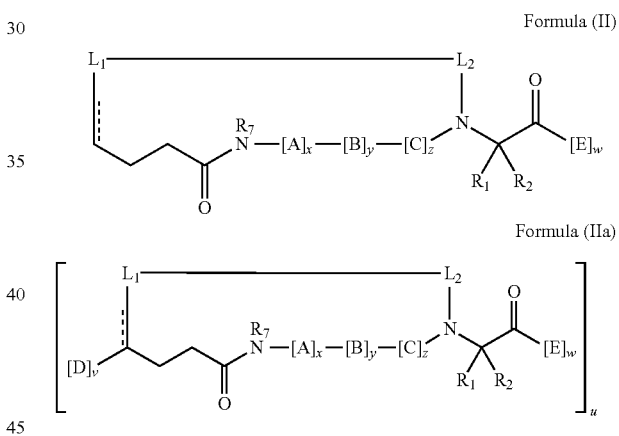

Formula (II)

Formula (IIa)

wherein:
each A, C, D, and E is independently an amino acid;
B is an amino acid,

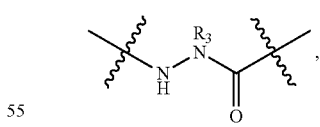

[—NH-$L_3$-CO—], [—NH-$L_3$-$SO_2$—], or [—NH-$L_3$-];
$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;
$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;
$L_1$ and $L_2$ are independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;

and wherein A, B, C, D, and E, taken together with the crosslinked amino acids connected by the macrocycle-forming linker -L$_1$-L$_2$-, form the amino acid sequence of the peptidomimetic macrocycle which is at least about 60%, 65%, 70%, 75%, 80%, 85%, 90%, 95%, 96%, 97%, 98%, or 99% identical to GHRH 1-44, GHRH 1-29 and/or to an amino acid sequence chosen from the group consisting of the amino acid sequences in Table 1, 2 or 4;

each R$_4$ is alkylene, alkenylene, alkynylene, heteroalkylene, cycloalkylene, heterocycloalkylene, arylene, or heteroarylene;

each K is O, S, SO, SO$_2$, CO, CO$_2$, or CONR$_3$;

each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope or a therapeutic agent;

each R$_6$ is independently —H, alkyl, alkenyl, alkynyl, arylalkyl, cycloalkylalkyl, heterocycloalkyl, a fluorescent moiety, a radioisotope or a therapeutic agent;

R$_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$;

v and w are independently integers from 1-1000, for example 1-100;

u, x, y and z are independently integers from 0-10, for example u is 1-3; and n is an integer from 1-5.

In one example, at least one of R$_1$ and R$_2$ is alkyl, unsubstituted or substituted with halo-. In another example, both R$_1$ and R$_2$ are independently alkyl, unsubstituted or substituted with halo-. In some embodiments, at least one of R$_1$ and R$_2$ is methyl. In other embodiments, R$_1$ and R$_2$ are methyl.

In some embodiments of the invention, the sum of x+y+z is at least 1. In other embodiments of the invention, the sum of x+y+z is at least 2. In other embodiments of the invention, the sum of x+y+z is 1, 2, 3, 4, 5, 6, 7, 8, 9 or 10. Each occurrence of A, B, C, D or E in a macrocycle or macrocycle precursor of the invention is independently selected. For example, a sequence represented by the formula [A]$_x$, when x is 3, encompasses embodiments where the amino acids are not identical, e.g. Gln-Asp-Ala as well as embodiments where the amino acids are identical, e.g. Gln-Gln-Gln. This applies for any value of x, y, or z in the indicated ranges.

In some embodiments, the peptidomimetic macrocycle of the invention comprises a secondary structure which is an α-helix and R$_8$ is —H, allowing intrahelical hydrogen bonding. In some embodiments, at least one of A, B, C, D or E is an α,α-disubstituted amino acid. In one example, B is an α,α-disubstituted amino acid. For instance, at least one of A, B, C, D or E is 2-aminoisobutyric acid. In other embodiments, at least one of A, B, C, D or E is

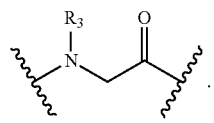

In other embodiments, the length of the macrocycle-forming linker -L$_1$-L$_2$- as measured from a first Cα to a second Cα is selected to stabilize a desired secondary peptide structure, such as an α-helix formed by residues of the peptidomimetic macrocycle including, but not necessarily limited to, those between the first Cα to a second Cα.

Exemplary embodiments of the macrocycle-forming linker -L$_1$-L$_2$- are shown below.

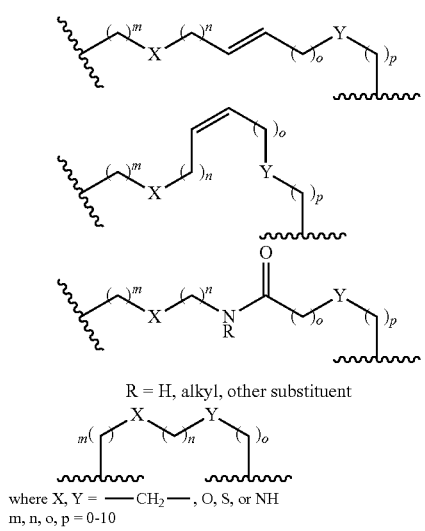

R = H, alkyl, other substituent where X, Y = —CH$_2$—, O, S, or NH
m, n, o, p = 0-10

Examples of peptidomimetic macrocycles of Formula (II) are shown in Table 4 and include SP-85, SP-86, SP-87, SP-88, SP-91, and SP-92.

Preparation of Peptidomimetic Macrocycles

Peptidomimetic macrocycles of the invention may be prepared by any of a variety of methods known in the art. For example, any of the residues indicated by "X", "Z" or "XX" in Tables 1, 2 or 4 may be substituted with a residue capable of forming a crosslinker with a second residue in the same molecule or a precursor of such a residue.

Various methods to effect formation of peptidomimetic macrocycles are known in the art. For example, the preparation of peptidomimetic macrocycles of Formula I is described in Schafmeister et al., J. Am. Chem. Soc. 122: 5891-5892 (2000); Schafmeister & Verdine, J. Am. Chem. Soc. 122:5891 (2005); Walensky et al., Science 305:1466-1470 (2004); U.S. Pat. No. 7,192,713 and PCT application WO 2008/121767. The α,α-disubstituted amino acids and amino acid precursors disclosed in the cited references may be employed in synthesis of the peptidomimetic macrocycle precursor polypeptides. For example, the "S5-olefin amino acid" is (S)-α-(2'-pentenyl) alanine and the "R8 olefin amino acid" is (R)-α-(2'-octenyl) alanine. Following incorporation of such amino acids into precursor polypeptides, the terminal olefins are reacted with a metathesis catalyst, leading to the formation of the peptidomimetic macrocycle. In various embodiments, the following amino acids may be employed in the synthesis of the peptidomimetic macrocycle:

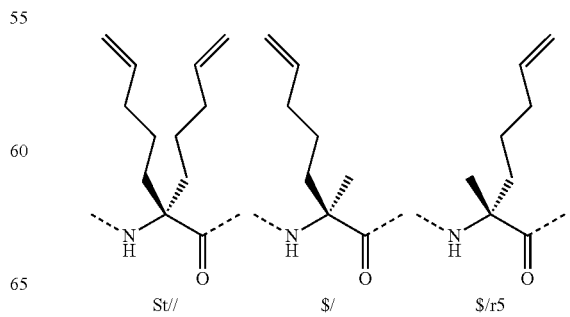

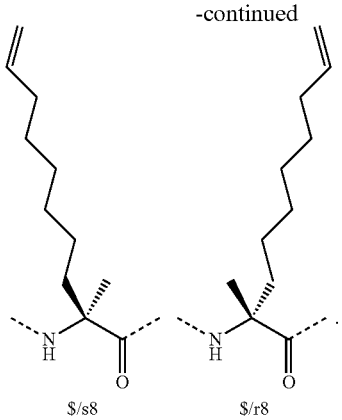

$/s8  $/r8

In some embodiments, x+y+z is 3, and A, B and C are independently natural or non-natural amino acids. In other embodiments, x+y+z is 6, and A, B and C are independently natural or non-natural amino acids.

In some embodiments, the contacting step is performed in a solvent selected from the group consisting of protic solvent, aqueous solvent, organic solvent, and mixtures thereof. For example, the solvent may be chosen from the group consisting of $H_2O$, THF, THF/$H_2O$, tBuOH/$H_2O$, DMF, DIPEA, $CH_3CN$ or $CH_2Cl_2$, $ClCH_2CH_2Cl$ or a mixture thereof. The solvent may be a solvent which favors helix formation.

Alternative but equivalent protecting groups, leaving groups or reagents are substituted, and certain of the synthetic steps are performed in alternative sequences or orders to produce the desired compounds. Synthetic chemistry transformations and protecting group methodologies (protection and deprotection) useful in synthesizing the compounds described herein include, for example, those such as described in Larock, *Comprehensive Organic Transformations*, VCH Publishers (1989); Greene and Wuts, *Protective Groups in Organic Synthesis*, 2d. Ed., John Wiley and Sons (1991); Fieser and Fieser, *Fieser and Fieser's Reagents for Organic Synthesis*, John Wiley and Sons (1994); and Paquette, ed., *Encyclopedia of Reagents for Organic Synthesis*, John Wiley and Sons (1995), and subsequent editions thereof.

The peptidomimetic macrocycles disclosed herein are made, for example, by chemical synthesis methods, such as described in Fields et al., Chapter 3 in *Synthetic Peptides: A User's Guide*, ed. Grant, W. H. Freeman & Co., New York, N. Y., 1992, p. 77. Hence, for example, peptides are synthesized using the automated Merrifield techniques of solid phase synthesis with the amine protected by either tBoc or Fmoc chemistry using side chain protected amino acids on, for example, an automated peptide synthesizer (e.g., Applied Biosystems (Foster City, Calif.), Model 430A, 431, or 433).

One manner of producing the peptidomimetic precursors and peptidomimetic macrocycles described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups.

Longer peptidomimetic precursors are produced, for example, by conjoining individual synthetic peptides using native chemical ligation. Alternatively, the longer synthetic peptides are biosynthesized by well known recombinant DNA and protein expression techniques. Such techniques are provided in well-known standard manuals with detailed protocols. To construct a gene encoding a peptidomimetic precursor of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptidomimetic precursors are made, for example, in a high-throughput, combinatorial fashion using, for example, a high-throughput polychannel combinatorial synthesizer (e.g., Thuramed TETRAS multichannel peptide synthesizer from CreoSalus, Louisville, Ky. or Model Apex 396 multichannel peptide synthesizer from AAPPTEC, Inc., Louisville, Ky.).

In some embodiments, the peptidomimetic macrocyles of the invention comprise triazole macrocycle-forming linkers. For example, the synthesis of such peptidomimetic macrocycles involves a multi-step process that features the synthesis of a peptidomimetic precursor containing an azide moiety and an alkyne moiety; followed by contacting the peptidomimetic precursor with a macrocyclization reagent to generate a triazole-linked peptidomimetic macrocycle. Such a process is described, for example, in U.S. application Ser. No. 12/037,041, filed on Feb. 25, 2008. Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in *Chemistry and Biochemistry of the Amino Acids*, edited by G. C. Barrett, Chapman and Hall, 1985.

In some embodiments, an azide is linked to the α-carbon of a residue and an alkyne is attached to the α-carbon of another residue. In some embodiments, the azide moieties are azido-analogs of amino acids L-lysine, D-lysine, alpha-methyl-L-lysine, alpha-methyl-D-lysine, L-ornithine, D-ornithine, alpha-methyl-L-ornithine or alpha-methyl-D-ornithine. In another embodiment, the alkyne moiety is L-propargylglycine. In yet other embodiments, the alkyne moiety is an amino acid selected from the group consisting of L-propargylglycine, D-propargylglycine, (S)-2-amino-2-methyl-4-pentynoic acid, (R)-2-amino-2-methyl-4-pentynoic acid, (S)-2-amino-2-methyl-5-hexynoic acid, (R)-2-amino-2-methyl-5-hexynoic acid, (S)-2-amino-2-methyl-6-heptynoic acid, (R)-2-amino-2-methyl-6-heptynoic acid, (S)-2-amino-2-methyl-7-octynoic acid, (R)-2-amino-2-methyl-7-octynoic acid, (S)-2-amino-2-methyl-8-nonynoic acid and (R)-2-amino-2-methyl-8-nonynoic acid.

The following synthetic schemes are provided solely to illustrate the present invention and are not intended to limit the scope of the invention, as described herein. To simplify the drawings, the illustrative schemes depict azido amino acid analogs ε-azido-α-methyl-L-lysine and ε-azido-α-methyl-D-lysine, and alkyne amino acid analogs L-propargylglycine, (S)-2-amino-2-methyl-4-pentynoic acid, and (S)-2-amino-2-methyl-6-heptynoic acid. Thus, in the following synthetic schemes, each $R_1$, $R_2$, $R_7$ and $R_8$ is —H; each $L_1$ is —$(CH_2)_4$—; and each $L_2$ is —$(CH_2)$—. However, as noted throughout the detailed description above, many other amino acid analogs can be employed in which $R_1$, $R_2$, $R_7$, $R_8$, $L_1$ and $L_2$ can be independently selected from the various structures disclosed herein.
Synthetic Scheme 1:
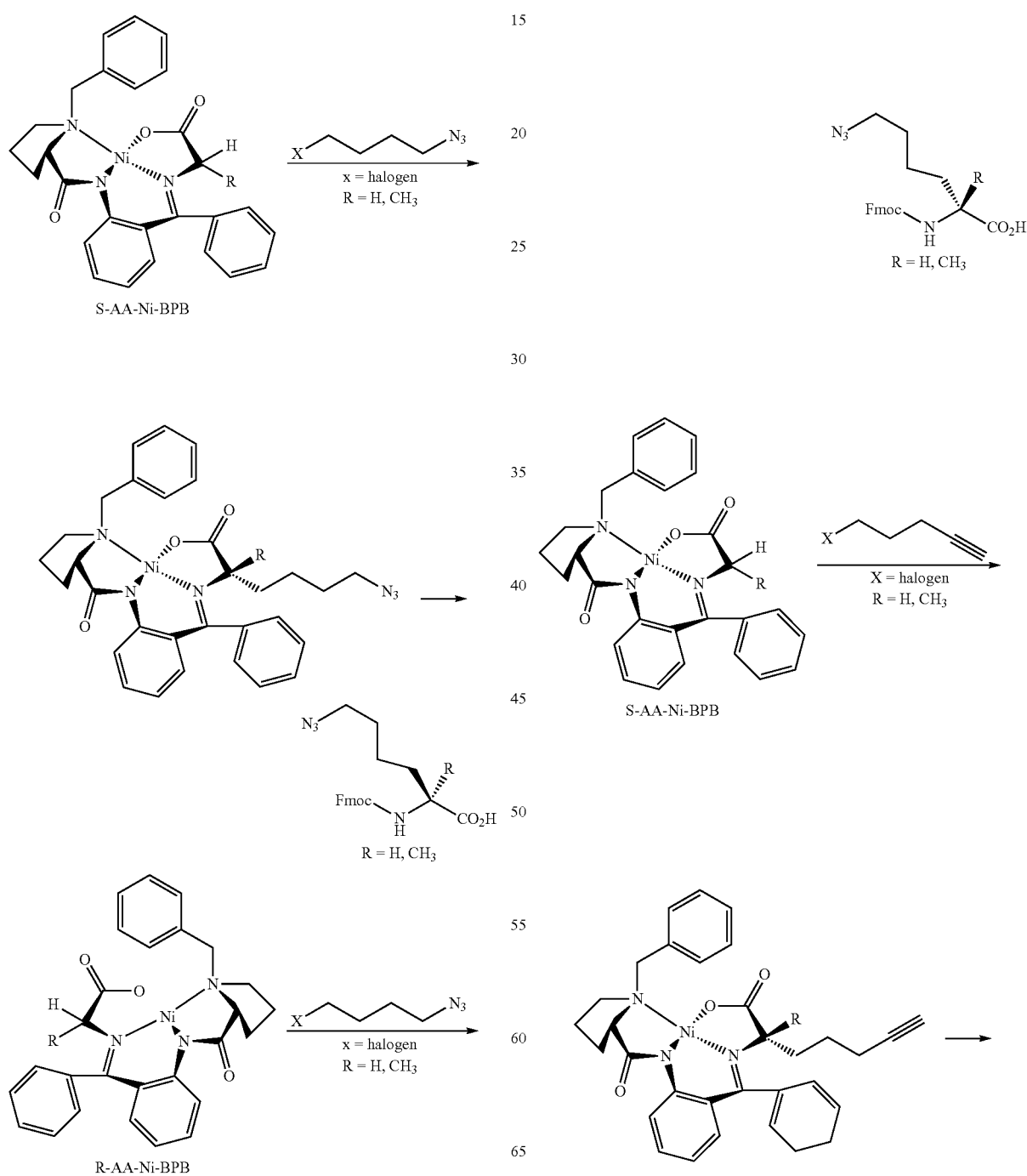

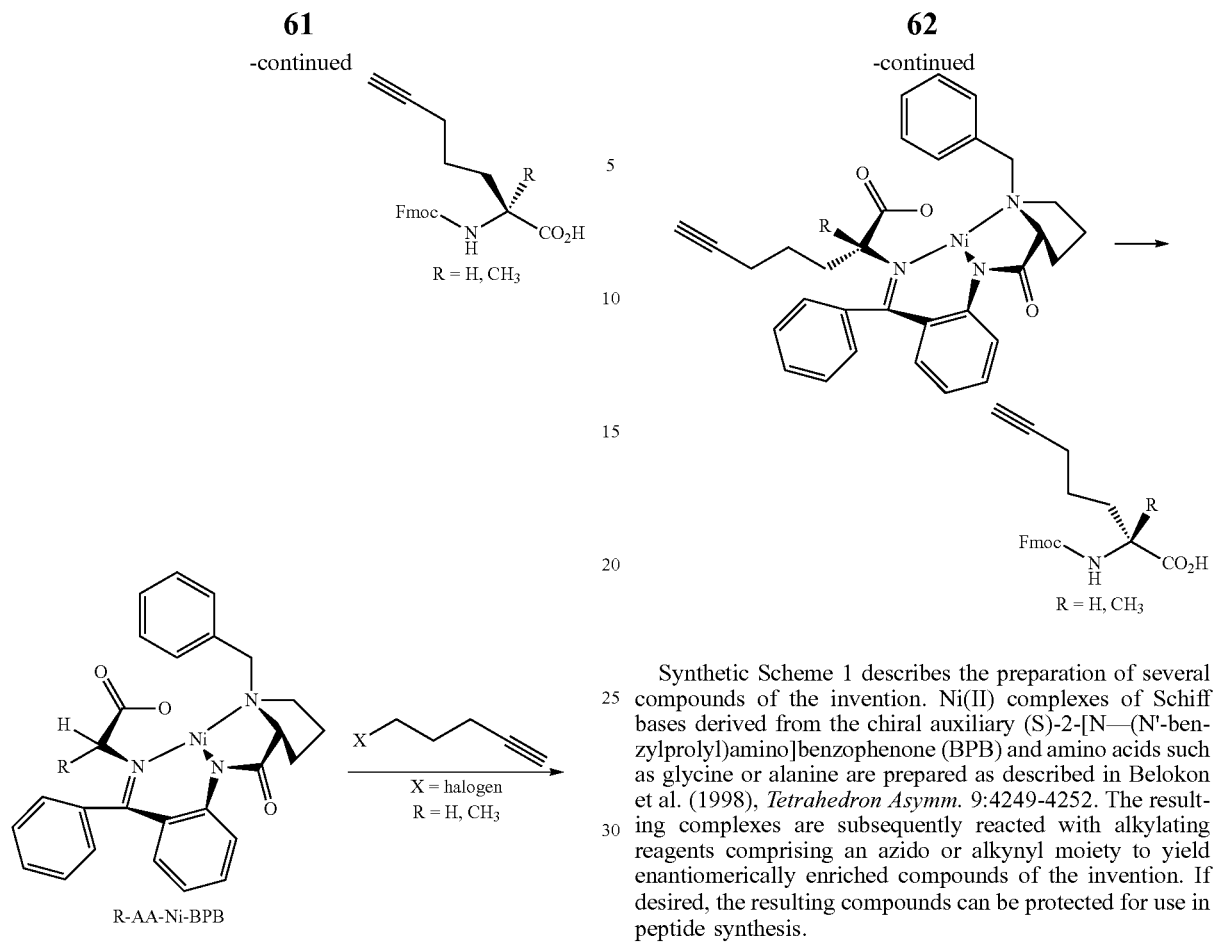

Synthetic Scheme 1 describes the preparation of several compounds of the invention. Ni(II) complexes of Schiff bases derived from the chiral auxiliary (S)-2-[N—(N'-benzylprolyl)amino]benzophenone (BPB) and amino acids such as glycine or alanine are prepared as described in Belokon et al. (1998), *Tetrahedron Asymm.* 9:4249-4252. The resulting complexes are subsequently reacted with alkylating reagents comprising an azido or alkynyl moiety to yield enantiomerically enriched compounds of the invention. If desired, the resulting compounds can be protected for use in peptide synthesis.

Synthetic Scheme 2:

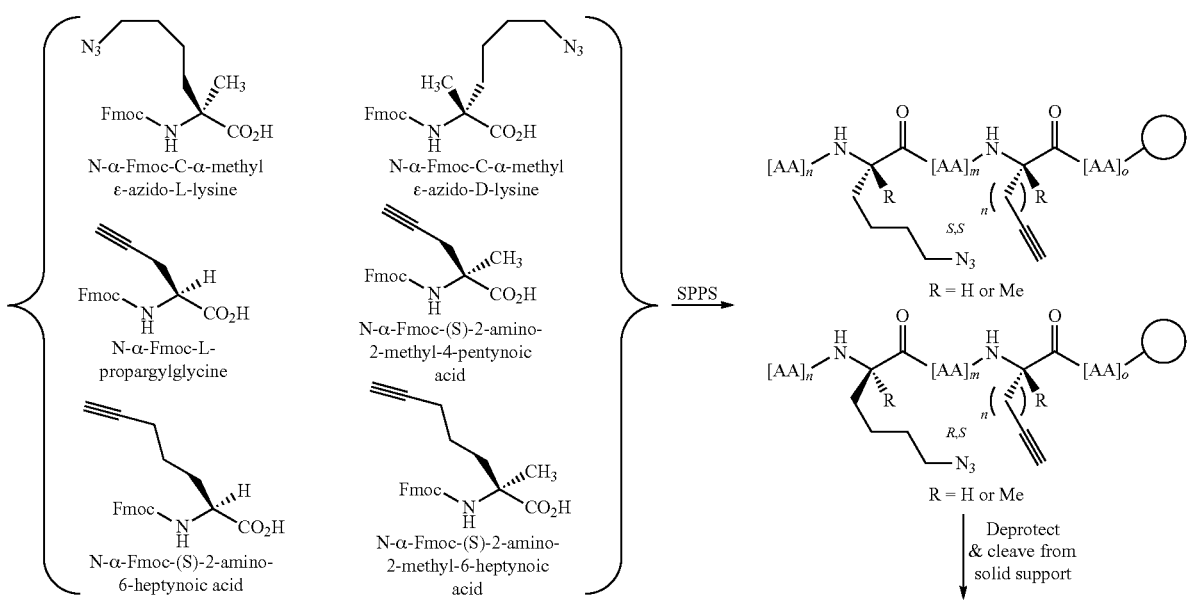

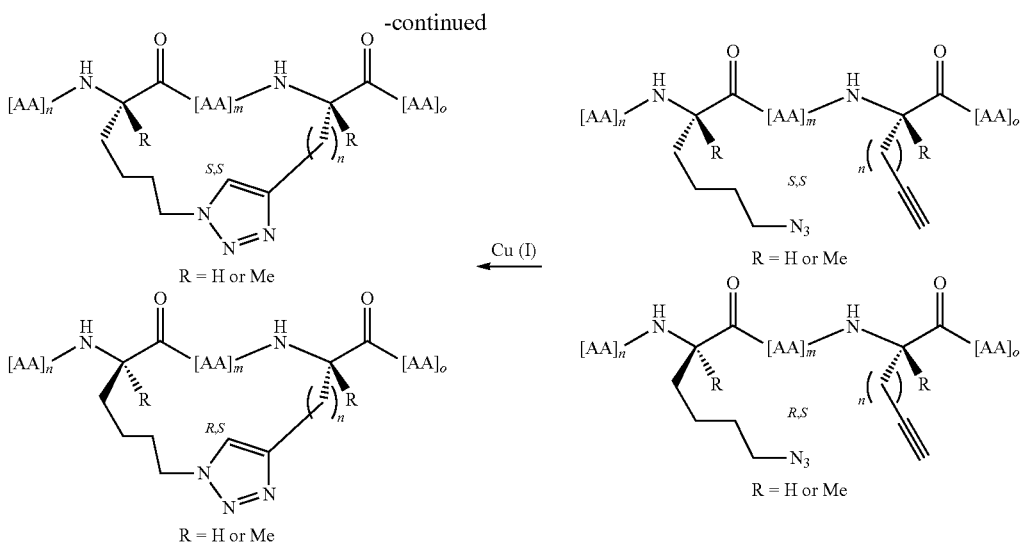

In the general method for the synthesis of peptidomimetic macrocycles shown in Synthetic Scheme 2, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ϵ-azido-L-lysine, and N-methyl-ϵ-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization reagent such as a Cu(I) in organic or aqueous solutions (Rostovtsev et al. (2002), Angew. Chem. Int. Ed. 41:2596-2599; Tornoe et al. (2002), J. Org. Chem. 67:3057-3064; Deiters et al. (2003), J. Am. Chem. Soc. 125:11782-11783; Punna et al. (2005), Angew. Chem. Int. Ed. 44:2215-2220). In one embodiment, the triazole forming reaction is performed under conditions that favor α-helix formation. In one embodiment, the macrocyclization step is performed in a solvent chosen from the group consisting of H₂O, THF, CH₃CN, DMF, DIPEA, tBuOH or a mixture thereof. In another embodiment, the macrocyclization step is performed in DMF. In some embodiments, the macrocyclization step is performed in a buffered aqueous or partially aqueous solvent.

Synthetic Scheme 3:

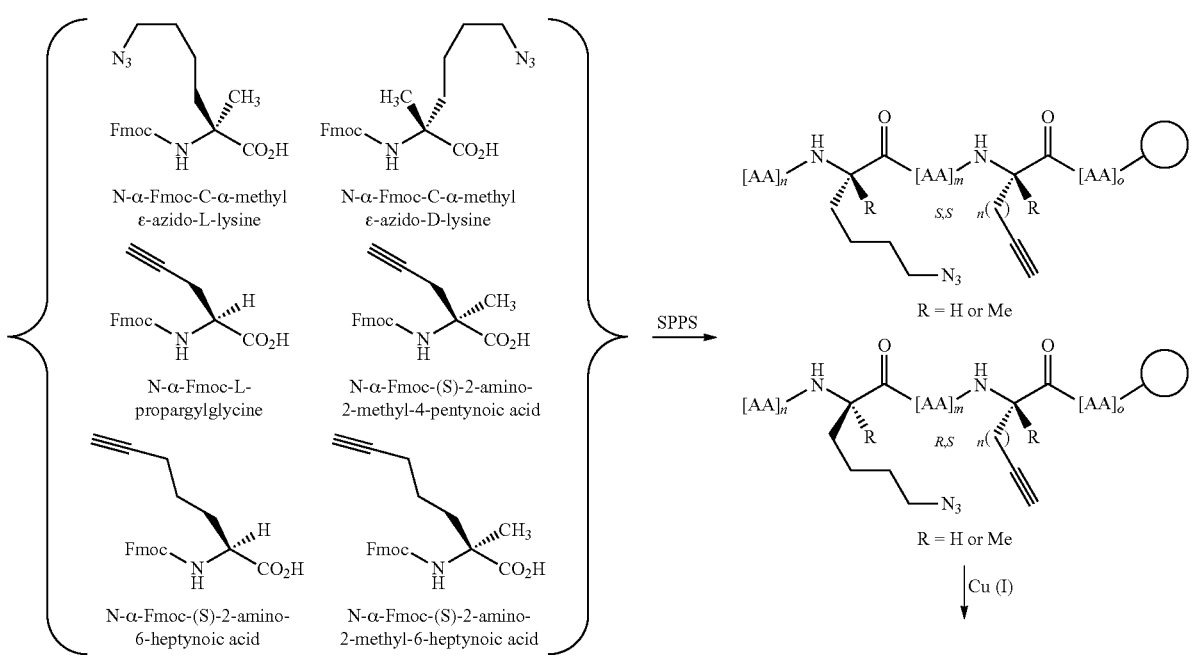

-continued

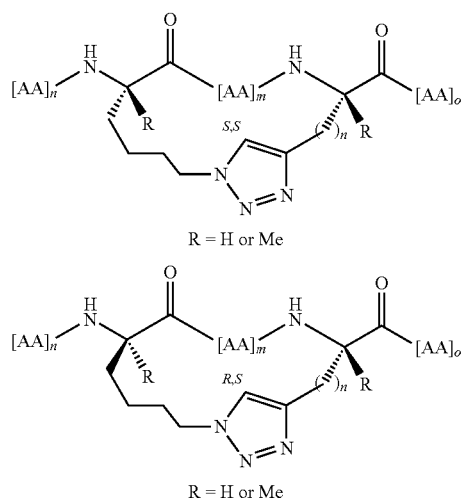

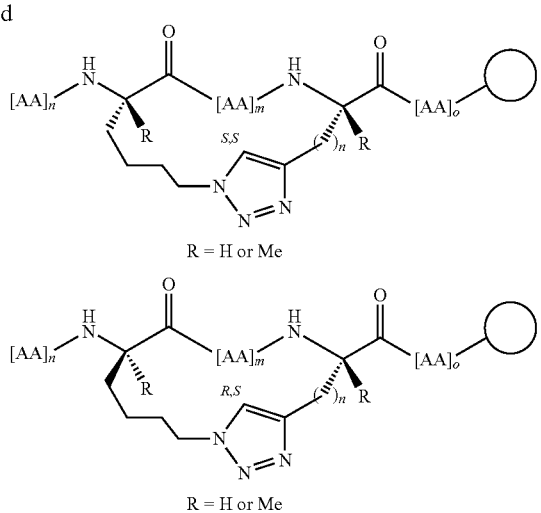

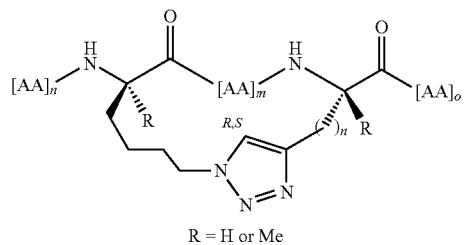

In the general method for the synthesis of peptidomimetic macrocycles shown in Synthetic Scheme 3, the peptidomimetic precursor contains an azide moiety and an alkyne moiety and is synthesized by solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization reagent such as a Cu(I) reagent on the resin as a crude mixture (Rostovtsev et al. (2002), Angew. Chem. Int. Ed. 41:2596-2599; Tornoe et al. (2002), J. Org. Chem. 67:3057-3064; Deiters et al. (2003), J. Am. Chem. Soc. 125:11782-11783; Punna et al. (2005), Angew. Chem. Int. Ed. 44:2215-2220). The resultant triazole-containing peptidomimetic macrocycle is then deprotected and cleaved from the solid-phase resin by standard conditions (e.g., strong acid such as 95% TFA). In some embodiments, the macrocyclization step is performed in a solvent chosen from the group consisting of $CH_2Cl_2$, $ClCH_2CH_2Cl$, DMF, THF, NMP, DIPEA, 2,6-lutidine, pyridine, DMSO, $H_2O$ or a mixture thereof. In some embodiments, the macrocyclization step is performed in a buffered aqueous or partially aqueous solvent.

Synthetic Scheme 4:

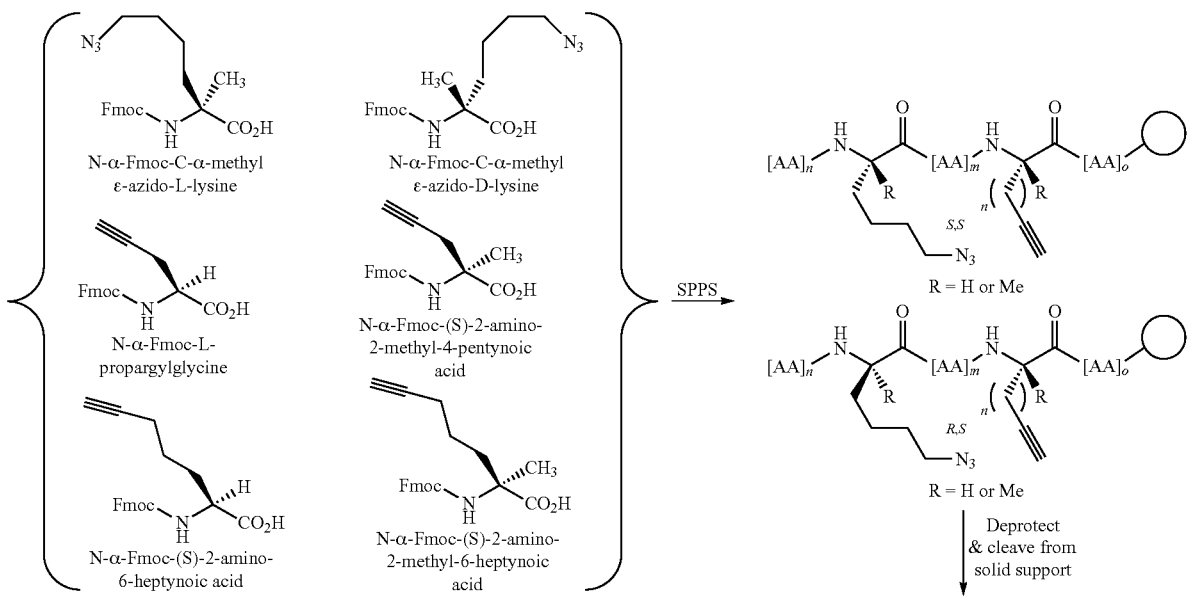

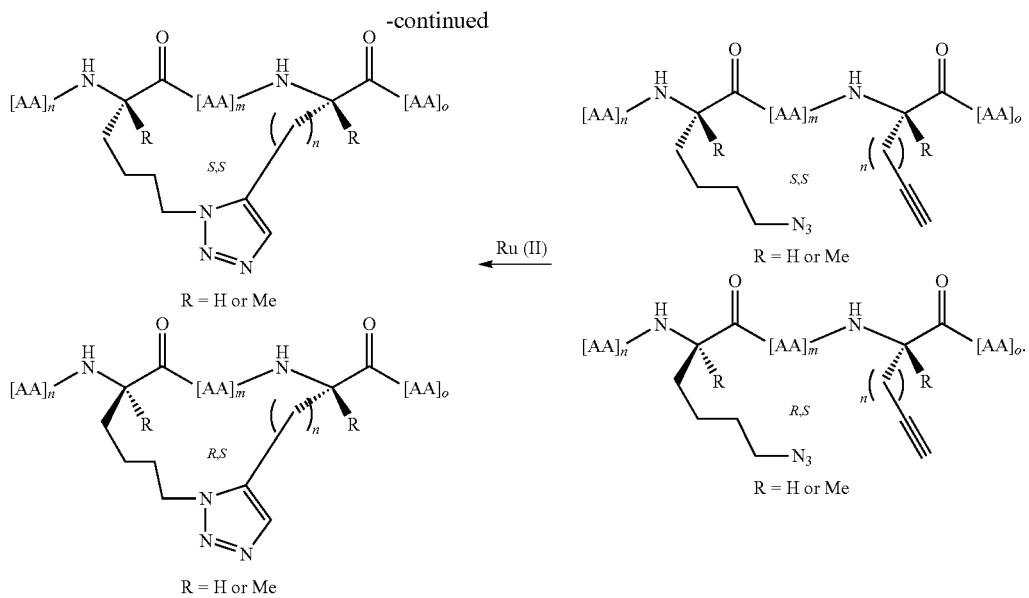

In the general method for the synthesis of peptidomimetic macrocycles shown in Synthetic Scheme 4, the peptidomimetic precursor contains an azide moiety and an alkyne moiety and is synthesized by solution-phase or solid-phase peptide synthesis (SPPS) using the commercially available amino acid N-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is then deprotected and cleaved from the solid-phase resin by standard conditions (e.g., strong acid such as 95% TFA). The peptidomimetic precursor is reacted as a crude mixture or is purified prior to reaction with a macrocyclization reagent such as a Ru(II) reagents, for example Cp*RuCl(PPh$_3$)$_2$ or [Cp*RuCl]$_4$ (Rasmussen et al. (2007), *Org. Lett.* 9:5337-5339; Zhang et al. (2005), *J. Am. Chem. Soc.* 127:15998-15999). In some embodiments, the macrocyclization step is performed in a solvent chosen from the group consisting of DMF, CH$_3$CN and THF.

Synthetic Scheme 5:

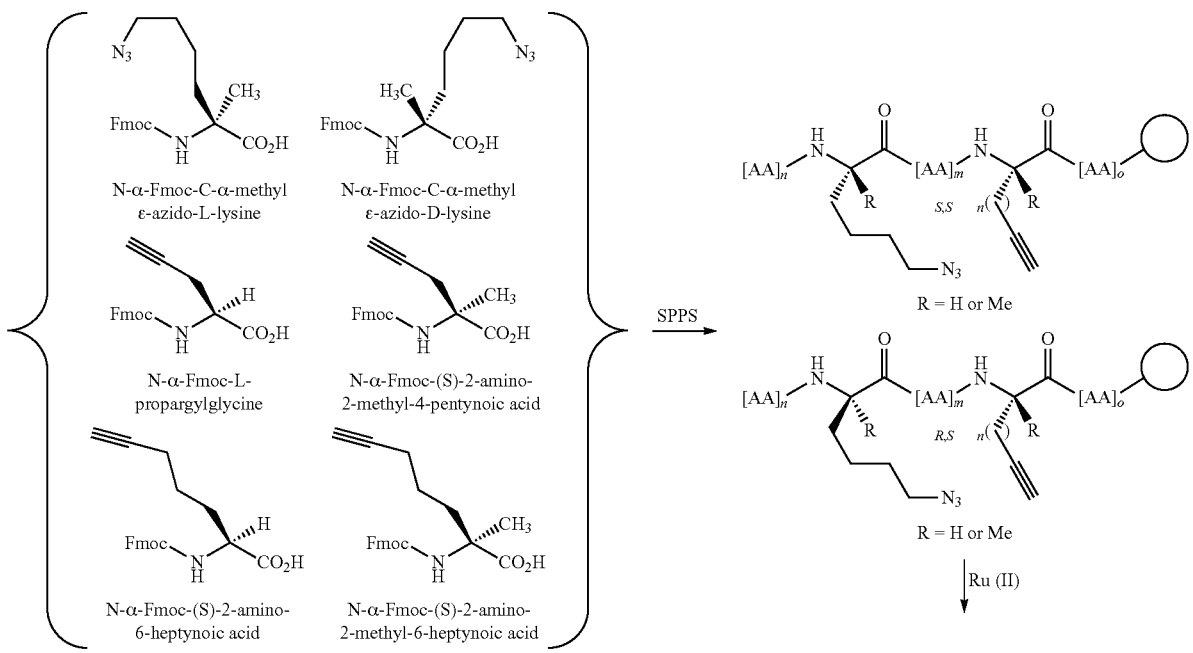

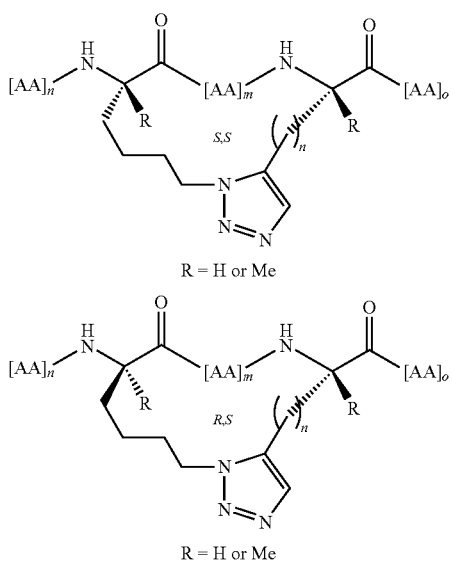

R = H or Me

R = H or Me

Deprotect & cleave from solid support

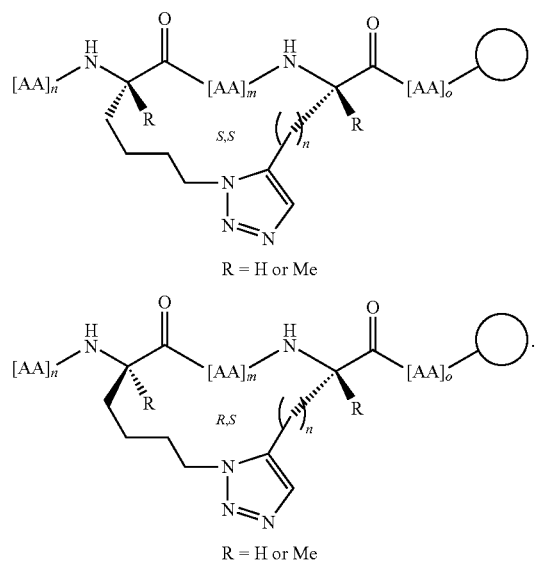

R = H or Me

R = H or Me

In the general method for the synthesis of peptidomimetic macrocycles shown in Synthetic Scheme 5, the peptidomimetic precursor contains an azide moiety and an alkyne moiety and is synthesized by solid-phase peptide synthesis (SPPS) using the commercially available amino acidN-α-Fmoc-L-propargylglycine and the N-α-Fmoc-protected forms of the amino acids (S)-2-amino-2-methyl-4-pentynoic acid, (S)-2-amino-6-heptynoic acid, (S)-2-amino-2-methyl-6-heptynoic acid, N-methyl-ε-azido-L-lysine, and N-methyl-ε-azido-D-lysine. The peptidomimetic precursor is reacted with a macrocyclization reagent such as a Ru(II) reagent on the resin as a crude mixture. For example, the reagent can be Cp*RuCl(PPh$_3$)$_2$ or [Cp*RuCl]$_4$ (Rasmussen et al. (2007), *Org. Lett.* 9:5337-5339; Zhang et al. (2005), *J. Am. Chem. Soc.* 127:15998-15999). In some embodiments, the macrocyclization step is performed in a solvent chosen from the group consisting of CH$_2$Cl$_2$, ClCH$_2$CH$_2$Cl, CH$_3$CN, DMF, and THF.

The present invention contemplates the use of non-naturally-occurring amino acids and amino acid analogs in the synthesis of the peptidomimetic macrocycles described herein. Any amino acid or amino acid analog amenable to the synthetic methods employed for the synthesis of stable triazole containing peptidomimetic macrocycles can be used in the present invention. For example, L-propargylglycine is contemplated as a useful amino acid in the present invention. However, other alkyne-containing amino acids that contain a different amino acid side chain are also useful in the invention. For example, L-propargylglycine contains one methylene unit between the α-carbon of the amino acid and the alkyne of the amino acid side chain. The invention also contemplates the use of amino acids with multiple methylene units between the α-carbon and the alkyne. Also, the azido-analogs of amino acids L-lysine, D-lysine, alpha-methyl-L-lysine, and alpha-methyl-D-lysine are contemplated as useful amino acids in the present invention. However, other terminal azide amino acids that contain a different amino acid side chain are also useful in the invention. For example, the azido-analog of L-lysine contains four methylene units between the α-carbon of the amino acid and the terminal azide of the amino acid side chain. The invention also contemplates the use of amino acids with fewer than or greater than four methylene units between the α-carbon and the terminal azide. Table 3 shows some amino acids useful in the preparation of peptidomimetic macrocycles disclosed herein.

TABLE 3

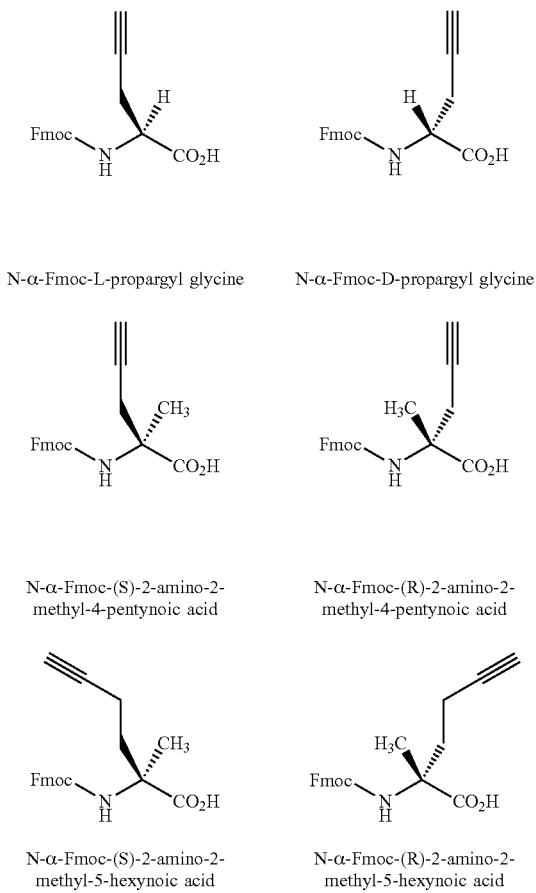

TABLE 3-continued

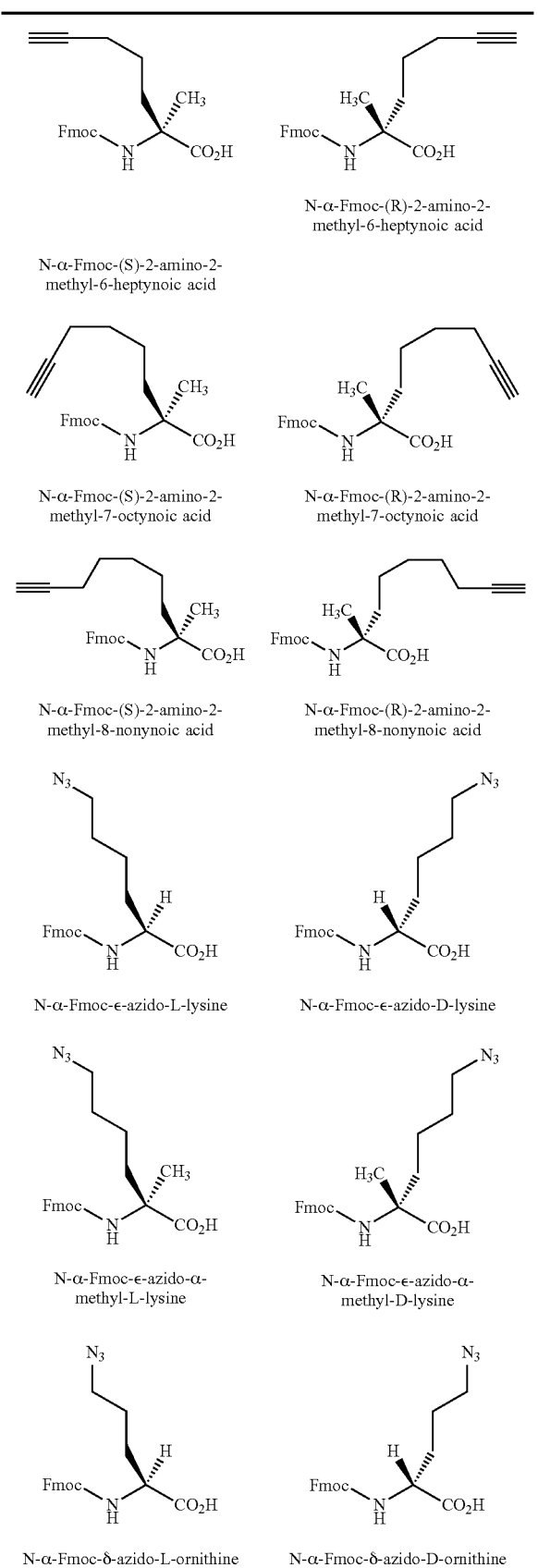

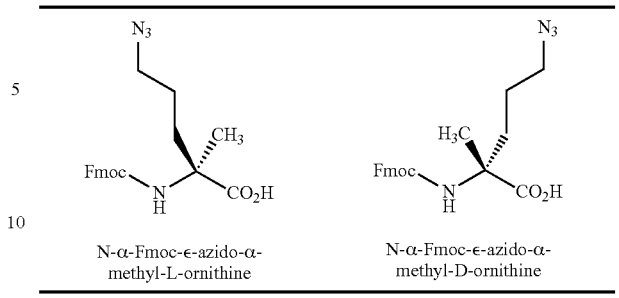

In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-propargylglycine, α-methyl-D-propargylglycine, ε-azido-alpha-methyl-L-lysine, and ε-azido-alpha-methyl-D-lysine. In some embodiments the amino acid analogs are N-alkylated, e.g., N-methyl-L-propargylglycine, N-methyl-D-propargylglycine, N-methyl-ε-azido-L-lysine, and N-methyl-ε-azido-D-lysine.

In some embodiments, the —NH moiety of the amino acid is protected using a protecting group, including without limitation -Fmoc and -Boc. In other embodiments, the amino acid is not protected prior to synthesis of the peptidomimetic macrocycle.

Additional methods of forming peptidomimetic macrocycles which are envisioned as suitable to perform the present invention include those disclosed by Mustapa, M. Firouz Mohd et al., J. Org. Chem (2003), 68, pp. 8193-8198; Yang, Bin et al. Bioorg Med. Chem. Lett. (2004), 14, pp. 1403-1406; U.S. Pat. No. 5,364,851; U.S. Pat. No. 5,446,128; U.S. Pat. No. 5,824,483; U.S. Pat. No. 6,713,280; and U.S. Pat. No. 7,202,332. In such embodiments, aminoacid precursors are used containing an additional substituent R— at the alpha position. Such aminoacids are incorporated into the macrocycle precursor at the desired positions, which may be at the positions where the crosslinker is substituted or, alternatively, elsewhere in the sequence of the macrocycle precursor. Cyclization of the precursor is then performed according to the indicated method.

For example, a peptidomimetic macrocycle of Formula (II) is prepared as indicated:

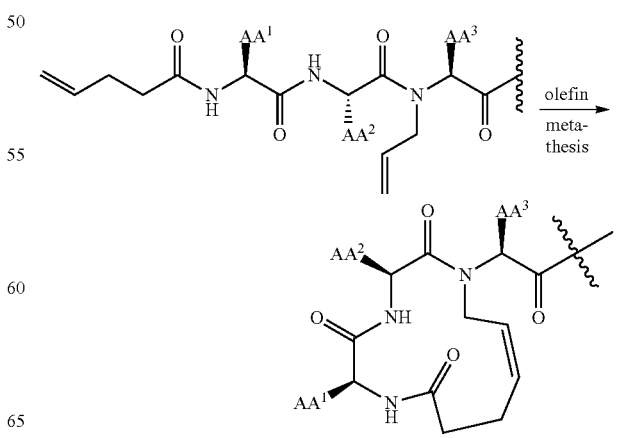

wherein each AA1, AA2, AA3 is independently an amino acid side chain.

In other embodiments, a peptidomimetic macrocycle of Formula (II) is prepared as indicated:

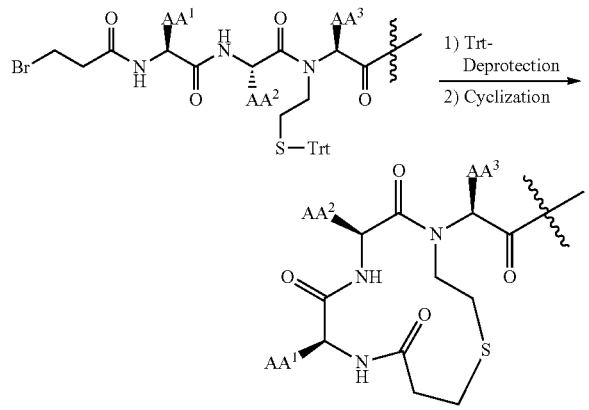

In some embodiments, a peptidomimetic macrocycle is obtained in more than one isomer, for example due to the configuration of a double bond within the structure of the crosslinker (E vs Z). Such isomers can or can not be separable by conventional chromatographic methods. In some embodiments, one isomer has improved biological properties relative to the other isomer. In one embodiment, an E crosslinker olefin isomer of a peptidomimetic macrocycle has better solubility, better target affinity, better in vivo or in vitro efficacy, higher helicity, or improved cell permeability relative to its Z counterpart. In another embodiment, a Z crosslinker olefin isomer of a peptidomimetic macrocycle has better solubility, better target affinity, better in vivo or in vitro efficacy, higher helicity, or improved cell permeability relative to its E counterpart.

Assays

The properties of the peptidomimetic macrocycles of the invention are assayed, for example, by using the methods described below. In some embodiments, a peptidomimetic macrocycle of the invention has improved biological properties relative to a corresponding polypeptide lacking the substituents described herein.

Assay to Determine α-Helicity.

In solution, the secondary structure of polypeptides with α-helical domains will reach a dynamic equilibrium between random coil structures and α-helical structures, often expressed as a "percent helicity". Thus, for example, alpha-helical domains are predominantly random coils in solution, with α-helical content usually under 25%. Peptidomimetic macrocycles with optimized linkers, on the other hand, possess, for example, an alpha-helicity that is at least two-fold greater than that of a corresponding uncrosslinked polypeptide. In some embodiments, macrocycles of the invention will possess an alpha-helicity of greater than 50%. To assay the helicity of peptidomimetic macrocyles of the invention, the compounds are dissolved in an aqueous solution (e.g. 50 mM potassium phosphate solution at pH 7, or distilled $H_2O$, to concentrations of 25-50 μM). Circular dichroism (CD) spectra are obtained on a spectropolarimeter (e.g., Jasco J-710) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity (e.g. [Φ]222obs) by the reported value for a model helical decapeptide (Yang et al. (1986), Methods Enzymol. 130:208)).

Assay to Determine Melting Temperature (Tm).

A peptidomimetic macrocycle of the invention comprising a secondary structure such as an α-helix exhibits, for example, a higher melting temperature than a corresponding uncrosslinked polypeptide. Typically peptidomimetic macrocycles of the invention exhibit Tm of >60° C. representing a highly stable structure in aqueous solutions. To assay the effect of macrocycle formation on meltine temperature, peptidomimetic macrocycles or unmodified peptides are dissolved in distilled $H_2O$ (e.g. at a final concentration of 50 μM) and the Tm is determined by measuring the change in ellipticity over a temperature range (e.g. 4 to 95° C.) on a spectropolarimeter (e.g., Jasco J-710) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

Protease Resistance Assay.

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention may be subjected to in vitro trypsin proteolysis to assess for any change in degradation rate compared to a corresponding uncrosslinked polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln [S] versus time (k=−1×slope).

Ex Vivo Stability Assay.

Peptidomimetic macrocycles with optimized linkers possess, for example, an ex vivo half-life that is at least two-fold greater than that of a corresponding uncrosslinked polypeptide, and possess an ex vivo half-life of 12 hours or more. For ex vivo serum stability studies, a variety of assays may be used. For example, a peptidomimetic macrocycle and a corresponding uncrosslinked polypeptide (2 mcg) are incubated with fresh mouse, rat and/or human serum (2 mL) at 37° C. for 0, 1, 2, 4, 8, and 24 hours. To determine the level of intact compound, the following procedure may be used: The samples are extracted by transferring 100 μl of sera to 2 ml centrifuge tubes followed by the addition of 10 μL of 50% formic acid and 500 μL acetonitrile and centrifugation at 14,000 RPM for 10 min at 4±2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis.

In Vitro Binding Assays.

To assess the binding and affinity of peptidomimetic macrocycles and peptidomimetic precursors to acceptor proteins, a fluorescence polarization assay (FPA) isused, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

For example, fluoresceinated peptidomimetic macrocycles (25 nM) are incubated with the acceptor protein (25-1000 nM) in binding buffer (140 mM NaCl, 50 mM Tris-HCL, pH 7.4) for 30 minutes at room temperature. Binding activity is measured, for example, by fluorescence polarization on a luminescence spectrophotometer (e.g. Perkin-Elmer LS50B). Kd values may be determined by non-linear regression analysis using, for example, Graphpad Prism software (GraphPad Software, Inc., San Diego, Calif.). A peptidomimetic macrocycle of the invention shows, in some instances, similar or lower Kd than a corresponding uncrosslinked polypeptide.

In Vitro Displacement Assays to Characterize Antagonists of Peptide-Protein Interactions.

To assess the binding and affinity of compounds that antagonize the interaction between a peptide and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). A compound that antagonizes the interaction between the fluoresceinated peptidomimetic macrocycle and an acceptor protein will be detected in a competitive binding FPA experiment.

For example, putative antagonist compounds (1 nM to 1 mM) and a fluoresceinated peptidomimetic macrocycle (25 nM) are incubated with the acceptor protein (50 nM) in binding buffer (140 mM NaCl, 50 mM Tris-HCL, pH 7.4) for 30 minutes at room temperature. Antagonist binding activity is measured, for example, by fluorescence polarization on a luminescence spectrophotometer (e.g. Perkin-Elmer LS50B). Kd values may be determined by nonlinear regression analysis using, for example, Graphpad Prism software (GraphPad Software, Inc., San Diego, Calif.).

Any class of molecule, such as small organic molecules, peptides, oligonucleotides or proteins can be examined as putative antagonists in this assay.

Assay for Protein-Ligand Binding by Affinity Selection-Mass Spectrometry

To assess the binding and affinity of test compounds for proteins, an affinity-selection mass spectrometry assay is used, for example. Protein-ligand binding experiments are conducted according to the following representative procedure outlined for a system-wide control experiment using 1 µM peptidomimetic macrocycle plus 5 µM target protein. A 1 µL DMSO aliquot of a 40 µM stock solution of peptidomimetic macrocycle is dissolved in 19 µL of PBS (Phosphate-buffered saline: 50 mM, pH 7.5 Phosphate buffer containing 150 mM NaCl). The resulting solution is mixed by repeated pipetting and clarified by centrifugation at 10 000 g for 10 min. To a 4 µL aliquot of the resulting supernatant is added 4 µL of 10 µM target protein in PBS. Each 8.0 µL experimental sample thus contains 40 pmol (1.5 µg) of protein at 5.0 µM concentration in PBS plus 1 µM peptidomimetic macrocycle and 2.5% DMSO. Duplicate samples thus prepared for each concentration point are incubated for 60 min at room temperature, and then chilled to 4° C. prior to size-exclusion chromatography-LC-MS analysis of 5.0 µL injections. Samples containing a target protein, protein-ligand complexes, and unbound compounds are injected onto an SEC column, where the complexes are separated from non-binding component by a rapid SEC step. The SEC column eluate is monitored using UV detectors to confirm that the early-eluting protein fraction, which elutes in the void volume of the SEC column, is well resolved from unbound components that are retained on the column. After the peak containing the protein and protein-ligand complexes elutes from the primary UV detector, it enters a sample loop where it is excised from the flow stream of the SEC stage and transferred directly to the LC-MS via a valving mechanism. The $(M+3H)^{3+}$ ion of the peptidomimetic macrocycle is observed by ESI-MS at the expected m/z, confirming the detection of the protein-ligand complex.

Assay for Protein-Ligand Kd Titration Experiments.

To assess the binding and affinity of test compounds for proteins, a protein-ligand Kd titration experiment is performed, for example. Protein-ligand $K_d$ titrations experiments are conducted as follows: 2 µL DMSO aliquots of a serially diluted stock solution of titrant peptidomimetic macrocycle (5, 2.5, . . . , 0.098 mM) are prepared then dissolved in 38 µL of PBS. The resulting solutions are mixed by repeated pipetting and clarified by centrifugation at 10 000 g for 10 min. To 4.0 µL aliquots of the resulting supernatants is added 4.0 µL of 10 µM target protein in PBS. Each 8.0 µL experimental sample thus contains 40 pmol (1.5 µg) of protein at 5.0 µM concentration in PBS, varying concentrations (125, 62.5, . . . , 0.24 µM) of the titrant peptide, and 2.5% DMSO. Duplicate samples thus prepared for each concentration point are incubated at room temperature for 30 min, then chilled to 4° C. prior to SEC-LC-MS analysis of 2.0 µL injections. The $(M+H)^{1+}$, $(M+2H)^{2+}$, $(M+3H)^{3+}$, and/or $(M+Na)^{1+}$ ion is observed by ESI-MS; extracted ion chromatograms are quantified, then fit to equations to derive the binding affinity $K_d$ as described in "*A General Technique to Rank Protein-Ligand Binding Affinities and Determine Allosteric vs. Direct Binding Site Competition in Compound Mixtures.*" Annis, D. A.; Nazef, N.; Chuang, C. C.; Scott, M. P.; Nash, H. M. *J. Am. Chem. Soc.* 2004, 126, 15495-15503; also in "*ALIS: An Affinity Selection-Mass Spectrometry System for the Discovery and Characterization of Protein-Ligand Interactions*" D. A. Annis, C.-C. Chuang, and N. Nazef. In Mass Spectrometry in Medicinal Chemistry. Edited by Wanner K, Höfner G: Wiley-VCH; 2007:121-184. Mannhold R, Kubinyi H, Folkers G (Series Editors): Methods and Principles in Medicinal Chemistry.

Assay for Competitive Binding Experiments by Affinity Selection-Mass Spectrometry To determine the ability of test compounds to bind competitively to proteins, an affinity selection mass spectrometry assay is performed, for example. A mixture of ligands at 40 µM per component is prepared by combining 2 µL aliquots of 400 µM stocks of each of the three compounds with 14 µL of DMSO. Then, 1 µL aliquots of this 40 µM per component mixture are combined with 1 µL DMSO aliquots of a serially diluted stock solution of titrant peptidomimetic macrocycle (10, 5, 2.5, . . . , 0.078 mM). These 2 µL samples are dissolved in 38 µL of PBS. The resulting solutions were mixed by repeated pipetting and clarified by centrifugation at 10 000 g for 10 min. To 4.0 µL aliquots of the resulting supernatants is added 4.0 µL of 10 µM target protein in PBS. Each 8.0 µL experimental sample thus contains 40 pmol (1.5 µg) of protein at 5.0 µM concentration in PBS plus 0.5 µM ligand, 2.5% DMSO, and varying concentrations (125, 62.5, . . . , 0.98 µM) of the titrant peptidomimetic macrocycle. Duplicate samples thus prepared for each concentration point are incubated at room temperature for 60 min, then chilled to 4° C. prior to SEC-LC-MS analysis of 2.0 µL injections. Additional details on these and other methods are provided in "*A General Technique to Rank Protein-Ligand Binding Affinities and Determine Allosteric vs. Direct Binding Site Competition in Compound Mixtures.*" Annis, D. A.; Nazef, N.; Chuang, C. C.; Scott, M. P.; Nash, H. M. *J. Am. Chem. Soc.* 2004, 126, 15495-15503; also in "*ALIS: An Affinity Selection-Mass Spectrometry System for the Discovery and Characterization of Protein-Ligand Interactions*" D. A. Annis, C.-C. Chuang, and N. Nazef. In Mass Spectrometry in Medicinal Chemistry. Edited by Wanner K, Höfner G: Wiley-VCH; 2007:121-184. Mannhold R, Kubinyi H, Folkers G (Series Editors): Methods and Principles in Medicinal Chemistry.

Binding Assays in Intact Cells.

It is possible to measure binding of peptides or peptidomimetic macrocycles to their natural acceptors in intact cells by immunoprecipitation experiments. For example, intact cells are incubated with fluoresceinated (FITC-labeled) compounds for 4 hrs in the absence of serum, followed by serum replacement and further incubation that ranges from 4-18 hrs. Cells are then pelleted and incubated in lysis buffer (50 mM Tris [pH 7.6], 150 mM NaCl, 1% CHAPS and protease inhibitor cocktail) for 10 minutes at 4° C. Extracts are centrifuged at 14,000 rpm for 15 minutes and supernatants collected and incubated with 10 µl goat anti-FITC antibody for 2 hrs, rotating at 4° C. followed by further 2 hrs incubation at 4° C. with protein A/G Sepharose (50 µl of 50% bead slurry). After quick centrifugation, the pellets are washed in lysis buffer containing increasing salt concentration (e.g., 150, 300, 500 mM). The beads are then re-equilibrated at 150 mM NaCl before addition of SDS-containing sample buffer and boiling. After centrifugation, the supernatants are optionally electrophoresed using 4%-12% gradient Bis-Tris gels followed by transfer into Immobilon-P membranes. After blocking, blots are optionally incubated with an antibody that detects FITC and also with one or more antibodies that detect proteins that bind to the peptidomimetic macrocycle.

Cellular Penetrability Assays.

To measure the cell penetrability of peptidomimetic macrocycles and corresponding uncrosslinked macrocycle, intact cells are incubated with fluoresceinated peptidomimetic macrocycles or corresponding uncrosslinked macrocycle (10 µM) for 4 hrs in serum free media at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader.

In Vivo Stability Assay.

To investigate the in vivo stability of the peptidomimetic macrocycles, the compounds are, for example, administered to mice and/or rats by IV, IP, PO or inhalation routes at concentrations ranging from 0.1 to 50 mg/kg and blood specimens withdrawn at 0', 5', 15', 30', 1 hr, 4 hrs, 8 hrs and 24 hours post-injection. Levels of intact compound in 25 µL of fresh serum are then measured by LC-MS/MS as above.

Clinical Trials.

To determine the suitability of the peptidomimetic macrocycles of the invention for treatment of humans, clinical trials are performed. For example, patients diagnosed with a muscle wasting disease or lipodystrophy and in need of treatment are selected and separated in treatment and one or more control groups, wherein the treatment group is administered a peptidomimetic macrocycle of the invention, while the control groups receive a placebo or a known GHRH or GH drug. The treatment safety and efficacy of the peptidomimetic macrocycles of the invention can thus be evaluated by performing comparisons of the patient groups with respect to factors such as survival and quality-of-life. In this example, the patient group treated with a peptidomimetic macrocyle show improved long-term survival compared to a patient control group treated with a placebo.

Pharmaceutical Compositions and Routes of Administration

The peptidomimetic macrocycles of the invention also include pharmaceutically acceptable derivatives or prodrugs thereof. A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention. Particularly favored pharmaceutically acceptable derivatives are those that increase the bioavailability of the compounds of the invention when administered to a mammal (e.g., by increasing absorption into the blood of an orally administered compound) or which increases delivery of the active compound to a biological compartment (e.g., the brain or lymphatic system) relative to the parent species. Some pharmaceutically acceptable derivatives include a chemical group which increases aqueous solubility or active transport across the gastrointestinal mucosa.

In some embodiments, the peptidomimetic macrocycles of the invention are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa.

In powders, the carrier is a finely divided solid, which is in a mixture with the finely divided active component. In tablets, the active component is mixed with the carrier having the necessary binding properties in suitable proportions and compacted in the shape and size desired.

Suitable solid excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents are added, such as the cross-linked polyvinyl pyrrolidone, agar, alginic acid, or a salt thereof, such as sodium alginate.

Liquid form preparations include solutions, suspensions, and emulsions, for example, water or water/propylene glycol solutions. For parenteral injection, liquid preparations can be formulated in solution in aqueous polyethylene glycol solution.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

When the compositions of this invention comprise a combination of a peptidomimetic macrocycle and one or more additional therapeutic or prophylactic agents, both the compound and the additional agent should be present at dosage levels of between about 1 to 100%, and more preferably between about 5 to 95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

In some embodiments, the compositions are present as unit dosage forms that can deliver, for example, from about 0.0001 mg to about 1,000 mg of the peptidomimetic macrocycles, salts thereof, prodrugs thereof, derivatives thereof, or any combination of these. Thus, the unit dosage forms can deliver, for example, in some embodiments, from about 1 mg to about 900 mg, from about 1 mg to about 800 mg, from about 1 mg to about 700 mg, from about 1 mg to about 600 mg, from about 1 mg to about 500 mg, from about 1 mg to about 400 mg, from about 1 mg to about 300 mg, from about 1 mg to about 200 mg, from about 1 mg to about 100 mg, from about 1 mg to about 10 mg, from about 1 mg to about 5 mg, from about 0.1 mg to about 10 mg, from about 0.1 mg to about 5 mg, from about 10 mg to about 1,000 mg, from about 50 mg to about 1,000 mg, from about 100 mg to about 1,000 mg, from about 200 mg to about 1,000 mg, from about 300 mg to about 1,000 mg, from about 400 mg to about 1,000 mg, from about 500 mg to about 1,000 mg, from about 600 mg to about 1,000 mg, from about 700 mg to about 1,000 mg, from about 800 mg to about 1,000 mg, from about 900 mg to about 1,000 mg, from about 10 mg to about 900 mg, from about 100 mg to about 800 mg, from about 200 mg to about 700 mg, or from about 300 mg to about 600 mg of the peptidomimetic macrocycles, salts thereof, prodrugs thereof, derivatives thereof, or any combination of these.

In some embodiments, the compositions are present as unit dosage forms that can deliver, for example, about 1 mg, about 2 mg, about 3 mg, about 4 mg, about 5 mg, about 6 mg, about 7 mg, about 8 mg, about 9 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 500 mg, about 600 mg, about 700 mg, about 800 mg, or about 800 mg of peptidomimetic macrocycles, salts thereof, prodrugs thereof, derivatives thereof, or any combination of these.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a composition as described herein is administered in a local rather than systemic manner, for example, via injection of the compound directly into an organ. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

In another embodiment, compositions described herein are formulated for oral administration. Compositions described herein are formulated by combining a peptidomimetic macrocycle with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the peptidomimetic macrocycles described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the peptidomimetic macrocycles described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the peptidomimetic macrocycles described herein are formulated for buccal or sublingual administration. Formulations suitable for buccal or sublingual administration include, by way of example only, tablets, lozenges, or gels. In still other embodiments, the peptidomimetic macrocycles described herein are formulated for parenertal injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, pharmaceutical compositions are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

Pharmaceutical compositions herein can be administered, for example, once or twice or three or four or five or six times per day, or once or twice or three or four or five or six times per week, and can be administered, for example, for a day, a week, a month, 3 months, six months, a year, five years, or for example ten years.

Methods of Use

In one aspect, the present invention provides novel peptidomimetic macrocycles that are useful in competitive binding assays to identify agents which bind to the natural ligand(s) of the proteins or peptides upon which the peptidomimetic macrocycles are modeled. For example, in the GHRH system, labeled peptidomimetic macrocycles based on GHRH can be used in a binding assay along with small molecules that competitively bind to the GHRH receptor. Competitive binding studies allow for rapid in vitro evaluation and determination of drug candidates specific for the GHRH system. Such binding studies may be performed with any of the peptidomimetic macrocycles disclosed herein and their binding partners.

The invention further provides for the generation of antibodies against the peptidomimetic macrocycles. In some embodiments, these antibodies specifically bind both the peptidomimetic macrocycle and the precursor peptides, such as GHRH, to which the peptidomimetic macrocycles are related. Such antibodies, for example, disrupt the native protein-protein interactions, for example, between GHRH and the GHRH receptor.

In another aspect, the present invention provides methods to activate the GHRH receptor, thereby stimulating production and release of growth hormone, which in turn can increase lean muscle mass or reduce adipose tissue, for example visceral and/or abdominal adipose tissue. In some embodiments, subject suffering from obesity, for example abdominal obesity, are treated using pharmaceutical compositions of the invention. See, e.g. Makimura et al., J. Clin. Endocrinol. Metab. 2009, 94(12): 5131-5138, which is hereby incorporated by reference.

In yet another aspect, the present invention provides methods for treating muscle wasting diseases that include anorexias, cachexias (such as cancer cachexia, chronic heart failure cachexia, chronic obstructive pulmonary disease cachexia, rheumatoid arthritis cachexia) and sarcopenias, methods for treating lipodystrophies that include HIV lipodystrophy, methods for treating growth hormone disorders that include adult and pediatric growth hormone deficiencies, or methods for treating gastroparesis or short bowel syndrome. These methods comprise administering an effective amount of a compound of the invention to a warm blooded animal, including a human. In some embodiments, a pharmaceutical composition provided herein used in the treatment of muscle wasting diseases is administered no more frequently than once daily, no more frequently than every other day, no more frequently than twice weekly, no more frequently than weekly, or no more frequently than every other week.

In some embodiments, provided herein are methods for treating adult growth hormone deficiencies. Such deficiencies may be cause, for example, by damage or injury to the pituitary gland or the hypothalamus. Frequently, adult-onset growth hormone deficiency is caused by pituitary tumors or treatment of such tumors, for example by cranial irradiation. Adult growth hormone deficiency may also be caused by a reduced blood supply to the pituitary gland. In some embodiments, a pharmaceutical composition of the invention used in treatment of adult growth hormone deficiency is administered no more frequently than once daily, no more frequently than every other day, no more frequently than twice weekly, no more frequently than weekly, or no more frequently than every other week.

In some embodiments, provided herein are methods for treating pediatric growth hormone deficiencies. Growth hormone deficiency in children is often idiophathic. However, possible causes include mutations in genes including GHRHR or GH1, congenital malformations involving the pituitary (such as septo-optic dysplasia or posterior pituitary ectopia), chronic kidney disease, intracranial tumors (e.g. in or near the sella turcica, such as craniopharyngioma), damage to the pituitary from radiation therapy to the cranium (for cancers such as leukemia or brain tumors), surgery, trauma or intracranial disease (e.g. hydrocephalus), autoimmune inflammation (hypophysitis), ischemic or hemorrhagic infarction from low blood pressure (Sheehan syndrome) or hemorrhage pituitary apoplexy. Growth hormone deficiency is observed in congenital diseases such as Prader-Willi syndrome, Turner syndrome, or short stature homeobox gene (SHOX) deficiency, idiopathic short stature, or in infants who are small for gestational age. In some embodiments, a composition of the invention used in treatment of pediatric growth hormone deficiency is administered no more frequently than once daily, no more frequently than every other day, no more frequently than twice weekly, no more frequently than weekly, or no more frequently than every other week.

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In some embodiments, the invention provides peptidomimetic macrocycles and methods of use as described in the items below.

Item 1. A peptidomimetic macrocycle comprising an amino acid sequence which is at least about 60% identical to an amino acid sequence chosen from the group consisting of the amino acid sequences in Tables 1, 2 or 4.

Item 2. The peptidomimetic macrocycle of item 1, wherein the amino acid sequence of said peptidomimetic macrocycle is at least about 80% identical to an amino acid sequence chosen from the group consisting of the amino acid sequences in Tables 1, 2 or 4.

Item 3. The peptidomimetic macrocycle of item 1, wherein the amino acid sequence of said peptidomimetic macrocycle is at least about 90% identical to an amino acid sequence chosen from the group consisting of the amino acid sequences in Tables 1, 2 or 4.

Item 4. The peptidomimetic macrocycle of item 1, wherein the amino acid sequence of said peptidomimetic macrocycle is chosen from the group consisting of the amino acid sequences in Tables 1, 2 or 4.

Item 5. The peptidomimetic macrocycle of item 1, wherein the peptidomimetic macrocycle comprises a helix.

Item 6. The peptidomimetic macrocycle of item 1, wherein the peptidomimetic macrocycle comprises an α-helix.

Item 7. The peptidomimetic macrocycle of item 1, wherein the peptidomimetic macrocycle comprises an α,α-disubstituted amino acid.

Item 8. The peptidomimetic macrocycle of item 1, wherein the peptidomimetic macrocycle comprises a crosslinker linking the α-positions of at least two amino acids.

Item 9. The peptidomimetic macrocycle of item 8, wherein at least one of said two amino acids is an α,α-disubstituted amino acid.

Item 10. The peptidomimetic macrocycle of item 8, wherein the peptidomimetic macrocycle has the formula:

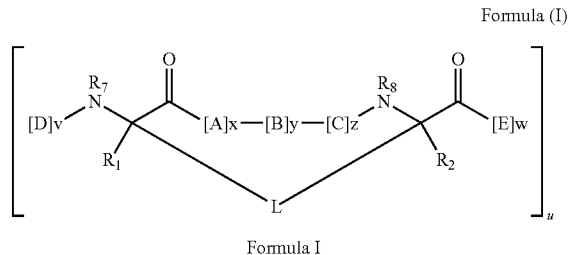

Formula I wherein:
each A, C, D, and E is independently a natural or non-natural amino acid;

B is a natural or non-natural amino acid, amino acid analog,

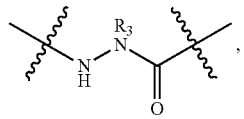

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

L is a macrocycle-forming linker of the formula -$L_1$-$L_2$-;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

$R_8$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

v and w are independently integers from 1-1000;

u, x, y and z are independently integers from 0-10; and n is an integer from 1-5.

Item 11. The peptidomimetic macrocycle of item 1, wherein the peptidomimetic macrocycle comprises a crosslinker linking a backbone amino group of a first amino acid to a second amino acid within the peptidomimetic macrocycle.

Item 12. The peptidomimetic macrocycle of item 11, wherein the peptidomimetic macrocycle has the formula (II) or (IIa):

Formula (II)

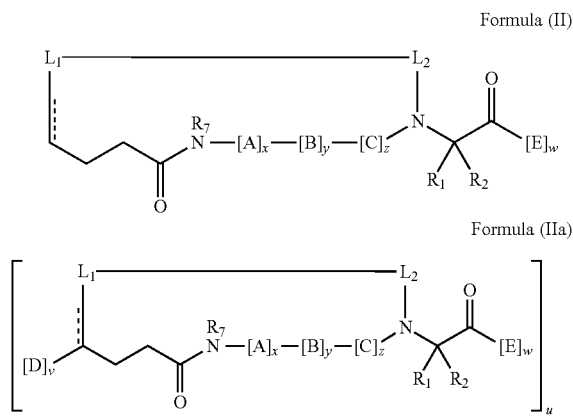

Formula (IIa)

wherein:
each A, C, D, and E is independently a natural or non-natural amino acid;
B is a natural or non-natural amino acid, amino acid analog,

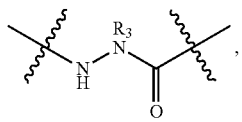

[—NH-$L_3$-CO—], [—NH-$L_3$-$SO_2$—], or [—NH-$L_3$-];

$R_1$ and $R_2$ are independently —H, alkyl, alkenyl, alkynyl, arylalkyl, cycloalkyl, cycloalkylalkyl, heteroalkyl, or heterocycloalkyl, unsubstituted or substituted with halo-, or part of a cyclic structure with an E residue;

$R_3$ is hydrogen, alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

$L_1$ and $L_2$ are independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each $R_4$ is alkylene, alkenylene, alkynylene, heteroalkylene, cycloalkylene, heterocycloalkylene, arylene, or heteroarylene;

each K is O, S, SO, $SO_2$, CO, $CO_2$, or $CONR_3$;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope or a therapeutic agent;

each $R_6$ is independently —H, alkyl, alkenyl, alkynyl, arylalkyl, cycloalkylalkyl, heterocycloalkyl, a fluorescent moiety, a radioisotope or a therapeutic agent;

$R_7$ is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$;

v and w are independently integers from 1-1000;
u, x, y and z are independently integers from 0-10; and
n is an integer from 1-5.

Item 13. A method of increasing the circulating level of growth hormone (GH) in a subject comprising administering to the subject a peptidomimetic macrocycle of item 1.

Item 14. A method of increasing lean muscle mass in a subject comprising administering to the subject a peptidomimetic macrocycle of item 1.

Item 15. A method of reducing adipose tissue in a subject comprising administering to the subject a peptidomimetic macrocycle of item 1.

Item 16. A method of treating muscle wasting diseases, including anorexias, cachexias (such as cancer cachexia, chronic heart failure cachexia, chronic obstructive pulmonary disease cachexia, rheumatoid arthritis cachexia) or sarcopenias in a subject comprising administering to the subject a peptidomimetic macrocycle of item 1.

Item 17. A method of treating lipodystrophies, including HIV lipodystrophy, in a subject comprising administering to the subject a peptidomimetic macrocycle of item 1.

Item 18. A method of treating growth hormone disorders, including adult growth hormone deficiency and pediatric growth hormone deficiency, in a subject comprising administering to the subject a peptidomimetic macrocycle of item 1.

Item 19. A method of treating gastroparesis or short bowel syndrome in a subject comprising administering to the subject a peptidomimetic macrocycle of item 1.

Item 20. A method of treating muscle wasting diseases, lipodystrophies, growth hormone disorders or gastroparesis/short bowel syndrome in a subject by administering an agonist of the GHRH receptor, wherein the agonist is administered no more frequently than once daily, no more frequently than every other day, no more frequently than twice weekly, no more frequently than weekly, or no more frequently than every other week.

Item 21. A method of treating muscle wasting diseases, lipodystrophies, growth hormone disorders or gastroparesis/short bowel syndrome in a subject by administering a GHRH analog, wherein the GHRH analog is administered no more frequently than once daily, no more frequently than every other day, no more frequently than twice weekly, no more frequently than weekly, or no more frequently than every other week.

Item 22. A method of increasing the circulating level of growth hormone (GH) in a subject by administering an agonist of the GHRH receptor, wherein the agonist is administered no more frequently than once daily, no more frequently than every other day, no more frequently than twice weekly, no more frequently than weekly, or no more frequently than every other week.

Item 23. A method of increasing the circulating level of growth hormone (GH) in a subject by administering a GHRH analog, wherein the GHRH analog is administered no more frequently than once daily, no more frequently than every other day, no more frequently than twice weekly, no more frequently than weekly, or no more frequently than every other week.

Item 24. The peptidomimetic macrocycle of item 10, wherein $L_1$ and $L_2$ are independently alkylene, alkenylene or alkynylene.

Item 25. The peptidomimetic macrocycle of item 24, wherein $L_1$ and $L_2$ are independently $C_3$-$C_{10}$ alkylene or alkenylene Item 26. The peptidomimetic macrocycle of item 24, wherein $L_1$ and $L_2$ are independently $C_3$-$C_6$ alkylene or alkenylene.

Item 27. The peptidomimetic macrocycle of item 10, wherein $R_1$ and $R_2$ are H.

Item 28. The peptidomimetic macrocycle of item 10, wherein $R_1$ and $R_2$ are independently alkyl.

Item 29. The peptidomimetic macrocycle of item 10, wherein $R_1$ and $R_2$ are methyl.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Peptidomimetic Macrocycles of the Invention

Peptidomimetic macrocycles were synthesized, purified and analyzed as previously described and as described below (Schafmeister et al., J. Am. Chem. Soc. 122:5891-5892 (2000); Schafmeister & Verdine, J. Am. Chem. Soc. 122:5891 (2005); Walensky et al., Science 305:1466-1470 (2004); and U.S. Pat. No. 7,192,713). Peptidomimetic macrocycles were designed by replacing two or more naturally occurring amino acids with the corresponding synthetic amino acids. Substitutions were made at i and i+4, and i and i+7 positions. Peptide synthesis was performed either manually or on an automated peptide synthesizer (Applied Biosystems, model 433A), using solid phase conditions, rink amide AM resin (Novabiochem), and Fmoc main-chain protecting group chemistry. For the coupling of natural Fmoc-protected amino acids (Novabiochem), 10 equivalents of amino acid and a 1:1:2 molar ratio of coupling reagents HBTU/HOBt (Novabiochem)/DIEA were employed. Non-natural amino acids (4 equiv) were coupled with a 1:1:2 molar ratio of HATU (Applied Biosystems)/HOBt/DIEA. The N-termini of the synthetic peptides were acetylated, while the C-termini were amidated.

Purification of cross-linked compounds was achieved by high performance liquid chromatography (HPLC) (Varian ProStar) on a reverse phase C18 column (Varian) to yield the pure compounds. Chemical composition of the pure products was confirmed by LC/MS mass spectrometry (Micromass LCT interfaced with Agilent 1100 HPLC system) and amino acid analysis (Applied Biosystems, model 420A).

Table 4 shows a list of peptidomimetic macrocycles of the invention prepared.

TABLE 4

| SP# | Sequence | | | | | | | | | | | | | | | | | | | |
|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 |
| SP-1 | H— | Y | a | D | $ | I | F | T | $ | S | Y | R | K | V | L | G | Q | L | S | A | R |
| SP-2 | H— | Y | a | D | $ | I | F | T | $ | S | Y | R | K | V | L | G | Q | L | S | A | R |
| SP-3 | H— | Y | A | D | $ | I | F | T | $ | S | Y | R | K | V | L | G | Q | L | S | A | R |
| SP-4 | H— | Y | A | D | $ | I | F | T | $ | S | Y | R | K | V | L | G | Q | L | S | A | R |
| SP-5 | H— | Y | a | D | $ | I | F | T | $ | S | Y | R | K | V | L | A | Q | L | S | A | R |
| SP-6 | H— | Y | a | D | $ | I | F | T | $ | S | Y | R | K | V | L | $r8 | Q | L | S | A | R |
| SP-7 | H— | Y | a | D | $ | I | F | T | $ | S | Y | R | K | V | L | G | Q | L | $r8 | A | R |
| SP-8 | H— | Y | a | D | $ | I | F | T | $ | S | Y | R | K | V | L | G | Q | L | S | A | R |
| SP-9 | H— | Y | a | D | $ | I | F | T | $ | S | Y | R | K | V | L | G | Q | L | S | A | R |
| SP-10 | H— | Y | a | D | $ | I | F | T | $ | S | Y | R | K | V | L | G | Q | L | S | A | R |
| SP-11 | H— | Y | a | D | A | I | F | T | $ | S | Y | R | $ | V | L | G | Q | L | S | A | R |
| SP-12 | H— | Y | a | D | A | I | F | T | $ | S | Y | R | $ | V | L | G | Q | L | S | A | R |
| SP-13 | H— | Y | a | D | A | I | F | T | $ | S | Y | R | $ | V | L | G | Q | L | $r8 | A | R |
| SP-14 | H— | Y | a | D | A | I | F | T | $ | S | Y | R | $ | V | L | G | Q | L | $r8 | A | R |
| SP-15 | H— | Y | a | D | A | I | F | T | $ | S | Y | R | $ | V | L | G | Q | L | S | A | R |
| SP-16 | H— | Y | a | D | A | I | F | T | $ | S | Y | R | $ | V | L | G | Q | L | S | A | R |
| SP-17 | H— | Y | a | D | A | I | F | T | $ | S | Y | R | $ | V | L | G | Q | L | S | A | R |
| SP-18 | H— | Y | a | D | A | I | F | T | $ | S | Y | R | $ | V | L | G | Q | L | S | A | R |
| SP-19 | H— | Y | a | D | A | I | F | T | N | S | Y | R | $ | V | L | G | $ | L | S | A | R |
| SP-20 | H— | Y | a | D | A | I | F | T | N | S | Y | R | $ | V | L | G | $ | L | S | A | R |
| SP-21 | H— | Y | a | D | A | $r8 | F | T | N | S | Y | R | $ | V | L | G | Q | L | S | A | R |
| SP-22 | H— | Y | a | D | A | $r8 | F | T | N | S | Y | R | $ | V | L | G | Q | L | S | A | R |
| SP-23 | H— | Y | a | D | A | I | F | T | $r8 | S | Y | R | K | V | L | $ | Q | L | S | A | R |
| SP-24 | H— | Y | a | D | A | I | F | T | $r8 | S | Y | R | K | V | L | $ | Q | L | S | A | R |
| SP-25 | H— | Y | a | D | A | I | F | T | N | $r8 | Y | R | K | V | L | G | $ | L | S | A | R |
| SP-26 | H— | Y | a | D | A | I | F | T | N | $r8 | Y | R | K | V | L | G | $ | L | S | A | R |
| SP-27 | H— | Y | a | D | A | I | F | T | N | $r8 | Y | R | K | V | L | G | $ | L | S | A | R |
| SP-28 | H— | Y | a | D | A | I | F | T | N | $r8 | Y | R | K | V | L | G | $ | L | S | A | R |
| SP-29 | H— | Y | a | D | A | I | F | T | N | $r8 | Y | R | K | V | L | G | $ | L | S | A | R |
| SP-30 | H— | Y | a | D | A | I | F | T | N | $r8 | Y | R | K | V | L | G | $ | L | S | A | R |
| SP-31 | H— | Y | a | D | A | I | F | T | N | S | Y | R | $r8 | V | L | G | Q | L | S | $ | R |
| SP-32 | H— | Y | a | D | A | I | F | T | N | S | Y | R | $r8 | V | L | G | Q | L | S | $ | R |
| SP-33 | H— | Y | a | D | A | I | F | T | N | S | Y | R | $r8 | V | L | G | Q | L | S | $ | R |
| SP-34 | H— | Y | a | D | $ | I | F | T | $ | S | Y | A | K | V | L | G | Q | L | S | A | R |
| SP-35 | H— | Y | a | D | $ | I | F | T | $ | S | Y | R | A | V | L | G | Q | L | S | A | R |
| SP-36 | H— | Y | a | D | $ | I | F | T | $ | S | Y | R | K | V | L | G | Q | L | S | A | A |
| SP-37 | H— | Y | a | D | $ | I | F | T | $ | S | Y | R | A | V | L | G | Q | L | S | A | R |
| SP-38 | H— | Y | a | D | $ | I | F | T | $ | S | Y | Q | K | V | L | G | Q | L | S | A | R |
| SP-39 | H— | Y | a | D | $ | I | F | T | $ | S | Y | R | Q | V | L | G | Q | L | S | A | R |
| SP-40 | H— | Y | a | D | $ | I | F | T | $ | S | Y | R | K | V | L | G | Q | L | S | A | Q |
| SP-41 | H— | Y | a | D | $ | I | F | T | $ | S | Y | R | K | V | L | G | Q | L | S | A | R |

TABLE 4-continued

| | | | | | | | | | | | | | | | | | | | | |
|---|---|---|---|---|---|---|---|---|---|---|---|---|---|---|---|---|---|---|---|---|
| SP-42 | H— | Y | a | D | $ | I | F | T | $ | S | Y | R | K | V | L | A | Q | L | S | A | R |
| SP-43 | H— | Y | a | D | $ | I | F | T | $ | S | Y | R | K | V | L | G | Q | L | S | A | R |
| SP-44 | H— | Y | a | D | % | I | F | T | % | S | Y | R | K | V | L | G | Q | L | S | A | R |
| SP-45 | H— | Y | a | D | $5a5 | I | F | T | $5n3 | S | Y | R | K | V | L | G | Q | L | S | A | R |
| SP-46 | H— | Y | a | D | $5n3 | I | F | T | $5a5 | S | Y | R | K | V | L | G | Q | L | S | A | R |
| SP-47 | H— | Y | a | D | $5a5 | I | F | T | $5n3 | S | Y | R | K | V | L | G | Q | L | S | A | R |
| SP-48 | H— | Y | a | D | $5n3 | I | F | T | $5a5 | S | Y | R | K | V | L | G | Q | L | S | A | R |
| SP-49 | H— | Y | a | D | A | I | F | T | N | S | Y | R | $4m6 | V | L | G | Q | L | S | $4a5 | R |

| | Sequence | | | | | | | | | Olefin Isomer | Exact mass | Calc'd (M + 3)/3 | Obsv'd (M + 3)/3 |
|---|---|---|---|---|---|---|---|---|---|---|---|---|---|
| SP # | 21 | 22 | 23 | 24 | 25 | 26 | 27 | 28 | 29 | | | | |
| SP-1 | $ | L | L | Q | $ | I | Nle | S | R | —NH2 | | 3410 | 1137.67 | 1137.42 |
| SP-2 | K | L | L | Q | $ | I | Nle | S | $ | —NH2 | | 3381.99 | 1128.34 | 1127.8 |
| SP-3 | $ | L | L | Q | $ | I | Nle | S | R | —NH2 | | 3410 | 1137.67 | 1137.05 |
| SP-4 | K | L | L | Q | $ | I | Nle | S | $ | —NH2 | | 3381.99 | 1128.34 | 1127.8 |
| SP-5 | K | L | L | Q | $ | I | Nle | S | $ | —NH2 | | 3396.01 | 1133.01 | 1132.86 |
| SP-6 | K | $ | L | Q | D | I | Nle | S | R | —NH2 | | 3525.06 | 1176.03 | 1175.76 |
| SP-7 | K | L | L | Q | $ | I | Nle | S | R | —NH2 | | 3493.11 | 1165.38 | 1165.02 |
| SP-8 | $r8 | L | L | Q | D | I | Nle | S | R | —NH2 | | 3480.04 | 1161.02 | 1160.66 |
| SP-9 | K | $r8 | L | Q | D | I | Nle | S | $ | —NH2 | | 3425.98 | 1143 | 1142.53 |
| SP-10 | K | $r8 | L | Q | D | I | Nle | S | $ | —NH2 | iso2 | 3425.98 | 1143 | 1142.6 |
| SP-11 | $ | L | L | Q | $ | I | Nle | S | R | —NH2 | | 3352.94 | 1118.65 | 1118.25 |
| SP-12 | K | L | L | Q | $ | I | Nle | S | $ | —NH2 | | 3324.93 | 1109.32 | 1108.93 |
| SP-13 | K | L | L | Q | $ | I | Nle | S | R | —NH2 | | 3436.05 | 1146.36 | 1146.15 |
| SP-14 | K | L | L | Q | $ | I | Nle | S | R | —NH2 | iso2 | 3436.05 | 1146.36 | 1146.08 |
| SP-15 | $r8 | L | L | Q | D | I | Nle | S | R | —NH2 | | 3422.98 | 1142 | 1141.94 |
| SP-16 | $r8 | L | L | Q | D | I | Nle | S | R | —NH2 | iso2 | 3422.98 | 1142 | 1141.79 |
| SP-17 | K | $r8 | L | Q | D | I | Nle | S | $ | —NH2 | | 3368.92 | 1123.98 | 1123.66 |
| SP-18 | K | $r8 | L | Q | D | I | Nle | S | $ | —NH2 | iso2 | 3368.92 | 1123.98 | 1123.73 |
| SP-19 | $ | L | L | Q | $ | I | Nle | S | R | —NH2 | | 3338.92 | 1113.98 | 1113.37 |
| SP-20 | K | L | L | Q | $ | I | Nle | S | $ | —NH2 | | 3310.92 | 1104.65 | 1104.34 |
| SP-21 | $ | L | L | Q | $ | I | Nle | S | R | —NH2 | | 3395.95 | 1132.99 | 1133.64 |
| SP-22 | K | L | L | Q | $ | I | Nle | S | $ | —NH2 | | 3367.94 | 1123.65 | 1123.36 |
| SP-23 | $ | L | L | Q | $ | I | Nle | S | R | —NH2 | | 3466.06 | 1156.36 | 1156.14 |
| SP-24 | K | L | L | Q | $ | I | Nle | S | $ | —NH2 | | 3438.05 | 1147.02 | 1146.75 |
| SP-25 | K | L | L | Q | $ | I | Nle | S | $ | —NH2 | | 3394.03 | 1132.35 | 1132.02 |
| SP-26 | K | L | L | Q | $ | I | Nle | S | $ | —NH2 | iso2 | 3394.03 | 1132.35 | 1132.09 |
| SP-27 | $ | L | L | Q | $ | I | Nle | S | R | —NH2 | | 3422.03 | 1141.68 | 1141.42 |
| SP-28 | $ | L | L | Q | $ | I | Nle | S | R | —NH2 | iso2 | 3422.03 | 1141.68 | 1141.42 |
| SP-29 | K | L | L | Q | D | I | Nle | S | R | —NH2 | | 3414.99 | 1139.34 | 1139.05 |
| SP-30 | K | L | L | Q | D | I | Nle | S | R | —NH2 | iso2 | 3414.99 | 1139.34 | 1139.05 |
| SP-31 | K | L | L | Q | D | I | Nle | S | R | —NH2 | | 3430.95 | 1144.66 | 1144.45 |
| SP-32 | K | L | L | Q | D | I | Nle | S | R | —NH2 | iso2 | 3430.95 | 1144.66 | 1145.3 |
| SP-33 | K | L | L | Q | $ | I | Nle | S | $ | —NH2 | | 3409.99 | 1137.67 | 1137.42 |
| SP-34 | $ | L | L | Q | $ | I | Nle | S | R | —NH2 | | 3324.93 | 1109.32 | 1110.29 |
| SP-35 | $ | L | L | Q | $ | I | Nle | S | R | —NH2 | | 3352.94 | 1118.65 | 1119.13 |
| SP-36 | $ | L | L | Q | $ | I | Nle | S | R | —NH2 | | 3324.93 | 1109.32 | 1110.2 |
| SP-37 | $ | L | L | Q | $ | I | Nle | S | A | —NH2 | | 3267.88 | 1090.3 | 1091.14 |
| SP-38 | $ | L | L | Q | $ | I | Nle | S | R | —NH2 | | 3381.96 | 1128.33 | 1129.16 |
| SP-39 | $ | L | L | Q | $ | I | Nle | S | R | —NH2 | | 3409.96 | 1137.66 | 1138.5 |
| SP-40 | $ | L | L | Q | $ | I | Nle | S | R | —NH2 | | 3381.96 | 1128.33 | 1129.16 |
| SP-41 | $ | L | L | Q | $ | I | Nle | S | Q | —NH2 | | 3381.96 | 1128.33 | 1129.16 |
| SP-42 | $ | A | L | Q | $ | I | Nle | S | R | —NH2 | | 3381.97 | 1128.33 | 1129.16 |
| SP-43 | $ | L | L | Q | $ | I | Nle | S | | —NH2 | | 3253.9 | 1085.64 | 1086.52 |
| SP-44 | % | L | L | Q | % | I | Nle | S | R | —NH2 | | | | |
| SP-45 | $5a5 | L | L | Q | $5n3 | I | Nle | S | R | —NH2 | | | | |
| SP-46 | $5n3 | L | L | Q | $5a3 | I | Nle | S | R | —NH2 | | | | |
| SP-47 | $5n3 | L | L | Q | $5a5 | I | Nle | S | R | —NH2 | | | | |
| SP-48 | $5a5 | L | L | Q | $5n3 | I | Nle | S | R | —NH2 | | | | |
| SP-49 | K | L | L | Q | D | I | Nle | S | R | —NH2 | | | | |

| | 0 | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| SP-50 | H— | Y | a | D | A | I | F | T | N | S | Y | Q | $r8 | V | L | G | Q | L | S |
| SP-51 | H— | Y | a | D | A | I | F | T | N | S | Y | R | $r8 | V | L | G | Q | L | S |
| SP-52 | H— | Y | a | D | A | I | F | T | N | S | Y | R | $r8 | V | L | G | Q | L | S |
| SP-53 | H— | Y | a | D | A | I | F | T | N | S | Y | R | $r8 | V | L | G | Q | L | S |
| SP-54 | H— | Y | a | D | A | I | F | T | N | S | Y | R | $r8 | V | L | G | Q | L | S |
| SP-55 | H— | Y | a | D | A | I | F | T | A | S | Y | Q | $r8 | V | L | G | Q | L | S |
| SP-56 | H— | Y | a | D | A | I | F | T | A | S | Y | R | $r8 | V | L | G | Q | L | S |
| SP-57 | H— | Y | a | D | A | I | F | T | A | S | Y | R | $r8 | V | L | G | Q | L | S |
| SP-58 | H— | Y | a | D | A | I | F | T | A | S | Y | R | $r8 | V | L | G | Q | L | S |
| SP-59 | H— | Y | a | D | A | I | F | T | A | S | Y | R | $r8 | V | L | G | Q | L | S |
| SP-60 | H— | Y | a | D | A | I | F | T | A | S | Y | R | $r8 | V | L | G | Q | L | S |
| SP-61 | H— | Y | a | D | A | I | F | T | A | S | Y | R | $r8 | V | L | G | Q | L | S |
| SP-62 | H— | Y | a | D | A | I | F | T | A | S | Y | R | $r8 | V | L | A | Q | L | S |

TABLE 4-continued

|  |  |  |  |  |  |  |  |  |  |  |  |  |  |  |  |  |  |  |
|---|---|---|---|---|---|---|---|---|---|---|---|---|---|---|---|---|---|---|
| SP-63 | H— | Y | a | D | $ | I | F | T | $ | S | Y | R | K | V | L | G | Q | L | S |
| SP-64 | H— | Y | a | D | $ | I | F | T | $ | S | Y | R | K | V | L | G | E | L | S |
| SP-65 | H— | Y | a | D | $ | I | F | T | $ | S | Y | R | K | V | L | G | E | L | S |
| SP-66 | H— | Y | a | D | $ | I | F | T | $ | S | Y | R | K | V | L | G | Q | L | S |
| SP-67 | H— | Y | a | D | $ | I | F | T | $ | S | Y | R | K | V | L | A | Q | L | S |
| SP-68 | H— | Y | a | D | $ | I | F | T | $ | S | Y | R | A | V | L | A | Q | L | S |
| SP-69 | H— | Y | a | D | $ | I | F | T | $ | S | Y | R | K | V | L | A | Q | L | S |
| SP-70 | H— | Y | a | D | $ | I | F | T | $ | S | Y | R | K | V | L | A | Q | L | S |
| SP-71 | H— | Y | a | D | A | I | F | T | D | S | Y | R | $r8 | V | L | G | E | L | S |
| SP-72 | H— | Y | a | D | A | I | F | T | D | S | Y | R | $r8 | V | L | G | Q | L | S |
| SP-73 | H— | Y | a | D | A | I | F | T | N | S | Y | R | $r8 | V | L | G | E | L | S |
| SP-74 | H— | Y | a | D | A | I | F | T | N | S | Y | R | $r8 | V | L | G | Q | L | S |
| SP-75 | H— | Y | a | D | A | I | F | T | D | S | Y | R | $r8 | V | L | G | E | L | S |
| SP-76 | H— | Y | a | D | A | I | F | T | N | S | Y | R | $r8 | V | L | G | E | L | S |
| SP-77 | H— | Y | a | D | A | I | F | T | D | S | Y | R | $r8 | V | L | G | Q | L | S |
| SP-78 | H— | Y | a | D | $ | I | F | T | $ | S | Y | R | K | V | L | G | E | L | S |
| SP-79 | H— | Y | a | D | $ | I | F | T | $ | S | Y | R | K | V | L | G | E | L | S |
| SP-80 | H— | Y | a | D | $ | I | F | T | $ | S | Y | R | K | V | L | G | Q | L | S |
| SP-81 | H— | Y | a | D | A | I | F | T | N | S | Y | Q | $r8 | V | L | G | Q | L | S |
| SP-82 | H— | Y | a | D | A | I | F | T | N | S | Y | R | $r8 | V | L | G | Q | L | S |
| SP-83 | H— | Y | a | D | A | I | F | T | N | S | Y | R | %r8 | V | L | G | Q | L | S |
| SP-84 | H— | Y | a | D | $ | I | F | T | $ | S | Y | R | K | V | L | G | Q | L | S |
| SP-85 | HBS— | Y | A | Aar | A | I | F | T | N | S | Y | R | K | V | L | G | Q | L | S |
| SP-86 | HBS— | Y | A | Dar | A | I | F | T | N | S | Y | R | K | V | L | G | Q | L | S |
| SP-87 | HBS— | Y | A | Gar | A | I | F | T | N | S | Y | R | K | V | L | G | Q | L | S |
| SP-88 | HBS— | Y | A | Gar | A | I | F | T | N | S | Y | R | K | V | L | G | Q | L | S |
| SP-89 | H— | Y | a | D | $5a5 | I | F | T | $5n3 | S | Y | R | K | V | L | G | Q | L | S |
| SP-90 | H— | Y | a | D | $5n3 | I | F | T | $5a5 | S | Y | R | K | V | L | G | Q | L | S |
| SP-91 | HBS— | Y | A | Dar | A | I | F | T | N | S | Y | R | K | V | L | G | Q | L | S |
| SP-92 | teHBS— | Y | A | teGar | A | I | F | T | N | S | Y | R | K | V | L | G | Q | L | S |

|  | 19 | 20 | 21 | 22 | 23 | 24 | 25 | 26 | 27 | 28 | 29 | 30 | Exact mass | Calc'd (M + 3)/ 3 | Obsv'd (M + 3)/3 |
|---|---|---|---|---|---|---|---|---|---|---|---|---|---|---|---|
| SP-50 | $ | R | K | L | L | Q | N | I | Nle | S | R | —NH2 | 3401.92 | 1134.98 | 1135.64 |
| SP-51 | $ | Q | K | L | L | Q | N | I | Nle | S | R | —NH2 | 3401.92 | 1134.98 | 1135.73 |
| SP-52 | $ | R | Q | L | L | Q | N | I | Nle | S | R | —NH2 | 3429.93 | 1144.32 | 1145.07 |
| SP-53 | $ | R | K | L | L | Q | N | I | Nle | S | Q | —NH2 | 3401.92 | 1134.98 | 1136.19 |
| SP-54 | $ | R | K | L | L | Q | N | I | Nle | S |  | —NH2 | 3273.86 | 1092.29 | 1093.18 |
| SP-55 | $ | R | K | L | L | Q | N | I | Nle | S | R | —NH2 | 3358.91 | 1120.64 | 1121.76 |
| SP-56 | $ | Q | K | L | L | Q | N | I | Nle | S | R | —NH2 | 3358.91 | 1120.64 | 1121.76 |
| SP-57 | $ | R | Q | L | L | Q | N | I | Nle | S | R | —NH2 | 3386.92 | 1129.98 | 1131.1 |
| SP-58 | $ | R | K | L | L | Q | N | I | Nle | S | Q | —NH2 | 3358.91 | 1120.64 | 1121.76 |
| SP-59 | $ | R | K | L | L | Q | N | I | Nle | S |  | —NH2 | 3230.86 | 1077.96 | 1079.12 |
| SP-60 | $ | R | Q | L | L | Q | N | I | Nle | S |  | —NH2 | 3230.82 | 1077.95 | 1079.02 |
| SP-61 | $ | R | K | L | L | Q | N | I | Nle | S | R | —NH2 | 3386.96 | 1129.99 | 1130.83 |
| SP-62 | $ | R | K | A | L | Q | N | I | Nle | S | R | —NH2 | 3358.93 | 1120.65 | 1121.48 |
| SP-63 | A | R | $ | L | L | Q | $ | I | Nle | S | R | —OH | 3410.98 | 1138 | 1138.08 |
| SP-64 | A | R | $ | L | L | E | $ | I | Nle | S | R | —OH | 3412.95 | 1138.66 | 1138.73 |
| SP-65 | A | R | $ | L | L | Q | $ | I | Nle | S | R | —OH | 3411.97 | 1138.33 | 1138.45 |
| SP-66 | A | R | $ | L | L | E | $ | I | Nle | S | R | —OH | 3411.97 | 1138.33 | 1138.36 |
| SP-67 | A | R | $ | L | L | Q | $ | I | Nle | S | R | —NH2 |  |  |  |
| SP-68 | A | R | $ | L | L | Q | $ | I | Nle | S | R | —NH2 |  |  |  |
| SP-69 | A | A | $ | L | L | Q | $ | I | Nle | S | R | —NH2 |  |  |  |
| SP-70 | A | R | $ | L | L | Q | $ | I | Nle | S | A | —NH2 |  |  |  |
| SP-71 | $ | R | K | L | L | E | D | I | Nle | S | R | —NH2 |  |  |  |
| SP-72 | $ | R | K | L | L | Q | D | I | Nle | S | R | —NH2 |  |  |  |
| SP-73 | $ | R | K | L | L | Q | D | I | Nle | S | R | —NH2 |  |  |  |
| SP-74 | $ | R | K | L | L | E | D | I | Nle | S | R | —NH2 |  |  |  |
| SP-75 | $ | R | K | L | L | Q | D | I | Nle | S | R | —NH2 |  |  |  |
| SP-76 | $ | R | K | L | L | E | D | I | Nle | S | R | —NH2 |  |  |  |
| SP-77 | $ | R | K | L | L | Q | D | I | Nle | S | R | —NH2 |  |  |  |
| SP-78 | A | R | $ | L | L | E | $ | I | Nle | S | R | —NH2 |  |  |  |
| SP-79 | A | R | $ | L | L | Q | $ | I | Nle | S | R | —NH2 |  |  |  |
| SP-80 | A | R | $ | L | L | E | $ | I | Nle | S | R | —NH2 |  |  |  |
| SP-81 | $ | R | K | L | L | Q | N | I | Nle | S | R | —NH2 |  |  |  |
| SP-82 | $ | Q | K | L | L | Q | N | I | Nle | S | R | —NH2 |  |  |  |
| SP-83 | % | R | K | L | L | Q | D | I | Nle | S | R | —NH2 |  |  |  |
| SP-84 | A | R | $ | L | L | Q | $ | I | Nle | S | R | —NH2 |  |  |  |
| SP-85 | A | R | $ | L | L | Q | $ | I | Nle | S | R | —NH2 |  |  |  |
| SP-86 | A | R | $ | L | L | Q | $ | I | Nle | S | R | —NH2 |  |  |  |
| SP-87 | A | R | K | L | L | Q | D | I | Nle | S | R | —NH2 |  |  |  |
| SP-88 | A | R | $ | L | L | Q | $ | I | Nle | S | R | —NH2 |  |  |  |
| SP-89 | A | R | $5n3 | L | L | Q | $5a5 | I | Nle | S | R | —NH2 |  |  |  |
| SP-90 | A | R | $5a5 | L | L | Q | $5n3 | I | Nle | S | R | —NH2 |  |  |  |
| SP-91 | A | R | K | L | L | Q | D | I | Nle | S | R | —NH2 |  |  |  |
| SP-92 | A | R | K | L | L | Q | D | I | Nle | S | R | —NH2 |  |  |  |

In the sequences shown above and elsewhere, the following abbreviations are used: amino acids represented as "$" are alpha-Me S5-pentenyl-alanine olefin amino acids connected by an all-carbon i to i+4 crosslinker comprising one double bond. "%" are alpha-Me S5-pentenyl-alanine olefin amino acids connected by an all-carbon i to i+4 crosslinker comprising no double bonds (fully saturated alkylene crosslinker). Amino acids represented as "$r8" are alpha-Me R8-octenyl-alanine olefin amino acids connected by an all-carbon i to i+7 crosslinker comprising one double bond. Amino acids represented as "% r8" are alpha-Me R8-octenyl-alanine olefin amino acids connected by an all-carbon i to i+7 crosslinker comprising no double bonds (fully saturated alkylene crosslinker). The designation "iso1" or "iso2" indicates that the peptidomimetic macrocycle is a single isomer. Amino acids designated as lower case "a" represent D-Alanine.

Amino acids which are used in the formation of triazole crosslinkers are represented according to the legend indicated below. Stereochemistry at the alpha position of each amino acid is S unless otherwise indicated. For azide amino acids, the number of carbon atoms indicated refers to the number of methylene units between the alpha carbon and the terminal azide. For alkyne amino acids, the number of carbon atoms indicated is the number of methylene units between the alpha position and the triazole moiety plus the two carbon atoms within the triazole group derived from the alkyne.

| | |
|---|---|
| $5a5 | Alpha-Me alkyne 1,5 triazole (5 carbon) |
| $5n3 | Alpha-Me azide 1,5 triazole (3 carbon) |
| $4rn6 | Alpha-Me R-azide 1,4 triazole (6 carbon) |
| $4a5 | Alpha-Me alkyne 1,4 triazole (5 carbon) |

Exemplary structures of several peptidomimetic macrocycles are shown in Table 5.

TABLE 5
| SP | Structure |
|---|---|
| SP-1 | 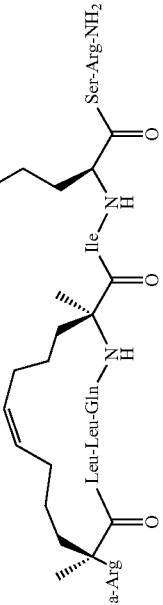<br>Chemical Formula: $C_{161}H_{264}N_{42}O_{39}$<br>Exact Mass: 3410.00<br>Molecular Weight: 3412.08 |
| SP-45 | 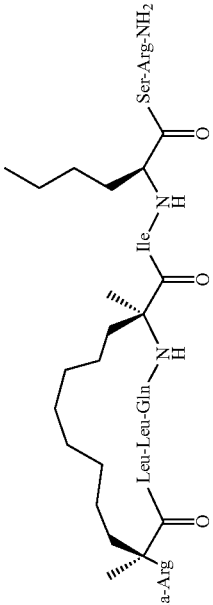<br>Chemical Formula: $C_{161}H_{268}N_{42}O_{39}$<br>Exact Mass: 3414.03<br>Molecular Weight: 3416.11 |

TABLE 5-continued

| SP | Structure |
|---|---|
| SP-46 | Chemical Formula: $C_{161}H_{262}N_{48}O_{39}$<br>Exact Mass: 3492.00<br>Molecular Weight: 3494.10 |
| SP-47 | Chemical Formula: $C_{161}H_{262}N_{48}O_{39}$<br>Exact Mass: 3492.00<br>Molecular Weight: 3494.10 |

Example 2

Metabolism by Purified Protease

Figure 1B:
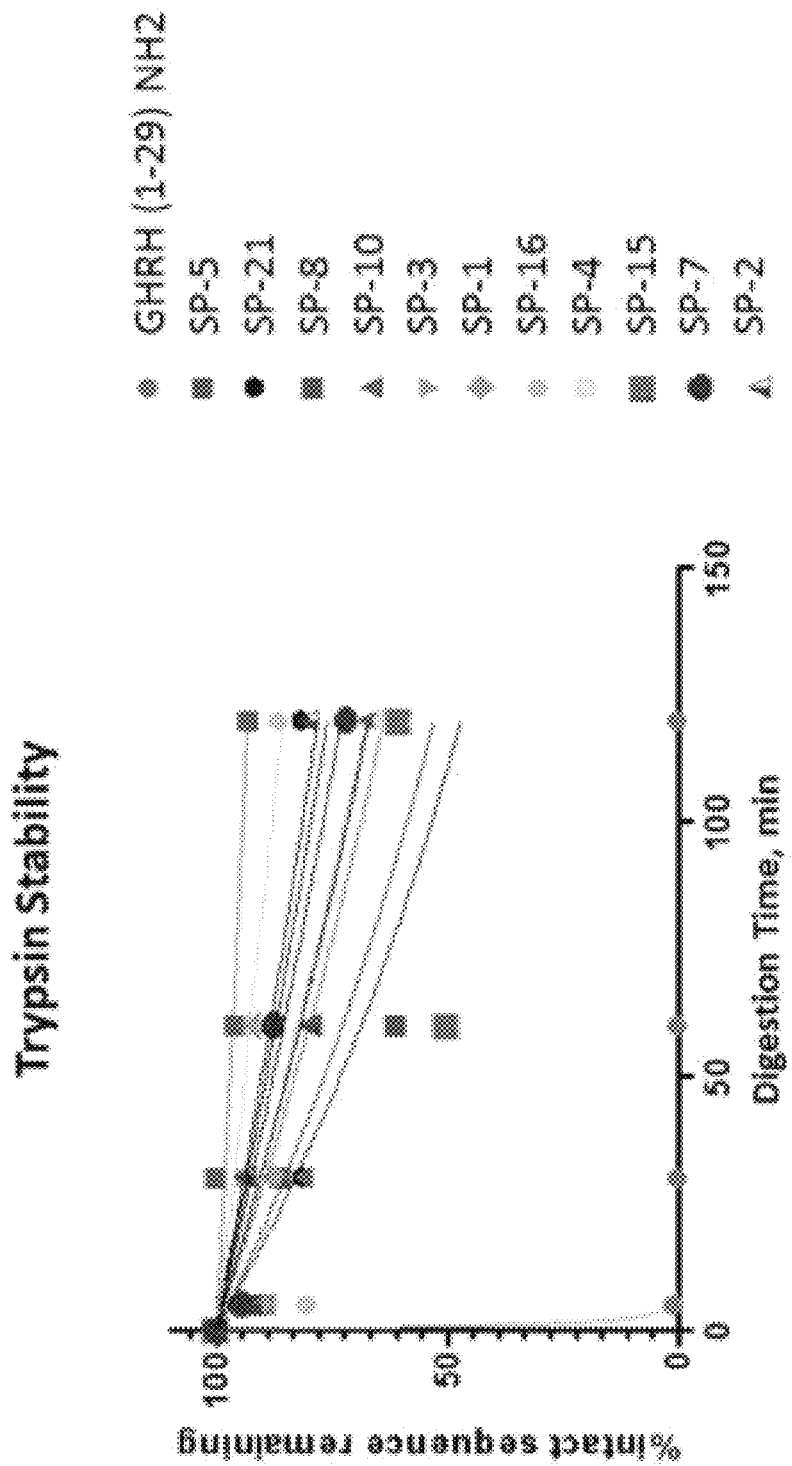
Figure 2:
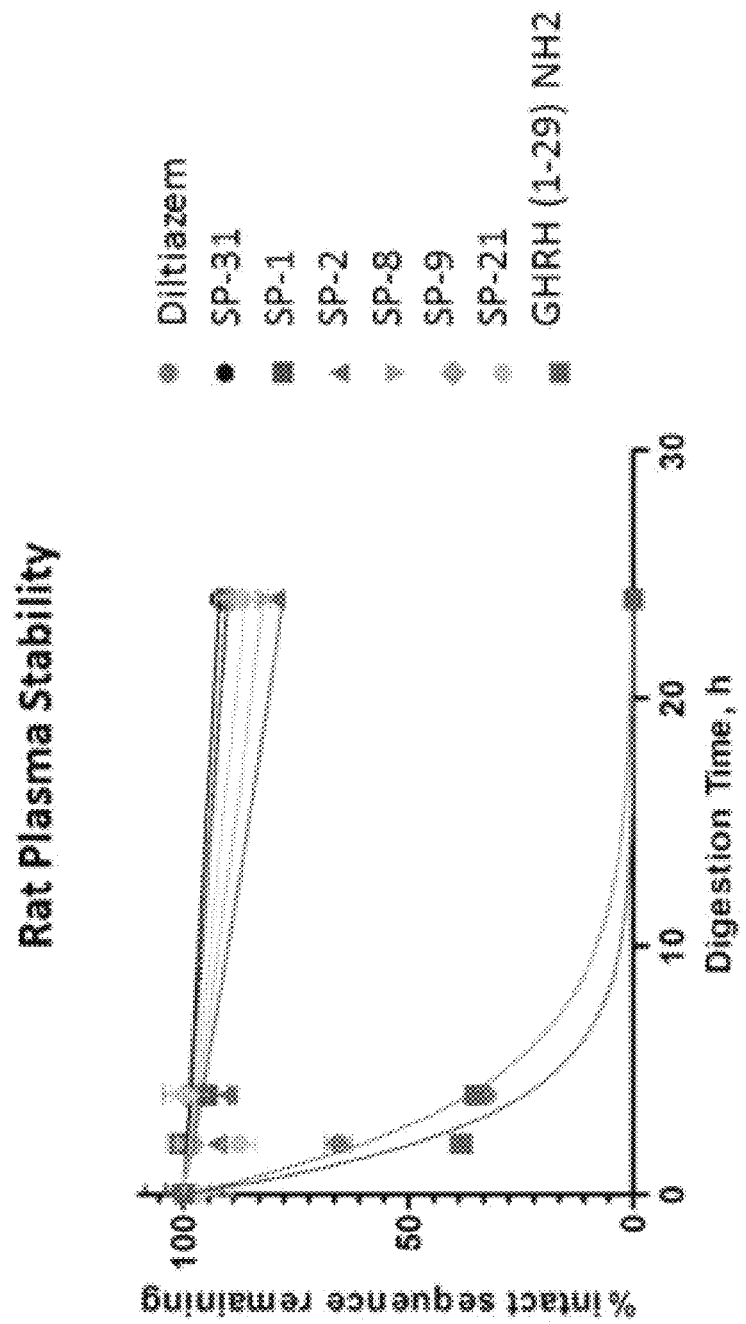
FIG. 2 shows improved serum stabilities of the peptidomimetic macrocycles of the invention.

Linear peptides and cross-linked peptidomimetic macrocycles were tested for stability to proteolysis by Trypsin (MP Biomedicals, Solon Ohio) by solubilizing each peptide at 10 μM concentration in 200 μL 100 mM NH4OAc (pH 7.5). The reaction was initiated by adding 3.5 μl of Trypsin (12.5 μg protease per 500 μL reaction) and shaking continually in sealed vials while incubating in a Room Temperature (22±2° C.). The enzyme/substrate ratio was 1:102 (w/w). After incubation times of 0, 5, 30, 60 and 135 min the reaction was stopped by addition of equal volume of 0.2% trifluoroacetic acid. Then, the solution was immediately analyzed by LC-MS in positive detection mode. The reaction half-life for each peptide was calculated in GraphPad Prism by a non-linear fit of uncalibrated MS response versus enzyme incubation time. Results are shown in FIGS. 1A and 1B.

Example 3

GHRHR Agonism Measured by cAMP

Figure 3:
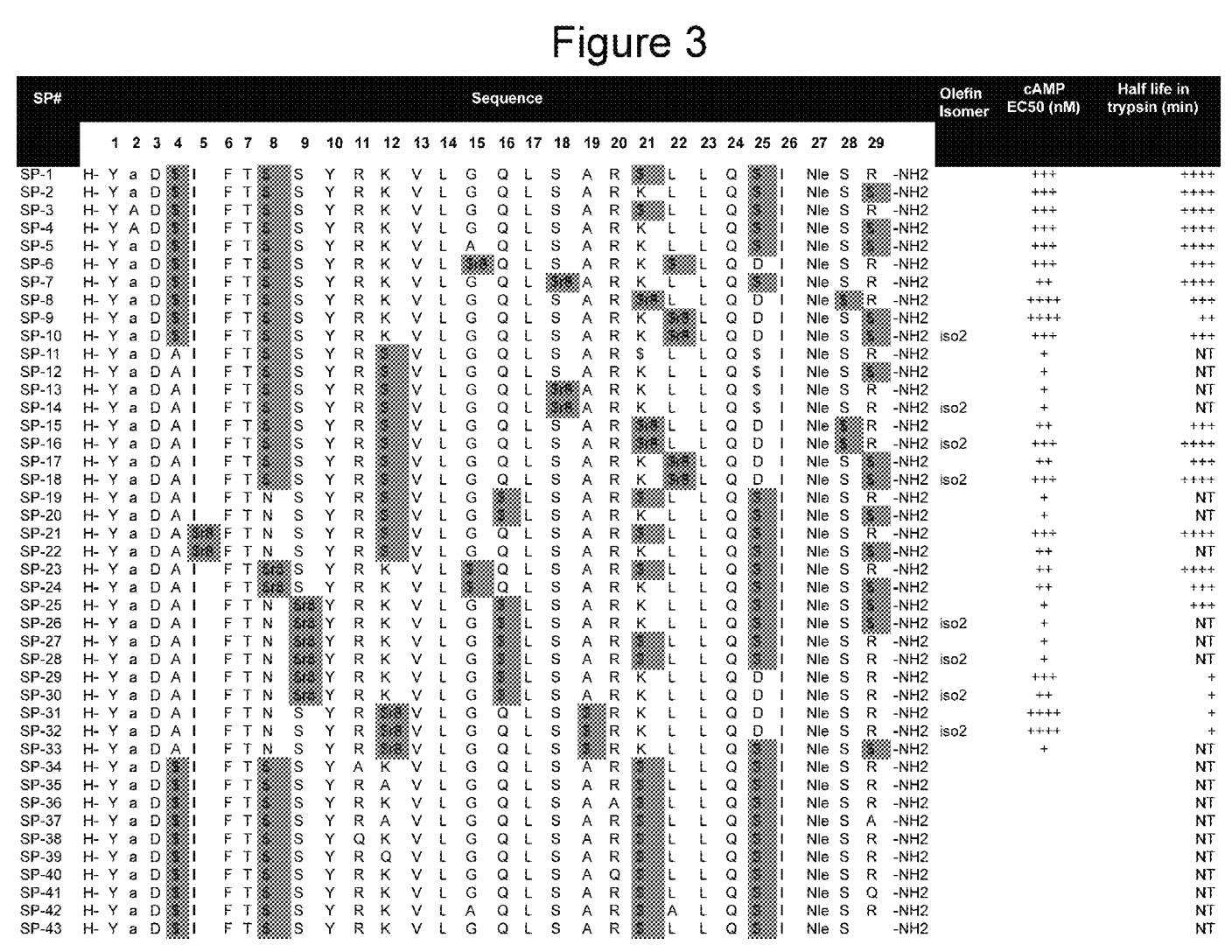
Figure 3A:
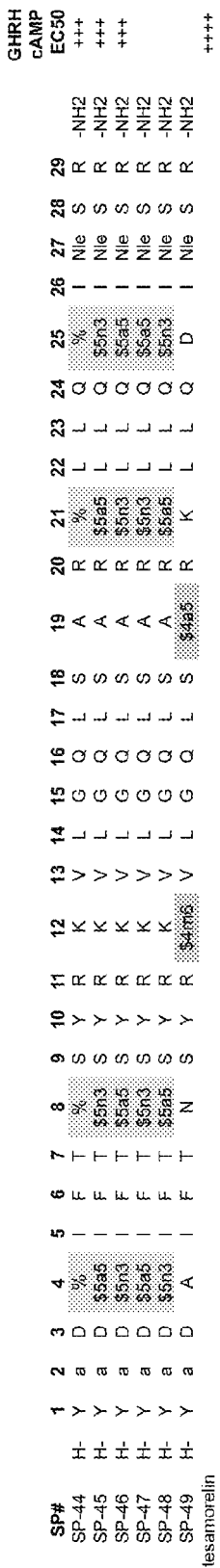
Figure 5:
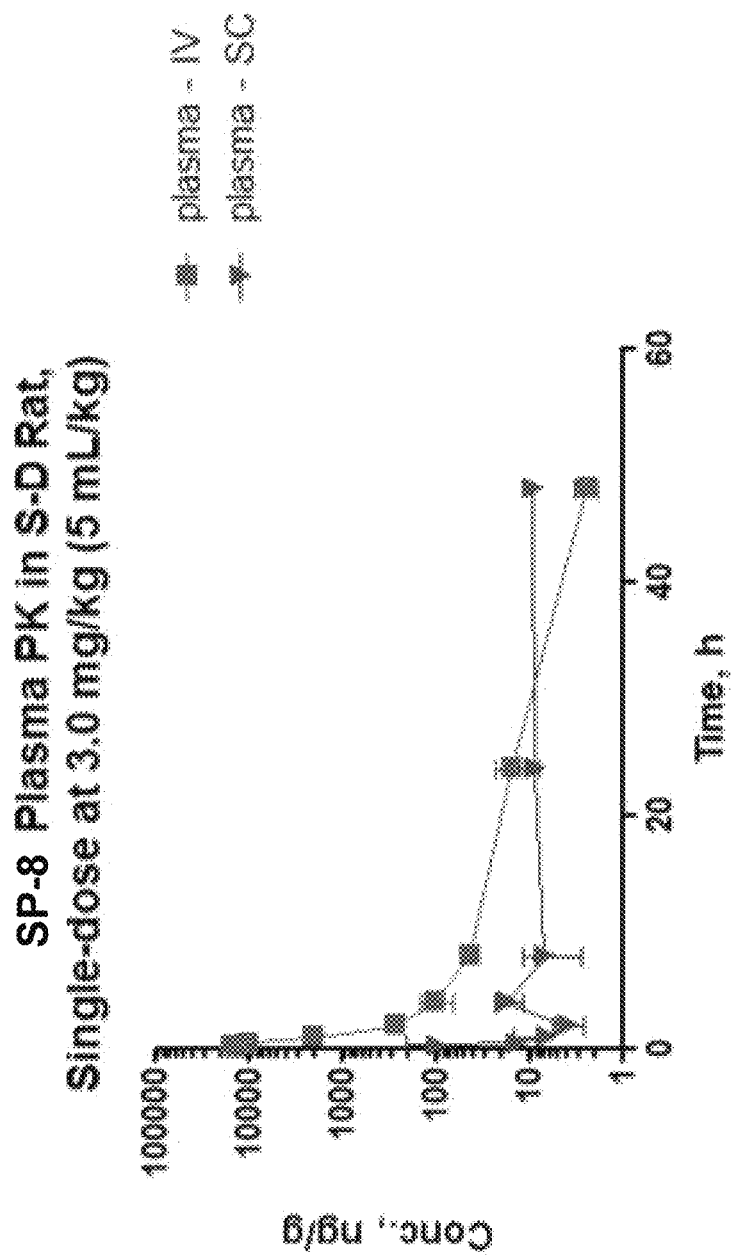
FIG. 5 shows the result of a plasma PK study performed with peptidomimetic macrocycle SP-8.
Figure 6:
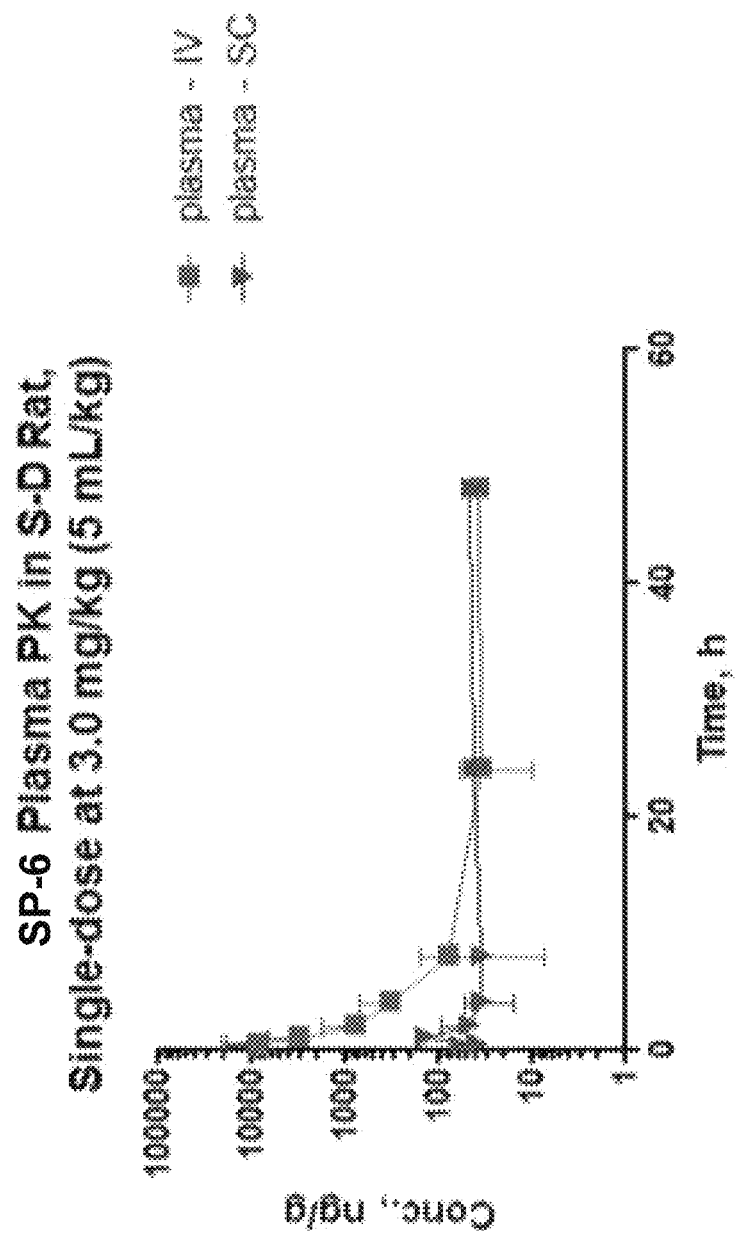
FIG. 6 shows the result of a plasma PK study performed with peptidomimetic macrocycle SP-6.
Figure 7:
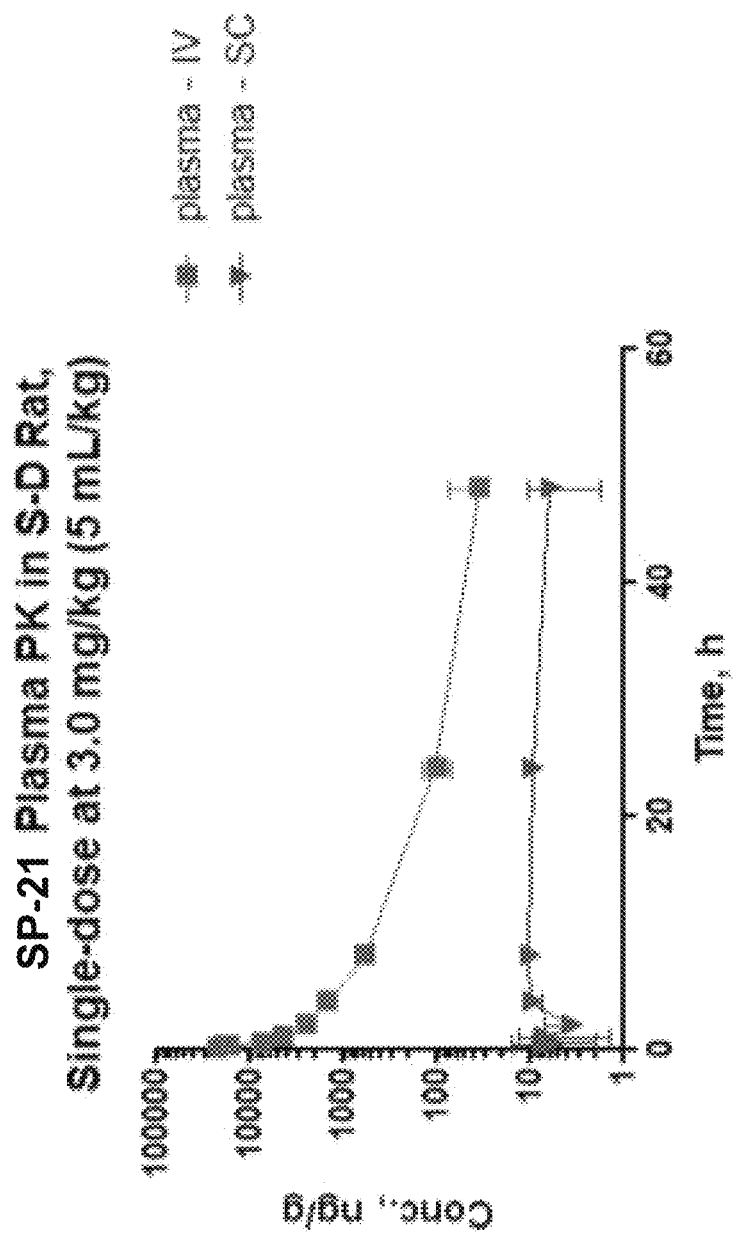
FIG. 7 shows the result of a plasma PK study performed with peptidomimetic macrocycle SP-21.
Figure 8:
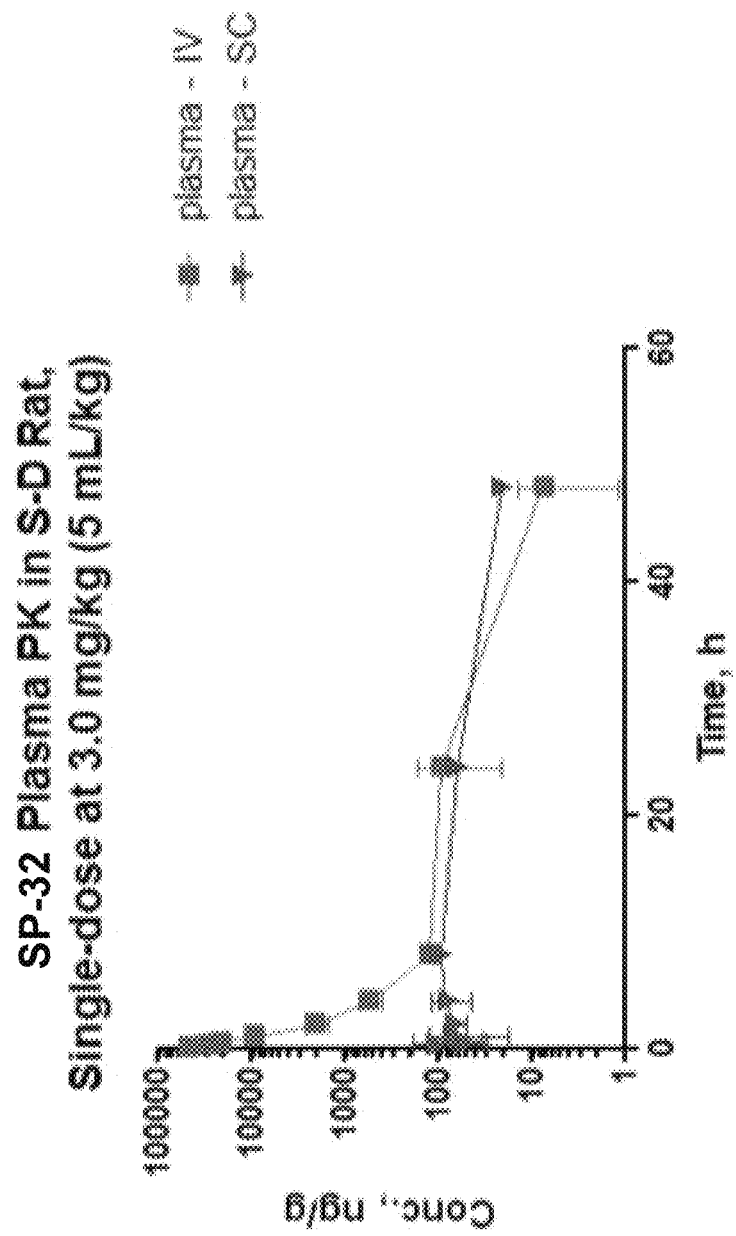
FIG. 8 shows the result of a plasma PK study performed with peptidomimetic macrocycle SP-32.
Figure 10:
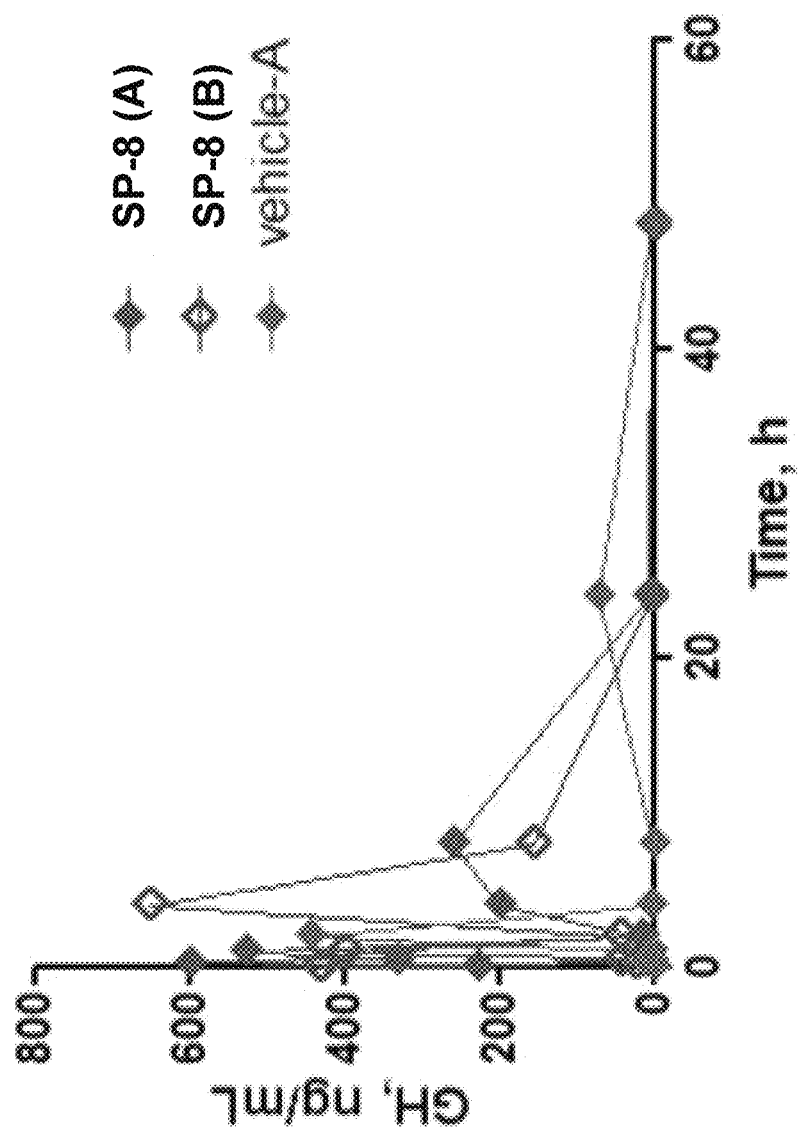
FIG. 10 shows stimulation of growth hormone production by peptidomimetic macrocycle SP-8.
Figure 11:
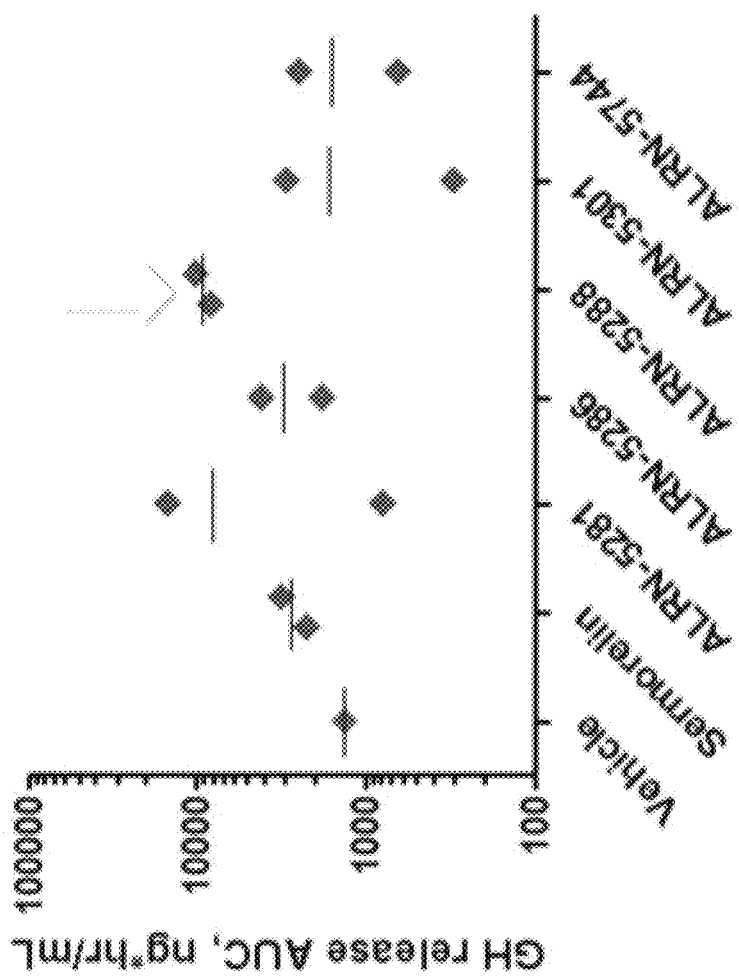
FIG. 11 shows growth hormone release (AUC) induced by sermorelin in comparison to peptidomimetic macrocycles SP-1, SP-6, SP-8, SP-21, and SP-32.

GHRH (1-29) and cross-linked peptidomimetic macrocycles were tested for agonism at the human GHRH receptor (hGHRHR) at various concentrations. Human 293 cells transiently or stably expressing hGHRHR were detached from cell culture flasks with versene (Lifetechnologies), suspended in serum-free medium (50 k cells/assay point), and stimulated for 30 min at RT with GHRH (1-29) (Bachem) or cross-linked peptidomimetic macrocycles. cAMP was quantified using an HTRF®-based assay (CisBio) and used according to the manufacturers instructions. An EC50% for each agonist was calculated from a non-linear fit of response vs dose (GraphPad Prism). The maximum response was determined by stimulating with 10 μM GHRH (1-29). Results are shown in FIG. 3.

Example 4

Plasma PK/PD Study in Rats

Five peptidomimetic macrocycles of the invention (SP-1, SP-6, SP-8, SP-21, SP-32), as well as sermorelin, were studied to determine pharmacokinetic and pharmacodynamic parameters in rats. Male Sprague-Dawley rats (300 g, non-fasted, cannulated) were used. The study had three arms: IV administration, SC administration, and SC administration (vehicle control). For experiments using sermorelin, a dose level of 3 mg/kg IV/SC bolus was used (dose volume of 3 mL/kg dose and dose concentration of 1 mg/mL). The vehicle used was: 10 wt % N, N-Dimethylacetamide, 10 wt % DMSO, 2 wt % Solutol HS 15 in water for injection containing 45 mg/mL (4.5 wt %) Mannitol and 25 mM (0.38 wt %) Histidine (pH 7.5; 320 mOsm/kg). The peptide was first dissolved at high concentration in DMA and DMSO before a second dilution in Solutol vehicle.

For experiments using peptidomimetic macrocycles, 0.1 mL of DMA and 0.1 mL of DMSO were used to combine with each mg of macrocycle (~4.3-4.5 mg of macrocycle used in each experiment). Sonication was used to ensure complete solubilization. 0.8 mL of Solutol vehicle was used for each mg of macrocycle in DMA/DMSO. The solutions were mixed gently with pipet or light vortexing. Fresh vials were used for each day of dosing, and macrocycles were stored solid at −20° C. prior to formulation.

For each study arm, 2 rats were bled (350 μL) at specific timepoints (5 min, 15 min, 30 min, 1 h, 2 h, 4 h, 8 h, 24 h, and 48 h) and a 150 μL bleed was performed just before dosing. Plasma was prepared into K2EDTA tubes by centrifuging for 20 minutes at 4° C. at 2000 G maximum 30 minutes after collection. From each 350 μL bleed, 120 μL were transferred to one tube for PK studies and 50 μL to another tube for PD studies and frozen immediately. From the 150 μL bleed, 70 μL were transferred to one tube for PD studies and frozen immediately.

Results are shown in FIGS. 4-11.

---

What is claimed is:

1. A peptidomimetic macrocycle comprising an amino acid sequence which is at least about 60% identical to GHRH 1-29, and a crosslinker that is a macrocycle-forming linker of the formula -$L_1$-$L_2$-, wherein:
   each $L_1$ and $L_2$ is independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;
   each K is independently O, S, SO, $SO_2$, CO, or $CO_2$;
   each $R_4$ is independently alkylene, alkenylene, alkynylene, heteroalkylene, cycloalkylene, heterocycloalkylene, arylene, or heteroarylene;
   each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope, or a therapeutic agent;
   each $R_6$ is independently —H, alkyl, alkenyl, alkynyl, arylalkyl, cycloalkylalkyl, heterocycloalkyl, a fluorescent moiety, a radioisotope, or a therapeutic agent; and
   each n is independently an integer from 1-5, wherein the peptidomimetic macrocycle comprises an α,α-disubstituted amino acid.

2. The peptidomimetic macrocycle of claim 1, wherein the macrocycle-forming linker connects a first amino acid and a second amino acid, wherein the first amino acid and the second amino acid are selected from amino acids corresponding to the following locations of amino acids: 4 and 8; 5 and 12; 8 and 12; 8 and 15; 9 and 16; 12 and 16; 12 and 19; 15 and 22; 18 and 25; 21 and 25; 21 and 28; 22 and 29; and 25 and 29 of GHRH 1-29.

3. The peptidomimetic macrocycle of claim 1, wherein the macrocycle-forming linker connects a first amino acid and a second amino acid, wherein the first amino acid and the second amino acid are selected from amino acids corresponding to the following locations of amino acids: 4 and 8; 5 and 12; 12 and 19; 15 and 22; 18 and 25; 21 and 25; and 21 and 28 of GHRH 1-29.

4. The peptidomimetic macrocycle of claim 1, wherein the macrocycle-forming linker connects a first amino acid and a second amino acid, wherein the first amino acid and the second amino acid correspond to the following locations of amino acids: 4 and 8 of GHRH 1-29.

5. The peptidomimetic macrocycle of claim 1, wherein the macrocycle-forming linker connects a first amino acid and a second amino acid, wherein the first amino acid and the second amino acid correspond to the following locations of amino acids: 21 and 25 of GHRH 1-29.

6. The peptidomimetic macrocycle of claim 1, comprising two macrocycle-forming linkers.

7. The peptidomimetic macrocycle of claim 1, comprising an amino acid sequence which is at least about 60% identical to an amino acid sequence chosen from the group consisting of the amino acid sequences in Tables 1, 2 or 4.

8. The peptidomimetic macrocycle of claim 1, wherein the amino acid sequence of said peptidomimetic macrocycle is at least about 80% identical to an amino acid sequence chosen from the group consisting of the amino acid sequences in Tables 1, 2 or 4.

9. The peptidomimetic macrocycle of claim 1, wherein the amino acid sequence of said peptidomimetic macrocycle is at least about 90% identical to an amino acid sequence chosen from the group consisting of the amino acid sequences in Tables 1, 2 or 4.

10. The peptidomimetic macrocycle of claim 1, wherein the peptidomimetic macrocycle comprises a helix.

11. The peptidomimetic macrocycle of claim 1, wherein the peptidomimetic macrocycle comprises an α-helix.

12. The peptidomimetic macrocycle of claim 1, wherein the peptidomimetic macrocycle comprises an α,α-disubstituted amino acid.

13. The peptidomimetic macrocycle of claim 1, wherein the macrocycle forming linker connects two α,α-disubstituted amino acids.

14. The peptidomimetic macrocycle of claim 1, wherein the peptidomimetic macrocycle has the formula:

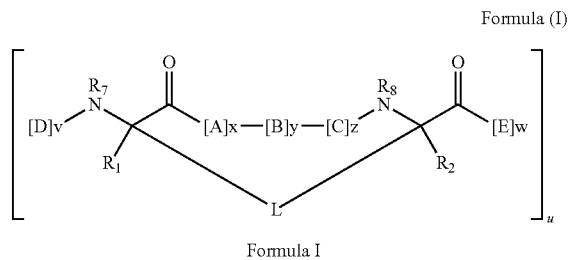

Formula I wherein:
each A, C, D, and E is independently an amino acid;
each B is independently an amino acid or

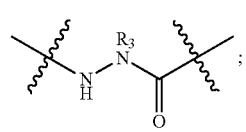

each L is independently a macrocycle-forming linker of the formula -$L_1$-$L_2$-;
A, B, C, D, and E, taken together with the crosslinked amino acids connected by the macrocycle-forming linker L, form the amino acid sequence of the peptidomimetic macrocycle;

each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-;

each $R_3$ is independently alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

each $R_7$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

each $R_8$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

each v and w is independently an integer from 1-100;
u is an integer from 1 to 3; and
each x, y and z is independently an integer from 0-10.

15. The peptidomimetic macrocycle of claim 14, wherein $R_1$ and $R_2$ are independently H.

16. The peptidomimetic macrocycle of claim 14, wherein $R_1$ and $R_2$ are independently alkyl.

17. The peptidomimetic macrocycle of claim 14, wherein $R_1$ and $R_2$ are independently methyl.

18. The peptidomimetic macrocycle of claim 14, wherein the sum of x+y+z is 2, 3, or 6.

19. The pharmaceutical composition of claim 14, wherein the peptidomimetic macrocycle has the formula:

21. A pharmaceutical composition comprising the peptidomimetic macrocycle of claim 1.

22. A method of treating a condition in a subject in need thereof, the method comprising administering to the subject a therapeutically-effective amount of a peptidomimetic macrocycle, wherein the peptidomimetic macrocycle comprises an amino acid sequence which is at least about 60% identical to GHRH 1-29, and a crosslinker that is a macrocycle-forming linker of the formula -$L_1$-$L_2$-, wherein:

each $L_1$ and $L_2$ is independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

each K is independently O, S, SO, $SO_2$, CO, or $CO_2$;

each $R_4$ is independently alkylene, alkenylene, alkynylene, heteroalkylene, cycloalkylene, heterocycloalkylene, arylene, or heteroarylene;

each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope, or a therapeutic agent;

each $R_6$ is independently —H, alkyl, alkenyl, alkynyl, arylalkyl, cycloalkylalkyl, heterocycloalkyl, a fluorescent moiety, a radioisotope, or a therapeutic agent; and each n is independently an integer from 1-5, wherein the peptidomimetic macrocycle comprises an α,α-disubstituted amino acid.

23. The method of claim 22, wherein the macrocycle-forming linker connects a first amino acid and a second amino acid, wherein the first amino acid and the second amino acid are selected from amino acids corresponding to

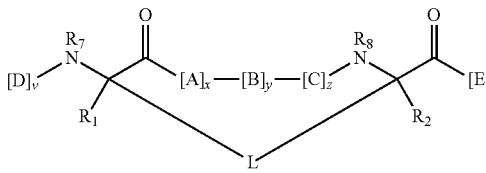
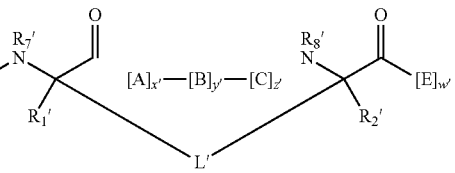

L' is a macrocycle-forming linker of the formula -$L_1$'-$L_2$'-;
A, B, C, D, and E, taken together with the crosslinked amino acids connected by the macrocycle-forming linkers L and L', form the amino acid sequence of the peptidomimetic macrocycle;

each $R_1$' and $R_2$' is independently —H, alkyl, alkenyl, alkynyl, arylalkyl, cycloalkyl, cycloalkylalkyl, heteroalkyl, or heterocycloalkyl, unsubstituted or substituted with halo-;

each $L_1$' and $L_2$' is independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;

$R_7$' is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

$R_8$' is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

each v' and w' is independently an integer from 1-100; and
each x', y' and z' is independently an integer from 0-10.

20. The peptidomimetic macrocycle of claim 19, wherein the sum of x'+y'+z' is 2, 3 or 6.

the following locations of amino acids: 4 and 8; 5 and 12; 8 and 12; 8 and 15; 9 and 16; 12 and 16; 12 and 19; 15 and 22; 18 and 25; 21 and 25; 21 and 28; 22 and 29; and 25 and 29 of GHRH 1-29.

24. The method of claim 22, wherein the macrocycle-forming linker connects a first amino acid and a second amino acid, wherein the first amino acid and the second amino acid are selected from amino acids corresponding to the following locations of amino acids: 4 and 8; 5 and 12; 12 and 19; 15 and 22; 18 and 25; 21 and 25; and 21 and 28 of GHRH 1-29.

25. The method of claim 22, wherein the macrocycle-forming linker connects a first amino acid and a second amino acid, wherein the first amino acid and the second amino acid correspond to the following locations of amino acids: 4 and 8 of GHRH 1-29.

26. The method of claim 22, wherein the macrocycle-forming linker connects a first amino acid and a second amino acid, wherein the first amino acid and the second amino acid correspond to the following locations of amino acids: 21 and 25 of GHRH 1-29.

27. The method of claim 22, wherein the peptidomimetic macrocycle comprises two macrocycle-forming linkers.

28. The method of claim 22, wherein the peptidomimetic macrocycle comprises an amino acid sequence which is at least about 60% identical to an amino acid sequence chosen from the group consisting of the amino acid sequences in Tables 1, 2, or 4.

29. The method of claim 22, wherein the amino acid sequence of said peptidomimetic macrocycle is at least about 80% identical to an amino acid sequence chosen from the group consisting of the amino acid sequences in Tables 1, 2, or 4.

30. The method of claim 22, wherein the amino acid sequence of said peptidomimetic macrocycle is at least about 90% identical to an amino acid sequence chosen from the group consisting of the amino acid sequences in Tables 1, 2, or 4.

31. The method of claim 22, wherein the peptidomimetic macrocycle comprises a helix.

32. The method of claim 22, wherein the peptidomimetic macrocycle comprises an α-helix.

33. The method of claim 22, wherein the peptidomimetic macrocycle comprises an α,α-disubstituted amino acid.

34. The method of claim 22, wherein the macrocycle forming linker connects two α,α-disubstituted amino acids.

35. The method of claim 22, wherein the peptidomimetic macrocycle has the formula:

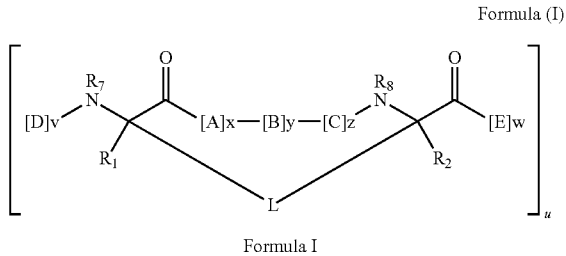

Formula I wherein:
each A, C, D, and E is independently an amino acid;
each B is independently an amino acid or

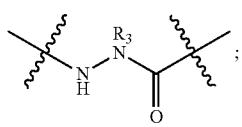

each L is independently a macrocycle-forming linker of the formula -$L_1$-$L_2$-;
A, B, C, D, and E, taken together with the crosslinked amino acids connected by the macrocycle-forming linker L, form the amino acid sequence of the peptidomimetic macrocycle;
each $R_1$ and $R_2$ is independently —H, alkyl, alkenyl, alkynyl, arylalkyl, cycloalkyl, cycloalkylalkyl, heteroalkyl, or heterocycloalkyl, unsubstituted or substituted with halo-;

each $R_3$ is independently alkyl, alkenyl, alkynyl, arylalkyl, heteroalkyl, cycloalkyl, heterocycloalkyl, cycloalkylalkyl, cycloaryl, or heterocycloaryl, optionally substituted with $R_5$;

each $R_7$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;

each $R_8$ is independently —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with an E residue;

each v and w is independently an integer from 1-100;
u is an integer from 1 to 3; and
each x, y and z is independently an integer from 0-10.

36. The method of claim 35, wherein $R_1$ and $R_2$ are independently H.

37. The method of claim 35, wherein $R_1$ and $R_2$ are independently alkyl.

38. The method of claim 35, wherein $R_1$ and $R_2$ are independently methyl.

39. The method of claim 35, wherein the sum of x+y+z is 2, 3, or 6.

40. The method of claim 35, wherein the peptidomimetic macrocycle has the formula:

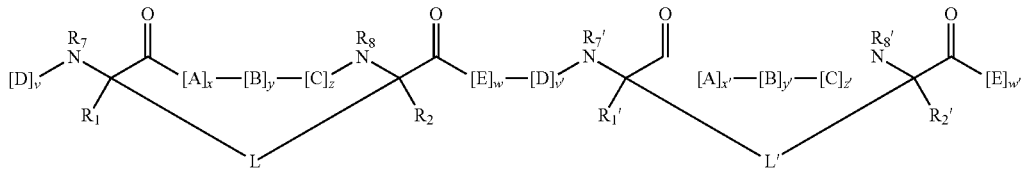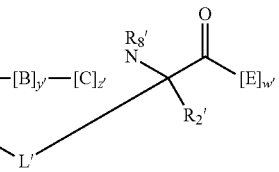

wherein:
L' is a macrocycle-forming linker of the formula -$L_1$'-$L_2$'-;
A, B, C, D, and E, taken together with the crosslinked amino acids connected by the macrocycle-forming linkers L and L', form the amino acid sequence of the peptidomimetic macrocycle;
each $R_1$' and $R_2$' is independently —H, alkyl, alkenyl, alkynyl, arylalkyl, cycloalkyl, cycloalkylalkyl, heteroalkyl, or heterocycloalkyl, unsubstituted or substituted with halo-;
each $L_1$' and $L_2$' is independently alkylene, alkenylene, alkynylene, heteroalkylene, cycloalkylene, heterocycloalkylene, cycloarylene, heterocycloarylene, or [—$R_4$—K—$R_4$—]$_n$, each being optionally substituted with $R_5$;
$R_7$' is —H, alkyl, alkenyl, alkynyl, arylalkyl, cycloalkyl, heteroalkyl, cycloalkylalkyl, heterocycloalkyl, cycloaryl, or heterocycloaryl, optionally substituted with $R_5$, or part of a cyclic structure with a D residue;
$R_8$' is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R$_5$, or part of a cyclic structure with an E residue; each v' and w' is independently an integer from 1-100; and each x', y' and z' is independently an integer from 0-10.

41. The method of claim 40, wherein the sum of x'+y'+z' is 2, 3, or 6.

42. The method of claim 22, wherein the condition is a cachexia.

43. The method of claim 42, wherein the cachexia is cancer cachexia, chronic heart failure cachexia, chronic obstructive pulmonary disease cachexia, or rheumatoid arthritis cachexia.

44. The method of claim 22, wherein the condition is a lipodystrophy.

45. The method of claim 44, wherein the lipodystrophy is a HIV lipodystrophy.

46. The method of claim 22, wherein the condition is a growth hormone disorder.

47. The method of claim 46, wherein the growth hormone disorder is an adult growth hormone deficiency.

48. The method of claim 46, wherein the growth hormone disorder is a pediatric growth hormone deficiency.

49. The method of claim 48, wherein the pediatric growth hormone deficiency is associated with idiopathic short stature, SGA (infant small for gestational age), chronic kidney disease, Prader-Willi syndrome Turner syndrome, short stature homeobox (SHOX) gene deficiency, or primary IGF-1 deficiency.

50. The method of claim 22, wherein the condition is gastroparesis/short bowel syndrome.

51. A method of treating a condition in a subject in need thereof, the method comprising administering to the subject a therapeutically-effective amount of a peptidomimetic macrocycle, wherein the peptidomimetic macrocycle comprises an amino acid sequence which is at least about 60% identical to GHRH 1-29, comprising at least two macrocycle-forming linkers, wherein the first of said two macrocycle-forming linkers connects a first amino acid to a second amino acid, and the second of said two macrocycle-forming linkers connects a third amino acid to a fourth amino acid, wherein the peptidomimetic macrocycle comprises an α,α-disubstituted amino acid.

52. A method of treating a condition in a subject in need thereof, the method comprising administering to the subject a therapeutically-effective amount of a peptidomimetic macrocycle, wherein the peptidomimetic macrocycle comprises:
   i) an amino acid sequence which is at least about 60% identical to GHRH 1-29; and
   ii) a macrocycle-forming linker connecting a first amino acid to a second amino acid, wherein the peptidomimetic macrocycle comprises an α,α-disubstituted amino acid, and wherein the first and second amino acids are selected from amino acids corresponding to the following locations of amino acids: 4 and 8; 5 and 12; 8 and 12; 8 and 15; 9 and 16; 12 and 16; 12 and 19; 15 and 22; 18 and 25; 21 and 25; 21 and 28; and 22 and 29 of GHRH 1-29.

53. A method of treating a condition in a subject in need thereof, the method comprising administering to the subject a therapeutically-effective amount of a peptidomimetic macrocycle, wherein the peptidomimetic macrocycle comprises an amino acid sequence of formula:

X1-X2-X3-X4-X5-X6-X7-X8-X9-X10-X11-X12-X13-X14-X15-X16-X17-X18-X19-X20-X21-X22-X23-X24-X25-X26-X27-X28-X29 wherein:
X1 is Tyr or His;
X2 is Ala, D-Ala, or Val;
X3 is Asp;
X4 is Ala or a crosslinked amino acid;
X5 is Ile;
X6 is Phe;
X7 is Thr;
X8 is Gln, Asn, or a crosslinked amino acid;
X9 is Ser or a crosslinked amino acid;
X10 is Tyr;
X11 is Arg, Ala or Gln;
X12 is Lys, Ala, Gln or a crosslinked amino acid;
X13 is Val or Ile;
X14 is Leu;
X15 is Gly, Ala or a crosslinked amino acid;
X16 is Gln, Glu or a crosslinked amino acid;
X17 is Leu;
X18 is Ser, Tyr or a crosslinked amino acid;
X19 is Ala or a crosslinked amino acid;
X20 is Arg or Gln;
X21 is Lys, Gln or a crosslinked amino acid;
X22 is Leu, Ala, or a crosslinked amino acid;
X23 is Leu;
X24 is Gln, Glu or His;
X25 is Asp, Glu or a crosslinked amino acid;
X26 is Ile;
X27 is Met, Ile, Leu or Nle;
X28 is Ser or a crosslinked amino acid;
X29 is Arg, Ala, Gln or a crosslinked amino acid;
wherein the peptidomimetic macrocycle comprises at least one macrocycle-forming linker L connecting at least one pair of amino acids;
each L is independently a macrocycle-forming linker of the formula -L$_1$-L$_2$-;
each L$_1$ and L$_2$ is independently alkylene, alkenylene, alkynylene, heteroalkylene, cycloalkylene, heterocycloalkylene, cycloarylene, heterocycloarylene, or [—R$_4$—K—R$_4$—]$_n$, each being optionally substituted with R$_5$;
each R$_4$ is independently alkylene, alkenylene, alkynylene, heteroalkylene, cycloalkylene, heterocycloalkylene, arylene, or heteroarylene;
each K is independently O, S, SO, SO$_2$, CO, or CO$_2$;
each R$_5$ is independently halogen, alkyl, —OR$_6$, —N(R$_6$)$_2$, —SR$_6$, —SOR$_6$, —SO$_2$R$_6$, —CO$_2$R$_6$, a fluorescent moiety, a radioisotope, or a therapeutic agent;
each R$_6$ is independently —H, alkyl, alkenyl, alkynyl, arylalkyl, cycloalkylalkyl, heterocycloalkyl, a fluorescent moiety, a radioisotope, or a therapeutic agent; and
each n is independently an integer from 1-5, wherein the peptidomimetic macrocycle comprises an α,α-disubstituted amino acid.

54. A pharmaceutical composition comprising a peptidomimetic macrocycle, wherein the peptidomimetic macrocycle comprises an amino acid sequence which is at least about 60% identical to GHRH 1-29, comprising at least two macrocycle-forming linkers, wherein the first of said two macrocycle-forming linkers connects a first amino acid to a second amino acid, and the second of said two macrocycle-forming linkers connects a third amino acid to a fourth amino acid, wherein the peptidomimetic macrocycle comprises an α,α-disubstituted amino acid.

55. A pharmaceutical composition comprising a peptidomimetic macrocycle, wherein the peptidomimetic macrocycle comprises:
   i) an amino acid sequence which is at least about 60% identical to GHRH 1-29; and ii) a macrocycle-forming linker connecting a first amino acid to a second amino acid, wherein the peptidomimetic macrocycle comprises an α,α-disubstituted amino acid, and wherein the first and second amino acids are selected from amino acids corresponding to the following locations of amino acids: 4 and 8; 5 and 12; 8 and 12; 8 and 15; 9 and 16; 12 and 16; 12 and 19; 15 and 22; 18 and 25; 21 and 25; 21 and 28; and 22 and 29 of GHRH 1-29.

56. A pharmaceutical composition comprising a peptidomimetic macrocycle, wherein the peptidomimetic macrocycle comprises an amino acid sequence of formula:

X1-X2-X3-X4-X5-X6-X7-X8-X9-X10-X11-X12-X13-X14-X15-X16-X17-X18-X19-X20-X21-X22-X23-X24-X25-X26-X27-X28-X29 wherein:
X1 is Tyr or His;
X2 is Ala, D-Ala, or Val;
X3 is Asp;
X4 is Ala or a crosslinked amino acid;
X5 is Ile;
X6 is Phe;
X7 is Thr;
X8 is Gln, Asn, or a crosslinked amino acid;
X9 is Ser or a crosslinked amino acid;
X10 is Tyr;
X11 is Arg, Ala or Gln;
X12 is Lys, Ala, Gln or a crosslinked amino acid;
X13 is Val or Ile;
X14 is Leu;
X15 is Gly, Ala or a crosslinked amino acid;
X16 is Gln, Glu or a crosslinked amino acid;
X17 is Leu;
X18 is Ser, Tyr or a crosslinked amino acid;
X19 is Ala or a crosslinked amino acid;
X20 is Arg or Gln;
X21 is Lys, Gln or a crosslinked amino acid;
X22 is Leu, Ala, or a crosslinked amino acid;
X23 is Leu;
X24 is Gln, Glu or His;
X25 is Asp, Glu or a crosslinked amino acid;
X26 is Ile;
X27 is Met, Ile, Leu or Nle;
X28 is Ser or a crosslinked amino acid;
X29 is Arg, Ala, Gln or a crosslinked amino acid;
wherein the peptidomimetic macrocycle comprises at least one macrocycle-forming linker L connecting at least one pair of amino acids;
each L is independently a macrocycle-forming linker of the formula $-L_1-L_2-$;
each $L_1$ and $L_2$ is independently alkylene, alkenylene, alkynylene, heteroalkylene, cycloalkylene, heterocycloalkylene, cycloarylene, heterocycloarylene, or $[-R_4-K-R_4-]_n$, each being optionally substituted with $R_5$;
each $R_4$ is independently alkylene, alkenylene, alkynylene, heteroalkylene, cycloalkylene, heterocycloalkylene, arylene, or heteroarylene;
each K is independently O, S, SO, $SO_2$, CO, or $CO_2$;
each $R_5$ is independently halogen, alkyl, —$OR_6$, —$N(R_6)_2$, —$SR_6$, —$SOR_6$, —$SO_2R_6$, —$CO_2R_6$, a fluorescent moiety, a radioisotope, or a therapeutic agent;
each $R_6$ is independently —H, alkyl, alkenyl, alkynyl, arylalkyl, cycloalkylalkyl, heterocycloalkyl, a fluorescent moiety, a radioisotope, or a therapeutic agent; and
each n is independently an integer from 1-5, wherein the peptidomimetic macrocycle comprises an α,α-disubstituted amino acid.

* * * * *

SEQUENCE LISTING

<160> NUMBER OF SEQ ID NOS: 180

<210> SEQ ID NO 1
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr or His
<220> FEATURE:
<221> NAME/KEY: MOD_RES
<222> LOCATION: (2)..(2)
<223> OTHER INFORMATION: Ala, D-Ala or Val
<220> FEATURE:
<221> NAME/KEY: MOD_RES
<222> LOCATION: (4)..(4)
<223> OTHER INFORMATION: Ala or a cross-linked amino acid
<220> FEATURE:
<221> NAME/KEY: MOD_RES
<222> LOCATION: (8)..(8)
<223> OTHER INFORMATION: Gln, Asn or a cross-linked amino acid
<220> FEATURE:
<221> NAME/KEY: MOD_RES
<222> LOCATION: (9)..(9)

-continued

```
<223> OTHER INFORMATION: Ser or a cross-linked amino acid
<220> FEATURE:
<221> NAME/KEY: MOD_RES
<222> LOCATION: (11)..(11)
<223> OTHER INFORMATION: Arg, Ala or Gln
<220> FEATURE:
<221> NAME/KEY: MOD_RES
<222> LOCATION: (12)..(12)
<223> OTHER INFORMATION: Lys, Ala, Gln or a cross-linked amino acid
<220> FEATURE:
<221> NAME/KEY: MOD_RES
<222> LOCATION: (13)..(13)
<223> OTHER INFORMATION: Val or Ile
<220> FEATURE:
<221> NAME/KEY: MOD_RES
<222> LOCATION: (15)..(15)
<223> OTHER INFORMATION: Gly, Ala or a cross-linked amino acid
<220> FEATURE:
<221> NAME/KEY: MOD_RES
<222> LOCATION: (16)..(16)
<223> OTHER INFORMATION: Gln, Glu or a cross-linked amino acid
<220> FEATURE:
<221> NAME/KEY: MOD_RES
<222> LOCATION: (18)..(18)
<223> OTHER INFORMATION: Ser, Tyr or a cross-linked amino acid
<220> FEATURE:
<221> NAME/KEY: MOD_RES
<222> LOCATION: (19)..(19)
<223> OTHER INFORMATION: Ala or a cross-linked amino acid
<220> FEATURE:
<221> NAME/KEY: MOD_RES
<222> LOCATION: (20)..(20)
<223> OTHER INFORMATION: Arg or Gln
<220> FEATURE:
<221> NAME/KEY: MOD_RES
<222> LOCATION: (21)..(21)
<223> OTHER INFORMATION: Lys, Gln or a cross-linked amino acid
<220> FEATURE:
<221> NAME/KEY: MOD_RES
<222> LOCATION: (22)..(22)
<223> OTHER INFORMATION: Leu, Ala or a cross-linked amino acid
<220> FEATURE:
<221> NAME/KEY: MOD_RES
<222> LOCATION: (24)..(24)
<223> OTHER INFORMATION: Gln, Glu or His
<220> FEATURE:
<221> NAME/KEY: MOD_RES
<222> LOCATION: (25)..(25)
<223> OTHER INFORMATION: Asp, Glu or a cross-linked amino acid
<220> FEATURE:
<221> NAME/KEY: MOD_RES
<222> LOCATION: (27)..(27)
<223> OTHER INFORMATION: Met, Ile, Leu or Nle
<220> FEATURE:
<221> NAME/KEY: MOD_RES
<222> LOCATION: (28)..(28)
<223> OTHER INFORMATION: Ser or a cross-linked amino acid
<220> FEATURE:
<221> NAME/KEY: MOD_RES
<222> LOCATION: (29)..(29)
<223> OTHER INFORMATION: Arg, Ala, Gln or a cross-linked amino acid
<220> FEATURE:
<223> OTHER INFORMATION: see specification as filed for detailed
      description of substitutions and preferred embodiments

<400> SEQUENCE: 1

Xaa Xaa Asp Xaa Ile Phe Thr Xaa Xaa Tyr Xaa Xaa Xaa Leu Xaa Xaa
1               5                   10                  15

Leu Xaa Xaa Xaa Xaa Xaa Leu Xaa Xaa Ile Xaa Xaa Xaa
            20                  25

<210> SEQ ID NO 2
<211> LENGTH: 29
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 2

Tyr Ala Asp Xaa Ile Phe Thr Xaa Ser Tyr Arg Lys Val Leu Xaa Gln
1               5                   10                  15

Leu Ser Ala Arg Xaa Leu Leu Gln Xaa Ile Leu Ser Arg
            20                  25

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
```

```
<222> LOCATION: (15)..(15)
<223> OTHER INFORMATION: L-Ala or Gly
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 3

Tyr Ala Asp Xaa Ile Phe Thr Xaa Ser Tyr Arg Lys Val Leu Xaa Gln
1               5                   10                  15
Leu Ser Ala Arg Lys Leu Leu Gln Xaa Ile Leu Ser Xaa
            20                  25

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 4
```

```
Tyr Ala Asp Ala Ile Phe Thr Xaa Ser Tyr Arg Xaa Val Leu Xaa Gln
1               5                   10                  15

Leu Ser Ala Arg Xaa Leu Leu Gln Xaa Ile Leu Ser Arg
            20                  25
```

<210> SEQ ID NO 5
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 5

```
Tyr Ala Asp Ala Ile Phe Thr Xaa Ser Tyr Arg Xaa Val Leu Xaa Gln
1               5                   10                  15

Leu Ser Ala Arg Lys Leu Leu Gln Xaa Ile Leu Ser Xaa
            20                  25
```

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:

```
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 6

Tyr Ala Asp Ala Ile Phe Thr Xaa Ser Tyr Xaa Lys Val Leu Xaa Gln
1               5                   10                  15

Leu Ser Ala Arg Xaa Leu Leu Gln Xaa Ile Leu Ser Arg
            20                  25

<210> SEQ ID NO 7
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
```

```
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 7

Tyr Ala Asp Ala Ile Phe Thr Xaa Ser Tyr Xaa Lys Val Leu Xaa Gln
1               5                   10                  15

Leu Ser Ala Arg Lys Leu Leu Gln Xaa Ile Leu Ser Xaa
            20                  25

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 8

Tyr Ala Asp Ala Ile Phe Thr Xaa Ser Tyr Arg Xaa Val Leu Xaa Xaa
1               5                   10                  15

Leu Ser Ala Arg Xaa Leu Leu Gln Xaa Ile Leu Ser Arg
```

```
                    20                  25

<210> SEQ ID NO 9
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 9

Tyr Ala Asp Ala Ile Phe Thr Xaa Ser Tyr Arg Xaa Val Leu Xaa Xaa
1               5                   10                  15

Leu Ser Ala Arg Lys Leu Leu Gln Xaa Ile Leu Ser Xaa
            20                  25

<210> SEQ ID NO 10
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
```

```
<222> LOCATION: (4)..(4)
<223> OTHER INFORMATION: Any amino acid available for cross-linking
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 10

Tyr Ala Asp Xaa Ile Phe Thr Xaa Ser Tyr Xaa Lys Val Leu Xaa Gln
1               5                   10                  15

Leu Ser Ala Arg Lys Leu Leu Gln Asp Ile Leu Ser Arg
            20                  25

<210> SEQ ID NO 11
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 11

Tyr Ala Asp Ala Xaa Phe Thr Xaa Ser Tyr Arg Xaa Val Leu Xaa Gln
1               5                   10                  15
```

Leu Ser Ala Arg Lys Leu Leu Gln Asp Ile Leu Ser Arg
            20                  25

<210> SEQ ID NO 12
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (6)..(6)
<223> OTHER INFORMATION: Any amino acid available for cross-linking
<220> FEATURE:
<221> NAME/KEY: misc_feature
<222> LOCATION: (6)..(13)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (13)..(13)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 12

Tyr Ala Asp Ala Ile Xaa Thr Xaa Ser Tyr Arg Lys Xaa Leu Xaa Gln
1               5                   10                  15

Leu Ser Ala Arg Lys Leu Leu Gln Asp Ile Leu Ser Arg
            20                  25

<210> SEQ ID NO 13
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (7)..(7)
<223> OTHER INFORMATION: Any amino acid available for cross-linking
<220> FEATURE:
<221> NAME/KEY: misc_feature
<222> LOCATION: (7)..(14)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:

```
<221> NAME/KEY: MOD_RES
<222> LOCATION: (14)..(14)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 13

Tyr Ala Asp Ala Ile Phe Xaa Xaa Ser Tyr Arg Lys Val Xaa Xaa Gln
1               5                   10                  15

Leu Ser Ala Arg Lys Leu Leu Gln Asp Ile Leu Ser Arg
            20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 14

Tyr Ala Asp Ala Ile Phe Thr Xaa Ser Tyr Arg Lys Val Leu Xaa Gln
1               5                   10                  15

Leu Ser Ala Arg Lys Leu Leu Gln Asp Ile Leu Ser Arg
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
```

```
<222> LOCATION: (8)..(8)
<223> OTHER INFORMATION: L-Asn or L-Gln
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 15

Tyr Ala Asp Ala Ile Phe Thr Xaa Xaa Tyr Arg Lys Val Leu Xaa Xaa
1               5                   10                  15

Leu Ser Ala Arg Lys Leu Leu Gln Asp Ile Leu Ser Arg
            20                  25

<210> SEQ ID NO 16
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (10)..(10)
<223> OTHER INFORMATION: Any amino acid available for cross-linking
<220> FEATURE:
<221> NAME/KEY: misc_feature
<222> LOCATION: (10)..(17)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (17)..(17)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 16

Tyr Ala Asp Ala Ile Phe Thr Xaa Ser Xaa Arg Lys Val Leu Xaa Gln
1               5                   10                  15
```

Xaa Ser Ala Arg Lys Leu Leu Gln Asp Ile Leu Ser Arg
        20                  25

<210> SEQ ID NO 17
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(18)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (18)..(18)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 17

Tyr Ala Asp Ala Ile Phe Thr Xaa Ser Tyr Xaa Lys Val Leu Xaa Gln
1               5                   10                  15

Leu Xaa Ala Arg Lys Leu Leu Gln Asp Ile Leu Ser Arg
        20                  25

<210> SEQ ID NO 18
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(19)
<223> OTHER INFORMATION: Crosslink between residues
<220> FEATURE:

```
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (19)..(19)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 18

Tyr Ala Asp Ala Ile Phe Thr Xaa Ser Tyr Arg Xaa Val Leu Xaa Gln
1               5                  10                  15

Leu Ser Xaa Arg Lys Leu Leu Gln Asp Ile Leu Ser Arg
            20                  25

<210> SEQ ID NO 19
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (13)..(13)
<223> OTHER INFORMATION: Any amino acid available for cross-linking
<220> FEATURE:
<221> NAME/KEY: misc_feature
<222> LOCATION: (13)..(20)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (20)..(20)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 19

Tyr Ala Asp Ala Ile Phe Thr Xaa Ser Tyr Arg Lys Xaa Leu Xaa Gln
1               5                  10                  15

Leu Ser Ala Xaa Lys Leu Leu Gln Asp Ile Leu Ser Arg
            20                  25

<210> SEQ ID NO 20
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (14)..(14)
<223> OTHER INFORMATION: Any amino acid available for cross-linking
<220> FEATURE:
<221> NAME/KEY: misc_feature
<222> LOCATION: (14)..(21)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 20

Tyr Ala Asp Ala Ile Phe Thr Xaa Ser Tyr Arg Lys Val Xaa Xaa Gln
1               5                   10                  15

Leu Ser Ala Arg Xaa Leu Leu Gln Asp Ile Leu Ser Arg
            20                  25

<210> SEQ ID NO 21
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: misc_feature
<222> LOCATION: (15)..(22)
<223> OTHER INFORMATION: Crosslink between residues
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 21
```

```
Tyr Ala Asp Ala Ile Phe Thr Xaa Ser Tyr Arg Lys Val Leu Xaa Gln
1               5                   10                  15

Leu Ser Ala Arg Lys Xaa Leu Gln Asp Ile Leu Ser Arg
            20                  25

<210> SEQ ID NO 22
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: misc_feature
<222> LOCATION: (16)..(23)
<223> OTHER INFORMATION: Crosslink between residues
<220> FEATURE:
<221> NAME/KEY: MOD_RES
<222> LOCATION: (23)..(23)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 22

Tyr Ala Asp Ala Ile Phe Thr Xaa Ser Tyr Arg Lys Val Leu Xaa Xaa
1               5                   10                  15

Leu Ser Ala Arg Lys Leu Xaa Gln Asp Ile Leu Ser Arg
            20                  25

<210> SEQ ID NO 23
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
```

```
<221> NAME/KEY: MOD_RES
<222> LOCATION: (17)..(17)
<223> OTHER INFORMATION: Any amino acid available for cross-linking
<220> FEATURE:
<221> NAME/KEY: misc_feature
<222> LOCATION: (17)..(24)
<223> OTHER INFORMATION: Crosslink between residues
<220> FEATURE:
<221> NAME/KEY: MOD_RES
<222> LOCATION: (24)..(24)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 23

Tyr Ala Asp Ala Ile Phe Thr Xaa Ser Tyr Arg Lys Val Leu Xaa Gln
1               5                   10                  15

Xaa Ser Ala Arg Lys Leu Leu Xaa Asp Ile Leu Ser Arg
            20                  25

<210> SEQ ID NO 24
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (18)..(18)
<223> OTHER INFORMATION: Any amino acid available for cross-linking
<220> FEATURE:
<221> NAME/KEY: misc_feature
<222> LOCATION: (18)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 24

Tyr Ala Asp Ala Ile Phe Thr Xaa Ser Tyr Arg Lys Val Leu Xaa Gln
1               5                   10                  15

Leu Xaa Ala Arg Lys Leu Leu Gln Xaa Ile Leu Ser Arg
            20                  25

<210> SEQ ID NO 25
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (19)..(19)
<223> OTHER INFORMATION: Any amino acid available for cross-linking
<220> FEATURE:
<221> NAME/KEY: misc_feature
<222> LOCATION: (19)..(26)
<223> OTHER INFORMATION: Crosslink between residues
<220> FEATURE:
<221> NAME/KEY: MOD_RES
<222> LOCATION: (26)..(26)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 25

Tyr Ala Asp Ala Ile Phe Thr Xaa Ser Tyr Arg Lys Val Leu Xaa Gln
1               5                   10                  15

Leu Ser Xaa Arg Lys Leu Leu Gln Asp Xaa Leu Ser Arg
            20                  25

<210> SEQ ID NO 26
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (20)..(20)
<223> OTHER INFORMATION: Any amino acid available for cross-linking
<220> FEATURE:
<221> NAME/KEY: misc_feature
<222> LOCATION: (20)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid available for cross-linking
```

```
<220> FEATURE:
<223> OTHER INFORMATION: C-term NH2

<400> SEQUENCE: 26

Tyr Ala Asp Ala Ile Phe Thr Xaa Ser Tyr Arg Lys Val Leu Xaa Gln
1               5                   10                  15

Leu Ser Ala Xaa Lys Leu Leu Gln Asp Ile Xaa Ser Arg
            20                  25

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (28)..(28)
<223> OTHER INFORMATION: Any amino acid available for cross-linking
<220> FEATURE:
<223> OTHER INFORMATION: C-term NH2

<400> SEQUENCE: 27

Tyr Ala Asp Ala Ile Phe Thr Xaa Ser Tyr Arg Lys Val Leu Xaa Gln
1               5                   10                  15

Leu Ser Ala Arg Xaa Leu Leu Gln Asp Ile Leu Xaa Arg
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
```

```
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 28

Tyr Ala Asp Ala Ile Phe Thr Xaa Ser Tyr Arg Lys Val Leu Xaa Gln
1               5                   10                  15

Leu Ser Ala Arg Lys Xaa Leu Gln Asp Ile Leu Ser Xaa
            20                  25

<210> SEQ ID NO 29
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
```

```
<223> OTHER INFORMATION: L-Nle or L-Leu
<220> FEATURE:
<223> OTHER INFORMATION: C-term NH2

<400> SEQUENCE: 29

Tyr Ala Asp Xaa Ile Phe Thr Xaa Ser Tyr Xaa Lys Val Leu Xaa Gln
1               5                   10                  15

Leu Ser Ala Arg Xaa Leu Leu Gln Xaa Ile Leu Ser Arg
            20                  25

<210> SEQ ID NO 30
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 30

Tyr Ala Asp Xaa Ile Phe Thr Xaa Ser Tyr Xaa Lys Val Leu Xaa Gln
1               5                   10                  15

Leu Ser Ala Arg Lys Leu Leu Gln Xaa Ile Leu Ser Xaa
            20                  25

<210> SEQ ID NO 31
<211> LENGTH: 29
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 31

Tyr Ala Asp Ala Xaa Phe Thr Xaa Ser Tyr Arg Xaa Val Leu Xaa Gln
1               5                   10                  15

Leu Ser Ala Arg Xaa Leu Leu Gln Xaa Ile Leu Ser Arg
            20                  25

<210> SEQ ID NO 32
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
```

```
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 32

Tyr Ala Asp Ala Xaa Phe Thr Xaa Ser Tyr Arg Xaa Val Leu Xaa Gln
1               5                   10                  15

Leu Ser Ala Arg Lys Leu Leu Gln Xaa Ile Leu Ser Xaa
            20                  25

<210> SEQ ID NO 33
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (6)..(6)
<223> OTHER INFORMATION: Any amino acid available for cross-linking
<220> FEATURE:
<221> NAME/KEY: misc_feature
<222> LOCATION: (6)..(13)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (13)..(13)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
```

```
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 33

Tyr Ala Asp Ala Ile Xaa Thr Xaa Ser Tyr Arg Lys Xaa Leu Xaa Gln
1               5                   10                  15

Leu Ser Ala Arg Xaa Leu Leu Gln Xaa Ile Leu Ser Arg
            20                  25

<210> SEQ ID NO 34
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (6)..(6)
<223> OTHER INFORMATION: Any amino acid available for cross-linking
<220> FEATURE:
<221> NAME/KEY: misc_feature
<222> LOCATION: (6)..(13)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (13)..(13)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 34

Tyr Ala Asp Ala Ile Xaa Thr Xaa Ser Tyr Arg Lys Xaa Leu Xaa Gln
1               5                   10                  15

Leu Ser Ala Arg Lys Leu Leu Gln Xaa Ile Leu Ser Xaa
            20                  25
```

```
<210> SEQ ID NO 35
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (7)..(7)
<223> OTHER INFORMATION: Any amino acid available for cross-linking
<220> FEATURE:
<221> NAME/KEY: misc_feature
<222> LOCATION: (7)..(14)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (14)..(14)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 35

Tyr Ala Asp Ala Ile Phe Xaa Xaa Ser Tyr Arg Lys Val Xaa Xaa Gln
1               5                   10                  15

Leu Ser Ala Arg Xaa Leu Leu Gln Xaa Ile Leu Ser Arg
            20                  25

<210> SEQ ID NO 36
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (7)..(7)
```

```
<223> OTHER INFORMATION: Any amino acid available for cross-linking
<220> FEATURE:
<221> NAME/KEY: misc_feature
<222> LOCATION: (7)..(14)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (14)..(14)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 36

Tyr Ala Asp Ala Ile Phe Xaa Xaa Ser Tyr Arg Lys Val Xaa Xaa Gln
1               5                   10                  15

Leu Ser Ala Arg Lys Leu Leu Gln Xaa Ile Leu Ser Xaa
            20                  25

<210> SEQ ID NO 37
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
```

```
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 37

Tyr Ala Asp Ala Ile Phe Thr Xaa Ser Tyr Arg Lys Val Leu Xaa Gln
1               5                   10                  15

Leu Ser Ala Arg Xaa Leu Leu Gln Xaa Ile Leu Ser Arg
            20                  25

<210> SEQ ID NO 38
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 38

Tyr Ala Asp Ala Ile Phe Thr Xaa Ser Tyr Arg Lys Val Leu Xaa Gln
1               5                   10                  15

Leu Ser Ala Arg Lys Leu Leu Gln Xaa Ile Leu Ser Xaa
            20                  25

<210> SEQ ID NO 39
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 39

Tyr Ala Asp Ala Ile Phe Thr Xaa Xaa Tyr Arg Lys Val Leu Xaa Xaa
1               5                   10                  15

Leu Ser Ala Arg Lys Leu Leu Gln Xaa Ile Leu Ser Xaa
            20                  25

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(16)
<223> OTHER INFORMATION: Crosslink between residues
```

```
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 40

Tyr Ala Asp Ala Ile Phe Thr Xaa Xaa Tyr Arg Lys Val Leu Xaa Xaa
1               5                   10                  15

Leu Ser Ala Arg Xaa Leu Leu Gln Xaa Ile Leu Ser Arg
            20                  25

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (19)..(19)
<223> OTHER INFORMATION: Any amino acid available for cross-linking
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
```

```
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 41

Tyr Ala Asp Ala Ile Phe Thr Xaa Ser Tyr Arg Xaa Val Leu Xaa Gln
1               5                   10                  15

Leu Ser Xaa Arg Lys Leu Leu Gln Xaa Ile Leu Ser Xaa
            20                  25

<210> SEQ ID NO 42
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: misc_feature
<222> LOCATION: (15)..(22)
<223> OTHER INFORMATION: Crosslink between residues
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 42

Tyr Ala Asp Xaa Ile Phe Thr Xaa Ser Tyr Arg Lys Val Leu Xaa Gln
1               5                   10                  15

Leu Ser Ala Arg Lys Xaa Leu Gln Asp Ile Leu Ser Arg
            20                  25

<210> SEQ ID NO 43
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (18)..(18)
<223> OTHER INFORMATION: Any amino acid available for cross-linking
<220> FEATURE:
<221> NAME/KEY: misc_feature
<222> LOCATION: (18)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 43

Tyr Ala Asp Xaa Ile Phe Thr Xaa Ser Tyr Arg Lys Val Leu Xaa Gln
1               5                   10                  15

Leu Xaa Ala Arg Lys Leu Leu Gln Xaa Ile Leu Ser Arg
            20                  25

<210> SEQ ID NO 44
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
```

```
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (28)..(28)
<223> OTHER INFORMATION: Any amino acid available for cross-linking
<220> FEATURE:
<223> OTHER INFORMATION: C-term NH2

<400> SEQUENCE: 44

Tyr Ala Asp Xaa Ile Phe Thr Xaa Ser Tyr Arg Lys Val Leu Xaa Gln
1               5                   10                  15

Leu Ser Ala Arg Xaa Leu Leu Gln Asp Ile Leu Xaa Arg
            20                  25

<210> SEQ ID NO 45
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 45

Tyr Ala Asp Xaa Ile Phe Thr Xaa Ser Tyr Arg Lys Val Leu Xaa Gln
1               5                   10                  15
```

Leu Ser Ala Arg Lys Xaa Leu Gln Asp Ile Leu Ser Xaa
            20                  25

<210> SEQ ID NO 46
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: misc_feature
<222> LOCATION: (15)..(22)
<223> OTHER INFORMATION: Crosslink between residues
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 46

Tyr Ala Asp Ala Ile Phe Thr Xaa Ser Tyr Arg Xaa Val Leu Xaa Gln
1               5                   10                  15

Leu Ser Ala Arg Lys Xaa Leu Gln Asp Ile Leu Ser Arg
            20                  25

<210> SEQ ID NO 47
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues

```
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (18)..(18)
<223> OTHER INFORMATION: Any amino acid available for cross-linking
<220> FEATURE:
<221> NAME/KEY: misc_feature
<222> LOCATION: (18)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 47

Tyr Ala Asp Ala Ile Phe Thr Xaa Ser Tyr Arg Xaa Val Leu Xaa Gln
1               5                   10                  15

Leu Xaa Ala Arg Lys Leu Leu Gln Xaa Ile Leu Ser Arg
            20                  25

<210> SEQ ID NO 48
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
```

```
<222> LOCATION: (28)..(28)
<223> OTHER INFORMATION: Any amino acid available for cross-linking
<220> FEATURE:
<223> OTHER INFORMATION: C-term NH2

<400> SEQUENCE: 48

Tyr Ala Asp Ala Ile Phe Thr Xaa Ser Tyr Arg Xaa Val Leu Xaa Gln
1               5                   10                  15

Leu Ser Ala Arg Xaa Leu Leu Gln Asp Ile Leu Xaa Arg
            20                  25

<210> SEQ ID NO 49
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 49

Tyr Ala Asp Ala Ile Phe Thr Xaa Ser Tyr Arg Xaa Val Leu Xaa Gln
1               5                   10                  15

Leu Ser Ala Arg Lys Xaa Leu Gln Asp Ile Leu Ser Xaa
            20                  25

<210> SEQ ID NO 50
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (28)..(28)
<223> OTHER INFORMATION: Any amino acid available for cross-linking
<220> FEATURE:
<223> OTHER INFORMATION: C-term NH2

<400> SEQUENCE: 50

Tyr Ala Asp Ala Ile Phe Thr Xaa Ser Tyr Arg Xaa Val Leu Xaa Xaa
1               5                   10                  15

Leu Ser Ala Arg Xaa Leu Leu Gln Asp Ile Leu Xaa Arg
            20                  25

<210> SEQ ID NO 51
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
```

```
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 51

Tyr Ala Asp Ala Ile Phe Thr Xaa Ser Tyr Arg Xaa Val Leu Xaa Xaa
1               5                   10                  15

Leu Ser Ala Arg Lys Xaa Leu Gln Asp Ile Leu Ser Xaa
            20                  25

<210> SEQ ID NO 52
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (28)..(28)
```

```
<223> OTHER INFORMATION: Any amino acid available for cross-linking
<220> FEATURE:
<223> OTHER INFORMATION: C-term NH2

<400> SEQUENCE: 52

Tyr Ala Asp Ala Ile Phe Thr Xaa Ser Tyr Xaa Lys Val Leu Xaa Gln
1               5                   10                  15

Leu Ser Ala Arg Xaa Leu Leu Gln Asp Ile Leu Xaa Arg
            20                  25

<210> SEQ ID NO 53
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 53

Tyr Ala Asp Ala Ile Phe Thr Xaa Ser Tyr Xaa Lys Val Leu Xaa Gln
1               5                   10                  15

Leu Ser Ala Arg Lys Xaa Leu Gln Asp Ile Leu Ser Xaa
            20                  25

<210> SEQ ID NO 54
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
```

```
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 54

Tyr Ala Asp Xaa Ile Phe Thr Xaa Ser Tyr Arg Xaa Val Leu Xaa Gln
1               5                   10                  15
Leu Ser Ala Arg Lys Leu Leu Gln Asp Ile Leu Ser Arg
            20                  25

<210> SEQ ID NO 55
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
```

```
<222> LOCATION: (16)..(16)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 55

Tyr Ala Asp Ala Ile Phe Thr Xaa Ser Tyr Arg Xaa Val Leu Xaa Xaa
1               5                   10                  15

Leu Ser Ala Arg Lys Leu Leu Gln Asp Ile Leu Ser Arg
            20                  25

<210> SEQ ID NO 56
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: misc_feature
<222> LOCATION: (16)..(20)
<223> OTHER INFORMATION: Crosslink between residues
<220> FEATURE:
<221> NAME/KEY: MOD_RES
<222> LOCATION: (20)..(20)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 56

Tyr Ala Asp Ala Ile Phe Thr Xaa Ser Tyr Arg Xaa Val Leu Xaa Xaa
1               5                   10                  15

Leu Ser Ala Xaa Lys Leu Leu Gln Asp Ile Leu Ser Arg
            20                  25

<210> SEQ ID NO 57
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 57

Tyr Ala Asp Ala Ile Phe Thr Xaa Ser Tyr Arg Lys Val Leu Xaa Gln
1               5                   10                  15

Leu Ser Ala Arg Xaa Leu Leu Gln Xaa Ile Leu Ser Xaa
            20                  25

<210> SEQ ID NO 58
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
```

```
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 58

Tyr Ala Asp Xaa Ile Phe Thr Xaa Ser Tyr Arg Lys Val Leu Xaa Gln
1               5                   10                  15
Leu Ser Ala Arg Lys Leu Leu Gln Asp Ile Leu Ser Arg
            20                  25

<210> SEQ ID NO 59
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 59

Tyr Ala Asp Xaa Ile Phe Thr Xaa Ser Tyr Xaa Lys Val Leu Xaa Gln
1               5                   10                  15
Leu Ser Ala Arg Lys Leu Leu Gln Asp Ile Leu Ser Arg
            20                  25

<210> SEQ ID NO 60
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (19)..(19)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 60

Tyr Ala Asp Ala Ile Phe Thr Xaa Ser Tyr Arg Xaa Val Leu Xaa Gln
1               5                   10                  15

Leu Ser Xaa Arg Lys Leu Leu Gln Asp Ile Leu Ser Arg
            20                  25

<210> SEQ ID NO 61
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: misc_feature
<222> LOCATION: (15)..(19)
<223> OTHER INFORMATION: Crosslink between residues
```

```
<220> FEATURE:
<221> NAME/KEY: MOD_RES
<222> LOCATION: (19)..(19)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 61

Tyr Ala Asp Ala Ile Phe Thr Xaa Ser Tyr Arg Lys Val Leu Xaa Gln
1               5                   10                  15

Leu Ser Xaa Arg Lys Leu Leu Gln Asp Ile Leu Ser Arg
            20                  25

<210> SEQ ID NO 62
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: misc_feature
<222> LOCATION: (16)..(20)
<223> OTHER INFORMATION: Crosslink between residues
<220> FEATURE:
<221> NAME/KEY: MOD_RES
<222> LOCATION: (20)..(20)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 62

Tyr Ala Asp Ala Ile Phe Thr Xaa Xaa Tyr Arg Lys Val Leu Xaa Xaa
1               5                   10                  15

Leu Ser Ala Xaa Lys Leu Leu Gln Asp Ile Leu Ser Arg
            20                  25

<210> SEQ ID NO 63
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(13)
<223> OTHER INFORMATION: Crosslink between residues
<220> FEATURE:
<221> NAME/KEY: MOD_RES
<222> LOCATION: (13)..(13)
<223> OTHER INFORMATION: Any amino acid available for cross-linking
<220> FEATURE:
<221> NAME/KEY: misc_feature
<222> LOCATION: (13)..(20)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (20)..(20)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 63

Tyr Ala Asp Ala Ile Phe Thr Xaa Xaa Tyr Arg Lys Xaa Leu Xaa Gln
1               5                   10                  15

Leu Ser Ala Xaa Lys Leu Leu Gln Asp Ile Leu Ser Arg
            20                  25

<210> SEQ ID NO 64
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(19)
```

```
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (19)..(19)
<223> OTHER INFORMATION: Any amino acid available for cross-linking
<220> FEATURE:
<221> NAME/KEY: misc_feature
<222> LOCATION: (19)..(23)
<223> OTHER INFORMATION: Crosslink between residues
<220> FEATURE:
<221> NAME/KEY: MOD_RES
<222> LOCATION: (23)..(23)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 64

Tyr Ala Asp Ala Ile Phe Thr Xaa Ser Tyr Arg Xaa Val Leu Xaa Gln
1               5                   10                  15

Leu Ser Xaa Arg Lys Leu Xaa Gln Asp Ile Leu Ser Arg
            20                  25

<210> SEQ ID NO 65
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: misc_feature
<222> LOCATION: (16)..(23)
<223> OTHER INFORMATION: Crosslink between residues
<220> FEATURE:
<221> NAME/KEY: MOD_RES
<222> LOCATION: (23)..(23)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
```

<223> OTHER INFORMATION: C-term NH2

<400> SEQUENCE: 65

Tyr Ala Asp Ala Ile Phe Thr Xaa Ser Tyr Arg Xaa Val Leu Xaa Xaa
1               5                   10                  15

Leu Ser Ala Arg Lys Leu Xaa Gln Asp Ile Leu Ser Arg
            20                  25

<210> SEQ ID NO 66
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: misc_feature
<222> LOCATION: (16)..(23)
<223> OTHER INFORMATION: Crosslink between residues
<220> FEATURE:
<221> NAME/KEY: MOD_RES
<222> LOCATION: (23)..(23)
<223> OTHER INFORMATION: Any amino acid available for cross-linking
<220> FEATURE:
<221> NAME/KEY: misc_feature
<222> LOCATION: (23)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid available for cross-linking
<220> FEATURE:
<223> OTHER INFORMATION: C-term NH2

<400> SEQUENCE: 66

Tyr Ala Asp Ala Ile Phe Thr Xaa Ser Tyr Arg Lys Val Leu Xaa Xaa
1               5                   10                  15

Leu Ser Ala Arg Lys Leu Xaa Gln Asp Ile Xaa Ser Arg
            20                  25

<210> SEQ ID NO 67
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES

```
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: misc_feature
<222> LOCATION: (16)..(20)
<223> OTHER INFORMATION: Crosslink between residues
<220> FEATURE:
<221> NAME/KEY: MOD_RES
<222> LOCATION: (20)..(20)
<223> OTHER INFORMATION: Any amino acid available for cross-linking
<220> FEATURE:
<221> NAME/KEY: misc_feature
<222> LOCATION: (20)..(27)
<223> OTHER INFORMATION: Crosslink between residues
<220> FEATURE:
<221> NAME/KEY: MOD_RES
<222> LOCATION: (27)..(27)
<223> OTHER INFORMATION: Any amino acid available for cross-linking
<220> FEATURE:
<223> OTHER INFORMATION: C-term NH2

<400> SEQUENCE: 67

Tyr Ala Asp Ala Ile Phe Thr Xaa Ser Tyr Arg Lys Val Leu Xaa Xaa
1               5                   10                  15

Leu Ser Ala Xaa Lys Leu Leu Gln Asp Ile Xaa Ser Arg
            20                  25

<210> SEQ ID NO 68
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (18)..(18)
<223> OTHER INFORMATION: Any amino acid available for cross-linking
<220> FEATURE:
<221> NAME/KEY: misc_feature
<222> LOCATION: (18)..(22)
<223> OTHER INFORMATION: Crosslink between residues
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
```

```
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 68

Tyr Ala Asp Ala Ile Phe Thr Xaa Ser Tyr Arg Lys Val Leu Xaa Gln
1               5                   10                  15

Leu Xaa Ala Arg Lys Xaa Leu Gln Asp Ile Leu Ser Xaa
            20                  25

<210> SEQ ID NO 69
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (18)..(18)
<223> OTHER INFORMATION: Any amino acid available for cross-linking
<220> FEATURE:
<221> NAME/KEY: misc_feature
<222> LOCATION: (18)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 69

Tyr Ala Asp Ala Ile Phe Thr Xaa Ser Tyr Arg Lys Val Leu Xaa Gln
1               5                   10                  15

Leu Xaa Ala Arg Lys Leu Leu Gln Xaa Ile Leu Ser Xaa
            20                  25

<210> SEQ ID NO 70
<211> LENGTH: 29
<212> TYPE: PRT
<213> ORGANISM: Artificial Sequence
<220> FEATURE:
<223> OTHER INFORMATION: Description of Artificial Sequence: Synthetic
```

```
                peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(11)
<223> OTHER INFORMATION: Crosslink between residues
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(18)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (18)..(18)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 70

Tyr Ala Asp Xaa Ile Phe Thr Xaa Ser Tyr Xaa Lys Val Leu Xaa Gln
1               5                   10                  15

Leu Xaa Ala Arg Lys Leu Leu Gln Asp Ile Leu Ser Arg
            20                  25

<210> SEQ ID NO 71
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: misc_feature
<222> LOCATION: (15)..(22)
```

```
<223> OTHER INFORMATION: Crosslink between residues
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 71

Tyr Ala Asp Ala Ile Phe Thr Xaa Ser Tyr Arg Lys Val Leu Xaa Gln
1               5                   10                  15

Leu Ser Ala Arg Lys Xaa Leu Gln Asp Ile Leu Ser Arg
            20                  25

<210> SEQ ID NO 72
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: misc_feature
<222> LOCATION: (16)..(23)
<223> OTHER INFORMATION: Crosslink between residues
<220> FEATURE:
<221> NAME/KEY: MOD_RES
<222> LOCATION: (23)..(23)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 72

Tyr Ala Asp Ala Ile Phe Thr Xaa Xaa Tyr Arg Lys Val Leu Xaa Xaa
1               5                   10                  15

Leu Ser Ala Arg Lys Leu Xaa Gln Asp Ile Leu Ser Arg
            20                  25

<210> SEQ ID NO 73
```

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (19)..(19)
<223> OTHER INFORMATION: Any amino acid available for cross-linking
<220> FEATURE:
<221> NAME/KEY: misc_feature
<222> LOCATION: (19)..(26)
<223> OTHER INFORMATION: Crosslink between residues
<220> FEATURE:
<221> NAME/KEY: MOD_RES
<222> LOCATION: (26)..(26)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 73

Tyr Ala Asp Ala Ile Phe Thr Xaa Ser Tyr Arg Xaa Val Leu Xaa Gln
1               5                   10                  15

Leu Ser Xaa Arg Lys Leu Leu Gln Asp Xaa Leu Ser Arg
            20                  25

<210> SEQ ID NO 74
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: misc_feature
```

```
<222> LOCATION: (15)..(22)
<223> OTHER INFORMATION: Crosslink between residues
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 74

Tyr Ala Asp Ala Ile Phe Thr Xaa Ser Tyr Arg Lys Val Leu Xaa Gln
1               5                   10                  15

Leu Ser Ala Arg Lys Xaa Leu Gln Asp Ile Leu Ser Xaa
            20                  25

<210> SEQ ID NO 75
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 75
```

-continued

```
Tyr Ala Asp Xaa Ile Phe Thr Xaa Ser Tyr Arg Lys Val Leu Xaa Gln
1               5                   10                  15

Leu Ser Ala Arg Xaa Leu Leu Gln Xaa Ile Leu Ser Arg Gln Gln Gly
            20                  25                  30

Glu Ser Asn Gln Glu Arg Gly Ala Arg Ala Arg Leu
35                  40

<210> SEQ ID NO 76
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 76

Tyr Ala Asp Xaa Ile Phe Thr Xaa Ser Tyr Arg Lys Val Leu Xaa Gln
1               5                   10                  15

Leu Ser Ala Arg Lys Leu Leu Gln Xaa Ile Leu Ser Xaa Gln Gln Gly
            20                  25                  30

Glu Ser Asn Gln Glu Arg Gly Ala Arg Ala Arg Leu
            35                  40

<210> SEQ ID NO 77
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: misc_feature
<222> LOCATION: (15)..(22)
<223> OTHER INFORMATION: Crosslink between residues
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 77

Tyr Ala Asp Xaa Ile Phe Thr Xaa Ser Tyr Arg Lys Val Leu Xaa Gln
1               5                   10                  15

Leu Ser Ala Arg Lys Xaa Leu Gln Asp Ile Leu Ser Arg Gln Gln Gly
            20                  25                  30

Glu Ser Asn Gln Glu Arg Gly Ala Arg Ala Arg Leu
        35                  40

<210> SEQ ID NO 78
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
```

```
<222> LOCATION: (18)..(18)
<223> OTHER INFORMATION: Any amino acid available for cross-linking
<220> FEATURE:
<221> NAME/KEY: misc_feature
<222> LOCATION: (18)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 78

Tyr Ala Asp Xaa Ile Phe Thr Xaa Ser Tyr Arg Lys Val Leu Xaa Gln
1               5                   10                  15

Leu Xaa Ala Arg Lys Leu Leu Gln Ala Ile Leu Ser Arg Gln Gln Gly
            20                  25                  30

Glu Ser Asn Gln Glu Arg Gly Ala Arg Ala Arg Leu
        35                  40

<210> SEQ ID NO 79
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (28)..(28)
<223> OTHER INFORMATION: Any amino acid available for cross-linking
<220> FEATURE:
<223> OTHER INFORMATION: C-term NH2
```

<400> SEQUENCE: 79

Tyr Ala Asp Xaa Ile Phe Thr Xaa Ser Tyr Arg Lys Val Leu Xaa Gln
1               5                   10                  15

Leu Ser Ala Arg Xaa Leu Leu Gln Asp Ile Leu Xaa Arg Gln Gln Gly
            20                  25                  30

Glu Ser Asn Gln Glu Arg Gly Ala Arg Ala Arg Leu
            35                  40

<210> SEQ ID NO 80
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (22)..(22)
<223> OTHER INFORMATION: Any amino acid available for cross-linking
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 80

Tyr Ala Asp Xaa Ile Phe Thr Xaa Ser Tyr Arg Lys Val Leu Xaa Gln
1               5                   10                  15

Leu Ser Ala Arg Lys Xaa Leu Gln Asp Ile Leu Ser Xaa Gln Gln Gly
            20                  25                  30

Glu Ser Asn Gln Glu Arg Gly Ala Arg Ala Arg Leu
            35                  40

<210> SEQ ID NO 81
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 81

Tyr Ala Asp Ala Ile Phe Thr Xaa Ser Tyr Arg Xaa Val Leu Xaa Gln
1               5                   10                  15

Leu Ser Ala Arg Xaa Leu Leu Gln Xaa Ile Leu Ser Arg Gln Gln Gly
            20                  25                  30

Glu Ser Asn Gln Glu Arg Gly Ala Arg Ala Arg Leu
        35                  40

<210> SEQ ID NO 82
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: Any amino acid available for cross-linking
<220> FEATURE:
```

```
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 82

Tyr Ala Asp Ala Ile Phe Thr Xaa Ser Tyr Arg Xaa Val Leu Xaa Gln
1               5                   10                  15

Leu Ser Ala Arg Lys Leu Leu Gln Xaa Ile Leu Ser Xaa Gln Gln Gly
            20                  25                  30

Glu Ser Asn Gln Glu Arg Gly Ala Arg Ala Arg Leu
            35                  40

<210> SEQ ID NO 83
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
```

```
<220> FEATURE:
<223> OTHER INFORMATION: C-term NH2

<400> SEQUENCE: 83

Tyr Ala Asp Ala Ile Phe Thr Xaa Ser Tyr Xaa Lys Val Leu Xaa Gln
1               5                   10                  15

Leu Ser Ala Arg Xaa Leu Leu Gln Xaa Ile Leu Ser Arg Gln Gln Gly
            20                  25                  30

Glu Ser Asn Gln Glu Arg Gly Ala Arg Ala Arg Leu
        35                  40

<210> SEQ ID NO 84
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: misc_feature
<222> LOCATION: (11)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 84

Tyr Ala Asp Ala Ile Phe Thr Xaa Ser Tyr Xaa Lys Val Leu Xaa Gln
1               5                   10                  15

Leu Ser Ala Arg Lys Leu Leu Gln Xaa Ile Leu Ser Xaa Gln Gln Gly
            20                  25                  30

Glu Ser Asn Gln Glu Arg Gly Ala Arg Ala Arg Leu
        35                  40

<210> SEQ ID NO 85
<211> LENGTH: 44
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 85

Tyr Ala Asp Ala Ile Phe Thr Xaa Ser Tyr Arg Xaa Val Leu Xaa Xaa
1               5                   10                  15

Leu Ser Ala Arg Xaa Leu Leu Gln Xaa Ile Leu Ser Arg Gln Gln Gly
            20                  25                  30

Glu Ser Asn Gln Glu Arg Gly Ala Arg Ala Arg Leu
        35                  40

<210> SEQ ID NO 86
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: L-Asn or L-Gln
<220> FEATURE:
<221> NAME/KEY: MOD_RES
```

```
<222> LOCATION: (12)..(12)
<223> OTHER INFORMATION: Any amino acid available for cross-linking
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (15)..(15)
<223> OTHER INFORMATION: L-Ala or Gly
<220> FEATURE:
<221> NAME/KEY: MOD_RES
<222> LOCATION: (16)..(16)
<223> OTHER INFORMATION: Any amino acid available for cross-linking
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 86

Tyr Ala Asp Ala Ile Phe Thr Xaa Ser Tyr Arg Xaa Val Leu Xaa Xaa
1               5                   10                  15

Leu Ser Ala Arg Lys Leu Leu Gln Xaa Ile Leu Ser Xaa Gln Gln Gly
            20                  25                  30

Glu Ser Asn Gln Glu Arg Gly Ala Arg Ala Arg Leu
        35                  40

<210> SEQ ID NO 87
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (21)..(21)
<223> OTHER INFORMATION: Any amino acid available for cross-linking
<220> FEATURE:
<221> NAME/KEY: misc_feature
<222> LOCATION: (21)..(25)
<223> OTHER INFORMATION: Crosslink between residues
<220> FEATURE:
```

```
<221> NAME/KEY: MOD_RES
<222> LOCATION: (25)..(25)
<223> OTHER INFORMATION: Any amino acid available for cross-linking
<220> FEATURE:
<221> NAME/KEY: MOD_RES
<222> LOCATION: (27)..(27)
<223> OTHER INFORMATION: L-Nle or L-Leu
<220> FEATURE:
<223> OTHER INFORMATION: C-term NH2

<400> SEQUENCE: 87

Tyr Ala Asp Ala Ile Phe Thr Xaa Ser Tyr Arg Lys Val Leu Xaa Gln
1               5                   10                  15

Leu Ser Ala Arg Xaa Leu Leu Gln Xaa Ile Leu Ser Arg Gln Gln Gly
            20                  25                  30

Glu Ser Asn Gln Glu Arg Gly Ala Arg Ala Arg Leu
            35                  40

<210> SEQ ID NO 88
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: L-Ala or D-Ala
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MOD_RES
<222> LOCATION: (25)..(25)
<223> OTHER INFORMATION: Any amino acid available for cross-linking
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: L-Nle or L-Leu
<220> FEATURE:
<221> NAME/KEY: MOD_RES
<222> LOCATION: (29)..(29)
<223> OTHER INFORMATION: Any amino acid available for cross-linking
<220> FEATURE:
<223> OTHER INFORMATION: C-term NH2

<400> SEQUENCE: 88

Tyr Ala Asp Ala Ile Phe Thr Xaa Ser Tyr Arg Lys Val Leu Xaa Gln
1               5                   10                  15

Leu Ser Ala Arg Lys Leu Leu Gln Xaa Ile Leu Ser Xaa Gln Gln Gly
            20                  25                  30

Glu Ser Asn Gln Glu Arg Gly Ala Arg Ala Arg Leu
            35                  40

<210> SEQ ID NO 89
```

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 89

Tyr Ala Asp Ala Ile Phe Thr Ala Ser Tyr Arg Lys Val Leu Gly Gln
1               5                   10                  15

Leu Ser Ala Arg Ala Leu Leu Gln Ala Ile Leu Ser Arg
            20                  25

<210> SEQ ID NO 90
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
```

```
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 90

Tyr Ala Asp Ala Ile Phe Thr Ala Ser Tyr Arg Lys Val Leu Gly Gln
1               5                   10                  15

Leu Ser Ala Arg Lys Leu Leu Gln Ala Ile Leu Ser Ala
            20                  25

<210> SEQ ID NO 91
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
```

```
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 91

Tyr Ala Asp Ala Ile Phe Thr Ala Ser Tyr Arg Lys Val Leu Gly Gln
1               5                   10                  15

Leu Ser Ala Arg Ala Leu Leu Gln Ala Ile Leu Ser Arg
            20                  25

<210> SEQ ID NO 92
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 92

Tyr Ala Asp Ala Ile Phe Thr Ala Ser Tyr Arg Lys Val Leu Gly Gln
1               5                   10                  15

Leu Ser Ala Arg Lys Leu Leu Gln Ala Ile Leu Ser Ala
            20                  25

<210> SEQ ID NO 93
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 93

Tyr Ala Asp Ala Ile Phe Thr Ala Ser Tyr Arg Lys Val Leu Ala Gln
1               5                   10                  15

Leu Ser Ala Arg Lys Leu Leu Gln Ala Ile Leu Ser Ala
            20                  25

<210> SEQ ID NO 94
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
```

```
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (15)..(15)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (15)..(22)
<223> OTHER INFORMATION: Crosslink between residues
<220> FEATURE:
<221> NAME/KEY: MOD_RES
<222> LOCATION: (22)..(22)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 94

Tyr Ala Asp Ala Ile Phe Thr Ala Ser Tyr Arg Lys Val Leu Ala Gln
1               5                   10                  15

Leu Ser Ala Arg Lys Ala Leu Gln Asp Ile Leu Ser Arg
            20                  25

<210> SEQ ID NO 95
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (18)..(18)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (18)..(25)
```

```
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 95

Tyr Ala Asp Ala Ile Phe Thr Ala Ser Tyr Arg Lys Val Leu Gly Gln
1               5                   10                  15

Leu Ala Ala Arg Lys Leu Leu Gln Ala Ile Leu Ser Arg
            20                  25

<210> SEQ ID NO 96
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (28)..(28)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 96

Tyr Ala Asp Ala Ile Phe Thr Ala Ser Tyr Arg Lys Val Leu Gly Gln
1               5                   10                  15
```

```
Leu Ser Ala Arg Ala Leu Leu Gln Asp Ile Leu Ala Arg
            20                  25

<210> SEQ ID NO 97
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (22)..(22)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 97

Tyr Ala Asp Ala Ile Phe Thr Ala Ser Tyr Arg Lys Val Leu Gly Gln
1               5                   10                  15

Leu Ser Ala Arg Lys Ala Leu Gln Asp Ile Leu Ser Ala
            20                  25

<210> SEQ ID NO 98
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
```

```
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (22)..(22)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 98

Tyr Ala Asp Ala Ile Phe Thr Ala Ser Tyr Arg Lys Val Leu Gly Gln
1               5                   10                  15

Leu Ser Ala Arg Lys Ala Leu Gln Asp Ile Leu Ser Ala
            20                  25

<210> SEQ ID NO 99
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
```

```
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 99

Tyr Ala Asp Ala Ile Phe Thr Ala Ser Tyr Arg Ala Val Leu Gly Gln
1               5                   10                  15

Leu Ser Ala Arg Ala Leu Leu Gln Ala Ile Leu Ser Arg
            20                  25

<210> SEQ ID NO 100
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
```

```
<220> FEATURE:
<223> OTHER INFORMATION: C-term NH2

<400> SEQUENCE: 100

Tyr Ala Asp Ala Ile Phe Thr Ala Ser Tyr Arg Ala Val Leu Gly Gln
1               5                   10                  15

Leu Ser Ala Arg Lys Leu Leu Gln Ala Ile Leu Ser Ala
            20                  25

<210> SEQ ID NO 101
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (18)..(18)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (18)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 101

Tyr Ala Asp Ala Ile Phe Thr Ala Ser Tyr Arg Ala Val Leu Gly Gln
1               5                   10                  15

Leu Ala Ala Arg Lys Leu Leu Gln Ala Ile Leu Ser Arg
            20                  25

<210> SEQ ID NO 102
<211> LENGTH: 29
<212> TYPE: PRT
<213> ORGANISM: Artificial Sequence
<220> FEATURE:
<223> OTHER INFORMATION: Description of Artificial Sequence: Synthetic
```

```
                           peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (18)..(18)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (18)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 102

Tyr Ala Asp Ala Ile Phe Thr Ala Ser Tyr Arg Ala Val Leu Gly Gln
1               5                   10                  15

Leu Ala Ala Arg Lys Leu Leu Gln Ala Ile Leu Ser Arg
            20                  25

<210> SEQ ID NO 103
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (8)..(12)
<223> OTHER INFORMATION: Crosslink between residues
<220> FEATURE:
```

```
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (28)..(28)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 103

Tyr Ala Asp Ala Ile Phe Thr Ala Ser Tyr Arg Ala Val Leu Gly Gln
1               5                   10                  15

Leu Ser Ala Arg Ala Leu Leu Gln Asp Ile Leu Ala Arg
            20                  25

<210> SEQ ID NO 104
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (21)..(28)
<223> OTHER INFORMATION: Crosslink between residues
<220> FEATURE:
<221> NAME/KEY: MOD_RES
<222> LOCATION: (27)..(27)
```

```
<223> OTHER INFORMATION: Nle
<220> FEATURE:
<221> NAME/KEY: MOD_RES
<222> LOCATION: (28)..(28)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 104

Tyr Ala Asp Ala Ile Phe Thr Ala Ser Tyr Arg Ala Val Leu Gly Gln
1               5                   10                  15

Leu Ser Ala Arg Ala Leu Leu Gln Asp Ile Leu Ala Arg
            20                  25

<210> SEQ ID NO 105
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (22)..(22)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 105

Tyr Ala Asp Ala Ile Phe Thr Ala Ser Tyr Arg Ala Val Leu Gly Gln
1               5                   10                  15

Leu Ser Ala Arg Lys Ala Leu Gln Asp Ile Leu Ser Ala
            20                  25
```

```
<210> SEQ ID NO 106
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (8)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (22)..(22)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (22)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 106

Tyr Ala Asp Ala Ile Phe Thr Ala Ser Tyr Arg Ala Val Leu Gly Gln
1               5                   10                  15

Leu Ser Ala Arg Lys Ala Leu Gln Asp Ile Leu Ser Ala
            20                  25

<210> SEQ ID NO 107
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me S5-pentenyl-alanine olefin amino
``` acid connected by an all-carbon i to i+4
crosslinker comprising one double bond
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 107

Tyr Ala Asp Ala Ile Phe Thr Asn Ser Tyr Arg Ala Val Leu Gly Ala
1               5                   10                  15
Leu Ser Ala Arg Ala Leu Leu Gln Ala Ile Leu Ser Arg
            20                  25

<210> SEQ ID NO 108
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (12)..(16)
<223> OTHER INFORMATION: Crosslink between residues
<220> FEATURE:
<221> NAME/KEY: MOD_RES
<222> LOCATION: (16)..(16)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond

```
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 108

Tyr Ala Asp Ala Ile Phe Thr Asn Ser Tyr Arg Ala Val Leu Gly Ala
1               5                   10                  15

Leu Ser Ala Arg Lys Leu Leu Gln Ala Ile Leu Ser Ala
            20                  25

<210> SEQ ID NO 109
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 109
```

```
Tyr Ala Asp Ala Ala Phe Thr Asn Ser Tyr Arg Ala Val Leu Gly Gln
1               5                   10                  15

Leu Ser Ala Arg Ala Leu Leu Gln Ala Ile Leu Ser Arg
            20                  25
```

<210> SEQ ID NO 110
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (5)..(12)
<223> OTHER INFORMATION: Crosslink between residues
<220> FEATURE:
<221> NAME/KEY: MOD_RES
<222> LOCATION: (12)..(12)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 110

```
Tyr Ala Asp Ala Ala Phe Thr Asn Ser Tyr Arg Ala Val Leu Gly Gln
1               5                   10                  15

Leu Ser Ala Arg Lys Leu Leu Gln Ala Ile Leu Ser Ala
            20                  25
```

<210> SEQ ID NO 111
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:

```
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 111

Tyr Ala Asp Ala Ile Phe Thr Ala Ser Tyr Arg Lys Val Leu Ala Gln
1               5                   10                  15

Leu Ser Ala Arg Ala Leu Leu Gln Ala Ile Leu Ser Arg
            20                  25

<210> SEQ ID NO 112
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (8)..(8)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (8)..(15)
<223> OTHER INFORMATION: Crosslink between residues
<220> FEATURE:
<221> NAME/KEY: MOD_RES
<222> LOCATION: (15)..(15)
<223> OTHER INFORMATION: alpha-Me S5-pentenyl-alanine olefin amino
      acid connected by an all-carbon i to i+4
```

```
crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 112

Tyr Ala Asp Ala Ile Phe Thr Ala Ser Tyr Arg Lys Val Leu Ala Gln
 1               5                  10                  15

Leu Ser Ala Arg Lys Leu Leu Gln Ala Ile Leu Ser Ala
            20                  25

<210> SEQ ID NO 113
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
```

```
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 113

Tyr Ala Asp Ala Ile Phe Thr Asn Ala Tyr Arg Lys Val Leu Gly Ala
1               5                   10                  15

Leu Ser Ala Arg Lys Leu Leu Gln Ala Ile Leu Ser Ala
            20                  25

<210> SEQ ID NO 114
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 114

Tyr Ala Asp Ala Ile Phe Thr Asn Ala Tyr Arg Lys Val Leu Gly Ala
1               5                   10                  15

Leu Ser Ala Arg Lys Leu Leu Gln Ala Ile Leu Ser Ala
            20                  25

<210> SEQ ID NO 115
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 115

Tyr Ala Asp Ala Ile Phe Thr Asn Ala Tyr Arg Lys Val Leu Gly Ala
1               5                   10                  15

Leu Ser Ala Arg Ala Leu Leu Gln Ala Ile Leu Ser Arg
            20                  25

<210> SEQ ID NO 116
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
```

-continued

```
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 116

Tyr Ala Asp Ala Ile Phe Thr Asn Ala Tyr Arg Lys Val Leu Gly Ala
1               5                   10                  15
Leu Ser Ala Arg Ala Leu Leu Gln Ala Ile Leu Ser Arg
            20                  25

<210> SEQ ID NO 117
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 117

Tyr Ala Asp Ala Ile Phe Thr Asn Ala Tyr Arg Lys Val Leu Gly Ala
```

Leu Ser Ala Arg Lys Leu Leu Gln Asp Ile Leu Ser Arg
            20                  25

<210> SEQ ID NO 118
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (9)..(9)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (9)..(16)
<223> OTHER INFORMATION: Crosslink between residues
<220> FEATURE:
<221> NAME/KEY: MOD_RES
<222> LOCATION: (16)..(16)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 118

Tyr Ala Asp Ala Ile Phe Thr Asn Ala Tyr Arg Lys Val Leu Gly Ala
1               5                   10                  15

Leu Ser Ala Arg Lys Leu Leu Gln Asp Ile Leu Ser Arg
            20                  25

<210> SEQ ID NO 119
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4 crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 119

Tyr Ala Asp Ala Ile Phe Thr Asn Ser Tyr Arg Ala Val Leu Gly Gln
1               5                   10                  15

Leu Ser Ala Arg Lys Leu Leu Gln Asp Ile Leu Ser Arg
            20                  25

<210> SEQ ID NO 120
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 120

Tyr Ala Asp Ala Ile Phe Thr Asn Ser Tyr Arg Ala Val Leu Gly Gln
1               5                   10                  15

Leu Ser Ala Arg Lys Leu Leu Gln Asp Ile Leu Ser Arg
            20                  25

<210> SEQ ID NO 121
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino

```
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (25)..(29)
<223> OTHER INFORMATION: Crosslink between residues
<220> FEATURE:
<221> NAME/KEY: MOD_RES
<222> LOCATION: (27)..(27)
<223> OTHER INFORMATION: Nle
<220> FEATURE:
<221> NAME/KEY: MOD_RES
<222> LOCATION: (29)..(29)
<223> OTHER INFORMATION: alpha-Me S5-pentenyl-alanine olefin amino
      acid connected by an all-carbon i to i+4
      crosslinker comprising one double bond
<220> FEATURE:
<223> OTHER INFORMATION: C-term NH2

<400> SEQUENCE: 121

Tyr Ala Asp Ala Ile Phe Thr Asn Ser Tyr Arg Ala Val Leu Gly Gln
1               5                   10                  15

Leu Ser Ala Arg Lys Leu Leu Gln Ala Ile Leu Ser Ala
            20                  25

<210> SEQ ID NO 122
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
```

```
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 122

Tyr Ala Asp Ala Ile Phe Thr Ala Ser Tyr Ala Lys Val Leu Gly Gln
1               5                   10                  15

Leu Ser Ala Arg Ala Leu Leu Gln Ala Ile Leu Ser Arg
            20                  25

<210> SEQ ID NO 123
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 123
```

-continued

```
Tyr Ala Asp Ala Ile Phe Thr Ala Ser Tyr Arg Ala Val Leu Gly Gln
1               5                   10                  15

Leu Ser Ala Arg Ala Leu Leu Gln Ala Ile Leu Ser Arg
            20                  25

<210> SEQ ID NO 124
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 124

Tyr Ala Asp Ala Ile Phe Thr Ala Ser Tyr Arg Lys Val Leu Gly Gln
1               5                   10                  15

Leu Ser Ala Ala Ala Leu Leu Gln Ala Ile Leu Ser Arg
            20                  25

<210> SEQ ID NO 125
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
```

```
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 125

Tyr Ala Asp Ala Ile Phe Thr Ala Ser Tyr Arg Ala Val Leu Gly Gln
1               5                   10                  15
Leu Ser Ala Arg Ala Leu Leu Gln Ala Ile Leu Ser Ala
            20                  25

<210> SEQ ID NO 126
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
```

```
          crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 126

Tyr Ala Asp Ala Ile Phe Thr Ala Ser Tyr Gln Lys Val Leu Gly Gln
1               5                   10                  15

Leu Ser Ala Arg Ala Leu Leu Gln Ala Ile Leu Ser Arg
            20                  25

<210> SEQ ID NO 127
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
```

```
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 127

Tyr Ala Asp Ala Ile Phe Thr Ala Ser Tyr Arg Gln Val Leu Gly Gln
1               5                   10                  15

Leu Ser Ala Arg Ala Leu Leu Gln Ala Ile Leu Ser Arg
            20                  25

<210> SEQ ID NO 128
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 128

Tyr Ala Asp Ala Ile Phe Thr Ala Ser Tyr Arg Lys Val Leu Gly Gln
1               5                   10                  15

Leu Ser Ala Gln Ala Leu Leu Gln Ala Ile Leu Ser Arg
            20                  25

<210> SEQ ID NO 129
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 129

Tyr Ala Asp Ala Ile Phe Thr Ala Ser Tyr Arg Lys Val Leu Gly Gln
1               5                   10                  15

Leu Ser Ala Arg Ala Leu Leu Gln Ala Ile Leu Ser Gln
            20                  25

<210> SEQ ID NO 130
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
```

```
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 130

Tyr Ala Asp Ala Ile Phe Thr Ala Ser Tyr Arg Lys Val Leu Ala Gln
1               5                   10                  15
Leu Ser Ala Arg Ala Ala Leu Gln Ala Ile Leu Ser Arg
            20                  25

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
```

```
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 131

Tyr Ala Asp Ala Ile Phe Thr Ala Ser Tyr Arg Lys Val Leu Gly Gln
1               5                   10                  15

Leu Ser Ala Arg Ala Leu Leu Gln Ala Ile Leu Ser
            20                  25

<210> SEQ ID NO 132
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising no double bonds
      (fully saturated alkylene crosslinker)
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising no double bonds
      (fully saturated alkylene crosslinker)
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising no double bonds
      (fully saturated alkylene crosslinker)
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising no double bonds
      (fully saturated alkylene crosslinker)
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 132
```

```
Tyr Ala Asp Ala Ile Phe Thr Ala Ser Tyr Arg Lys Val Leu Gly Gln
1               5                   10                  15

Leu Ser Ala Arg Ala Leu Leu Gln Ala Ile Leu Ser Arg
                20                  25
```

<210> SEQ ID NO 133
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Alpha-Me alkyne 1,5 triazole (5 carbon) amino
      acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Alpha-Me azide 1,5 triazole (3 carbon) amino
      acid
<220> FEATURE:
<221> NAME/KEY: MOD_RES
<222> LOCATION: (21)..(21)
<223> OTHER INFORMATION: Alpha-Me alkyne 1,5 triazole (5 carbon) amino
      acid
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Alpha-Me azide 1,5 triazole (3 carbon) amino
      acid
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 133

```
Tyr Ala Asp Xaa Ile Phe Thr Xaa Ser Tyr Arg Lys Val Leu Gly Gln
1               5                   10                  15

Leu Ser Ala Arg Xaa Leu Leu Gln Xaa Ile Leu Ser Arg
                20                  25
```

<210> SEQ ID NO 134
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:

```
<221> NAME/KEY: MOD_RES
<222> LOCATION: (4)..(4)
<223> OTHER INFORMATION: Alpha-Me azide 1,5 triazole (3 carbon) amino
      acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Alpha-Me alkyne 1,5 triazole (5 carbon) amino
      acid
<220> FEATURE:
<221> NAME/KEY: MOD_RES
<222> LOCATION: (21)..(21)
<223> OTHER INFORMATION: Alpha-Me azide 1,5 triazole (3 carbon) amino
      acid
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Alpha-Me alkyne 1,5 triazole (5 carbon) amino
      acid
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 134

Tyr Ala Asp Xaa Ile Phe Thr Xaa Ser Tyr Arg Lys Val Leu Gly Gln
1               5                   10                  15

Leu Ser Ala Arg Xaa Leu Leu Gln Xaa Ile Leu Ser Arg
            20                  25

<210> SEQ ID NO 135
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Alpha-Me alkyne 1,5 triazole (5 carbon) amino
      acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Alpha-Me azide 1,5 triazole (3 carbon) amino
      acid
<220> FEATURE:
<221> NAME/KEY: MOD_RES
<222> LOCATION: (21)..(21)
<223> OTHER INFORMATION: Alpha-Me azide 1,5 triazole (3 carbon) amino
      acid
<220> FEATURE:
<221> NAME/KEY: misc_feature
<222> LOCATION: (21)..(25)
<223> OTHER INFORMATION: Crosslink between residues
```

```
<220> FEATURE:
<221> NAME/KEY: MOD_RES
<222> LOCATION: (25)..(25)
<223> OTHER INFORMATION: Alpha-Me alkyne 1,5 triazole (5 carbon) amino
      acid
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 135

Tyr Ala Asp Xaa Ile Phe Thr Xaa Ser Tyr Arg Lys Val Leu Gly Gln
1               5                   10                  15

Leu Ser Ala Arg Xaa Leu Leu Gln Xaa Ile Leu Ser Arg
            20                  25

<210> SEQ ID NO 136
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Alpha-Me azide 1,5 triazole (3 carbon) amino
      acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Alpha-Me alkyne 1,5 triazole (5 carbon) amino
      acid
<220> FEATURE:
<221> NAME/KEY: MOD_RES
<222> LOCATION: (21)..(21)
<223> OTHER INFORMATION: Alpha-Me alkyne 1,5 triazole (5 carbon) amino
      acid
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Alpha-Me azide 1,5 triazole (3 carbon) amino
      acid
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 136

Tyr Ala Asp Xaa Ile Phe Thr Xaa Ser Tyr Arg Lys Val Leu Gly Gln
1               5                   10                  15

Leu Ser Ala Arg Xaa Leu Leu Gln Xaa Ile Leu Ser Arg
            20                  25

<210> SEQ ID NO 137
```

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: Alpha-Me R-azide 1,4 triazole (6 carbon) amino
      acid
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: Alpha-Me alkyne 1,4 triazole (5 carbon) amino
      acid
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 137

Tyr Ala Asp Ala Ile Phe Thr Asn Ser Tyr Arg Xaa Val Leu Gly Gln
1               5                   10                  15

Leu Ser Xaa Arg Lys Leu Leu Gln Asp Ile Leu Ser Arg
            20                  25

<210> SEQ ID NO 138
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 138
```

```
Tyr Ala Asp Ala Ile Phe Thr Asn Ser Tyr Gln Ala Val Leu Gly Gln
1               5                   10                  15

Leu Ser Ala Arg Lys Leu Leu Gln Asn Ile Leu Ser Arg
            20                  25

<210> SEQ ID NO 139
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 139

Tyr Ala Asp Ala Ile Phe Thr Asn Ser Tyr Arg Ala Val Leu Gly Gln
1               5                   10                  15

Leu Ser Ala Gln Lys Leu Leu Gln Asn Ile Leu Ser Arg
            20                  25

<210> SEQ ID NO 140
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
```

```
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 140

Tyr Ala Asp Ala Ile Phe Thr Asn Ser Tyr Arg Ala Val Leu Gly Gln
1               5                   10                  15

Leu Ser Ala Arg Gln Leu Leu Gln Asn Ile Leu Ser Arg
            20                  25

<210> SEQ ID NO 141
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 141

Tyr Ala Asp Ala Ile Phe Thr Asn Ser Tyr Arg Ala Val Leu Gly Gln
1               5                   10                  15

Leu Ser Ala Arg Lys Leu Leu Gln Asn Ile Leu Ser Gln
            20                  25

<210> SEQ ID NO 142
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
```

-continued

```
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 142

Tyr Ala Asp Ala Ile Phe Thr Asn Ser Tyr Arg Ala Val Leu Gly Gln
1               5                   10                  15

Leu Ser Ala Arg Lys Leu Leu Gln Asn Ile Leu Ser
            20                  25

<210> SEQ ID NO 143
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 143

Tyr Ala Asp Ala Ile Phe Thr Ala Ser Tyr Gln Ala Val Leu Gly Gln
1               5                   10                  15

Leu Ser Ala Arg Lys Leu Leu Gln Asn Ile Leu Ser Arg
            20                  25

<210> SEQ ID NO 144
<211> LENGTH: 29
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 144

Tyr Ala Asp Ala Ile Phe Thr Ala Ser Tyr Arg Ala Val Leu Gly Gln
1               5                   10                  15

Leu Ser Ala Gln Lys Leu Leu Gln Asn Ile Leu Ser Arg
            20                  25

<210> SEQ ID NO 145
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 145
```

Tyr Ala Asp Ala Ile Phe Thr Ala Ser Tyr Arg Ala Val Leu Gly Gln
1               5                   10                  15

Leu Ser Ala Arg Gln Leu Leu Gln Asn Ile Leu Ser Arg
                20                  25

<210> SEQ ID NO 146
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 146

Tyr Ala Asp Ala Ile Phe Thr Ala Ser Tyr Arg Ala Val Leu Gly Gln
1               5                   10                  15

Leu Ser Ala Arg Lys Leu Leu Gln Asn Ile Leu Ser Gln
                20                  25

<210> SEQ ID NO 147
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino

```
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 147

Tyr Ala Asp Ala Ile Phe Thr Ala Ser Tyr Arg Ala Val Leu Gly Gln
1               5                   10                  15

Leu Ser Ala Arg Lys Leu Leu Gln Asn Ile Leu Ser
            20                  25

<210> SEQ ID NO 148
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 148

Tyr Ala Asp Ala Ile Phe Thr Ala Ser Tyr Arg Ala Val Leu Gly Gln
1               5                   10                  15

Leu Ser Ala Arg Gln Leu Leu Gln Asn Ile Leu Ser
            20                  25

<210> SEQ ID NO 149
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
```

```
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 149

Tyr Ala Asp Ala Ile Phe Thr Ala Ser Tyr Arg Ala Val Leu Gly Gln
1               5                   10                  15

Leu Ser Ala Arg Lys Leu Leu Gln Asn Ile Leu Ser Arg
            20                  25

<210> SEQ ID NO 150
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 150

Tyr Ala Asp Ala Ile Phe Thr Ala Ser Tyr Arg Ala Val Leu Ala Gln
1               5                   10                  15

Leu Ser Ala Arg Lys Ala Leu Gln Asn Ile Leu Ser Arg
            20                  25

<210> SEQ ID NO 151
<211> LENGTH: 29
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term OH

<400> SEQUENCE: 151

Tyr Ala Asp Ala Ile Phe Thr Ala Ser Tyr Arg Lys Val Leu Gly Gln
1               5                   10                  15

Leu Ser Ala Arg Ala Leu Leu Gln Ala Ile Leu Ser Arg
            20                  25

<210> SEQ ID NO 152
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
```

```
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term OH

<400> SEQUENCE: 152

Tyr Ala Asp Ala Ile Phe Thr Ala Ser Tyr Arg Lys Val Leu Gly Glu
1               5                   10                  15

Leu Ser Ala Arg Ala Leu Leu Glu Ala Ile Leu Ser Arg
                20                  25

<210> SEQ ID NO 153
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
```

```
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term OH

<400> SEQUENCE: 153

Tyr Ala Asp Ala Ile Phe Thr Ala Ser Tyr Arg Lys Val Leu Gly Glu
1               5                   10                  15

Leu Ser Ala Arg Ala Leu Leu Gln Ala Ile Leu Ser Arg
            20                  25

<210> SEQ ID NO 154
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term OH

<400> SEQUENCE: 154

Tyr Ala Asp Ala Ile Phe Thr Ala Ser Tyr Arg Lys Val Leu Gly Gln
1               5                   10                  15

Leu Ser Ala Arg Ala Leu Leu Glu Ala Ile Leu Ser Arg
            20                  25
```

```
<210> SEQ ID NO 155
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 155

Tyr Ala Asp Ala Ile Phe Thr Ala Ser Tyr Arg Lys Val Leu Ala Gln
1               5                   10                  15

Leu Ser Ala Arg Ala Leu Leu Gln Ala Ile Leu Ser Arg
            20                  25

<210> SEQ ID NO 156
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
```

```
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 156

Tyr Ala Asp Ala Ile Phe Thr Ala Ser Tyr Arg Ala Val Leu Ala Gln
1               5                   10                  15

Leu Ser Ala Arg Ala Leu Leu Gln Ala Ile Leu Ser Arg
            20                  25

<210> SEQ ID NO 157
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
```

```
            crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 157

Tyr Ala Asp Ala Ile Phe Thr Ala Ser Tyr Arg Lys Val Leu Ala Gln
1               5                   10                  15

Leu Ser Ala Ala Ala Leu Leu Gln Ala Ile Leu Ser Arg
            20                  25

<210> SEQ ID NO 158
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2
```

<400> SEQUENCE: 158

Tyr Ala Asp Ala Ile Phe Thr Ala Ser Tyr Arg Lys Val Leu Ala Gln
1               5                   10                  15

Leu Ser Ala Arg Ala Leu Leu Gln Ala Ile Leu Ser Ala
            20                  25

<210> SEQ ID NO 159
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 159

Tyr Ala Asp Ala Ile Phe Thr Asp Ser Tyr Arg Ala Val Leu Gly Glu
1               5                   10                  15

Leu Ser Ala Arg Lys Leu Leu Glu Asp Ile Leu Ser Arg
            20                  25

<210> SEQ ID NO 160
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES

```
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 160

Tyr Ala Asp Ala Ile Phe Thr Asp Ser Tyr Arg Ala Val Leu Gly Gln
1               5                   10                  15

Leu Ser Ala Arg Lys Leu Leu Gln Asp Ile Leu Ser Arg
            20                  25

<210> SEQ ID NO 161
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 161

Tyr Ala Asp Ala Ile Phe Thr Asn Ser Tyr Arg Ala Val Leu Gly Glu
1               5                   10                  15

Leu Ser Ala Arg Lys Leu Leu Gln Asp Ile Leu Ser Arg
            20                  25

<210> SEQ ID NO 162
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
```

```
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 162

Tyr Ala Asp Ala Ile Phe Thr Asn Ser Tyr Arg Ala Val Leu Gly Gln
1               5                   10                  15

Leu Ser Ala Arg Lys Leu Leu Glu Asp Ile Leu Ser Arg
            20                  25

<210> SEQ ID NO 163
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 163

Tyr Ala Asp Ala Ile Phe Thr Asp Ser Tyr Arg Ala Val Leu Gly Glu
1               5                   10                  15

Leu Ser Ala Arg Lys Leu Leu Gln Asp Ile Leu Ser Arg
            20                  25

<210> SEQ ID NO 164
<211> LENGTH: 29
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 164

Tyr Ala Asp Ala Ile Phe Thr Asn Ser Tyr Arg Ala Val Leu Gly Glu
1               5                   10                  15

Leu Ser Ala Arg Lys Leu Leu Glu Asp Ile Leu Ser Arg
            20                  25

<210> SEQ ID NO 165
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 165
```

Tyr Ala Asp Ala Ile Phe Thr Asp Ser Tyr Arg Ala Val Leu Gly Gln
1               5                   10                  15

Leu Ser Ala Arg Lys Leu Leu Glu Asp Ile Leu Ser Arg
            20                  25

<210> SEQ ID NO 166
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 166

Tyr Ala Asp Ala Ile Phe Thr Ala Ser Tyr Arg Lys Val Leu Gly Glu
1               5                   10                  15

Leu Ser Ala Arg Ala Leu Leu Glu Ala Ile Leu Ser Arg
            20                  25

<210> SEQ ID NO 167
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:

```
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 167

Tyr Ala Asp Ala Ile Phe Thr Ala Ser Tyr Arg Lys Val Leu Gly Glu
1               5                   10                  15

Leu Ser Ala Arg Ala Leu Leu Gln Ala Ile Leu Ser Arg
            20                  25

<210> SEQ ID NO 168
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
```

```
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 168

Tyr Ala Asp Ala Ile Phe Thr Ala Ser Tyr Arg Lys Val Leu Gly Gln
1               5                   10                  15

Leu Ser Ala Arg Ala Leu Leu Glu Ala Ile Leu Ser Arg
            20                  25

<210> SEQ ID NO 169
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 169

Tyr Ala Asp Ala Ile Phe Thr Asn Ser Tyr Gln Ala Val Leu Gly Gln
1               5                   10                  15

Leu Ser Ala Arg Lys Leu Leu Gln Asn Ile Leu Ser Arg
            20                  25

<210> SEQ ID NO 170
```

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising one double bond
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 170

Tyr Ala Asp Ala Ile Phe Thr Asn Ser Tyr Arg Ala Val Leu Gly Gln
1               5                   10                  15

Leu Ser Ala Gln Lys Leu Leu Gln Asn Ile Leu Ser Arg
            20                  25

<210> SEQ ID NO 171
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (12)..(12)
<223> OTHER INFORMATION: alpha-Me R8-octenyl-alanine olefin amino
      acid connected by an all-carbon i to i+7
      crosslinker comprising no double bonds
      (fully saturated alkylene crosslinker)
<220> FEATURE:
<221> NAME/KEY: misc_feature
<222> LOCATION: (12)..(19)
<223> OTHER INFORMATION: Crosslink between residues
<220> FEATURE:
<221> NAME/KEY: MOD_RES
<222> LOCATION: (19)..(19)
<223> OTHER INFORMATION: alpha-Me S5-pentenyl-alanine olefin amino
      acid connected by an all-carbon i to i+4
      crosslinker comprising no double bonds
      (fully saturated alkylene crosslinker)
<220> FEATURE:
<221> NAME/KEY: MOD_RES
<222> LOCATION: (27)..(27)
<223> OTHER INFORMATION: Nle
```

```
<220> FEATURE:
<223> OTHER INFORMATION: C-term NH2

<400> SEQUENCE: 171

Tyr Ala Asp Ala Ile Phe Thr Asn Ser Tyr Arg Ala Val Leu Gly Gln
1               5                   10                  15

Leu Ser Ala Arg Lys Leu Leu Gln Asp Ile Leu Ser Arg
            20                  25

<210> SEQ ID NO 172
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 172

Tyr Ala Asp Ala Ile Phe Thr Ala Ser Tyr Arg Lys Val Leu Gly Gln
1               5                   10                  15

Leu Ser Ala Arg Ala Leu Leu Gln Ala Ile Leu Ser Arg
            20                  25

<210> SEQ ID NO 173
<211> LENGTH: 29
<212> TYPE: PRT
<213> ORGANISM: Artificial Sequence
<220> FEATURE:
<223> OTHER INFORMATION: Description of Artificial Sequence: Synthetic
```

```
                         peptide
<220> FEATURE:
<223> OTHER INFORMATION: N-term HBS
<220> FEATURE:
<221> NAME/KEY: MOD_RES
<222> LOCATION: (3)..(3)
<223> OTHER INFORMATION: Aar
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 173

Tyr Ala Xaa Ala Ile Phe Thr Asn Ser Tyr Arg Lys Val Leu Gly Gln
1               5                   10                  15

Leu Ser Ala Arg Ala Leu Leu Gln Ala Ile Leu Ser Arg
            20                  25

<210> SEQ ID NO 174
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HBS
<220> FEATURE:
<221> NAME/KEY: MOD_RES
<222> LOCATION: (3)..(3)
<223> OTHER INFORMATION: N-allylaspartic acid
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 174

Tyr Ala Asp Ala Ile Phe Thr Asn Ser Tyr Arg Lys Val Leu Gly Gln
1               5                   10                  15
```

```
Leu Ser Ala Arg Ala Leu Leu Gln Ala Ile Leu Ser Arg
            20                  25

<210> SEQ ID NO 175
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HBS
<220> FEATURE:
<221> NAME/KEY: MOD_RES
<222> LOCATION: (3)..(3)
<223> OTHER INFORMATION: N-allylglycine
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 175

Tyr Ala Gly Ala Ile Phe Thr Asn Ser Tyr Arg Lys Val Leu Gly Gln
1               5                   10                  15

Leu Ser Ala Arg Lys Leu Leu Gln Asp Ile Leu Ser Arg
            20                  25

<210> SEQ ID NO 176
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HBS
<220> FEATURE:
<221> NAME/KEY: MOD_RES
<222> LOCATION: (3)..(3)
<223> OTHER INFORMATION: N-allylglycine
<220> FEATURE:
<221> NAME/KEY: MOD_RES
<222> LOCATION: (21)..(21)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: alpha-Me S5-pentenyl-alanine olefin amino
      acid connected by an all-carbon i to i+4
      crosslinker comprising one double bond
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 176

Tyr Ala Gly Ala Ile Phe Thr Asn Ser Tyr Arg Lys Val Leu Gly Gln
1               5                   10                  15

Leu Ser Ala Arg Ala Leu Leu Gln Ala Ile Leu Ser Arg
            20                  25
```

```
<210> SEQ ID NO 177
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Alpha-Me alkyne 1,5 triazole (5 carbon) amino
      acid
<220> FEATURE:
<221> NAME/KEY: misc_feature
<222> LOCATION: (4)..(8)
<223> OTHER INFORMATION: Crosslink between residues
<220> FEATURE:
<221> NAME/KEY: MOD_RES
<222> LOCATION: (8)..(8)
<223> OTHER INFORMATION: Alpha-Me azide 1,5 triazole (3 carbon) amino
      acid
<220> FEATURE:
<221> NAME/KEY: MOD_RES
<222> LOCATION: (21)..(21)
<223> OTHER INFORMATION: Alpha-Me azide 1,5 triazole (3 carbon) amino
      acid
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Alpha-Me alkyne 1,5 triazole (5 carbon) amino
      acid
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 177

Tyr Ala Asp Xaa Ile Phe Thr Xaa Ser Tyr Arg Lys Val Leu Gly Gln
1               5                   10                  15

Leu Ser Ala Arg Xaa Leu Leu Gln Xaa Ile Leu Ser Arg
            20                  25

<210> SEQ ID NO 178
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (4)..(4)
<223> OTHER INFORMATION: Alpha-Me azide 1,5 triazole (3 carbon) amino
      acid
<220> FEATURE:
<221> NAME/KEY: misc_feature
<222> LOCATION: (4)..(8)
<223> OTHER INFORMATION: Crosslink between residues
```

```
<220> FEATURE:
<221> NAME/KEY: MOD_RES
<222> LOCATION: (8)..(8)
<223> OTHER INFORMATION: Alpha-Me alkyne 1,5 triazole (5 carbon) amino
      acid
<220> FEATURE:
<221> NAME/KEY: MOD_RES
<222> LOCATION: (21)..(21)
<223> OTHER INFORMATION: Alpha-Me alkyne 1,5 triazole (5 carbon) amino
      acid
<220> FEATURE:
<221> NAME/KEY: misc_feature
<222> LOCATION: (21)..(25)
<223> OTHER INFORMATION: Crosslink between residues
<220> FEATURE:
<221> NAME/KEY: MOD_RES
<222> LOCATION: (25)..(25)
<223> OTHER INFORMATION: Alpha-Me azide 1,5 triazole (3 carbon) amino
      acid
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 178

Tyr Ala Asp Xaa Ile Phe Thr Xaa Ser Tyr Arg Lys Val Leu Gly Gln
1               5                   10                  15

Leu Ser Ala Arg Xaa Leu Leu Gln Xaa Ile Leu Ser Arg
            20                  25

<210> SEQ ID NO 179
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term HBS
<220> FEATURE:
<221> NAME/KEY: MOD_RES
<222> LOCATION: (3)..(3)
<223> OTHER INFORMATION: N-allylaspartic acid
<220> FEATURE:
<221> NAME/KEY: MOD_RES
<222> LOCATION: (27)..(27)
<223> OTHER INFORMATION: Nle
<220> FEATURE:
<223> OTHER INFORMATION: C-term NH2

<400> SEQUENCE: 179

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Leu Ser Arg
            20                  25

<210> SEQ ID NO 180
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term teHBS
<220> FEATURE:
<221> NAME/KEY: MOD_RES
<222> LOCATION: (3)..(3)
<223> OTHER INFORMATION: N-(2-sulfhydryleth-1yl)glycine
<220> FEATURE:
<221> NAME/KEY: MOD_RES
```

```
<222> LOCATION: (27)..(27)
<223> OTHER INFORMATION: Nle
<220> FEATURE:
<223> OTHER INFORMATION: C-term NH2

<400> SEQUENCE: 180

Tyr Ala Gly Ala Ile Phe Thr Asn Ser Tyr Arg Lys Val Leu Gly Gln
1               5                   10                  15

Leu Ser Ala Arg Lys Leu Leu Gln Asp Ile Leu Ser Arg
            20                  25
```